US012298304B2

(12) United States Patent
Mahler

(10) Patent No.: US 12,298,304 B2
(45) Date of Patent: May 13, 2025

(54) COMPOSITIONS AND METHODS FOR DIAGNOSING AND ASSESSING RHEUMATOID ARTHRITIS

(71) Applicant: Inova Diagnostics, Inc., San Diego, CA (US)

(72) Inventor: Michael Mahler, Bad Neuenahr (DE)

(73) Assignee: Inova Diagnostics, Inc., San Diego, CA (US)

( * ) Notice: Subject to any disclaimer, the term of this patent is extended or adjusted under 35 U.S.C. 154(b) by 392 days.

(21) Appl. No.: 16/791,779

(22) Filed: Feb. 14, 2020

(65) Prior Publication Data

US 2020/0264177 A1 Aug. 20, 2020

Related U.S. Application Data

(60) Provisional application No. 62/806,607, filed on Feb. 15, 2019.

(51) Int. Cl.
*G01N 33/573* (2006.01)
*G01N 33/58* (2006.01)

(52) U.S. Cl.
CPC .......... *G01N 33/573* (2013.01); *G01N 33/58* (2013.01); *G01N 2458/00* (2013.01); *G01N 2800/105* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 4,208,479 | A * | 6/1980 | Zuk | C07J 41/0016 436/826 |
| 2003/0153013 | A1 | 8/2003 | Huang | |
| 2004/0253640 | A1 | 12/2004 | Chen et al. | |
| 2008/0280785 | A1 | 11/2008 | Tseng et al. | |
| 2011/0003880 | A1 * | 1/2011 | Bhattacharya | C12N 15/1137 800/9 |
| 2013/0274125 | A1 | 10/2013 | Binder et al. | |
| 2014/0127720 | A1 * | 5/2014 | Rosen | G01N 33/564 435/7.92 |
| 2018/0284118 | A1 | 10/2018 | Darrah et al. | |
| 2019/0048086 | A1 * | 2/2019 | Mobley | A61K 45/06 |

FOREIGN PATENT DOCUMENTS

| | | |
|---|---|---|
| WO | WO 2009/039170 | 3/2009 |
| WO | 2017202879 A1 | 11/2017 |

OTHER PUBLICATIONS

"An Assay Panel Combining Anti-Protein Arginine Deiminase4 with Rheumatoid Factor Isotypes Distinguishes Anti-Citrullinated Peptide Antibody Negative RheumatoidArthritis" By Dervieux 2018 ACR Abstract No. 1858 (Year: 2018).*

"Peptidyl Arginine Deiminase Type 2 (PAD-2) and PAD-4 but Not PAD-1, PAD-3, and PAD-6 Are Expressed in Rheumatoid Arthritis Synovium in Close Association With Tissue Inflammation" By Foulquier Arthritis & Rheumatism 2007 56: 3541-3553 (Year: 2007).*

Zhao (Chin J Rheumatol. 2014 vol. 18, p. 734-737 (original Chinese text); Note both English translation and original Chinese text ) (Year: 2014).*

Floulquier et al. ("Peptidyl Arginine Deimanase Type 2 (PAD2) and PAD4 but Not PAD1, PAD3 and PAD6 are expressed in Rheumatoid Arthritis Synovium in Close Association with Tissue Inflammation" Arthritis & Rheumatism 2007 56:3541 (Year: 2007).*

Reyes-Castillo et al., "Comparative analysis of autoantibodies targeting peptidylarginine deiminase type 4, mutated citrullinated vimentin and cyclic citrullinated peptides in rheumatoid arthritis: associations with cytokine profiles, clinical and genetic features," *Clin. Exp. Immunol.*, 182(2):119-131 (2015).

Annonymous, "PAD4 Autoantibody ELISA Kit," *Cayman Chemical*, pp. 1-12 (2019). Retrieved from the internet: https://www.caymanchem.com/pdfs/500930.pdf.

Rantapaa-Dahlqvist et al., "Antibodies against cyclic citrullinated peptide and IgA rheumatoid factor predict the development of rheumatoid arthritis," *Arthritis Rheum.*, 48(10):2741-2749 (2003).

Kokkonen et al., "Antibodies of IgG, IgA and IgM isotypes against cyclic citrullinated peptide precede the development of rheumatoid arthritis," *Arthritis Res. Ther.*, 13(1):R13 (2011).

Aletaha et al., "2010 Rheumatoid arthritis classifi cation criteria: an American College of Rheumatology/European League Against Rheumatism collaborative initiative," *Ann. Rheum.*, 69:1580-1588 (2010).

Aletaha et al., "Diagnosis and Management of Rheumatoid Arthritis: A Review," *JAMA*, 320(13):1360-1372 (2018).

Asaga et al., "Immunocytochemical localization of peptidylarginine deiminase in human eosinophils and neutrophils," *J. Leukoc. Biol.*, 70(1):46-51 (2001).

Brower, "Use of the radiograph to measure the course of rheumatoid arthritis. The gold standard versus fool's gold.," *Arthritis Rheum.*, 33(3):316-324 (1990).

Bruce et al., "The Stanford Health Assessment Questionnaire: dimensions and practical applications," *Health Qual. Life Outcomes*, 1(1):20 (2003).

Chavanas et al., "Peptidylarginine deiminases and deimination in biology and pathology: relevance to skin homeostasis," *J. Dermatol. Sci.*, 44(2):63-72 (2006).

Darrah et al., "Autoantibodies to Peptidylarginine Deiminase 2 Are Associated With Less Severe Disease in Rheumatoid Arthritis," *Front. Immunol.* 9:2696 (2018).

Darrah et al., "Erosive rheumatoid arthritis is associated with antibodies that activate PAD4 by increasing calcium sensitivity," *Sci. Transl. Med.*, 5(186):186ra65 (2013).

(Continued)

*Primary Examiner* — Changhwa J Cheu
(74) *Attorney, Agent, or Firm* — ArentFox Schiff LLP

(57) ABSTRACT

The present disclosure relates to the use of anti-PAD IgA as a clinical biomarker for diagnostic and prognostic information in rheumatoid arthritis (RA) patients. The disclosure further provides methods and compositions for the detection anti-PAD IgA in a biological sample.

16 Claims, 18 Drawing Sheets

Specification includes a Sequence Listing.

(56) References Cited

OTHER PUBLICATIONS

Dennler et al., "Antibody Conjugates: From Heterogeneous Populations to Defined Reagents," *Antibodies*, 4(3):197-224 (2015).
Fries et al., "Measurement of patient outcome in arthritis," *Arthritis Rheum.*, 23(3):137-145 (1980).
GenBank Accession No. NM_007365.3, GI No. 1519245591, "*Homo sapiens* peptidyl arginine deiminase 2 (PADI2), mRNA," Dec. 29, 2018.
GenBank Accession No. NM_012387.2, GI No. 216548486, "*Homo sapiens* peptidyl arginine deiminase 4 (PADI4), mRNA," Sep. 2, 2018.
GenBank Accession No. NM_012387.3, GI No. 1519314340, "*Homo sapiens* peptidyl arginine deiminase 4 (PADI4), mRNA," Nov. 23, 2018.
GenBank Accession No. NM_016233.2, GI No. 122939160, "*Homo sapiens* peptidyl arginine deiminase 3 (PADI3), mRNA," Jun. 24, 2018.
GenBank Accession No. NP_031391.2, GI No. 122939159, "protein-arginine deiminase type-2 [*Homo sapiens*]," Dec. 29, 2018.
GenBank Accession No. NP_036519.2, GI No. 216548487, "protein-arginine deiminase type-4 [*Homo sapiens*]," Nov. 23, 2018.
GenBank Accession No. NP_057317.2, GI No. 122939161, "protein-arginine deiminase type-3 [*Homo sapiens*]," Jun. 24, 2018.
GenBank Accession No. XM_011541150.1, GI No. 767903519, "Predicted: *Homo sapiens* peptidyl arginine deiminase 4 (PADI4), transcript variant X1, mRNA," Mar. 26, 2018.
GenBank Accession No. XM_011541151.1, GI No. 767903521, "Predicted: *Homo sapiens* peptidyl arginine deiminase 4 (PADI4), transcript variant X2, mRNA," Mar. 26, 2018.
GenBank Accession No. XM_011541152.1, GI No. 767903523, "Predicted: *Homo sapiens* peptidyl arginine deiminase 4 (PADI4), transcript variant X3, mRNA," Mar. 26, 2018.
GenBank Accession No. XM_011541153.1, GI No. 767903525, "Predicted: *Homo sapiens* peptidyl arginine deiminase 4 (PADI4), transcript variant X4, mRNA," Mar. 26, 2018.
GenBank Accession No. XM_011541154.2, GI No. 1034557308, "Predicted: *Homo sapiens* peptidyl arginine deiminase 4 (PADI4), transcript variant X5, mRNA," Mar. 26, 2018.
GenBank Accession No. XM_011541155.1, GI No. 767903529, "Predicted: *Homo sapiens* peptidyl arginine deiminase 4 (PADI4), transcript variant X6, mRNA," Mar. 26, 2018.
GenBank Accession No. XM_011541156.1, GI No. 767903531, "Predicted: *Homo sapiens* peptidyl arginine deiminase 4 (PADI4), transcript variant X7, mRNA," Mar. 26, 2018.
GenBank Accession No. XM_011541157.1, GI No. 767903533, "Predicted: *Homo sapiens* peptidyl arginine deiminase 4 (PADI4), transcript variant X8, mRNA," Mar. 26, 2018.
GenBank Accession No. XM_011541571.2, GI No. 1034559140, "Predicted: *Homo sapiens* peptidyl arginine deiminase 3 (PADI3), transcript variant X1, mRNA," Mar. 26, 2018.
GenBank Accession No. XM_011541572.2, GI No. 1034559143, "Predicted: *Homo sapiens* peptidyl arginine deiminase 3 (PADI3), transcript variant X3, mRNA," Mar. 26, 2018.
GenBank Accession No. XM_017000148.2, GI No. 1370451734, "Predicted: *Homo sapiens* peptidyl arginine deiminase 2 (PADI2), transcript variant X2, mRNA," Mar. 26, 2018.
GenBank Accession No. XM_017001463.1, GI No. 1034559141, "Predicted: *Homo sapiens* peptidyl arginine deiminase 3 (PADI3), transcript variant X2, mRNA," Mar. 26, 2018.
GenBank Accession No. XP_011539452.1, GI No. 767903520, "protein-arginine deiminase type-4 isoform X1 [*Homo sapiens*]," Mar. 26, 2018.
GenBank Accession No. XP_011539453.1, GI No. 767903522, "protein-arginine deiminase type-4 isoform X2 [*Homo sapiens*]," Mar. 26, 2018.
GenBank Accession No. XP_011539455.1, GI No. 767903526, "protein-arginine deiminase type-4 isoform X4 [*Homo sapiens*]," Mar. 26, 2018.
GenBank Accession No. XP_011539456.1, GI No. 767903528, "protein-arginine deiminase type-4 isoform X4 [*Homo sapiens*]," Mar. 26, 2018.
GenBank Accession No. XP_011539457.1, GI No. 767903530, "protein-arginine deiminase type-4 isoform X5 [*Homo sapiens*]," Mar. 26, 2018.
GenBank Accession No. XP_011539458.1, GI No. 767903532, "protein-arginine deiminase type-4 isoform X6 [*Homo sapiens*]," Mar. 26, 2018.
GenBank Accession No. XP_011539873.1, GI No. 767904616, "protein-arginine deiminase type-3 isoform X1 [*Homo sapiens*]," Mar. 26, 2018.
GenBank Accession No. XP_011539874.1, GI No. 767904618, "protein-arginine deiminase type-3 isoform X3 [*Homo sapiens*]," Mar. 26, 2018.
GenBank Accession No. XP_016855637.1, GI No. 1034554998, "protein-arginine deiminase type-2 isoform X1 [*Homo sapiens*]," Mar. 26, 2018.
GenBank Accession No. XP_016856952.1, GI No. 1034559142, "protein-arginine deiminase type-3 isoform X2 [*Homo sapiens*]," Mar. 26, 2018.
Grassi et al., "The clinical features of rheumatoid arthritis," *Eur. J. Radiol.*, 27:S18-S24 (1998).
Halvorsen et al., "Serum IgG antibodies to peptidylarginine deiminase 4 in rheumatoid arthritis and associations with disease severity," *Ann. Rheum. Dis.*, 67(3):414-417 (2008).
Huston et al., "Antigen recognition and targeted delivery by the single-chain Fv," *Cell Biophys.*, 22(1-3):189-224 (1993).
Kanno et al., "Human peptidylarginine deiminase type III: molecular cloning and nucleotide sequence of the cDNA, properties of the recombinant enzyme, and immunohistochemical localization in human skin," *J. Invest. Dermatol.*, 115(5):813-823 (2000).
Kruljec et al., "Alternative Affinity Ligands for Immunoglobulins," *Bioconjug. Chem.*, 28(8):2009-2030 (2017).
Nacaht et al., "Peptidylarginine deiminase isoforms are differentially expressed in the anagen hair follicles and other human skin appendages," *J. Invest. Dermatol.*, 125(1):34-41 (2005).
Nagata et al., "Peptidylarginine deiminase in rat and mouse hemopoietic cells," *Experientia*, 46(1):72-74 (1990).
Nakashima et al., "Nuclear localization of peptidylarginine deiminase V and histone deimination in granulocytes," *J. Biol. Chem.*, 277(51):49562-49568 (2002).
Pluckthun et al., "Expression of functional antibody Fv and Fab fragments in *Escherichia coli," Methods Enzymol.*, 178:497-515 (1989).
Ronnmark et al., "Human immunoglobulin A (IgA)-specific ligands from combinatorial engineering of protein A," *Eur. J. Biochem.*, 269(11):2647-2655 (2002).
Roth et al., "Antibodies against transglutaminases, peptidylarginine deiminase and citrulline in rheumatoid arthritis—new pathways to epitope spreading," *Clin. Exp. Rheumatol.*, 24(1):12-18 (2006).
Sasse et al., "How to Define and Determine Reference Intervals in the Clinical Laboratory; Approved Guideline," *Clinical and Laboratory Standards Institute*, C28-A2, 20(13):1-38 (2000).
Sharp, "Radiologic assessment as an outcome measure in rheumatoid arthritis," *Arthritis Rheum.*, 32(2):221-229 (1989).
Takizawa et al., "Peptidylarginine deiminase 4 (PADI4) identified as a conformation-dependent autoantigen in rheumatoid arthritis," *Scand. J. Reumatol.* ,34(3):212-215 (2005).
Taylor et al., "A systematic review of serum biomarkers anti-cyclic citrullinated Peptide and rheumatoid factor as tests for rheumatoid arthritis," *Autoimmune Dis.*, 2011:815038 (2011).
Urano et al., "Immunohistochemical demonstration of peptidylarginine deiminase in human sweat glands," *Am. J. Dermatopathol.*, 12(3):249-255 (1990).
Vossenaar et al., "Citrullination of synovial proteins in murine models of rheumatoid arthritis," *Arthritis Rheum.*, 48(9):2489-2500 (2003).
Vossenaar et al., "Expression and activity of citrullinating peptidylarginine deiminase enzymes in monocytes and macrophages," *Ann. Rheum. Dis.*, 63(4):373-381 (2004).

(56) References Cited

OTHER PUBLICATIONS

Wang et al., "Peptidylarginine deiminases in citrullination, gene regulation, health and pathogenesis," *Biochim. Biophys. Acta*, 1829(10):1126-1135 (2013).
Watanabe et al., "Combined biochemical and immunochemical comparison of peptidylarginine deiminases present in various tissues," *Biochim. Biophys. Acta*, 966(3):375-383 (1988).
Watanabe et al., "Isolation and characterization of cDNA clones encoding rat skeletal muscle peptidylarginine deiminase.," *J. Biol. Chem.*, 264(26):15255-15260 (1989).
Zhao et al., "Prevalence and significance of anti-peptidylarginine deiminase 4 antibodies in rheumatoid arthritis," *J. Rheumatol.*, 35(6):969-974 (2008).
JP Appln. No. JP2021-547276, Office Action, Feb. 6, 2024, 5 pages.
International Preliminary Report on Patentability received for PCT Patent Application No. PCT/US2020/018251, mailed on Aug. 10, 2021, 9 pages.
International Search Report and Written Opinion received for PCT Patent Application No. PCT/US2020/018251 , mailed on Jul. 31, 2020, 13 pages.
Office Action received for European Patent Application No. 20711700.3, Mailed on Oct. 1, 2024, 7 Pages.
Office Action received for Japanese Patent Application No. 2021-547276, mailed on Oct. 22, 2024, 8 pages (4 pages of English Translation and 4 pages of Original Document).
Office Action received for Canadian Patent Application No. 3,129,624, Mailed on Jan. 21, 2025, 6 Pages.

* cited by examiner

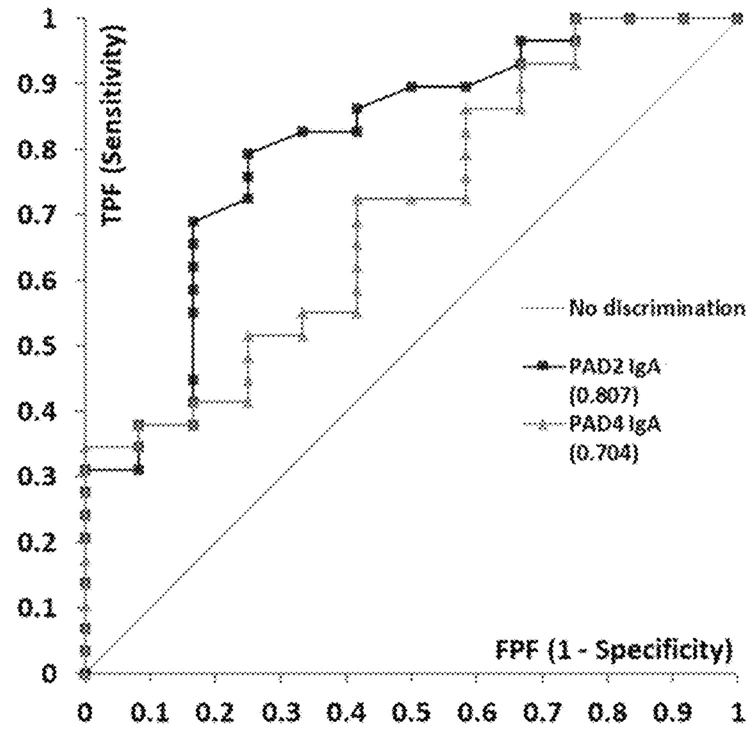

FIG. 3

```
DEFINITION  Homo sapiens peptidyl arginine deiminase 2 (PADI2), mRNA.
ACCESSION   NM_007365
VERSION     NM_007365.3
sequence number-1

   1 aggctgctgg agaaggcgca cctgctgcag gtgctcccgg ccgcccccgga ccagcgagcg
  61 cgggcactgc ggcggggagg atgctgcgcg agcggaccgt gcggctgcag tacgggagcc
 121 gcgtggaggc ggtgtacgtg ctgggcacct acctctggac cgatgtctac agcgcggccc
 181 cagccggggc ccaaaccttc agcctgaagc actcggaaca cgtgtgggtg gaggtggtgc
 241 gtgatgggga ggctgaggag gtggccacca atggcaagca gcgctggctt ctctcgccca
 301 gcaccaccct gcgggtcacc atgagccagg cgagcaccga ggccagcagt gacaaggtca
 361 ccgtcaacta ctatgacgag gaagggagca ttcccatcga ccaggcgggg ctcttcctca
 421 cagccattga gatctccctg gatgtggacg cagaccggga tggtgtggtg gagaagaaca
 481 acccaaagaa ggcatcctgg acctggggcc ccgagggcca gggggccatc ctgctggtga
 541 actgtgaccg agagacaccc tggttgccca aggaggactg ccgtgatgag aaggtctaca
 601 gcaaggaaga tctcaaggac atgtcccaga tgatcctgcg gaccaaaggc cccgaccgcc
 661 tccccgccgg atacgagata gttctgtaca tttccatgtc agactcagac aaagtgggcg
 721 tgttctacgt ggagaacccg ttcttcggcc aacgctatat ccacatcctg ggccggcgga
 781 agctctacca tgtggtcaag tacacgggtg gctccgcgga gctgctgttc ttcgtggaag
 841 gcctctgttt ccccgacgag ggcttctcag gcctggtctc catccatgtc agcctgctgg
 901 agtacatggc ccaggacatt cccctgactc ccatcttcac ggacaccgtg atattccgga
 961 ttgctccgtg gatcatgacc cccaacatcc tgcctcccgt gtcggtgttt gtgtgctgca
1021 tgaaggataa ttacctgttc ctgaaagagg tgaagaacct tgtggagaaa accaactgtg
1081 agctgaaggt ctgcttccag tacctaaacc gaggcgatcg ctggatccag gatgaaattg
1141 agtttggcta catcgaggcc ccccataaag gcttccccgt ggtgctggac tctccccgag
1201 atggaaacct aaaggacttc cctgtgaagg agctcctggg cccagatttt ggctacgtga
1261 cccgggagcc cctctttgag tctgtcacca gccttgactc atttggaaac ctggaggtca
1321 gtcccccagt gaccgtgaac ggcaagacat acccgcttgg ccgcatcctc atcgggagca
1381 gctttcctct gtctggtggt cggaggatga ccaaggtggt gcgtgacttc ctgaaggccc
```

```
1441 agcaggtgca ggcgcccgtg gagctctact cagactggct gactgtgggc cacgtggatg
1501 agttcatgtc ctttgtcccc atccccggca caaagaaatt cctgctactc atggccagca
1561 cctcggcctg ctacaagctc ttccgagaga agcagaagga cggccatgga gaggccatca
1621 tgttcaaagg cttgggtggg atgagcagca agcgaatcac catcaacaag attctgtcca
1681 acgagagcct tgtgcaggag aacctgtact tccagcgctg cctagactgg aaccgtgaca
1741 tcctcaagaa ggagctggga ctgacagagc aggacatcat tgacctgccc gctctgttca
1801 agatggacga ggaccaccgt gccagagcct tcttcccaaa catggtgaac atgatcgtgc
1861 tggacaagga cctgggcatc cccaagccat tcgggccaca ggttgaggag gaatgctgcc
1921 tggagatgca cgtgcgtggc ctcctggagc ccctgggcct cgaatgcacc ttcatcgacg
1981 acatttctgc ctaccacaaa tttctggggg aagtccactg tggcaccaac gtccgcagga
2041 agcccttcac cttcaagtgg tggcacatgg tgccctgacc tgccaggggc cctggcgttt
2101 gcctccttcg cttagttctc cagaccctcc ctcacacgcc cagagccttc tgctgacatg
2161 gactggacag ccccgctggg agacctttgg gacgtggggt ggaatttggg gtatctgtgc
2221 cttgccctcc ctgagagggg cctcagtgtc ctctgaagcc atccccagtg agcctcgact
2281 ctgtccctgc tgaaaatagc tgggccagtg tctctgtagc cctgacataa ggaacagaac
2341 acaacaaaac acagcaaacc atgtgcccaa actgctcccc aaagaatttt gagtctctaa
2401 tctgacactg aatgagggga gaagggaagg agattctggg attgccagtt cttccagcag
2461 ccatgctctg aaaatcaagg tagaatccat ggaaagggac cccaggaccc cgggacccta
2521 gacgtatctt gaactgccat cgtcatttca aatacatctc cctcagggtt tccaggtggc
2581 cacccccaat tattcattcc ttaccaacct ctcaaatcct cttggctttc tctctgcagt
2641 gtggacactg ttggctagtc ctccccactc cctgagggtc cagtaagtta gcttagaacc
2701 ttcctggaaa catttcatct gagcaggttt ccccacgtgt gggatgctcc ttttgcctca
2761 tctgtctcag ggatgcaggc tcccccgcat gcatggggat ttctccccag accagcatac
2821 ttgtgacctg agagttcaat gcgtaaagat gcccctggtc agccatatcc atcttctctt
2881 gcctggtcct tgattctctg gccgctccct gaccttcctc cttccactgc cttgactttc
2941 ttcctttta ttcctggtgc catctgtcca ggcagctaga caagaacttg ttcgccagca
3001 gccagattca ggccttccca ggggcataat aagtgaccag cccctcctct ccggacatca
3061 gatccaacac ataaggaccc tggcctaccc tccagcccaa cagccagttc tgggtcagct
3121 gccaacttag ggtggtttg attatcccat tgaaattcac cagtgccttt gccaaagacc
3181 ctctcatttg gacataccca gattcattcc ctggctccaa ctgaaaagac tcagtttcaa
3241 tcgttaaaag ttcctttagg gccagaagaa taaatgaatt ataatcccat tttgaagaac
3301 cgatttataa ccaatgaaaa ggttataatg taatttatat tcttggagga acaagatttt
3361 catttgggat tatttccttc aaccattcaa caaacatttg ttgtatgcca ctaagcgcca
3421 ggcacggcgt tgggctctgc aaacacagtg gttagtagca gtctggacct ggtccctact
3481 ggcatggaac ccatcactcc ccaacatgca aagcccacat ttaaaggcca gcctctgccc
3541 cttcagtgat gcgctcttta gaaatgccag tccactatat tcagaaatcc gcagggcaca
3601 aaacttccag caagtcactg ttgtggtgaa atgggcagtg ggggtggggg gtcttcttta
3661 aacaggcccc cttcccatct acctagccag tacccatcca atgagtcccc agagcctcca
3721 gaagctgttg tctcctctct ggggacagca gctcctgcct ttggaggcca aagccccaga
3781 tctctccagc cccagagctg aaaacaccaa gtgcctattt gagggtgtct gtctggagac
3841 ttagagtttg tcatgtgtgt gtgtgtgttt ggttaatgtg ggtttatggg ttttctttct
3901 tttttttctt ttttttttta gtctacatta gggggaagtg agcgcctccc atgtgcagac
3961 agtgtgtctt tatagatttt tctaaggctt tccccaatga tgtcggtaat ttctgatgtt
4021 tctgaagttc ccaggactca cacacccgtt cccatctcac ttgcccaccc agtgtgacaa
4081 ccctcggtgt ggatataccc ccgtggactc atggctcttc cccaccccca ctttctataa
4141 atgtaggcct agaatacgct tctctgttgc aaaactcagc taagttcctg cttccacctt
4201 gatgttgaaa tatcttatgt aagagggcag gggatgtcgt gaagatggca agaagaacac
4261 agtttcaaat ttctggaaaa gagcctgtgg tggagatcta aagatgttta gggaagagct
4321 cgactaaaga acaatgaaat aaatggtcca aggggaagtc a
```

FIG. 4

```
DEFINITION  protein-arginine deiminase type-2 [Homo sapiens].
ACCESSION   NP_031391
VERSION     NP_031391.2
sequence number-2

        1 mlrertvrlq ygsrveavyv lgtylwtdvy saapagaqtf slkhsehvwv evvrdgeaee
       61 vatngkqrwl lspsttlrvt msqasteass dkvtvnyyde egsipidqag lfltaieisl
      121 dvdadrdgvv eknnpkkasw twgpegqgai llvncdretp wlpkedcrde kvyskedlkd
      181 msqmilrtkg pdrlpagyei vlyismsdsd kvgvfyvenp ffgqryihil grrklyhvvk
      241 ytggsaellf fveglcfpde gfsglvsihv slleymaqdi pltpiftdtv ifriapwimt
      301 pnilppvsvf vccmkdnylf lkevknlvek tncelkvcfq ylnrgdrwiq deiefgyiea
      361 phkgfpvvld sprdgnlkdf pvkellgpdf gyvtreplfe svtsldsfgn levsppvtvn
      421 gktyplgril igssfplsgg rrmtkvvrdf lkaqqvqapv elysdwltvg hvdefmsfvp
      481 ipgtkkflll mastsacykl frekqkdghg eaimfkglgg msskritink ilsneslvqe
      541 nlyfqrcldw nrdilkkelg lteqdiidlp alfkmdedhr araffpnmvn mivldkdlgi
      601 pkpfgpqvee ecclemhvrg lleplglect fiddisayhk flgevhcgtn vrrkpftfkw
      661 whmvp
```

FIG. 5

```
DEFINITION  PREDICTED: Homo sapiens peptidyl arginine deiminase 2 (PADI2),
            transcript variant X2, mRNA.
ACCESSION   XM_017000148
VERSION     XM_017000148.2
sequence number-3

        1 agcagctctg cagatgggga ttcttctgtc agctcatatc tgcacatgtg cacaaagaca
       61 taaacataca agtgcactac agtgctgctt cttgtagtag caaaagattg caaagcaacc
      121 taaatgtcca tctgtggagg actgagtaac ggccttcccg gaagttctgt gcaaccgcta
      181 aaaaggatga agccagtctc tcaatatgga tacaggatgt gcttcaagga tgaaattgag
      241 tttggctaca tcgaggcccc ccataaaggc ttccccgtgg tgctggactc tccccgagat
      301 ggaaacctaa aggacttccc tgtgaaggag ctcctgggcc cagattttgg ctacgtgacc
      361 cgggagcccc tctttgagtc tgtcaccagc cttgactcat ttggaaacct ggaggtcagt
      421 cccccagtga ccgtgaacgg caagacatac ccgcttggcc gcatcctcat cgggagcagc
      481 tttcctctgt ctggtggtcg gaggatgacc aaggtggtgc gtgacttcct gaaggcccag
      541 caggtgcagg cgcccgtgga gctctactca gactggctga ctgtgggcca cgtggatgag
      601 ttcatgtcct ttgtccccat ccccggcaca aagaaattcc tgctactcat ggccagcacc
      661 tcggcctgct acaagctctt ccgagagaag cagaaggacg gccatggaga ggccatcatg
      721 ttcaaaggct tgggtgggat gagcagcaag cgaatcacca tcaacaagat tctgtccaac
      781 gagagccttg tgcaggagaa cctgtacttc cagcgctgcc tagactggaa ccgtgacatc
      841 ctcaagaagg agctgggact gacagagcag gacatcattg acctgcccgc tctgttcaag
      901 atggacgagg accaccgtgc cagagccttc ttcccaaaca tggtgaacat gatcgtgctg
      961 gacaaggacc tgggcatccc caagccattc gggccacagg ttgaggagga atgctgcctg
     1021 gagatgcacg tgcgtggcct cctggagccc ctgggcctcg aatgcacctt catcgacgac
     1081 atttctgcct accacaaatt tctgggggaa gtccactgtg gcaccaacgt ccgcaggaag
     1141 cccttcacct tcaagtggtg gcacatggtg ccctgacctg ccaggggccc tggcgtttgc
     1201 ctccttcgct tagttctcca gaccctccct cacacgccca gagccttctg ctgacatgga
     1261 ctggacagcc ccgctgggag acctttggga cgtggggtgg aatttggggt atctgtgcct
     1321 tgccctccct gagaggggcc tcagtgtcct ctgaagccat ccccagtgag cctcgactct
     1381 gtccctgctg aaaatagctg ggccagtgtc tctgtagccc tgacataagg aacagaacac
     1441 aacaaaacac agcaaaccat gtgcccaaac tgctccccaa agaattttga gtctctaatc
     1501 tgacactgaa tgagggagaa agggaaggag attctgggat tgccagttct tccagcagcc
     1561 atgctctgaa aatcaaggta gaatccatgg aaagggaccc caggaccccg ggaccctaga
     1621 cgtatcttga actgccatcg tcatttcaaa tacatctccc tcagggtttc caggtggcca
     1681 cccccaatta ttcattcctt accaacctct caaatcctct tggctttctc tctgcagtgt
     1741 ggacactgtt ggctagtcct ccccactccc tgagggtcca gtaagttagc ttagaacctt
     1801 cctggaaaca tttcatctga gcaggtttcc ccacgtgtgg gatgctcctt ttgcctcatc
     1861 tgtctcaggg atgcaggctc ccccgcatgc atggggattt ctccccagac cagcatactt
     1921 gtgacctgag agttcaatgc gtaaagatgc ccctggtcag ccatatccat cttctcttgc
     1981 ctggtccttg attctctggc cgctccctga ccttcctcct tccactgcct tgactttctt
```

```
2041 ccttttatt cctggtgcca tctgtccagg cagctagaca agaacttgtt cgccagcagc
2101 cagattcagg ccttcccagg ggcataataa gtgaccagcc cctcctctcc ggacatcaga
2161 tccaacacat aaggaccctg gcctaccctc cagcccaaca gccagttctg ggtcagctgc
2221 caacttaggg gtggtttgat tatcccattg aaattcacca gtgcctttgc caaagaccct
2281 ctcatttgga catacccaga ttcattccct ggctccaact gaaaagactc agtttcaatc
2341 gttaaaagtt cctttagggc cagaagaata aatgaattat aatcccattt tgaagaaccg
2401 atttataacc aatgaaaagg ttataatgta atttatattc ttggaggaac aagattttca
2461 tttgggatta tttccttcaa ccattcaaca aacatttgtt gtatgccact aagcgccagg
2521 cacggcgttg ggctctgcaa acacagtggt tagtagcagt ctggacctgg tccctactgg
2581 catggaaccc atcactcccc aacatgcaaa gcccacattt aaaggccagc ctctgcccct
2641 tcagtgatgc gctctttaga aatgccagtc cactatattc agaaatccgc agggcacaaa
2701 acttccagca agtcactgtt gtggtgaaat gggcagtggg ggtgggggt cttctttaaa
2761 caggccccct tcccatctac ctagccagta cccatccaat gagtccccag agcctccaga
2821 agctgttgtc tcctctctgg ggacagcagc tcctgccttt ggaggccaaa gccccagatc
2881 tctccagccc cagagctgaa aacaccaagt gcctatttga gggtgtctgt ctggagactt
2941 agagtttgtc atgtgtgtgt gtgtgtttgg ttaatgtggg tttatgggtt ttctttcttt
3001 tttttctttt ttttttagt ctacattagg gggaagtgag cgcctcccat gtgcagacag
3061 tgtgtcttta tagattttc taaggctttc cccaatgatg tcggtaattt ctgatgtttc
3121 tgaagttccc aggactcaca cacccgttcc catctcactt gcccacccag tgtgacaacc
3181 ctcggtgtgg atatacccc gtggactcat ggctcttccc cacccccact ttctataaat
3241 gtaggcctag aatacgcttc tctgttgcaa aactcagcta agttcctgct tccaccttga
3301 tgttgaaata tcttatgtaa gagggcaggg gatgtcgtga agatggcaag aagaacacag
3361 tttcaaattt ctggaaaaga gcctgtggtg gagatctaaa gatgtttagg gaagagctcg
3421 actaaagaac aatgaaataa atggtccaag gggaagtca
```

FIG. 6

```
DEFINITION  protein-arginine deiminase type-2 isoform X1 [Homo sapiens].
ACCESSION   XP_016855637
VERSION     XP_016855637.1
sequence number-4

  1 msicgglsng lpgssvqplk rmkpvsqygy rmcfkdeief gyieaphkgf pvvldsprdg
 61 nlkdfpvkel lgpdfgyvtr eplfesvtsl dsfgnlevsp pvtvngktyp lgriligssf
121 plsggrrmtk vvrdflkaqq vqapvelysd wltvghvdef msfvpipgtk kflllmasts
181 acyklfrekq kdghgeaimf kglggmsskr itinkilsne slvqenlyfq rcldwnrdil
241 kkelglteqd iidlpalfkm dedhraraff pnmvnmivld kdlgipkpfg pqveeeccle
301 mhvrgllepl glectfiddi sayhkflgev hcgtnvrrkp ftfkwwhmvp
```

FIG. 7

```
DEFINITION  Homo sapiens peptidyl arginine deiminase 3 (PADI3), mRNA.
ACCESSION   NM_016233
VERSION     NM_016233.2
sequence number-5

  1 agtgttgggg ttggcggcca cagctaagtc caacaccagc atgtcgctgc agagaatcgt
 61 gcgtgtgtcc ctggagcatc ccaccagcgc ggtgtgtgtg gctggcgtgg agaccctcgt
121 ggacatttat gggtcagtgc ctgagggcac agaaatgttt gaggtctatg ggacgcctgg
181 cgtggacatc tacatctctc ccaacatgga gaggggccgg gagcgtgcag acaccaggcg
241 gtggcgcttt gacgcgactt tggagatcat cgtggtcatg aactccccca gcaatgacct
301 caacgacagc catgttcaga tttcctacca ctccagccat gagcctctgc ccctggccta
361 tgcggtgctc tacctcacct gtgttgacat ctctctggat tgcgacctga actgtgaggg
421 aaggcaggac aggaactttg tagacaagcg gcagtgggtc tgggggccca gtgggtatgg
481 cggcatcttg ctggtgaact gtgaccgtga tgatccgagc tgtgatgtcc aggacaattg
541 tgaccagcac gtgcactgcc tgcaagacct ggaagacatg tctgtcatgg tcctgcggac
601 gcagggccct gcagccctct ttgatgacca caaacttgtc ctccatacct ccagctatga
```

```
 661 tgccaaacgg gcacaggtct tccacatctg cggtcctgag gatgtgtgtg aggcctatag
 721 gcatgtgctg ggccaagata aggtgtccta tgaggtaccc cgcttgcatg gggatgagga
 781 gcgcttcttc gtggaaggcc tgtccttccc tgatgccggc ttcacaggac tcatctcctt
 841 ccatgtcact ctgctggacg actccaacga ggatttctcg gcatccccta tcttcactga
 901 cactgtggtg ttccgagtgg caccctggat catgacgccc agcactctgc cacccctaga
 961 ggtgtatgtg tgccgtgtga ggaacaacac gtgttttgtg gatgcggtgg cagagctggc
1021 caggaaggcc ggctgcaagc tgaccatctg cccacaggcc gagaaccgca acgaccgctg
1081 gatccaggat gagatggagc tgggctacgt tcaggcgccg cacaagaccc tcccggtggt
1141 ctttgactcc ccaaggaatg gggaactgca ggatttccct tacaaaagaa tcctgggtcc
1201 agattttggt tacgtgactc gggaaccacg cgacaggtct gtgagtggcc tggactcctt
1261 tgggaacctg gaggtcagcc ctccagtggt ggccaatggg aaagagtacc ccctggggag
1321 gatcctcatt gggggcaacc tgcctgggtc aagtggccgc agggtcaccc aggtggtgcg
1381 ggacttcctc catgcccaga aggtgcagcc ccccgtggag ctctttgtgg actggttggc
1441 cgtgggccat gtggatgagt ttctgagctt tgtccctgcc cccgatggga agggcttccg
1501 gatgctcctg gccagccctg ggcctgctt caagctcttc caggaaaagc agaagtgtgg
1561 ccacgggagg gccctcctgt tccagggggt tgttgatgat gagcaggtca agaccatctc
1621 catcaaccag gtgctctcca ataaagacct catcaactac aataagtttg tgcagagctg
1681 catcgactgg aaccgtgagg tgctgaagcg ggagctgggc ctggcagagt gtgacatcat
1741 tgacatccca cagctcttca agaccgagag gaaaaaagca acggccttct tccctgactt
1801 ggtgaacatg ctggtgctgg ggaagcacct gggcatcccc aagccctttg ggcccatcat
1861 caatggctgc tgctgcctgg aggagaaggt gcggtccctg ctggagccgc tgggcctcca
1921 ctgcaccttc attgatgact tcactccata ccacatgctg catggggagg tgcactgtgg
1981 caccaatgtg tgcagaaagc ccttctcttt caagtggtgg aacatggtgc cctgagacag
2041 ctcccaccca ccatcctgtc cccctggggc gggcattggc ccaggtggtg gagacagaga
2101 caggcccctg aacgataagc accaagagac cccaaggctc cagatggaac actgagggtg
2161 accgtccctc tcagaagcct tttccctgga agtgtccatg cctcacctgc aacccatgtg
2221 gttctcagac ttgaatcttc tcggcccccc aaaaagaagg acctcatttc ttatagcctc
2281 tcctgtgatt caacacaacc catggagatg tccccttctc actctgaaat catccatttg
2341 gggacaaatc cacattgggg tctagaaaca tccacgtatc tcatcagcca tcttgtcctg
2401 tgcatcctaa cagaggaagg atccatgatt ctgctttggt ccaattgctt cctctctgca
2461 gaggaacaac cctaaaacca gaccactcca cgcaggacag gcaggagaga ttcttcctaa
2521 agcctccccc ataaaaaggg agctgtggat ccacttagat cagggcggaa ccatctttca
2581 cccggccaag ctcctgccca gatgttgacc ctcacccagc gtgagctgtc acatagtagg
2641 agcttctaga tgcatgtgga agcaatgaga gttgtccctt agccttataa actccccatg
2701 atctgacatg cagaaatcca gccttgtcca gaatcctcct ggaatttctt ggagacgaaa
2761 gtatctgggg gattgttggg tactagggag actgggtaca agggtgaaaa gtagttccca
2821 taatacacat ggttgactat ggtgatccac cttgtgatgg ttaatattag gtgtctggag
2881 aaggttgctt cattggccct gggacttctc tctgcaggag gagagaacgc tgcctctcct
2941 ctggattggt ctcaggctct ctgttggcct ttggtcagcg tttccacatc ctgctctgct
3001 gcaggagagg gggctaaggg gctggatcca ccaaggcagc tcacagcggg aaaactctgg
3061 gaatgaacca ctgaattcag ggatgggggg tgggggggcg gttctcgagg tgtgtgccag
3121 ctacacgtgt gttctgtatg ggtccagctg cgtttccatc actcgctaat aaatcaacag
3181 aaacacaaa
```

FIG. 8

```
DEFINITION  protein-arginine deiminase type-3 [Homo sapiens].
ACCESSION   NP_057317
VERSION     NP_057317.2
sequence number-6

      1 mslqrivrvs lehptsavcv agvetlvdiy gsvpegtemf evygtpgvdi yispnmergr
     61 eradtrrwrf datleiivvm nspsndlnds hvqisyhssh eplplayavl yltcvdisld
    121 cdlncegrqd rnfvdkrqwv wgpsgyggil lvncdrddps cdvqdncdqh vhclqdledm
    181 svmvlrtqgp aalfddhklv lhtssydakr aqvfhicgpe dvceayrhvl gqdkvsyevp
    241 rlhgdeerff veglsfpdag ftglisfhvt llddsnedfs aspiftdtvv frvapwimtp
    301 stlpplevyv crvrnntcfv davaelarka gckltiepqa enrndrwiqd emelgyvqap
    361 hktlpvvfds prngelqdfp ykrilgpdfg yvtreprdrs vsgldsfgnl evsppvvang
    421 keyplgrili ggnlpgssgr rvtqvvrdfl haqkvqppve lfvdwlavgh vdeflsfvpa
    481 pdgkgfrmll aspgacfklf qekqkcghgr allfqgvvdd eqvktisinq vlsnkdliny
    541 nkfvqscidw nrevlkrelg laecdiidip qlfkterkka taffpdlvnm lvlgkhlgip
    601 kpfgpiingc ccleekvrsl leplglhctf iddftpyhml hgevhcgtnv crkpfsfkww
    661 nmvp
```

FIG. 9

```
DEFINITION  PREDICTED: Homo sapiens peptidyl arginine deiminase 3 (PADI3),
            transcript variant X1, mRNA.
ACCESSION   XM_011541571
VERSION     XM_011541571.2
sequence number-21

      1 tctccctggt tctgccattt cccctgtggg gggctgccca gggccaaaca ggccagaggg
     61 ctccaccagc cctggaaatt acaggctttg ggagtagggt tgccagataa aataaaagat
    121 gcctagttaa aattgaattt caggtaaata attaataatt tttttagtat aagtgtatcc
    181 caaatacttc acgggagtac caaacaatga ttgactgttc acttgaaatt caagtccaac
    241 tgagctttct gtatttttat ttgctaagtc tggcagccct gcttaggagg agaaacaggt
    301 gtgtctgtcc ctcccaactg gtgaggacac ctgacagggg cccagacacc agagtgggac
    361 ctgcctgatg gagagaagct tgggcttggt ttatttccct tttcataaaa aagctgcttt
    421 gagatgtaag agaatcatgt tggtggaaga gtgaagaggt tgttttgggg gaggtctgcc
    481 ttactctgag ggaagatggg aagcgggggg agtggccagc tgtggaaatt tggggtagtc
    541 ccctacgtat cctgtgcctc agtttcccca tgtgtaaaca ggagtaatta tctcatcctg
    601 gggctgcagt gaggatcaga tgagctaatg tacaaaaagg cttaggcagg cctgccgtga
    661 taagagtgca gaggctgggg gctttttatg ttatggtatt gttgttatta ttactcctgg
    721 ggaggtggtg ggcaagagtg tggactgagg agccacatgg ctgggtttgg atcccagccc
    781 ggccacagac cttgggcaag ttacttaacc tcggctttct catctgtata atgggagaca
    841 ataatagata gtgcctccct tctaggttta ttgagaggat tgcatgatgg gctggcacac
    901 agcatgagct cagtaagtgt cagtcactgt tatcccccag gggcatgcat gccgctgcct
    961 ccaggaggcc ctccaactcg cagtggcctc tccctacatg ggttcccact gagctgtgat
   1021 cctgtggcct tgagccccat ctggctgccc tggacaatgt tggtcctcag ctccccagcg
   1081 ggatcaacag tggggagagc agtgggtgga tctgcccgcc aggcagtacc tgagtgcaca
   1141 gtgggcaccc cacagtcaaa ggatgcatag tctggtttcc aaggaggaac cccaggctag
   1201 gtggaatgag ggaaatgcaa tctcagggcc agataacatc acagatactt taaacctgca
   1261 attaatttct ggttgtttga ccaaatccgg ccaagtttcc cgggtgacac tgcagagctg
   1321 tggaacagca tgggcttgga gtcagacctg ttgcacatct ggctctgcca tgtgatgcaa
   1381 cctcaggctt gtcacgaggc ctccttgagc ctcagttgct aatatgccaa atggggatga
   1441 tattgctcac cttacagctt gtaagagtgg agggagctgc gtgcgccagg tgcctggcat
   1501 gcagcgggca ctcaaccaga ttgaattccc ttcccaggga agaattcaag gatatcttcc
   1561 cacccactaa ggagacatgt gatgggatct ggggtgagaa ttgctctttt taaagctctc
   1621 agaactgtaa ggggctccac ccaccaatgg ctggtgttca ctgagctctt cgtgcccaga
   1681 cctgcactgg ggatttatcg agcacatggc tggcttctga cttccgaaga gctcgccatt
   1741 ctggtcagtg cctgagggca cagaaatgtt tgaggtctat gggacgcctg gcgtggacat
   1801 ctacatctct cccaacatgg agagggccg ggagcgtgca gacaccaggc ggtggcgctt
   1861 tgacgcgact ttggagatca tcgtggtcat gaactccccc agcaatgacc tcaacgacag
   1921 ccatgttcag atttcctacc actccagcca tgagcctctg cccctggcct atgcggtgct
   1981 ctacctcacc tgtgttgaca tctctctgga ttgcgacctg aactgtgagg gaaggcagga
```

```
2041 caggaacttt gtagacaagc ggcagtgggt ctgggggccc agtgggtatg gcggcatctt
2101 gctggtgaac tgtgaccgtg atgatccgag ctgtgatgtc caggacaatt gtgaccagca
2161 cgtgcactgc ctgcaagacc tggaagacat gtctgtcatg gtcctgcgga cgcagggccc
2221 tgcagccctc tttgatgacc acaaacttgt cctccatacc tccagctatg atgccaaacg
2281 ggcacaggtc ttccacatct gcggtcctga ggatgtgtgt gaggcctata ggcatgtgct
2341 gggccaagat aaggtgtcct atgaggtacc ccgcttgcat ggggatgagg agcgcttctt
2401 cgtggaaggc ctgtccttcc ctgatgccgg cttcacagga ctcatctcct tccatgtcac
2461 tctgctggac gactccaacg aggatttctc ggcatcccct atcttcactg acactgtggt
2521 gttccgagtg gcaccctgga tcatgacgcc cagcactctg ccacccctag aggtgtatgt
2581 gtgccgtgtg aggaacaaca cgtgttttgt ggatgcggtg gcagagctgg ccaggaaggc
2641 cggctgcaag ctgaccatct gcccacaggc cgagaaccgc aacgaccgct ggatccagga
2701 tgagatggag ctgggctacg ttcaggcgcc gcacaagacc ctcccggtgg tctttgactc
2761 cccaaggaat ggggaactgc aggatttccc ttacaaaaga atcctgggtc cagattttgg
2821 ttacgtgact cgggaaccac gcgacaggtc tgtgagtggc ctggactcct ttgggaacct
2881 ggaggtcagc cctccagtgg tggccaatgg gaaagagtac cccctgggga ggatcctcat
2941 tgggggcaac ctgcctgggt caagtggccg cagggtcacc caggtggtgc gggacttcct
3001 ccatgcccag aaggtgcagc cccccgtgga gctctttgtg gactggttgg ccgtgggcca
3061 tgtggatgag tttctgagct ttgtccctgc ccccgatggg aagggcttcc ggatgctcct
3121 ggccagccct ggggcctgct tcaagctctt ccaggaaaag cagaagtgtg gccacgggag
3181 ggccctcctg ttccaggggg ttgttgatga tgagcaggtc aagaccatct ccatcaacca
3241 ggtgctctcc aataaagacc tcatcaacta caataagttt gtgcagagct gcatcgactg
3301 gaaccgtgag gtgctgaagc gggagctggg cctggcagag tgtgacatca ttgacatccc
3361 acagctcttc aagaccgaga ggaaaaaagc aacggccttc ttccctgact tggtgaacat
3421 gctggtgctg gggaagcacc tgggcatccc caagcccttt gggcccatca tcaatggctg
3481 ctgctgcctg gaggagaagg tgcggtccct gctggagccg ctgggcctcc actgcacctt
3541 cattgatgac ttcactccat accacatgct gcatggggag gtgcactgtg gcaccaatgt
3601 gtgcagaaag cccttctctt tcaagtggtg gaacatggtg ccctgagaca gctcccaccc
3661 accatcctgt ccccctgggg cgggcattgg cccaggtggt ggagacagag acaggcccct
3721 gaacgataag caccaagaga ccccaaggct ccagatggaa cactgagggt gaccgtccct
3781 ctcagaagcc ttttccctgg aagtgtccat gcctcacctg caacccatgt ggttctcaga
3841 cttgaatctt ctcggccccc caaaaagaag gacctcattt cttatagcct ctcctgtgat
3901 tcaacacaac ccatggagat gtccccttct cactctgaaa tcatccattt ggggacaaat
3961 ccacattggg gtctagaaac atccacgtat ctcatcagcc atcttgtcct gtgcatccta
4021 acagaggaag gatccatgat tctgctttgg tccaattgct tcctctctgc agaggaacaa
4081 ccctaaaacc agaccactcc acgcaggaca ggcaggagag attcttccta aagcctcccc
4141 cataaaaagg gagctgtgga tccacttaga tcagggcgga accatctttc acccggccaa
4201 gctcctgccc agatgttgac cctcacccag cgtgagctgt cacatagtag gagcttctag
4261 atgcatgtgg aagcaatgag agttgtccct tagccttata aactccccat gatctgacat
4321 gcagaaatcc agccttgtcc agaatcctcc tggaatttct tggagacgaa agtatctggg
4381 ggattgttgg gtactaggga gactgggtac aagggtgaaa agtagttccc ataatacaca
4441 tggttgacta tggtgatcca ccttgtgatg gttaatatta ggtgtctgga gaaggttgct
4501 tcattggccc tgggacttct ctctgcagga ggagagaacg ctgcctctcc tctggattgg
4561 tctcaggctc tctgttggcc tttggtcagc gtttccacat cctgctctgc tgcaggagag
4621 ggggctaagg ggctggatcc accaaggcag ctcacagcgg gaaaactctg ggaatgaacc
4681 actgaattca ggggatgggg gtgggggggc ggttctcgag gtgtgtgcca gctacacgtg
4741 tgttctgtat gggtccagct gcgtttccat cactcgctaa taaatcaaca gaaacacaaa
```

FIG. 10

```
DEFINITION  protein-arginine deiminase type-3 isoform X1 [Homo sapiens].
ACCESSION   XP_011539873
VERSION     XP_011539873.1
sequence number-22

      1 mfevygtpgv diyispnmer greradtrrw rfdatleiiv vmnspsndln dshvqisyhs
     61 sheplplaya vlyltcvdis ldcdlncegr qdrnfvdkrq wvwgpsgygg illvncdrdd
    121 pscdvqdncd qhvhclqdle dmsvmvlrtq gpaalfddhk lvlhtssyda kraqvfhicg
    181 pedvceayrh vlgqdkvsye vprlhgdeer ffveglsfpd agftglisfh vtllddsned
    241 fsaspiftdt vvfrvapwim tpstlpplev yvcrvrnntc fvdavaelar kagckltìcp
    301 qaenrndrwi qdemelgyvq aphktlpvvf dsprngelqd fpykrilgpd fgyvtreprd
    361 rsvsgldsfg nlevsppvva ngkeyplgri liggnlpgss grrvtqvvrd flhaqkvqpp
    421 velfvdwlav ghvdeflsfv papdgkgfrm llaspgacfk lfqekqkcgh grallfqgvv
    481 ddeqvktisi nqvlsnkdli nynkfvqsci dwnrevlkre lglaecdiid ipqlfkterk
    541 kataffpdlv nmlvlgkhlg ipkpfgpiin gcccleekvr sllepiglhc tfiddftpyh
    601 mlhgevhcgt nvcrkpfsfk wwnmvp
```

FIG. 11

```
DEFINITION  PREDICTED: Homo sapiens peptidyl arginine deiminase 3 (PADI3),
            transcript variant X2, mRNA.
ACCESSION   XM_017001463
VERSION     XM_017001463.1
sequence number-37

      1 agaaatggat ggatgtgact gtgtgctaat aaaactttat ttatacaaac aggcagtagg
     61 ccagatttgg cccacagttc ataatgtgct gatcctgacc taggcgagaa gagaaaccaa
    121 atatgaaact gttgaagaac ttgggactga attatgttgg aacttggtgc cctgggagtt
    181 aagaggagaa ggtcgagcgg cagtgggtct gggggcccag tgggtatggc ggcatcttgc
    241 tggtgaactg tgaccgtgat gatccgagct gtgatgtcca ggacaattgt gaccagcacg
    301 tgcactgcct gcaagacctg gaagacatgt ctgtcatggt cctgcggacg cagggccctg
    361 cagccctctt tgatgaccac aaacttgtcc tccatacctc cagctatgat gccaaacggg
    421 cacaggtctt ccacatctgc ggtcctgagg atgtgtgtga ggcctatagg catgtgctgg
    481 gccaagataa ggtgtcctat gaggtacccc gcttgcatgg ggatgaggag cgcttcttcg
    541 tggaaggcct gtccttccct gatgccggct tcacaggact catctccttc catgtcactc
    601 tgctggacga ctccaacgag gatttctcgg catcccctat cttcactgac actgtggtgt
    661 tccgagtggc accctggatc atgacgccca gcactctgcc acccctagag gtgtatgtgt
    721 gccgtgtgag gaacaacacg tgttttgtgg atgcggtggc agagctggcc aggaaggccg
    781 gctgcaagct gaccatctgc ccacaggccg agaaccgcaa cgaccgctgg atccaggatg
    841 agatggagct gggctacgtt caggcgccgc acaagaccct cccggtggtc tttgactccc
    901 caaggaatgg ggaactgcag gatttccctt acaaaagaat cctgggtcca gattttggtt
    961 acgtgactcg ggaaccacgc gacaggtctg tgagtggcct ggactccttt gggaacctgg
   1021 aggtcagccc tccagtggtg gccaatggga aagagtaccc cctggggagg atcctcattg
   1081 ggggcaacct gcctgggtca agtggccgca gggtcaccca ggtggtgcgg gacttcctcc
   1141 atgcccagaa ggtgcagccc cccgtggagc tctttgtgga ctggttggcc gtgggccatg
   1201 tggatgagtt tctgagcttt gtccctgccc ccgatgggaa gggcttccgg atgctcctgg
   1261 ccagccctgg ggcctgcttc aagctcttcc aggaaaagca gaagtgtggc cacgggaggg
   1321 ccctcctgtt ccaggggğtt gttgatgatg agcaggtcaa gaccatctcc atcaaccagg
   1381 tgctctccaa taaagacctc atcaactaca ataagtttgt gcagagctgc atcgactgga
   1441 accgtgaggt gctgaagcgg gagctgggcc tggcagagtg tgacatcatt gacatcccac
   1501 agctcttcaa gaccgagagg aaaaaagcaa cggccttctt ccctgacttg gtgaacatgc
   1561 tggtgctggg gaagcacctg ggcatcccca agccctttgg gcccatcatc aatggctgct
   1621 gctgcctgga ggagaaggtg cggtccctgc tggagccgct gggcctccac tgcaccttca
   1681 ttgatgactt cactccatac cacatgctgc atggggaggt gcactgtggc accaatgtgt
   1741 gcagaaagcc cttctctttc aagtggtgga acatggtgcc ctgagacagc tcccacccac
   1801 catcctgtcc ccctggggcg ggcattggcc caggtggtgg agacagagac aggcccctga
   1861 acgataagca ccaagagacc ccaaggctcc agatggaaca ctgagggtga ccgtccctct
   1921 cagaagcctt ttccctggaa gtgtccatgc ctcacctgca acccatgtgg ttctcagact
   1981 tgaatcttct cggcccccca aaaagaagga cctcatttct tatagcctct cctgtgattc
```

```
2041 aacacaaccc atggagatgt cccctctca ctctgaaatc atccatttgg ggacaaatcc
2101 acattggggt ctagaaacat ccacgtatct catcagccat cttgtcctgt gcatcctaac
2161 agaggaagga tccatgattc tgctttggtc caattgcttc ctctctgcag aggaacaacc
2221 ctaaaaccag accactccac gcaggacagg caggagagat tcttcctaaa gcctccccca
2281 taaaaaggga gctgtggatc cacttagatc agggcggaac catctttcac ccggccaagc
2341 tcctgcccag atgttgaccc tcacccagcg tgagctgtca catagtagga gcttctagat
2401 gcatgtggaa gcaatgagag ttgtccctta gccttataaa ctccccatga tctgacatgc
2461 agaaatccag ccttgtccag aatcctcctg gaatttcttg gagacgaaag tatctggggg
2521 attgttgggt actagggaga ctgggtacaa gggtgaaaag tagttcccat aatacacatg
2581 gttgactatg gtgatccacc ttgtgatggt taatattagg tgtctggaga aggttgcttc
2641 attggccctg ggacttctct ctgcaggagg agagaacgct gcctctcctc tggattggtc
2701 tcaggctctc tgttggcctt tggtcagcgt ttccacatcc tgctctgctg caggagaggg
2761 ggctaagggg ctggatccac caaggcagct cacagcggga aaactctggg aatgaaccac
2821 tgaattcagg ggatggggt ggggggcgg ttctcgaggt gtgtgccagc tacacgtgtg
2881 ttctgtatgg gtccagctgc gtttccatca ctcgctaata aatcaacaga aacacaaa
```

FIG. 12

```
DEFINITION  protein-arginine deiminase type-3 isoform X2 [Homo sapiens].
ACCESSION   XP_016856952
VERSION     XP_016856952.1
sequence number-38

  1 msvmvlrtqg paalfddhkl vlhtssydak raqvfhicgp edvceayrhv lgqdkvsyev
 61 prlhgdeerf fveglsfpda gftglisfhv tlldds nedf saspiftdtv vfrvapwimt
121 pstlpplevy vcrvrnntcf vdavaelark agckltlcpq aenrndrwiq demelgyvqa
181 phktlpvvfd sprngelqdf pykrilgpdf gyvtreprdr svsgldsfgn levsppvvan
241 gkeyplgril iggnlpgssg rrvtqvvrdf lhaqkvqppv elfvdwlavg hvdeflsfvp
301 apdgkgfrml laspgacfkl fqekqkcghg rallfqgvvd deqvktisin qvlsnkdlin
361 ynkfvqscid wnrevlkrel glaecdiidi pqlfkterkk ataffpdlvn mlvlgkhlgi
421 pkpfgpiing cccleekvrs llepiglhct fiddftpyhm lhgevhcgtn vcrkpfsfkw
481 wnmvp
```

FIG. 13

```
DEFINITION  PREDICTED: Homo sapiens peptidyl arginine deiminase 3 (PADI3),
            transcript variant X2, mRNA.
ACCESSION   XM_017001463
VERSION     XM_017001463.1:c
sequence number-39

  1 agaaatggat ggatgtgact gtgtgctaat aaaactttat ttatacaaac aggcagtagg
 61 ccagatttgg cccacagttc ataatgtgct gatcctgacc taggcgagaa gagaaaccaa
121 atatgaaact gttgaagaac ttgggactga attatgttgg aacttggtgc cctgggagtt
181 aagaggagaa ggtcgagcgg cagtgggtct gggggcccag tgggtatggc ggcatcttgc
241 tggtgaactg tgaccgtgat gatccgagct gtgatgtcca ggacaattgt gaccagcacg
301 tgcactgcct gcaagacctg gaagacatgt ctgtcatggt cctgcggacg cagggccctg
361 cagccctctt tgatgaccac aaacttgtcc tccatacctc cagctatgat gccaaacggg
421 cacaggtctt ccacatctgc ggtcctgagg atgtgtgtga ggcctatagg catgtgctgg
481 gccaagataa ggtgtcctat gaggtacccc gcttgcatgg ggatgaggag cgcttcttcg
541 tggaaggcct gtccttccct gatgccggct tcacaggact catctccttc catgtcactc
601 tgctggacga ctccaacgag gatttctcgg catcccctat cttcactgac actgtggtgt
661 tccgagtggc accctggatc atgacgccca gcactctgcc accccctagag gtgtatgtgt
721 gccgtgtgag gaacaacacg tgttttgtgg atgcggtggc agagctggcc aggaaggccg
781 gctgcaagct gaccatctgc ccacaggccg agaaccgcaa cgaccgctgg atccaggatg
841 agatggagct gggctacgtt caggcgccgc acaagaccct cccggtggtc tttgactccc
```

```
 901 caaggaatgg ggaactgcag gatttccctt acaaaagaat cctgggtcca gattttggtt
 961 acgtgactcg ggaaccacgc gacaggtctg tgagtggcct ggactccttt gggaacctgg
1021 aggtcagccc tccagtggtg gccaatggga aagagtaccc cctggggagg atcctcattg
1081 ggggcaacct gcctgggtca agtggccgca gggtcaccca ggtggtgcgg gacttcctcc
1141 atgcccagaa ggtgcagccc cccgtggagc tctttgtgga ctggttggcc gtgggccatg
1201 tggatgagtt tctgagcttt gtccctgccc ccgatgggaa gggcttccgg atgctcctgg
1261 ccagccctgg ggcctgcttc aagctcttcc aggaaaagca gaagtgtggc cacgggaggg
1321 ccctcctgtt ccaggggtt gttgatgatg agcaggtcaa gaccatctcc atcaaccagg
1381 tgctctccaa taaagacctc atcaactaca ataagtttgt gcagagctgc atcgactgga
1441 accgtgaggt gctgaagcgg gagctgggcc tggcagagtg tgacatcatt gacatcccac
1501 agctcttcaa gaccgagagg aaaaaagcaa cggccttctt ccctgacttg gtgaacatgc
1561 tggtgctggg gaagcacctg ggcatcccca agccctttgg gcccatcatc aatggctgct
1621 gctgcctgga ggagaaggtg cggtccctgc tggagccgct gggcctccac tgcaccttca
1681 ttgatgactt cactccatac cacatgctgc atggggaggt gcactgtggc accaatgtgt
1741 gcagaaagcc cttctctttc aagtggtgga acatggtgcc ctgagacagc tcccacccac
1801 catcctgtcc ccctggggcg ggcattggcc caggtggtgg agacagagac aggcccctga
1861 acgataagca ccaagagacc ccaaggctcc agatggaaca ctgagggtga ccgtccctct
1921 cagaagcctt ttccctggaa gtgtccatgc ctcacctgca acccatgtgg ttctcagact
1981 tgaatcttct cggcccccca aaaagaagga cctcatttct tatagcctct cctgtgattc
2041 aacacaaccc atggagatgt ccccttctca ctctgaaatc atccatttgg ggacaaatcc
2101 acattggggt ctagaaacat ccacgtatct catcagccat cttgtcctgt gcatcctaac
2161 agaggaagga tccatgattc tgctttggtc caattgcttc ctctctgcag aggaacaacc
2221 ctaaaaccag accactccac gcaggacagg caggagagat tcttcctaaa gcctccccca
2281 taaaaaggga gctgtggatc cacttagatc agggcggaac catctttcac ccggccaagc
2341 tcctgcccag atgttgaccc tcacccagcg tgagctgtca catagtagga gcttctagat
2401 gcatgtggaa gcaatgagag ttgtccctta gccttataaa ctccccatga tctgacatgc
2461 agaaatccag ccttgtccag aatcctcctg gaatttcttg gagacgaaag tatctggggg
2521 attgttgggt actagggaga ctgggtacaa gggtgaaaag tagttcccat aatacacatg
2581 gttgactatg gtgatccacc ttgtgatggt taatattagg tgtctggaga aggttgcttc
2641 attggccctg ggacttctct ctgcaggagg agagaacgct gcctctcctc tggattggtc
2701 tcaggctctc tgttggcctt tggtcagcgt ttccacatcc tgctctgctg caggagaggg
2761 ggctaagggg ctggatccac caaggcagct cacagcggga aaactctggg aatgaaccac
2821 tgaattcagg ggatggggt gggggggcgg ttctcgaggt gtgtgccagc tacacgtgtg
2881 ttctgtatgg gtccagctgc gtttccatca ctcgctaata aatcaacaga aacacaaa
```

FIG. 14

```
DEFINITION  PREDICTED: Homo sapiens peptidyl arginine deiminase 3 (PADI3),
            transcript variant X2, mRNA.
ACCESSION   XM_017001463
VERSION     XM_017001463.1:c
sequence number-40

  1 agaaatggat ggatgtgact gtgtgctaat aaaactttat ttatacaaac aggcagtagg
 61 ccagatttgg cccacagttc ataatgtgct gatcctgacc taggcgagaa gagaaaccaa
121 atatgaaact gttgaagaac ttgggactga attatgttgg aacttggtgc cctgggagtt
181 aagaggagaa ggtcgagcgg cagtgggtct gggggcccag tgggtatggc ggcatcttgc
241 tggtgaactg tgaccgtgat gatccgagct gtgatgtcca ggacaattgt gaccagcacg
301 tgcactgcct gcaagacctg gaagacatgt ctgtcatggt cctgcggacg cagggccctg
361 cagccctctt tgatgaccac aaacttgtcc tccatacctc cagctatgat gccaaacggg
421 cacaggtctt ccacatctgc ggtcctgagg atgtgtgtga ggcctatagg catgtgctgg
481 gccaagataa ggtgtcctat gaggtacccc gcttgcatgg ggatgaggag cgcttcttcg
541 tggaaggcct gtccttccct gatgccggct tcacaggact catctccttc catgtcactc
601 tgctggacga ctccaacgag gatttctcgg catcccctat cttcactgac actgtggtgt
661 tccgagtggc accctggatc atgacgccca gcactctgcc acccctagag gtgtatgtgt
721 gccgtgtgag gaacaacacg tgttttgtgg atgcggtggc agagctggcc aggaaggccg
781 gctgcaagct gaccatctgc ccacaggccg agaaccgcaa cgaccgctgg atccaggatg
841 agatggagct gggctacgtt caggcgccgc acaagaccct cccggtggtc tttgactccc
```

```
 901 caaggaatgg ggaactgcag gatttccctt acaaaagaat cctgggtcca gattttggtt
 961 acgtgactcg ggaaccacgc gacaggtctg tgagtggcct ggactccttt gggaacctgg
1021 aggtcagccc tccagtggtg gccaatggga aagagtaccc cctggggagg atcctcattg
1081 ggggcaacct gcctgggtca agtggccgca gggtcaccca ggtggtgcgg gacttcctcc
1141 atgcccagaa ggtgcagccc cccgtggagc tctttgtgga ctggttggcc gtgggccatg
1201 tggatgagtt tctgagcttt gtccctgccc ccgatgggaa gggcttccgg atgctcctgg
1261 ccagccctgg ggcctgcttc aagctcttcc aggaaaagca gaagtgtggc cacgggaggg
1321 ccctcctgtt ccaggggggtt gttgatgatg agcaggtcaa gaccatctcc atcaaccagg
1381 tgctctccaa taaagacctc atcaactaca ataagtttgt gcagagctgc atcgactgga
1441 accgtgaggt gctgaagcgg gagctgggcc tggcagagtg tgacatcatt gacatcccac
1501 agctcttcaa gaccgagagg aaaaaagcaa cggccttctt ccctgacttg gtgaacatgc
1561 tggtgctggg gaagcacctg ggcatcccca agccctttgg gcccatcatc aatggctgct
1621 gctgcctgga ggagaaggtg cggtccctgc tggagccgct gggcctccac tgcaccttca
1681 ttgatgactt cactccatac cacatgctgc atggggaggt gcactgtggc accaatgtgt
1741 gcagaaagcc cttctctttc aagtggtgga acatggtgcc ctgagacagc tcccacccac
1801 catcctgtcc ccctggggcg ggcattggcc caggtggtgg agacagagac aggcccctga
1861 acgataagca ccaagagacc ccaaggctcc agatggaaca ctgagggtga ccgtccctct
1921 cagaagcctt ttccctggaa gtgtccatgc ctcacctgca acccatgtgg ttctcagact
1981 tgaatcttct cggcccccca aaaagaagga cctcatttct tatagcctct cctgtgattc
2041 aacacaaccc atggagatgt ccccttctca ctctgaaatc atccatttgg ggacaaatcc
2101 acattggggt ctagaaacat ccacgtatct catcagccat cttgtcctgt gcatcctaac
2161 agaggaagga tccatgattc tgctttggtc caattgcttc ctctctgcag aggaacaacc
2221 ctaaaaccag accactccac gcaggacagg caggagagat tcttcctaaa gcctccccca
2281 taaaaaggga gctgtggatc cacttagatc agggcggaac catctttcac ccggccaagc
2341 tcctgcccag atgttgaccc tcacccagcg tgagctgtca catagtagga gcttctagat
2401 gcatgtggaa gcaatgagag ttgtccctta gccttataaa ctccccatga tctgacatgc
2461 agaaatccag ccttgtccag aatcctcctg gaatttcttg gagacgaaag tatctggggg
2521 attgttgggt actagggaga ctgggtacaa gggtgaaaag tagttcccat aatacacatg
2581 gttgactatg gtgatccacc ttgtgatggt taatattagg tgtctggaga aggttgcttc
2641 attggccctg ggacttctct ctgcaggagg agagaacgct gcctctcctc tggattggtc
2701 tcaggctctc tgttggcctt tggtcagcgt ttccacatcc tgctctgctg caggagaggg
2761 ggctaagggg ctggatccac caaggcagct cacagcggga aaactctggg aatgaaccac
2821 tgaattcagg ggatgggggt gggggggcgg ttctcgaggt gtgtgccagc tacacgtgtg
2881 ttctgtatgg gtccagctgc gtttccatca ctcgctaata aatcaacaga aacacaaa
```

FIG. 15

```
DEFINITION  PREDICTED: Homo sapiens peptidyl arginine deiminase 3 (PADI3),
            transcript variant X3, mRNA.
ACCESSION   XM_011541572
VERSION     XM_011541572.2
sequence number-49

  1 cctaaggggc ctcaggggca gtgttggggt tggcggccac agctaagtcc aacaccagca
 61 tgtcgctgca gagaatcgtg cgtgtgtccc tggagcatcc caccagcgcg gtgtgtgtgg
121 ctggcgtgga gaccctcgtg gacatttatg ggtcagtgcc tgagggcaca gaaatgtttg
181 aggtctatgg gacgcctggc gtggacatct acatctctcc caacatggag aggggccggg
241 agcgtgcaga caccaggcgg tggcgctttg acgcgacttt ggagatcatc gtggtcatga
301 actcccccag caatgacctc aacgacagcc atgttcagat ttcctaccac tccagccatg
361 agcctctgcc cctggcctat gcggtgctct acctcacctg tgttgacatc tctctggatt
421 gcgacctgaa ctgtgaggga aggcaggaca ggaactttgt agacaagcgg cagtgggtct
481 gggggcccag tgggtatggc ggcatcttgc tggtgaactg tgaccgtgat gatccgagct
541 gtgatgtcca ggacaattgt gaccagcacg tgcactgcct gcaagacctg gaagacatgt
601 ctgtcatggt cctgcggacg cagggccctg cagccctctt tgatgaccac aaacttgtcc
661 tccatacctc cagctatgat gccaaacggg cacaggtctt ccacatctgc ggtcctgagg
721 atgtgtgtga ggcctatagg catgtgctgg gccaagataa ggtgtcctat gaggtacccc
781 gcttgcatgg ggatgaggag cgcttcttcg tggaaggcct gtccttccct gatgccggct
841 tcacaggact catctccttc catgtcactc tgctggacga ctccaacgag gatttctcgg
```

```
 901 catcccctat cttcactgac actgtggtgt tccgagtggc accctggatc atgacgccca
 961 gcactctgcc accccctagag gtgtatgtgt gccgtgtgag gaacaacacg tgttttgtgg
1021 atgcggtggc agagctggcc aggaaggccg gctgcaagct gaccatctgc ccacaggccg
1081 agaaccgcaa cgaccgctgg atccaggatg agatggagct gggctacgtt caggcgccgc
1141 acaagaccct cccggtggtc tttgactccc caaggaatgg ggaactgcag gatttccctt
1201 acaaaagaat cctggtcaag tggccgcagg gtcacccagg tggtgcggga cttcctccat
1261 gcccagaagg tgcagccccc cgtggagctc tttgtggact ggttggccgt gggccatgtg
1321 gatgagtttc tgagctttgt ccctgccccc gatgggaagg gcttccggat gctcctggcc
1381 agccctgggg cctgcttcaa gctcttccag gaaaagcaga agtgtggcca cgggagggcc
1441 ctcctgttcc ag
```

FIG. 16

```
DEFINITION  protein-arginine deiminase type-3 isoform X3 [Homo sapiens].
ACCESSION   XP_011539874
VERSION     XP_011539874.1
sequence number-50

  1 mslqrivrvs lehptsavcv agvetlvdiy gsvpegtemf evygtpgvdi yispnmergr
 61 eradtrrwrf datleiivvm nspsndlnds hvqisyhssh eplplayavl yltcvdisld
121 cdlncegrqd rnfvdkrqwv wgpsgyggil lvncdrddps cdvqdncdqh vhclqdledm
181 svmvlrtqgp aalfddhklv lhtssydakr aqvfhicgpe dvceayrhvl gqdkvsyevp
241 rlhgdeerff veglsfpdag ftglisfhvt llddsnedfs aspiftdtvv frvapwimtp
301 stlpplevyv crvrnntcfv davaelarka gckltlcpqa enrndrwiqd emelgyvqap
361 hktlpvvfds prngelqdfp ykrilvkwpq ghpggaglpp cpegaaprga lcglvgrgpc
421 g
```

FIG. 17

```
DEFINITION  PREDICTED: Homo sapiens peptidyl arginine deiminase 3 (PADI3),
            transcript variant X3, mRNA.
ACCESSION   XM_011541572
VERSION     XM_011541572.2:c.
sequence number-59

   1 cctaaggggc ctcaggggca gtgttggggt tggcggccac agctaagtcc aacaccagca
  61 tgtcgctgca gagaatcgtg cgtgtgtccc tggagcatcc caccagcgcg gtgtgtgtgg
 121 ctggcgtgga gaccctcgtg gacatttatg ggtcagtgcc tgagggcaca gaaatgtttg
 181 aggtctatgg gacgcctggc gtggacatct acatctctcc caacatggag aggggccggg
 241 agcgtgcaga caccaggcgg tggcgctttg acgcgacttt ggagatcatc gtggtcatga
 301 actcccccag caatgacctc aacgacagcc atgttcagat ttcctaccac tccagccatg
 361 agcctctgcc cctggcctat gcggtgctct acctcacctg tgttgacatc tctctggatt
 421 gcgacctgaa ctgtgaggga aggcaggaca ggaactttgt agacaagcgg cagtgggtct
 481 gggggcccag tgggtatggc ggcatcttgc tggtgaactg tgaccgtgat gatccgagct
 541 gtgatgtcca ggacaattgt gaccagcacg tgcactgcct gcaagacctg gaagacatgt
 601 ctgtcatggt cctgcggacg cagggccctg cagccctctt tgatgaccac aaacttgtcc
 661 tccatacctc cagctatgat gccaaacggg cacaggtctt ccacatctgc ggtcctgagg
 721 atgtgtgtga ggcctatagg catgtgctgg gccaagataa ggtgtcctat gaggtacccc
 781 gcttgcatgg ggatgaggag cgcttcttcg tggaaggcct gtccttccct gatgccggct
 841 tcacaggact catctccttc catgtcactc tgctggacga ctccaacgag gatttctcgg
 901 catcccctat cttcactgac actgtggtgt tccgagtggc accctggatc atgacgccca
 961 gcactctgcc acccctagag gtgtatgtgt gccgtgtgag gaacaacacg tgttttgtgg
1021 atgcggtggc agagctggcc aggaaggccg gctgcaagct gaccatctgc ccacaggccg
```

```
1081 agaaccgcaa cgaccgctgg atccaggatg agatggagct gggctacgtt caggcgccgc
1141 acaagaccct cccggtggtc tttgactccc caaggaatgg ggaactgcag gatttccctt
1201 acaaaagaat cctggtcaag tggccgcagg gtcacccagg tggtgcggga cttcctccat
1261 gcccagaagg tgcagccccc cgtggagctc tttgtggact ggttggccgt gggccatgtg
1321 gatgagtttc tgagctttgt ccctgccccc gatgggaagg gcttccggat gctcctggcc
1381 agccctgggg cctgcttcaa gctcttccag gaaaagcaga agtgtggcca cgggagggcc
1441 ctcctgttcc ag
```

FIG. 18

```
DEFINITION  Homo sapiens peptidyl arginine deiminase 4 (PADI4), mRNA.
ACCESSION   NM_012387
VERSION     NM_012387.3
sequence number-61

   1 agccagaggg acgagctagc ccgacgatgg cccaggggac attgatccgt gtgaccccag
  61 agcagcccac ccatgccgtg tgtgtgctgg gcaccttgac tcagcttgac atctgcagct
 121 ctgcccctga ggactgcacg tccttcagca tcaacgcctc cccaggggtg gtcgtggata
 181 ttgcccacgg ccctccagcc aagaagaaat ccacaggttc ctccacatgg cccctggacc
 241 ctggggtaga ggtgaccctg acgatgaaag tggccagtgg tagcacaggc gaccagaagg
 301 ttcagatttc atactacgga cccaagactc caccagtcaa agctctactc tacctcaccg
 361 gggtggaaat ctccttgtgc gcagacatca cccgcaccgg caaagtgaag ccaaccagag
 421 ctgtgaaaga tcagaggacc tggacctggg gcccttgtgg acagggtgcc atcctgctgg
 481 tgaactgtga cagagacaat ctcgaatctt ctgccatgga ctgcgaggat gatgaagtgc
 541 ttgacagcga agacctgcag gacatgtcgc tgatgaccct gagcacgaag acccccaagg
 601 acttcttcac aaaccataca ctggtgctcc acgtggccag gtctgagatg gacaaagtga
 661 gggtgtttca ggccacacgg ggcaaactgt cctccaagtg cagcgtagtc ttgggtccca
 721 agtggccctc tcactacctg atggtccccg gtggaaagca caacatggac ttctacgtgg
 781 aggccctcgc tttcccggac accgacttcc cggggctcat taccctcacc atctccctgc
 841 tggacacgtc caacctggag ctccccgagg ctgtggtgtt ccaagacagc gtggtcttcc
 901 gcgtggcgcc ctggatcatg acccccaaca cccagccccc gcaggaggtg tacgcgtgca
 961 gtatttttga aaatgaggac ttcctgaagt cagtgactac tctggccatg aaagccaagt
1021 gcaagctgac catctgccct gaggaggaga acatggatga ccagtggatg caggatgaaa
1081 tggagatcgg ctacatccaa gccccacaca aaacgctgcc cgtggtcttc gactctccaa
1141 ggaacagagg cctgaaggag tttcccatca aacgcgtgat gggtccagat tttggctatg
1201 taactcgagg gccccaaaca gggggtatca gtggactgga ctcctttggg aacctggaag
1261 tgagcccccc agtcacagtc aggggcaagg aataccccgct gggcaggatt ctcttcgggg
1321 acagctgtta tcccagcaat gacagccggc agatgcacca ggccctgcag gacttcctca
1381 gtgcccagca ggtgcaggcc cctgtgaagc tctattctga ctggctgtcc gtgggccacg
1441 tggacgagtt cctgagcttt gtgccagcac ccgacaggaa gggcttccgg ctgctcctgg
1501 ccagccccag gtcctgctac aaactgttcc aggagcagca gaatgagggc cacgggggagg
1561 ccctgctgtt cgaagggatc aagaaaaaaa aacagcagaa aataaagaac attctgtcaa
1621 acaagacatt gagagaacat aattcatttg tggagagatg catcgactgg aaccgcgagc
1681 tgctgaagcg ggagctgggc ctggccgaga gtgacatcat tgacatcccg cagctcttca
1741 agctcaaaga gttctctaag gcggaagctt ttttccccaa catggtgaac atgctggtgc
1801 tagggaagca cctgggcatc cccaagccct tcgggcccgt catcaacggc cgctgctgcc
1861 tggaggagaa ggtgtgttcc ctgctggagc cactgggcct ccagtgcacc ttcatcaacg
1921 acttcttcac ctaccacatc aggcatgggg aggtgcactg cggcaccaac gtgcgcagaa
1981 agcccttctc cttcaagtgg tggaacatgg tgccctgagc ccatcttccc tggcgtcctc
2041 tccctcctgg ccagatgtcg ctgggtcctc tgcagtgtgg caagcaagag ctcttgtgaa
2101 tattgtggct ccctgggggc ggccagccct cccagcagtg gcttgctttc ttctcctgtg
2161 atgtcccagt ttcccactct gaagatccca acatggtcct agcactgcac actcagttct
2221 gctctaagaa gctgcaataa agtttttta agtcactttg tacatga
```

FIG. 19

```
DEFINITION  protein-arginine deiminase type-4 [Homo sapiens].
ACCESSION   NP_036519
VERSION     NP_036519.2
sequence number-62

      1 maqgtlirvt peqpthavcv lgtltqldic ssapedctsf sinaspgvvv diahgppakk
     61 kstgsstwpl dpgvevtltm kvasgstgdq kvqisyygpk tppvkallyl tgveislcad
    121 itrtgkvkpt ravkdqrtwt wgpcgqgail lvncdrdnle ssamdcedde vldsedlqdm
    181 slmtlstktp kdfftnhtlv lhvarsemdk vrvfqatrgk lsskcsvvlg pkwpshylmv
    241 pggkhnmdfy vealafpdtd fpglitltis lldtsnleip eavvfqdsvv frvapwimtp
    301 ntqppqevya csifenedfl ksvttlamka kckltícpee enmddqwmqd emeigyiqap
    361 hktlpvvfds prnrglkefp ikrvmgpdfg yvtrgpqtgg isgldsfgnl evsppvtvrg
    421 keyplgrilf gdscypsnds rqmhqalqdf lsaqqvqapv klysdwlsvg hvdeflsfvp
    481 apdrkgfrll lasprscykl fqeqqneghg eallfegikk kkqqkiknil snktlrehns
    541 fvercidwnr ellkrelgla esdiidipql fklkefskae affpnmvnml vlgkhlgipk
    601 pfgpvingrc cleekvcsll eplglqctfi ndfftyhirh gevhcgtnvr rkpfsfkwwn
    661 mvp
```

FIG. 20

```
DEFINITION  PREDICTED: Homo sapiens peptidyl arginine deiminase 4 (PADI4),
            transcript variant X3, mRNA.
ACCESSION   XM_011541152
VERSION     XM_011541152.1:c
sequence number-67

      1 tctacctcac cggggtggaa atctccttgt gcgcagacat cacccgcacc ggcaaagtga
     61 agccaaccag agctgtgaaa gatcagacct gcaggacatg tcgctgatga ccctgagcac
    121 gaagaccccc aaggacttct tcacaaacca tacactggtg ctccacgtgg ccaggtctga
    181 gatggacaaa gtgagggtgt ttcaggccac acggggcaaa ctgtcctcca agtgcagcgt
    241 agtcttgggt cccaagtggc cctctcacta cctgatggtc cccggtggaa agcacaacat
    301 ggacttctac gtggaggccc tcgctttccc ggacaccgac ttcccggggc tcattaccct
    361 caccatctcc ctgctggaca cgtccaacct ggagctcccc gaggctgtgg tgttccaaga
    421 cagcgtggtc ttccgcgtgg cgccctggat catgaccccc aacacccagc cccgcagga
    481 ggtgtacgcg tgcagtattt ttgaaaatga ggacttcctg aagtcagtga ctactctggc
    541 catgaaagcc aagtgcaagc tgaccatctg ccctgaggag gagaacatgg atgaccagtg
    601 gatgcaggat gaaatggaga tcggctacat ccaagcccca cacaaaacgc tgcccgtggt
    661 cttcgactct ccaaggaaca gaggcctgaa ggagtttccc atcaaacgcg tgatgggtcc
    721 agattttggc tatgtaactc gagggcccca aacaggggt atcagtggac tggactcctt
    781 tgggaacctg gaagtgagcc ccccagtcac agtcaggggc aaggaatacc cgctgggcag
    841 gattctcttc ggggacagct gttatcccag caatgacagc cggcagatgc accaggccct
    901 gcaggacttc ctcagtgccc agcaggtgca ggcccctgtg aagctctatt ctgactggct
    961 gtccgtgggc cacgtggacg agttcctgag ctttgtgcca gcacccgaca ggaagggctt
   1021 ccggctgctc ctggccagcc ccaggtcctg ctacaaactg ttccaggagc agcagaatga
   1081 gggccacggg gaggccctgc tgttcgaagg gatcaagaaa aaaaaacagc agaaaataaa
   1141 gaacattctg tcaaacaaga cattgagaga acataattca tttgtggaga gatgcatcga
   1201 ctggaaccgc gagctgctga agcgggagct gggcctggcc gagagtgaca tcattgacat
   1261 cccgcagctc ttcaagctca aagagttctc taaggcggaa gctttttcc ccaacatggt
   1321 gaacatgctg gtgctaggga agcacctggg catccccaag cccttcgggc ccgtcatcaa
   1381 cggccgctgc tgcctggagg agaaggtgtg ttccctgctg gagccactgg gcctccagtg
   1441 caccttcatc aacgacttct tcacctacca catcaggcat ggggaggtgc actgcggcac
   1501 caacgtgcgc agaaagccct tctccttcaa gtggtggaac atggtgccct gagcccatct
   1561 tccctggcgt cctctccctc ctggccagat gtcgctgggt cctctgcagt gtggcaagca
   1621 agagctcttg tgaatattgt ggctccctgg gggcggccag ccctcccagc agtggcttgc
   1681 tttcttctcc tgtgatgtcc cagtttccca ctctgaagat cccaacatgg tcctagcact
   1741 gcacactcag ttctgctcta agaagctgca ataaagtttt tttaagtcac tttgtacatg
   1801 a
```

FIG. 21

```
DEFINITION   PREDICTED: Homo sapiens peptidyl arginine deiminase 4 (PADI4),
             transcript variant X8, mRNA.
ACCESSION    XM_011541157
VERSION      XM_011541157.1:c
sequence number-68

        1 agctctactc tacctcaccg gggtggaaat ctccttgtgc gcagacatca cccgcaccgg
       61 caaagtgaag ccaaccagag ctgtgaaaga tcagaggacc tggacctggg gcccttgtgg
      121 acagggtgcc atcctgctgg tgaactgtga cagagacaat ctcgaatctt ctgccatgga
      181 ctgcgaggat gatgaagtgc ttgacagcga agacctgcag gacatgtcgc tgatgaccct
      241 gagcacgaag acccccaagg acttcttcac aaaccataca ctggtgctcc acgtggccag
      301 gtctgagatg gacaaagtga gggtgtttca ggccacacga gctccccgag gctgtggtgt
      361 tccaagacag cgtggtcttc cgcgtggcgc cctggatcat gacccccaac acccagcccc
      421 cgcaggaggt gtacgcgtgc agtatttttg aaaatgagga cttcctgaag tcagtgacta
      481 ctctggccat gaaagccaag tgcaagctga ccatctgccc tgaggaggag aacatggatg
      541 accagtggat gcaggatgaa atggagatcg gctacatcca agccccacac aaaacgctgc
      601 ccgtggtctt cgactctcca aggaacagag gcctgaagga gtttcccatc aaacgcgtga
      661 tgggtccaga ttttggctat gtaactcgag ggccccaaac aggggtatc agtggactgg
      721 actcctttgg gaacctggaa gtgagccccc cagtcacagt caggggcaag gaatacccgc
      781 tgggcaggat tctcttcggg gacagctgtt atcccagcaa tgacagccgg cagatgcacc
      841 aggccctgca ggacttcctc agtgcccagc aggtgcaggc ccctgtgaag ctctattctg
      901 actggctgtc cgtgggccac gtggacgagt tcctgagctt tgtgccagca cccgacagga
      961 agggcttccg gctgctcctg gccagcccca ggtcctgcta caaactgttc caggagcagc
     1021 agaatgaggg ccacggggag gccctgctgt tcgaagggat caagaaaaaa aaacagcaga
     1081 aaataaagaa cattctgtca aacaagacat tgagagaaca taattcattt gtggagagat
     1141 gcatcgactg gaaccgcgag ctgctgaagc gggagctggg cctggccgag agtgacatca
     1201 ttgacatccc gcagctcttc aagctcaaag agttctctaa ggcggaagct tttttcccca
     1261 acatggtgaa catgctggtg ctagggaagc acctgggcat ccccaagccc ttcgggcccg
     1321 tcatcaacgg ccgctgctgc ctggaggaga aggtgtgttc cctgctggag ccactgggcc
     1381 tccagtgcac cttcatcaac gacttcttca cctaccacat caggcatggg gaggtgcact
     1441 gcggcaccaa cgtgcgcaga aagcccttct ccttcaagtg gtggaacatg gtgccctgag
     1501 cccatcttcc ctggcgtcct ctccctcctg gccagatgtc gctgggtcct ctgcagtgtg
     1561 gcaagcaaga gctcttgtga atattgtggc tccctggggg cggccagccc tcccagcagt
     1621 ggcttgcttt cttctcctgt gatgtcccag tttcccactc tgaagatccc aacatggtcc
     1681 tagcactgca cactcagttc tgctctaaga agctgcaata aagtttttt aagtcacttt
     1741 gtacatga
```

FIG. 22

SEQUENCE LISTING

<160> NUMBER OF SEQ ID NOS: 92

<210> SEQ ID NO 1
<211> LENGTH: 4361
<212> TYPE: DNA
<213> ORGANISM: Homo sapiens
<220> FEATURE:
<223> OTHER INFORMATION: Homo sapiens peptidyl arginine deiminase 2 (PADI2), mRNA

<400> SEQUENCE: 1
aggctgctgg agaaggcgca cctgctgcag gtgctcccgg ccgccccgga ccagcgagcg 60
cgggcactgc ggcggggagg atgctgcgcg agcggaccgt gcggctgcag tacgggagcc 120
gcgtggaggc ggtgtacgtg ctgggcacct acctctggac cgatgtctac agcgcggccc 180
cagccggggc ccaaaccttc agcctgaagc actcggaaca cgtgtgggtg gaggtggtgc 240
gtgatgggga ggctgaggag gtggccacca atggcaagca gcgctggctt ctctcgccca 300
gcaccaccct gcgggtcacc atgagccagg cgagcaccga ggccagcagt gacaaggtca 360
ccgtcaacta ctatgacgag gaagggagca ttcccatcga ccaggcgggg ctcttcctca 420
cagccattga gatctccctg gatgtggacg cagaccggga tggtgtggtg gagaagaaca 480
acccaaagaa ggcatcctgg acctggggcc ccgagggcca gggggccatc ctgctggtga 540
actgtgaccg agagacaccc tggttgccca aggaggactg ccgtgatgag aaggtctaca 600
gcaaggaaga tctcaaggac atgtcccaga tgatcctgcg gaccaaaggc cccgaccgcc 660
tccccgccgg atacgagata gttctgtaca tttccatgtc agactcagac aaagtgggcg 720
tgttctacgt ggagaacccg ttcttcggcc aacgctatat ccacatcctg ggccggcgga 780
agctctacca tgtggtcaag tacacgggtg gctccgcgga gctgctgttc ttcgtggaag 840
gcctctgttt ccccgacgag ggcttctcag gcctggtctc catccatgtc agcctgctgg 900
agtacatggc ccaggacatt cccctgactc ccatcttcac ggacaccgtg atattccgga 960
ttgctccgtg gatcatgacc cccaacatcc tgcctcccgt gtcggtgttt gtgtgctgca 1020
tgaaggataa ttacctgttc ctgaaagagg tgaagaacct tgtggagaaa accaactgtg 1080
agctgaaggt ctgcttccag tacctaaacc gaggcgatcg ctggatccag gatgaaattg 1140

-continued

```
agtttggcta catcgaggcc ccccataaag gcttccccgt ggtgctggac tctccccgag   1200
atggaaacct aaaggacttc cctgtgaagg agctcctggg cccagatttt ggctacgtga   1260
cccgggagcc cctctttgag tctgtcacca gccttgactc atttggaaac ctggaggtca   1320
gtcccccagt gaccgtgaac ggcaagacat acccgcttgg ccgcatcctc atcgggagca   1380
gctttcctct gtctggtggt cggaggatga ccaaggtggt gcgtgacttc ctgaaggccc   1440
agcaggtgca ggcgcccgtg gagctctact cagactggct gactgtgggc cacgtggatg   1500
agttcatgtc ctttgtcccc atccccggca caaagaaatt cctgctactc atggccagca   1560
cctcggcctg ctacaagctc ttccgagaga agcagaagga cggccatgga gaggccatca   1620
tgttcaaagg cttgggtggg atgagcagca agcgaatcac catcaacaag attctgtcca   1680
acgagagcct tgtgcaggag aacctgtact tccagcgctg cctagactgg aaccgtgaca   1740
tcctcaagaa ggagctggga ctgacagagc aggacatcat tgacctgccc gctctgttca   1800
agatggacga ggaccaccgt gccagagcct tcttcccaaa catggtgaac atgatcgtgc   1860
tggacaagga cctgggcatc cccaagccat tcgggccaca ggttgaggag gaatgctgcc   1920
tggagatgca cgtgcgtggc ctcctggagc ccctgggcct cgaatgcacc ttcatcgacg   1980
acatttctgc ctaccacaaa tttctggggg aagtccactg tggcaccaac gtccgcagga   2040
agcccttcac cttcaagtgg tggcacatgg tgccctgacc tgccaggggc cctggcgttt   2100
gcctccttcg cttagttctc cagaccctcc ctcacacgcc cagagccttc tgctgacatg   2160
gactggacag ccccgctggg agacctttgg gacgtggggt ggaatttggg gtatctgtgc   2220
cttgccctcc ctgagagggg cctcagtgtc ctctgaagcc atccccagtg agcctcgact   2280
ctgtccctgc tgaaaatagc tgggccagtg tctctgtagc cctgacataa ggaacagaac   2340
acaacaaaac acagcaaacc atgtgcccaa actgctcccc aaagaatttt gagtctctaa   2400
tctgacactg aatgagggga gaagggaagg agattctggg attgccagtt cttccagcag   2460
ccatgctctg aaaatcaagg tagaatccat ggaaagggac cccaggaccc cgggacccta   2520
gacgtatctt gaactgccat cgtcatttca aatacatctc cctcagggtt tccaggtggc   2580
cacccccaat tattcattcc ttaccaacct ctcaaatcct cttggctttc tctctgcagt   2640
gtggacactg ttggctagtc ctccccactc cctgagggtc cagtaagtta gcttagaacc   2700
ttcctggaaa catttcatct gagcaggttt ccccacgtgt gggatgctcc ttttgcctca   2760
tctgtctcag ggatgcaggc tcccccgcat gcatggggat ttctccccag accagcatac   2820
ttgtgacctg agagttcaat gcgtaaagat gcccctggtc agccatatcc atcttctctt   2880
gcctggtcct tgattctctg gccgctccct gaccttcctc cttccactgc cttgactttc   2940
ttcctttta ttcctggtgc catctgtcca ggcagctaga caagaacttg ttcgccagca   3000
gccagattca ggccttccca ggggcataat aagtgaccag cccctcctct ccggacatca   3060
gatccaacac ataaggaccc tggcctaccc tccagcccaa cagccagttc tgggtcagct   3120
gccaacttag ggtggtttg attatcccat tgaaattcac cagtgccttt gccaaagacc   3180
ctctcatttg gacataccca gattcattcc ctggctccaa ctgaaaagac tcagtttcaa   3240
tcgttaaaag ttcctttagg gccagaagaa taaatgaatt ataatcccat tttgaagaac   3300
cgatttataa ccaatgaaaa ggttataatg taatttatat tcttggagga acaagatttt   3360
catttgggat tatttccttc aaccattcaa caaacatttg ttgtatgcca ctaagcgcca   3420
ggcacggcgt tgggctctgc aaacacagtg gttagtagca gtctggacct ggtccctact   3480
```

-continued

```
ggcatggaac ccatcactcc ccaacatgca aagcccacat ttaaaggcca gcctctgccc   3540

cttcagtgat gcgctcttta gaaatgccag tccactatat tcagaaatcc gcagggcaca   3600

aaacttccag caagtcactg ttgtggtgaa atgggcagtg ggggtggggg gtcttcttta   3660

aacaggcccc cttcccatct acctagccag tacccatcca atgagtcccc agagcctcca   3720

gaagctgttg tctcctctct ggggacagca gctcctgcct ttggaggcca aagccccaga   3780

tctctccagc cccagagctg aaaacaccaa gtgcctattt gagggtgtct gtctggagac   3840

ttagagtttg tcatgtgtgt gtgtgtgttt ggttaatgtg ggtttatggg ttttctttct   3900

tttttttctt ttttttttta gtctacatta gggggaagtg agcgcctccc atgtgcagac   3960

agtgtgtctt tatagatttt tctaaggctt tccccaatga tgtcggtaat ttctgatgtt   4020

tctgaagttc ccaggactca cacacccgtt cccatctcac ttgcccaccc agtgtgacaa   4080

ccctcggtgt ggatataccc ccgtggactc atggctcttc cccaccccca ctttctataa   4140

atgtaggcct agaatacgct tctctgttgc aaaactcagc taagttcctg cttccacctt   4200

gatgttgaaa tatcttatgt aagagggcag gggatgtcgt gaagatggca agaagaacac   4260

agtttcaaat ttctggaaaa gagcctgtgg tggagatcta aagatgttta gggaagagct   4320

cgactaaaga acaatgaaat aaatggtcca aggggaagtc a                        4361


<210> SEQ ID NO 2
<211> LENGTH: 665
<212> TYPE: PRT
<213> ORGANISM: Homo sapiens
<220> FEATURE:
<223> OTHER INFORMATION: protein-arginine deiminase type-2 [Homo
      sapiens]

<400> SEQUENCE: 2

Met Leu Arg Glu Arg Thr Val Arg Leu Gln Tyr Gly Ser Arg Val Glu
1               5                   10                  15

Ala Val Tyr Val Leu Gly Thr Tyr Leu Trp Thr Asp Val Tyr Ser Ala
            20                  25                  30

Ala Pro Ala Gly Ala Gln Thr Phe Ser Leu Lys His Ser Glu His Val
        35                  40                  45

Trp Val Glu Val Val Arg Asp Gly Glu Ala Glu Glu Val Ala Thr Asn
    50                  55                  60

Gly Lys Gln Arg Trp Leu Leu Ser Pro Ser Thr Thr Leu Arg Val Thr
65                  70                  75                  80

Met Ser Gln Ala Ser Thr Glu Ala Ser Ser Asp Lys Val Thr Val Asn
                85                  90                  95

Tyr Tyr Asp Glu Glu Gly Ser Ile Pro Ile Asp Gln Ala Gly Leu Phe
            100                 105                 110

Leu Thr Ala Ile Glu Ile Ser Leu Asp Val Asp Ala Asp Arg Asp Gly
        115                 120                 125

Val Val Glu Lys Asn Asn Pro Lys Lys Ala Ser Trp Thr Trp Gly Pro
    130                 135                 140

Glu Gly Gln Gly Ala Ile Leu Leu Val Asn Cys Asp Arg Glu Thr Pro
145                 150                 155                 160

Trp Leu Pro Lys Glu Asp Cys Arg Asp Glu Lys Val Tyr Ser Lys Glu
                165                 170                 175

Asp Leu Lys Asp Met Ser Gln Met Ile Leu Arg Thr Lys Gly Pro Asp
            180                 185                 190

Arg Leu Pro Ala Gly Tyr Glu Ile Val Leu Tyr Ile Ser Met Ser Asp
        195                 200                 205
```

-continued

```
Ser Asp Lys Val Gly Val Phe Tyr Val Glu Asn Pro Phe Phe Gly Gln
    210                 215                 220

Arg Tyr Ile His Ile Leu Gly Arg Arg Lys Leu Tyr His Val Val Lys
225                 230                 235                 240

Tyr Thr Gly Gly Ser Ala Glu Leu Leu Phe Phe Val Glu Gly Leu Cys
                245                 250                 255

Phe Pro Asp Glu Gly Phe Ser Gly Leu Val Ser Ile His Val Ser Leu
            260                 265                 270

Leu Glu Tyr Met Ala Gln Asp Ile Pro Leu Thr Pro Ile Phe Thr Asp
        275                 280                 285

Thr Val Ile Phe Arg Ile Ala Pro Trp Ile Met Thr Pro Asn Ile Leu
    290                 295                 300

Pro Pro Val Ser Val Phe Val Cys Cys Met Lys Asp Asn Tyr Leu Phe
305                 310                 315                 320

Leu Lys Glu Val Lys Asn Leu Val Glu Lys Thr Asn Cys Glu Leu Lys
                325                 330                 335

Val Cys Phe Gln Tyr Leu Asn Arg Gly Asp Arg Trp Ile Gln Asp Glu
            340                 345                 350

Ile Glu Phe Gly Tyr Ile Glu Ala Pro His Lys Gly Phe Pro Val Val
        355                 360                 365

Leu Asp Ser Pro Arg Asp Gly Asn Leu Lys Asp Phe Pro Val Lys Glu
    370                 375                 380

Leu Leu Gly Pro Asp Phe Gly Tyr Val Thr Arg Glu Pro Leu Phe Glu
385                 390                 395                 400

Ser Val Thr Ser Leu Asp Ser Phe Gly Asn Leu Glu Val Ser Pro Pro
                405                 410                 415

Val Thr Val Asn Gly Lys Thr Tyr Pro Leu Gly Arg Ile Leu Ile Gly
            420                 425                 430

Ser Ser Phe Pro Leu Ser Gly Gly Arg Arg Met Thr Lys Val Val Arg
        435                 440                 445

Asp Phe Leu Lys Ala Gln Gln Val Gln Ala Pro Val Glu Leu Tyr Ser
    450                 455                 460

Asp Trp Leu Thr Val Gly His Val Asp Glu Phe Met Ser Phe Val Pro
465                 470                 475                 480

Ile Pro Gly Thr Lys Lys Phe Leu Leu Leu Met Ala Ser Thr Ser Ala
                485                 490                 495

Cys Tyr Lys Leu Phe Arg Glu Lys Gln Lys Asp Gly His Gly Glu Ala
            500                 505                 510

Ile Met Phe Lys Gly Leu Gly Gly Met Ser Ser Lys Arg Ile Thr Ile
        515                 520                 525

Asn Lys Ile Leu Ser Asn Glu Ser Leu Val Gln Glu Asn Leu Tyr Phe
    530                 535                 540

Gln Arg Cys Leu Asp Trp Asn Arg Asp Ile Leu Lys Lys Glu Leu Gly
545                 550                 555                 560

Leu Thr Glu Gln Asp Ile Ile Asp Leu Pro Ala Leu Phe Lys Met Asp
                565                 570                 575

Glu Asp His Arg Ala Arg Ala Phe Phe Pro Asn Met Val Asn Met Ile
            580                 585                 590

Val Leu Asp Lys Asp Leu Gly Ile Pro Lys Pro Phe Gly Pro Gln Val
        595                 600                 605

Glu Glu Glu Cys Cys Leu Glu Met His Val Arg Gly Leu Leu Glu Pro
    610                 615                 620
```

-continued

```
Leu Gly Leu Glu Cys Thr Phe Ile Asp Asp Ile Ser Ala Tyr His Lys
625                 630                 635                 640

Phe Leu Gly Glu Val His Cys Gly Thr Asn Val Arg Arg Lys Pro Phe
                645                 650                 655

Thr Phe Lys Trp Trp His Met Val Pro
            660                 665


<210> SEQ ID NO 3
<211> LENGTH: 3459
<212> TYPE: DNA
<213> ORGANISM: Homo sapiens
<220> FEATURE:
<223> OTHER INFORMATION: PREDICTED: Homo sapiens peptidyl arginine
      deiminase 2 (PADI2), transcript variant X2, mRNA

<400> SEQUENCE: 3

agcagctctg cagatgggga ttcttctgtc agctcatatc tgcacatgtg cacaaagaca     60

taaacataca agtgcactac agtgctgctt cttgtagtag caaaagattg caaagcaacc    120

taaatgtcca tctgtggagg actgagtaac ggccttcccg gaagttctgt gcaaccgcta    180

aaaaggatga agccagtctc tcaatatgga tacaggatgt gcttcaagga tgaaattgag    240

tttggctaca tcgaggcccc ccataaaggc ttccccgtgg tgctggactc tccccgagat    300

ggaaacctaa aggacttccc tgtgaaggag ctcctgggcc cagattttgg ctacgtgacc    360

cgggagcccc tctttgagtc tgtcaccagc cttgactcat ttggaaacct ggaggtcagt    420

cccccagtga ccgtgaacgg caagacatac ccgcttggcc gcatcctcat cgggagcagc    480

tttcctctgt ctggtggtcg gaggatgacc aaggtggtgc gtgacttcct gaaggcccag    540

caggtgcagg cgcccgtgga gctctactca gactggctga ctgtgggcca cgtggatgag    600

ttcatgtcct ttgtccccat ccccggcaca aagaaattcc tgctactcat ggccagcacc    660

tcggcctgct acaagctctt ccgagagaag cagaaggacg gccatggaga ggccatcatg    720

ttcaaaggct tgggtgggat gagcagcaag cgaatcacca tcaacaagat tctgtccaac    780

gagagccttg tgcaggagaa cctgtacttc cagcgctgcc tagactggaa ccgtgacatc    840

ctcaagaagg agctgggact gacagagcag gacatcattg acctgcccgc tctgttcaag    900

atggacgagg accaccgtgc cagagccttc ttcccaaaca tggtgaacat gatcgtgctg    960

gacaaggacc tgggcatccc caagccattc gggccacagg ttgaggagga atgctgcctg   1020

gagatgcacg tgcgtggcct cctggagccc ctgggcctcg aatgcacctt catcgacgac   1080

atttctgcct accacaaatt tctgggggaa gtccactgtg gcaccaacgt ccgcaggaag   1140

cccttcacct tcaagtggtg gcacatggtg ccctgacctg ccaggggccc tggcgtttgc   1200

ctccttcgct tagttctcca gaccctccct cacacgccca gagccttctg ctgacatgga   1260

ctggacagcc ccgctgggag acctttggga cgtggggtgg aatttggggt atctgtgcct   1320

tgccctccct gagaggggcc tcagtgtcct ctgaagccat ccccagtgag cctcgactct   1380

gtccctgctg aaaatagctg ggccagtgtc tctgtagccc tgacataagg aacagaacac   1440

aacaaaacac agcaaaccat gtgcccaaac tgctccccaa agaattttga gtctctaatc   1500

tgacactgaa tgaggggaga agggaaggag attctgggat tgccagttct tccagcagcc   1560

atgctctgaa aatcaaggta gaatccatgg aaaagggaccc caggaccccg ggaccctaga   1620

cgtatcttga actgccatcg tcatttcaaa tacatctccc tcagggtttc caggtggcca   1680

cccccaatta ttcattcctt accaacctct caaatcctct tggctttctc tctgcagtgt   1740

ggacactgtt ggctagtcct ccccactccc tgagggtcca gtaagttagc ttagaacctt   1800
```

-continued

```
cctggaaaca tttcatctga gcaggtttcc ccacgtgtgg gatgctcctt ttgcctcatc   1860

tgtctcaggg atgcaggctc ccccgcatgc atggggattt ctccccagac cagcatactt   1920

gtgacctgag agttcaatgc gtaaagatgc ccctggtcag ccatatccat cttctcttgc   1980

ctggtccttg attctctggc cgctccctga ccttcctcct tccactgcct tgactttctt   2040

cctttttatt cctggtgcca tctgtccagg cagctagaca agaacttgtt cgccagcagc   2100

cagattcagg ccttcccagg ggcataataa gtgaccagcc cctcctctcc ggacatcaga   2160

tccaacacat aaggaccctg gcctaccctc cagcccaaca gccagttctg ggtcagctgc   2220

caacttaggg gtggtttgat tatcccattg aaattcacca gtgcctttgc caaagaccct   2280

ctcatttgga catacccaga ttcattccct ggctccaact gaaaagactc agtttcaatc   2340

gttaaaagtt cctttagggc cagaagaata aatgaattat aatcccattt tgaagaaccg   2400

atttataacc aatgaaaagg ttataatgta atttatattc ttggaggaac aagattttca   2460

tttgggatta tttccttcaa ccattcaaca aacatttgtt gtatgccact aagcgccagg   2520

cacggcgttg ggctctgcaa acacagtggt tagtagcagt ctggacctgg tccctactgg   2580

catggaaccc atcactcccc aacatgcaaa gcccacattt aaaggccagc ctctgcccct   2640

tcagtgatgc gctctttaga aatgccagtc cactatattc agaaatccgc agggcacaaa   2700

acttccagca agtcactgtt gtggtgaaat gggcagtggg ggtggggggt cttctttaaa   2760

caggcccccct tcccatctac ctagccagta cccatccaat gagtccccag agcctccaga   2820

agctgttgtc tcctctctgg ggacagcagc tcctgccttt ggaggccaaa gccccagatc   2880

tctccagccc cagagctgaa aacaccaagt gcctatttga gggtgtctgt ctggagactt   2940

agagtttgtc atgtgtgtgt gtgtgtttgg ttaatgtggg tttatgggtt ttctttcttt   3000

tttttctttt ttttttagt ctacattagg gggaagtgag cgcctcccat gtgcagacag   3060

tgtgtcttta tagatttttc taaggctttc cccaatgatg tcggtaattt ctgatgtttc   3120

tgaagttccc aggactcaca cacccgttcc catctcactt gcccacccag tgtgacaacc   3180

ctcggtgtgg atataccccc gtggactcat ggctcttccc cacccccact ttctataaat   3240

gtaggcctag aatacgcttc tctgttgcaa aactcagcta agttcctgct tccaccttga   3300

tgttgaaata tcttatgtaa gagggcaggg gatgtcgtga agatggcaag aagaacacag   3360

tttcaaattt ctggaaaaga gcctgtggtg gagatctaaa gatgtttagg gaagagctcg   3420

actaaagaac aatgaaataa atggtccaag gggaagtca                          3459
```

<210> SEQ ID NO 4
<211> LENGTH: 350
<212> TYPE: PRT
<213> ORGANISM: Homo sapiens
<220> FEATURE:
<223> OTHER INFORMATION: protein-arginine deiminase type-2 isoform X1 [Homo sapiens]

<400> SEQUENCE: 4

```
Met Ser Ile Cys Gly Gly Leu Ser Asn Gly Leu Pro Gly Ser Ser Val
1               5                   10                  15

Gln Pro Leu Lys Arg Met Lys Pro Val Ser Gln Tyr Gly Tyr Arg Met
            20                  25                  30

Cys Phe Lys Asp Glu Ile Glu Phe Gly Tyr Ile Glu Ala Pro His Lys
        35                  40                  45

Gly Phe Pro Val Val Leu Asp Ser Pro Arg Asp Gly Asn Leu Lys Asp
    50                  55                  60
```

```
Phe Pro Val Lys Glu Leu Leu Gly Pro Asp Phe Gly Tyr Val Thr Arg
65                  70                  75                  80

Glu Pro Leu Phe Glu Ser Val Thr Ser Leu Asp Ser Phe Gly Asn Leu
                85                  90                  95

Glu Val Ser Pro Pro Val Thr Val Asn Gly Lys Thr Tyr Pro Leu Gly
            100                 105                 110

Arg Ile Leu Ile Gly Ser Ser Phe Pro Leu Ser Gly Gly Arg Arg Met
        115                 120                 125

Thr Lys Val Val Arg Asp Phe Leu Lys Ala Gln Gln Val Gln Ala Pro
    130                 135                 140

Val Glu Leu Tyr Ser Asp Trp Leu Thr Val Gly His Val Asp Glu Phe
145                 150                 155                 160

Met Ser Phe Val Pro Ile Pro Gly Thr Lys Lys Phe Leu Leu Leu Met
                165                 170                 175

Ala Ser Thr Ser Ala Cys Tyr Lys Leu Phe Arg Glu Lys Gln Lys Asp
            180                 185                 190

Gly His Gly Glu Ala Ile Met Phe Lys Gly Leu Gly Gly Met Ser Ser
        195                 200                 205

Lys Arg Ile Thr Ile Asn Lys Ile Leu Ser Asn Glu Ser Leu Val Gln
    210                 215                 220

Glu Asn Leu Tyr Phe Gln Arg Cys Leu Asp Trp Asn Arg Asp Ile Leu
225                 230                 235                 240

Lys Lys Glu Leu Gly Leu Thr Glu Gln Asp Ile Ile Asp Leu Pro Ala
                245                 250                 255

Leu Phe Lys Met Asp Glu Asp His Arg Ala Arg Ala Phe Phe Pro Asn
            260                 265                 270

Met Val Asn Met Ile Val Leu Asp Lys Asp Leu Gly Ile Pro Lys Pro
        275                 280                 285

Phe Gly Pro Gln Val Glu Glu Glu Cys Cys Leu Glu Met His Val Arg
    290                 295                 300

Gly Leu Leu Glu Pro Leu Gly Leu Glu Cys Thr Phe Ile Asp Asp Ile
305                 310                 315                 320

Ser Ala Tyr His Lys Phe Leu Gly Glu Val His Cys Gly Thr Asn Val
                325                 330                 335

Arg Arg Lys Pro Phe Thr Phe Lys Trp Trp His Met Val Pro
            340                 345                 350
```

<210> SEQ ID NO 5
<211> LENGTH: 3189
<212> TYPE: DNA
<213> ORGANISM: Homo sapiens
<220> FEATURE:
<223> OTHER INFORMATION: Homo sapiens peptidyl arginine deiminase 3 (PADI3), mRNA

<400> SEQUENCE: 5

```
agtgttgggg ttggcggcca cagctaagtc caacaccagc atgtcgctgc agagaatcgt      60

gcgtgtgtcc ctggagcatc ccaccagcgc ggtgtgtgtg gctggcgtgg agaccctcgt     120

ggacatttat gggtcagtgc ctgagggcac agaaatgttt gaggtctatg ggacgcctgg     180

cgtggacatc tacatctctc ccaacatgga gaggggccgg gagcgtgcag acaccaggcg     240

gtggcgcttt gacgcgactt tggagatcat cgtggtcatg aactccccca gcaatgacct     300

caacgacagc catgttcaga tttcctacca ctccagccat gagcctctgc ccctggccta     360

tgcggtgctc tacctcacct gtgttgacat ctctctggat tgcgacctga actgtgaggg     420
```

-continued

```
aaggcaggac aggaactttg tagacaagcg gcagtgggtc tgggggccca gtgggtatgg    480
cggcatcttg ctggtgaact gtgaccgtga tgatccgagc tgtgatgtcc aggacaattg    540
tgaccagcac gtgcactgcc tgcaagacct ggaagacatg tctgtcatgg tcctgcggac    600
gcagggccct gcagccctct ttgatgacca caaacttgtc ctccatacct ccagctatga    660
tgccaaacgg gcacaggtct tccacatctg cggtcctgag gatgtgtgtg aggcctatag    720
gcatgtgctg ggccaagata aggtgtccta tgaggtaccc cgcttgcatg gggatgagga    780
gcgcttcttc gtggaaggcc tgtccttccc tgatgccggc ttcacaggac tcatctcctt    840
ccatgtcact ctgctggacg actccaacga ggatttctcg gcatccccta tcttcactga    900
cactgtggtg ttccgagtgg caccctggat catgacgccc agcactctgc cacccctaga    960
ggtgtatgtg tgccgtgtga ggaacaacac gtgttttgtg gatgcggtgg cagagctggc   1020
caggaaggcc ggctgcaagc tgaccatctg cccacaggcc gagaaccgca acgaccgctg   1080
gatccaggat gagatggagc tgggctacgt tcaggcgccg cacaagaccc tcccggtggt   1140
ctttgactcc ccaaggaatg gggaactgca ggatttccct tacaaaagaa tcctgggtcc   1200
agattttggt tacgtgactc gggaaccacg cgacaggtct gtgagtggcc tggactcctt   1260
tgggaacctg gaggtcagcc ctccagtggt ggccaatggg aaagagtacc ccctggggag   1320
gatcctcatt gggggcaacc tgcctgggtc aagtggccgc agggtcaccc aggtggtgcg   1380
ggacttcctc catgcccaga aggtgcagcc ccccgtggag ctctttgtgg actggttggc   1440
cgtgggccat gtggatgagt ttctgagctt tgtccctgcc cccgatggga agggcttccg   1500
gatgctcctg gccagccctg gggcctgctt caagctcttc caggaaaagc agaagtgtgg   1560
ccacgggagg gccctcctgt tccagggggt tgttgatgat gagcaggtca agaccatctc   1620
catcaaccag gtgctctcca ataaagacct catcaactac aataagtttg tgcagagctg   1680
catcgactgg aaccgtgagg tgctgaagcg ggagctgggc ctggcagagt gtgacatcat   1740
tgacatccca cagctcttca agaccgagag gaaaaaagca acggccttct tccctgactt   1800
ggtgaacatg ctggtgctgg ggaagcacct gggcatcccc aagccctttg ggcccatcat   1860
caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc cctgagacag   2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
gttctcagac ttgaatcttc tcggcccccc aaaaagaagg acctcatttc ttatagcctc   2280
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaaaggg agctgtggat ccacttagat cagggcggaa ccatctttca   2580
cccggccaag ctcctgccca gatgttgacc ctcacccagc gtgagctgtc acatagtagg   2640
agcttctaga tgcatgtgga agcaatgaga gttgtccctt agccttataa actccccatg   2700
atctgacatg cagaaatcca gccttgtcca gaatcctcct ggaatttctt ggagacgaaa   2760
```

```
gtatctgggg gattgttggg tactagggag actgggtaca agggtgaaaa gtagttccca   2820

taatacacat ggttgactat ggtgatccac cttgtgatgg ttaatattag gtgtctggag   2880

aaggttgctt cattggccct gggacttctc tctgcaggag gagagaacgc tgcctctcct   2940

ctggattggt ctcaggctct ctgttggcct ttggtcagcg tttccacatc ctgctctgct   3000

gcaggagagg gggctaaggg gctggatcca ccaaggcagc tcacagcggg aaaactctgg   3060

gaatgaacca ctgaattcag gggatggggg tggggggcg gttctcgagg tgtgtgccag    3120

ctacacgtgt gttctgtatg ggtccagctg cgtttccatc actcgctaat aaatcaacag   3180

aaacacaaa                                                           3189


<210> SEQ ID NO 6
<211> LENGTH: 664
<212> TYPE: PRT
<213> ORGANISM: Homo sapiens
<220> FEATURE:
<223> OTHER INFORMATION: protein-arginine deiminase type-3 [Homo
      sapiens]

<400> SEQUENCE: 6

Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
```

-continued

```
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660
```

<210> SEQ ID NO 7
<211> LENGTH: 3189
<212> TYPE: DNA
<213> ORGANISM: Homo sapiens -continued
<220> FEATURE:
<223> OTHER INFORMATION: Homo sapiens peptidyl arginine deiminase 3
(PADI3)transcript, mRNA

<400> SEQUENCE: 7

```
agtgttgggg ttggcggcca cagctaagtc caacaccagc atgtcgctgc agagaatcgt     60
gcgtgtgtcc ctggagcatc ccaccagcgc ggtgtgtgtg gctggcgtgg agaccctcgt    120
ggacatttat gggtcagtgc ctgagggcac agaaatgttt gaggtctatg ggacgcctgg    180
cgtggacatc tacgtctctc ccaacatgga gaggggccgg gagcgtgcag acaccaggcg    240
gtggcgcttt gacgcgactt tggagatcat cgtggtcatg aactccccca gcaatgacct    300
caacgacagc catgttcaga tttcctacca ctccagccat gagcctctgc ccctggccta    360
tgcggtgctc tacctcacct gtgttgacat ctctctggat tgcgacctga actgtgaggg    420
aaggcaggac aggaactttg tagacaagcg gcagtgggtc tgggggccca gtgggtatgg    480
cggcatcttg ctggtgaact gtgaccgtga tgatccgagc tgtgatgtcc aggacaattg    540
tgaccagcac gtgcactgcc tgcaagacct ggaagacatg tctgtcatgg tcctgcggac    600
gcagggccct gcagccctct ttgatgacca caaacttgtc ctccatacct ccagctatga    660
tgccaaacgg gcacaggtct tccacatctg cggtcctgag gatgtgtgtg aggcctatag    720
gcatgtgctg ggccaagata aggtgtccta tgaggtaccc cgcttgcatg gggatgagga    780
gcgcttcttc gtggaaggcc tgtccttccc tgatgccggc ttcacaggac tcatctcctt    840
ccatgtcact ctgctggacg actccaacga ggatttctcg gcatccccta tcttcactga    900
cactgtggtg ttccgagtgg caccctggat catgacgccc agcactctgc cacccctaga    960
ggtgtatgtg tgccgtgtga ggaacaacac gtgttttgtg gatgcggtgg cagagctggc   1020
caggaaggcc ggctgcaagc tgaccatctg cccacaggcc gagaaccgca acgaccgctg   1080
gatccaggat gagatggagc tgggctacgt tcaggcgccg cacaagaccc tcccggtggt   1140
ctttgactcc ccaaggaatg gggaactgca ggatttccct tacaaaagaa tcctgggtcc   1200
agattttggt tacgtgactc gggaaccacg cgacaggtct gtgagtggcc tggactcctt   1260
tgggaacctg gaggtcagcc ctccagtggt ggccaatggg aaagagtacc ccctggggag   1320
gatcctcatt gggggcaacc tgcctgggtc aagtggccgc agggtcaccc aggtggtgcg   1380
ggacttcctc catgcccaga aggtgcagcc ccccgtggag ctctttgtgg actggttggc   1440
cgtgggccat gtggatgagt ttctgagctt tgtccctgcc cccgatggga agggcttccg   1500
gatgctcctg gccagccctg ggcctgcttt caagctcttc caggaaaagc agaagtgtgg   1560
ccacgggagg gccctcctgt tccagggggt tgttgatgat gagcaggtca agaccatctc   1620
catcaaccag gtgctctcca ataaagacct catcaactac aataagtttg tgcagagctg   1680
catcgactgg aaccgtgagg tgctgaagcg ggagctgggc ctggcagagt gtgacatcat   1740
tgacatccca cagctcttca agaccgagag gaaaaaagca acggccttct tccctgactt   1800
ggtgaacatg ctggtgctgg ggaagcacct gggcatcccc aagccctttg ggcccatcat   1860
caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc cctgagacag   2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
```

-continued

```
gttctcagac ttgaatcttc tcggcccccc aaaaagaagg acctcatttc ttatagcctc   2280

tcctgtgatt caacacaacc catggagatg tccccttctc actctgaaat catccatttg   2340

gggacaaatc cacattgggg tctagaaaca tccacgtatc tcatcagcca tcttgtcctg   2400

tgcatcctaa cagaggaagg atccatgatt ctgctttggt ccaattgctt cctctctgca   2460

gaggaacaac cctaaaacca gaccactcca cgcaggacag gcaggagaga ttcttcctaa   2520

agcctccccc ataaaaaggg agctgtggat ccacttagat cagggcggaa ccatctttca   2580

cccggccaag ctcctgccca gatgttgacc ctcacccagc gtgagctgtc acatagtagg   2640

agcttctaga tgcatgtgga agcaatgaga gttgtccctt agccttataa actccccatg   2700

atctgacatg cagaaatcca gccttgtcca gaatcctcct ggaatttctt ggagacgaaa   2760

gtatctgggg gattgttggg tactagggag actgggtaca agggtgaaaa gtagttccca   2820

taatacacat ggttgactat ggtgatccac cttgtgatgg ttaatattag gtgtctggag   2880

aaggttgctt cattggccct gggacttctc tctgcaggag gagagaacgc tgcctctcct   2940

ctggattggt ctcaggctct ctgttggcct ttggtcagcg tttccacatc ctgctctgct   3000

gcaggagagg gggctaaggg gctggatcca ccaaggcagc tcacagcggg aaaactctgg   3060

gaatgaacca ctgaattcag gggatggggg tggggggggcg gttctcgagg tgtgtgccag   3120

ctacacgtgt gttctgtatg ggtccagctg cgtttccatc actcgctaat aaatcaacag   3180

aaacacaaa                                                           3189
```

```
<210> SEQ ID NO 8
<211> LENGTH: 664
<212> TYPE: PRT
<213> ORGANISM: Homo sapiens
<220> FEATURE:
<223> OTHER INFORMATION: protein-arginine deiminase type-3 [Homo
      sapiens]

<400> SEQUENCE: 8

Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Val Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175
```

-continued

```
Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
```

-continued

```
        595                 600                 605

Gly Cys Cys Cys Leu Glu Glu Lys Val Arg Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660


<210> SEQ ID NO 9
<211> LENGTH: 3189
<212> TYPE: DNA
<213> ORGANISM: Homo sapiens
<220> FEATURE:
<223> OTHER INFORMATION: Homo sapiens peptidyl arginine deiminase 3
      (PADI3)transcript, mRNA

<400> SEQUENCE: 9

agtgttgggg ttggcggcca cagctaagtc caacaccagc atgtcgctgc agagaatcgt      60

gcgtgtgtcc ctggagcatc ccaccagcgc ggtgtgtgtg gctggcgtgg agaccctcgt     120

ggacatttat gggtcagtgc ctgagggcac agaaatgttt gaggtctatg ggacgcctgg     180

cgtggacatc tacatctctc ccaacatgga gaggggccgg gagcgtgcag acaccaggcg     240

gtggcgcttt gacgcgactt tggagatcat cgtggtcatg aactccccca gcaatgacct     300

caacgacagc catgttcaga tttcctacca ctccagccat gagcctctgc ccctggccta     360

tgcggtgctc taccacacct gtgttgacat ctctctggat tgcgacctga actgtgaggg     420

aaggcaggac aggaactttg tagacaagcg gcagtgggtc tgggggccca gtgggtatgg     480

cggcatcttg ctggtgaact gtgaccgtga tgatccgagc tgtgatgtcc aggacaattg     540

tgaccagcac gtgcactgcc tgcaagacct ggaagacatg tctgtcatgg tcctgcggac     600

gcagggccct gcagccctct ttgatgacca caaacttgtc ctccatacct ccagctatga     660

tgccaaacgg gcacaggtct tccacatctg cggtcctgag gatgtgtgtg aggcctatag     720

gcatgtgctg ggccaagata aggtgtccta tgaggtaccc cgcttgcatg gggatgagga     780

gcgcttcttc gtggaaggcc tgtccttccc tgatgccggc ttcacaggac tcatctcctt     840

ccatgtcact ctgctggacg actccaacga ggatttctcg gcatccccta tcttcactga     900

cactgtggtg ttccgagtgg caccctggat catgacgccc agcactctgc caccccctaga    960

ggtgtatgtg tgccgtgtga ggaacaacac gtgttttgtg gatgcggtgg cagagctggc    1020

caggaaggcc ggctgcaagc tgaccatctg cccacaggcc gagaaccgca acgaccgctg    1080

gatccaggat gagatggagc tgggctacgt tcaggcgccg cacaagaccc tcccggtggt    1140

ctttgactcc ccaaggaatg gggaactgca ggatttccct tacaaaagaa tcctgggtcc    1200

agattttggt tacgtgactc gggaaccacg cgacaggtct gtgagtggcc tggactcctt    1260

tgggaacctg gaggtcagcc ctccagtggt ggccaatggg aaagagtacc ccctggggag    1320

gatcctcatt gggggcaacc tgcctgggtc aagtggccgc agggtcaccc aggtggtgcg    1380

ggacttcctc catgcccaga aggtgcagcc ccccgtggag ctctttgtgg actggttggc    1440

cgtgggccat gtggatgagt ttctgagctt tgtccctgcc cccgatggga agggcttccg    1500

gatgctcctg gccagccctg ggcctgctt caagctcttc caggaaaagc agaagtgtgg     1560

ccacgggagg gccctcctgt tccagggggt tgttgatgat gagcaggtca agaccatctc    1620
```

-continued

```
catcaaccag gtgctctcca ataaagacct catcaactac aataagtttg tgcagagctg   1680
catcgactgg aaccgtgagg tgctgaagcg ggagctgggc ctggcagagt gtgacatcat   1740
tgacatccca cagctcttca agaccgagag gaaaaaagca acggccttct tccctgactt   1800
ggtgaacatg ctggtgctgg ggaagcacct gggcatcccc aagccctttg ggcccatcat   1860
caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc cctgagacag   2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
gttctcagac ttgaatcttc tcggcccccc aaaaagaagg acctcatttc ttatagcctc   2280
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaaaggg agctgtggat ccacttagat cagggcggaa ccatctttca   2580
cccggccaag ctcctgccca gatgttgacc ctcacccagc gtgagctgtc acatagtagg   2640
agcttctaga tgcatgtgga agcaatgaga gttgtccctt agccttataa actccccatg   2700
atctgacatg cagaaatcca gccttgtcca gaatcctcct ggaatttctt ggagacgaaa   2760
gtatctgggg gattgttggg tactagggag actgggtaca agggtgaaaa gtagttccca   2820
taatacacat ggttgactat ggtgatccac cttgtgatgg ttaatattag gtgtctggag   2880
aaggttgctt cattggccct gggacttctc tctgcaggag gagagaacgc tgcctctcct   2940
ctggattggt ctcaggctct ctgttggcct ttggtcagcg tttccacatc ctgctctgct   3000
gcaggagagg gggctaaggg gctggatcca ccaaggcagc tcacagcggg aaaactctgg   3060
gaatgaacca ctgaattcag gggatggggg tggggggcg gttctcgagg tgtgtgccag   3120
ctacacgtgt gttctgtatg ggtccagctg cgtttccatc actcgctaat aaatcaacag   3180
aaacacaaa                                                           3189
```

<210> SEQ ID NO 10
<211> LENGTH: 664
<212> TYPE: PRT
<213> ORGANISM: Homo sapiens
<220> FEATURE:
<223> OTHER INFORMATION: protein-arginine deiminase type-3 [Homo sapiens]

<400> SEQUENCE: 10

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80
```

-continued

```
Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr His
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495
```

```
Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660
```

```
<210> SEQ ID NO 11
<211> LENGTH: 3189
<212> TYPE: DNA
<213> ORGANISM: Homo sapiens
<220> FEATURE:
<223> OTHER INFORMATION: Homo sapiens peptidyl arginine deiminase 3
      (PADI3) transcript, mRNA

<400> SEQUENCE: 11

agtgttgggg ttggcggcca cagctaagtc caacaccagc atgtcgctgc agagaatcgt      60

gcgtgtgtcc ctggagcatc ccaccagcgc ggtgtgtgtg gctggcgtgg agaccctcgt     120

ggacatttat gggtcagtgc ctgagggcac agaaatgttt gaggtctatg ggacgcctgg     180

cgtggacatc tacatctctc ccaacatgga gaggggccgg gagcgtgcag acaccaggcg     240

gtggcgcttt gacgcgactt tggagatcat cgtggtcatg aactccccca gcaatgacct     300

caacgacagc catgttcaga tttcctacca ctccagccat gagcctctgc ccctggccta     360

tgcggtgctc tacctcacct gtgttgacat ctctctggat tgcgacctga actgtgaggg     420

aaggcaggac aggaactttg tagacaagcg gcagtgggtc tgggggccca gtgggtatgg     480

cggcatcttg ctggtgaact gtgaccgtga tgatccgagc tgtgatgtcc aggacaattg     540

tgaccagcac atgcactgcc tgcaagacct ggaagacatg tctgtcatgg tcctgcggac     600

gcagggccct gcagccctct ttgatgacca caaacttgtc ctccatacct ccagctatga     660

tgccaaacgg gcacaggtct tccacatctg cggtcctgag gatgtgtgtg aggcctatag     720

gcatgtgctg ggccaagata aggtgtccta tgaggtaccc cgcttgcatg gggatgagga     780

gcgcttcttc gtggaaggcc tgtccttccc tgatgccggc ttcacaggac tcatctcctt     840

ccatgtcact ctgctggacg actccaacga ggatttctcg gcatccccta tcttcactga     900

cactgtggtg ttccgagtgg caccctggat catgacgccc agcactctgc cacccctaga     960

ggtgtatgtg tgccgtgtga ggaacaacac gtgttttgtg gatgcggtgg cagagctggc    1020

caggaaggcc ggctgcaagc tgaccatctg cccacaggcc gagaaccgca acgaccgctg    1080
```

-continued

```
gatccaggat gagatggagc tgggctacgt tcaggcgccg cacaagaccc tcccggtggt   1140
ctttgactcc ccaaggaatg gggaactgca ggatttccct tacaaaagaa tcctgggtcc   1200
agattttggt tacgtgactc gggaaccacg cgacaggtct gtgagtggcc tggactcctt   1260
tgggaacctg gaggtcagcc ctccagtggt ggccaatggg aaagagtacc ccctggggag   1320
gatcctcatt gggggcaacc tgcctgggtc aagtggccgc agggtcaccc aggtggtgcg   1380
ggacttcctc catgcccaga aggtgcagcc ccccgtggag ctctttgtgg actggttggc   1440
cgtgggccat gtggatgagt ttctgagctt tgtccctgcc cccgatggga agggcttccg   1500
gatgctcctg gccagccctg ggcctgcttc caagctcttc caggaaaagc agaagtgtgg   1560
ccacgggagg gccctcctgt tccagggggt tgttgatgat gagcaggtca agaccatctc   1620
catcaaccag gtgctctcca ataaagacct catcaactac aataagtttg tgcagagctg   1680
catcgactgg aaccgtgagg tgctgaagcg ggagctgggc ctggcagagt gtgacatcat   1740
tgacatccca cagctcttca agaccgagag gaaaaaagca acggccttct tccctgactt   1800
ggtgaacatg ctggtgctgg ggaagcacct gggcatcccc aagccctttg ggcccatcat   1860
caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc cctgagacag   2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
gttctcagac ttgaatcttc tcggcccccc aaaaagaagg acctcatttc ttatagcctc   2280
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaaaggg agctgtggat ccacttagat cagggcggaa ccatctttca   2580
cccggccaag ctcctgccca gatgttgacc ctcacccagc gtgagctgtc acatagtagg   2640
agcttctaga tgcatgtgga agcaatgaga gttgtccctt agccttataa actccccatg   2700
atctgacatg cagaaatcca gccttgtcca gaatcctcct ggaatttctt ggagacgaaa   2760
gtatctgggg gattgttggg tactagggag actgggtaca agggtgaaaa gtagttccca   2820
taatacacat ggttgactat ggtgatccac cttgtgatgg ttaatattag gtgtctggag   2880
aaggttgctt cattggccct gggacttctc tctgcaggag gagagaacgc tgcctctcct   2940
ctggattggt ctcaggctct ctgttggcct ttggtcagcg tttccacatc ctgctctgct   3000
gcaggagagg gggctaaggg gctggatcca ccaaggcagc tcacagcggg aaaactctgg   3060
gaatgaacca ctgaattcag gggatggggg tgggggggcg gttctcgagg tgtgtgccag   3120
ctacacgtgt gttctgtatg ggtccagctg cgtttccatc actcgctaat aaatcaacag   3180
aaacacaaa                                                          3189
```

<210> SEQ ID NO 12
<211> LENGTH: 664
<212> TYPE: PRT
<213> ORGANISM: Homo sapiens
<220> FEATURE:

<223> OTHER INFORMATION: protein-arginine deiminase type-3 [Homo sapiens]

<400> SEQUENCE: 12

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Met His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400
```

-continued

```
Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660
```

```
<210> SEQ ID NO 13
<211> LENGTH: 3189
<212> TYPE: DNA
<213> ORGANISM: Homo sapiens
<220> FEATURE:
<223> OTHER INFORMATION: Homo sapiens peptidyl arginine deiminase 3
      (PADI3)transcript, mRNA

<400> SEQUENCE: 13

agtgttgggg ttggcggcca cagctaagtc caacaccagc atgtcgctgc agagaatcgt      60

gcgtgtgtcc ctggagcatc ccaccagcgc ggtgtgtgtg gctggcgtgg agaccctcgt     120

ggacatttat gggtcagtgc ctgagggcac agaaatgttt gaggtctatg ggacgcctgg     180

cgtggacatc tacatctctc ccaacatgga gaggggccgg gagcgtgcag acaccaggcg     240

gtggcgcttt gacgcgactt tggagatcat cgtggtcatg aactccccca gcaatgacct     300

caacgacagc catgttcaga tttcctacca ctccagccat gagcctctgc cctggccta     360

tgcggtgctc tacctcacct gtgttgacat ctctctggat tgcgacctga actgtgaggg     420

aaggcaggac aggaactttg tagacaagcg gcagtgggtc tgggggccca gtgggtatgg     480
```

-continued

```
cggcatcttg ctggtgaact gtgaccgtga tgatccgagc tgtgatgtcc aggacaattg    540
tgaccagcac gtgcactgcc tgcaagacct ggaagacatg tctgtcatgg tcctgcggac    600
gcagggccct gcagccctct ttgatgacca caaacttgtc ctccatacct ccagctatga    660
tgccaaacgg gcacaggtct tccacatctg cggtcctgag gatgtgtgtg aggcctatag    720
gcatgtgctg ggccaagata aggtgtccta tgaggtaccc cgcttgcatg gggatgagga    780
gcgcttcttc gtggaaggcc tgtccttccc tgatgccggc ttcacaggac tcatctcctt    840
ccatgtcact ctgctggacg actccaacga ggatttctcg gcatccccta tcttcactga    900
cactgtggtg ttccgagtgg taccctggat catgacgccc agcactctgc cacccctaga    960
ggtgtatgtg tgccgtgtga ggaacaacac gtgttttgtg gatgcggtgg cagagctggc   1020
caggaaggcc ggctgcaagc tgaccatctg cccacaggcc gagaaccgca acgaccgctg   1080
gatccaggat gagatggagc tgggctacgt tcaggcgccg cacaagaccc tcccggtggt   1140
ctttgactcc ccaaggaatg gggaactgca ggatttccct tacaaaagaa tcctgggtcc   1200
agattttggt tacgtgactc gggaaccacg cgacaggtct gtgagtggcc tggactcctt   1260
tgggaacctg gaggtcagcc ctccagtggt ggccaatggg aaagagtacc ccctggggag   1320
gatcctcatt gggggcaacc tgcctgggtc aagtggccgc agggtcaccc aggtggtgcg   1380
ggacttcctc catgcccaga aggtgcagcc ccccgtggag ctctttgtgg actggttggc   1440
cgtgggccat gtggatgagt ttctgagctt tgtccctgcc cccgatggga agggcttccg   1500
gatgctcctg gccagccctg ggcctgcttt caagctcttc caggaaaagc agaagtgtgg   1560
ccacgggagg gccctcctgt tccagggggt tgttgatgat gagcaggtca agaccatctc   1620
catcaaccag gtgctctcca ataaagacct catcaactac aataagtttg tgcagagctg   1680
catcgactgg aaccgtgagg tgctgaagcg ggagctgggc ctggcagagt gtgacatcat   1740
tgacatccca cagctcttca agaccgagag gaaaaaagca acggccttct tccctgactt   1800
ggtgaacatg ctggtgctgg ggaagcacct gggcatcccc aagccctttg ggcccatcat   1860
caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc cctgagacag   2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
gttctcagac ttgaatcttc tcggcccccc aaaaagaagg acctcatttc ttatagcctc   2280
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaaaggg agctgtggat ccacttagat cagggcggaa ccatctttca   2580
cccggccaag ctcctgccca gatgttgacc ctcacccagc gtgagctgtc acatagtagg   2640
agcttctaga tgcatgtgga agcaatgaga gttgtccctt agccttataa actccccatg   2700
atctgacatg cagaaatcca gccttgtcca gaatcctcct ggaatttctt ggagacgaaa   2760
gtatctgggg gattgttggg tactagggag actgggtaca agggtgaaaa gtagttccca   2820
taatacacat ggttgactat ggtgatccac cttgtgatgg ttaatattag gtgtctggag   2880
```

-continued aaggttgctt cattggccct gggacttctc tctgcaggag gagagaacgc tgcctctcct 2940
ctggattggt ctcaggctct ctgttggcct ttggtcagcg tttccacatc ctgctctgct 3000
gcaggagagg gggctaaggg gctggatcca ccaaggcagc tcacagcggg aaaactctgg 3060
gaatgaacca ctgaattcag gggatggggg tggggggcg gttctcgagg tgtgtgccag 3120
ctacacgtgt gttctgtatg ggtccagctg cgtttccatc actcgctaat aaatcaacag 3180
aaacacaaa 3189

<210> SEQ ID NO 14
<211> LENGTH: 664
<212> TYPE: PRT
<213> ORGANISM: Homo sapiens
<220> FEATURE:
<223> OTHER INFORMATION: protein-arginine deiminase type-3 [Homo sapiens]

<400> SEQUENCE: 14

Met Ser Leu Gln Arg Ile Val Arg Val Ser Leu Glu His Pro Thr Ser
1 5 10 15

Ala Val Cys Val Ala Gly Val Glu Thr Leu Val Asp Ile Tyr Gly Ser
20 25 30

Val Pro Glu Gly Thr Glu Met Phe Glu Val Tyr Gly Thr Pro Gly Val
35 40 45

Asp Ile Tyr Ile Ser Pro Asn Met Glu Arg Gly Arg Glu Arg Ala Asp
50 55 60

Thr Arg Arg Trp Arg Phe Asp Ala Thr Leu Glu Ile Ile Val Val Met
65 70 75 80

Asn Ser Pro Ser Asn Asp Leu Asn Asp Ser His Val Gln Ile Ser Tyr
85 90 95

His Ser Ser His Glu Pro Leu Pro Leu Ala Tyr Ala Val Leu Tyr Leu
100 105 110

Thr Cys Val Asp Ile Ser Leu Asp Cys Asp Leu Asn Cys Glu Gly Arg
115 120 125

Gln Asp Arg Asn Phe Val Asp Lys Arg Gln Trp Val Trp Gly Pro Ser
130 135 140

Gly Tyr Gly Gly Ile Leu Leu Val Asn Cys Asp Arg Asp Asp Pro Ser
145 150 155 160

Cys Asp Val Gln Asp Asn Cys Asp Gln His Val His Cys Leu Gln Asp
165 170 175

Leu Glu Asp Met Ser Val Met Val Leu Arg Thr Gln Gly Pro Ala Ala
180 185 190

Leu Phe Asp Asp His Lys Leu Val Leu His Thr Ser Ser Tyr Asp Ala
195 200 205

Lys Arg Ala Gln Val Phe His Ile Cys Gly Pro Glu Asp Val Cys Glu
210 215 220

Ala Tyr Arg His Val Leu Gly Gln Asp Lys Val Ser Tyr Glu Val Pro
225 230 235 240

Arg Leu His Gly Asp Glu Glu Arg Phe Phe Val Glu Gly Leu Ser Phe
245 250 255

Pro Asp Ala Gly Phe Thr Gly Leu Ile Ser Phe His Val Thr Leu Leu
260 265 270

Asp Asp Ser Asn Glu Asp Phe Ser Ala Ser Pro Ile Phe Thr Asp Thr
275 280 285

Val Val Phe Arg Val Val Pro Trp Ile Met Thr Pro Ser Thr Leu Pro 290 295 300

Pro Leu Glu Val Tyr Val Cys Arg Val Arg Asn Asn Thr Cys Phe Val
305 310 315 320

Asp Ala Val Ala Glu Leu Ala Arg Lys Ala Gly Cys Lys Leu Thr Ile
325 330 335

Cys Pro Gln Ala Glu Asn Arg Asn Asp Arg Trp Ile Gln Asp Glu Met
340 345 350

Glu Leu Gly Tyr Val Gln Ala Pro His Lys Thr Leu Pro Val Val Phe
355 360 365

Asp Ser Pro Arg Asn Gly Glu Leu Gln Asp Phe Pro Tyr Lys Arg Ile
370 375 380

Leu Gly Pro Asp Phe Gly Tyr Val Thr Arg Glu Pro Arg Asp Arg Ser
385 390 395 400

Val Ser Gly Leu Asp Ser Phe Gly Asn Leu Glu Val Ser Pro Pro Val
405 410 415

Val Ala Asn Gly Lys Glu Tyr Pro Leu Gly Arg Ile Leu Ile Gly Gly
420 425 430

Asn Leu Pro Gly Ser Ser Gly Arg Arg Val Thr Gln Val Val Arg Asp
435 440 445

Phe Leu His Ala Gln Lys Val Gln Pro Pro Val Glu Leu Phe Val Asp
450 455 460

Trp Leu Ala Val Gly His Val Asp Glu Phe Leu Ser Phe Val Pro Ala
465 470 475 480

Pro Asp Gly Lys Gly Phe Arg Met Leu Leu Ala Ser Pro Gly Ala Cys
485 490 495

Phe Lys Leu Phe Gln Glu Lys Gln Lys Cys Gly His Gly Arg Ala Leu
500 505 510

Leu Phe Gln Gly Val Val Asp Asp Glu Gln Val Lys Thr Ile Ser Ile
515 520 525

Asn Gln Val Leu Ser Asn Lys Asp Leu Ile Asn Tyr Asn Lys Phe Val
530 535 540

Gln Ser Cys Ile Asp Trp Asn Arg Glu Val Leu Lys Arg Glu Leu Gly
545 550 555 560

Leu Ala Glu Cys Asp Ile Ile Asp Ile Pro Gln Leu Phe Lys Thr Glu
565 570 575

Arg Lys Lys Ala Thr Ala Phe Phe Pro Asp Leu Val Asn Met Leu Val
580 585 590

Leu Gly Lys His Leu Gly Ile Pro Lys Pro Phe Gly Pro Ile Ile Asn
595 600 605

Gly Cys Cys Cys Leu Glu Glu Lys Val Arg Ser Leu Leu Glu Pro Leu
610 615 620

Gly Leu His Cys Thr Phe Ile Asp Asp Phe Thr Pro Tyr His Met Leu
625 630 635 640

His Gly Glu Val His Cys Gly Thr Asn Val Cys Arg Lys Pro Phe Ser
645 650 655

Phe Lys Trp Trp Asn Met Val Pro
660

<210> SEQ ID NO 15
<211> LENGTH: 3189
<212> TYPE: DNA
<213> ORGANISM: Homo sapiens
<220> FEATURE:
<223> OTHER INFORMATION: Homo sapiens peptidyl arginine deiminase 3
(PADI3) transcript, mRNA

<400> SEQUENCE: 15
agtgttgggg ttggcggcca cagctaagtc caacaccagc atgtcgctgc agagaatcgt 60
gcgtgtgtcc ctggagcatc ccaccagcgc ggtgtgtgtg gctggcgtgg agaccctcgt 120
ggacatttat gggtcagtgc ctgagggcac agaaatgttt gaggtctatg ggacgcctgg 180
cgtggacatc tacatctctc ccaacatgga gaggggccgg gagcgtgcag acaccaggcg 240
gtggcgcttt gacgcgactt tggagatcat cgtggtcatg aactccccca gcaatgacct 300
caacgacagc catgttcaga tttcctacca ctccagccat gagcctctgc ccctggccta 360
tgcggtgctc tacctcacct gtgttgacat ctctctggat tgcgacctga actgtgaggg 420
aaggcaggac aggaactttg tagacaagcg gcagtgggtc tgggggccca gtgggtatgg 480
cggcatcttg ctggtgaact gtgaccgtga tgatccgagc tgtgatgtcc aggacaattg 540
tgaccagcac gtgcactgcc tgcaagacct ggaagacatg tctgtcatgg tcctgcggac 600
gcagggccct gcagccctct ttgatgacca caaacttgtc ctccatacct ccagctatga 660
tgccaaacgg gcacaggtct tccacatctg cggtcctgag gatgtgtgtg aggcctatag 720
gcatgtgctg ggccaagata aggtgtccta tgaggtaccc cgcttgcatg gggatgagga 780
gcgcttcttc gtggaaggcc tgtccttccc tgatgccggc ttcacaggac tcatctcctt 840
ccatgtcact ctgctggacg actccaacga ggatttctcg gcatccccta tcttcactga 900
cactgtggtg ttccgagtgg caccctggat catgacgccc agcactctgc caccccctaga 960
ggtgtatgtg tgccgtgtga ggaacaacac gtgttttgtg gatgcggtgg cagagctggc 1020
caggaaggcc ggctgcaagc tgaccatctg cccacaggcc gagaaccgca acgaccgctg 1080
gatccaggat gagatggagc tgggctacgt tcaggcgccg cacaagaccc tcccggtggt 1140
ctttgactcc ccaaggaatg gggaactgca ggatttccct tacaaaagaa tcctgggtcc 1200
agattttggt tacgtgactc gggaaccacg cgacaggtct gtgagtggcc tggactcctt 1260
tgggaacctg gaggtcagcc ctccagtggt ggccaatggg aaagagtacc ccctggggag 1320
gatcctcatt gggggcaacc tgcctgggtc aagtggccgc agggtcaccc aggtggtgcg 1380
ggacttcctc catgcccaga aggtgcagcc ccccgtggag ctctttgtgg actggttggc 1440
cgtgggccat gtggatgagt ttctgagctt tgtccctgcc cccgatggga agggcttccg 1500
gatgctcctg gccagccctg ggcctgctt caagctcttc caggaaaagc agaagtgtgg 1560
ccacgggagg gccctcctgt tccagggggt tgttgatgat gagcaggtca agaccatctc 1620
catcaaccag gtgctctcca ataaagacct catcaactac aataagtttg tgcagagctg 1680
catcgactgg aaccgtgagg tgctgaagcg ggagctgggc ctggcagagt gtgacatcat 1740
tgacatccca cagctcttca agaccgagag gaaaaaaaca acggccttct tccctgactt 1800
ggtgaacatg ctggtgctgg ggaagcacct gggcatcccc aagccctttg ggcccatcat 1860
caatggctgc tgctgcctgg aggagaaggt gcggtccctg ctggagccgc tgggcctcca 1920
ctgcaccttc attgatgact tcactccata ccacatgctg catggggagg tgcactgtgg 1980
caccaatgtg tgcagaaagc ccttctcttt caagtggtgg aacatggtgc cctgagacag 2040
ctcccaccca ccatcctgtc cccctggggc gggcattggc ccaggtggtg gagacagaga 2100
caggcccctg aacgataagc accaagagac cccaaggctc cagatggaac actgagggtg 2160
accgtccctc tcagaagcct tttccctgga agtgtccatg cctcacctgc aacccatgtg 2220
gttctcagac ttgaatcttc tcggcccccc aaaaagaagg acctcatttc ttatagcctc 2280

-continued

```
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaaaggg agctgtggat ccacttagat cagggcggaa ccatctttca   2580
cccggccaag ctcctgccca gatgttgacc ctcacccagc gtgagctgtc acatagtagg   2640
agcttctaga tgcatgtgga agcaatgaga gttgtccctt agccttataa actccccatg   2700
atctgacatg cagaaatcca gccttgtcca gaatcctcct ggaatttctt ggagacgaaa   2760
gtatctgggg gattgttggg tactagggag actgggtaca agggtgaaaa gtagttccca   2820
taatacacat ggttgactat ggtgatccac cttgtgatgg ttaatattag gtgtctggag   2880
aaggttgctt cattggccct gggacttctc tctgcaggag gagagaacgc tgcctctcct   2940
ctggattggt ctcaggctct ctgttggcct ttggtcagcg tttccacatc ctgctctgct   3000
gcaggagagg gggctaaggg gctggatcca ccaaggcagc tcacagcggg aaaactctgg   3060
gaatgaacca ctgaattcag gggatggggg tggggggcg gttctcgagg tgtgtgccag   3120
ctacacgtgt gttctgtatg ggtccagctg cgtttccatc actcgctaat aaatcaacag   3180
aaacacaaa                                                           3189
```

<210> SEQ ID NO 16
<211> LENGTH: 664
<212> TYPE: PRT
<213> ORGANISM: Homo sapiens
<220> FEATURE:
<223> OTHER INFORMATION: protein-arginine deiminase type-3 [Homo sapiens]

<400> SEQUENCE: 16

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190
```

```
Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Thr Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
```

610 615 620

Gly Leu His Cys Thr Phe Ile Asp Asp Phe Thr Pro Tyr His Met Leu
625 630 635 640

His Gly Glu Val His Cys Gly Thr Asn Val Cys Arg Lys Pro Phe Ser
645 650 655

Phe Lys Trp Trp Asn Met Val Pro
660

<210> SEQ ID NO 17
<211> LENGTH: 3189
<212> TYPE: DNA
<213> ORGANISM: Homo sapiens
<220> FEATURE:
<223> OTHER INFORMATION: Homo sapiens peptidyl arginine deiminase 3
(PADI3)transcript, mRNA

<400> SEQUENCE: 17
agtgttgggg ttggcggcca cagctaagtc caacaccagc atgtcgctgc agagaatcgt 60
gcgtgtgtcc ctggagcatc ccaccagcgc ggtgtgtgtg gctggcgtgg agaccctcgt 120
ggacatttat gggtcagtgc ctgagggcac agaaatgttt gaggtctatg ggacgcctgg 180
cgtggacatc tacatctctc ccaacatgga gaggggccgg gagcgtgcag acaccaggcg 240
gtggcgcttt gacgcgactt tggagatcat cgtggtcatg aactccccca gcaatgacct 300
caacgacagc catgttcaga tttcctacca ctccagccat gagcctctgc cctggccta 360 tgcggtgctc tacctcacct gtgttgacat ctctctggat tgcgacctga actgtgaggg 420
aaggcaggac aggaactttg tagacaagcg gcagtgggtc tgggggccca gtgggtatgg 480
cggcatcttg ctggtgaact gtgaccgtga tgatccgagc tgtgatgtcc aggacaattg 540
tgaccagcac gtgcactgcc tgcaagacct ggaagacatg tctgtcatgg tcctgcggac 600
gcagggccct gcagccctct ttgatgacca caaacttgtc ctccatacct ccagctatga 660
tgccaaacgg gcacaggtct tccacatctg cggtcctgag gatgtgtgtg aggcctatag 720
gcatgtgctg ggccaagata aggtgtccta tgaggtaccc cgcttgcatg gggatgagga 780
gcgcttcttc gtggaaggcc tgtccttccc tgatgccggc ttcacaggac tcatctcctt 840
ccatgtcact ctgctggacg actccaacga ggatttctcg gcatccccta tcttcactga 900
cactgtggtg ttccgagtgg caccctggat catgacgccc agcactctgc caccccctaga 960 ggtgtatgtg tgccgtgtga ggaacaacac gtgttttgtg gatgcggtgg cagagctggc 1020
caggaaggcc ggctgcaagc tgaccatctg cccacaggcc gagaaccgca acgaccgctg 1080
gatccaggat gagatggagc tgggctacgt tcaggcgccg cacaagaccc tcccggtggt 1140
ctttgactcc ccaaggaatg gggaactgca ggatttccct tacaaaagaa tcctgggtcc 1200
agattttggt tacgtgactc gggaaccacg cgacaggtct gtgagtggcc tggactcctt 1260
tgggaacctg gaggtcagcc ctccagtggt ggccaatggg aaagagtacc ccctggggag 1320
gatcctcatt gggggcaacc tgcctgggtc aagtggccgc agggtcaccc aggtggtgcg 1380
ggacttcctc catgcccaga aggtgcagcc ccccgtggag ctctttgtgg actggttggc 1440
cgtgggccat gtggatgagt ttctgagctt tgtccctgcc cccgatggga agggcttccg 1500
gatgctcctg gccagccctg ggcctgcttt caagctcttc caggaaaagc agaagtgtgg 1560
ccacgggagg gccctcctgt tccagggggt tgttgatgat gagcaggtca agaccatctc 1620
catcaaccag gtgctctcca ataaagacct catcaactac aataagtttg tgcagagctg 1680
catcgactgg aaccgtgagg tgctgaagcg ggagctgggc ctggcagagt gtgacatcat 1740

```
tgacatccca cagctcttca agaccgagag gaaaaaagca acggccttct tccctgactt   1800

ggtgaacatg ctggtgctgg ggaagcacct gggcataccc aagccctttg ggcccatcat   1860

caatggctgc tgctgcctgg aggagaaggt gcggtccctg ctggagccgc tgggcctcca   1920

ctgcaccttc attgatgact tcactccata ccacatgctg catggggagg tgcactgtgg   1980

caccaatgtg tgcagaaagc ccttctcttt caagtggtgg aacatggtgc cctgagacag   2040

ctcccaccca ccatcctgtc cccctggggc gggcattggc ccaggtggtg gagacagaga   2100

caggcccctg aacgataagc accaagagac cccaaggctc cagatggaac actgagggtg   2160

accgtccctc tcagaagcct tttccctgga agtgtccatg cctcacctgc aacccatgtg   2220

gttctcagac ttgaatcttc tcggcccccc aaaaagaagg acctcatttc ttatagcctc   2280

tcctgtgatt caacacaacc catggagatg tccccttctc actctgaaat catccatttg   2340

gggacaaatc cacattgggg tctagaaaca tccacgtatc tcatcagcca tcttgtcctg   2400

tgcatcctaa cagaggaagg atccatgatt ctgctttggt ccaattgctt cctctctgca   2460

gaggaacaac cctaaaacca gaccactcca cgcaggacag gcaggagaga ttcttcctaa   2520

agcctccccc ataaaaaggg agctgtggat ccacttagat cagggcggaa ccatctttca   2580

cccggccaag ctcctgccca gatgttgacc ctcacccagc gtgagctgtc acatagtagg   2640

agcttctaga tgcatgtgga agcaatgaga gttgtccctt agccttataa actccccatg   2700

atctgacatg cagaaatcca gccttgtcca gaatcctcct ggaatttctt ggagacgaaa   2760

gtatctgggg gattgttggg tactagggag actgggtaca agggtgaaaa gtagttccca   2820

taatacacat ggttgactat ggtgatccac cttgtgatgg ttaatattag gtgtctggag   2880

aaggttgctt cattggccct gggacttctc tctgcaggag gagagaacgc tgcctctcct   2940

ctggattggt ctcaggctct ctgttggcct ttggtcagcg tttccacatc ctgctctgct   3000

gcaggagagg gggctaaggg gctggatcca ccaaggcagc tcacagcggg aaaactctgg   3060

gaatgaacca ctgaattcag gggatggggg tggggggcg gttctcgagg tgtgtgccag   3120

ctacacgtgt gttctgtatg ggtccagctg cgtttccatc actcgctaat aaatcaacag   3180

aaacacaaa                                                           3189
```

<210> SEQ ID NO 18
<211> LENGTH: 664
<212> TYPE: PRT
<213> ORGANISM: Homo sapiens
<220> FEATURE:
<223> OTHER INFORMATION: protein-arginine deiminase type-3 [Homo sapiens]

<400> SEQUENCE: 18

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95
```

-continued

```
His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510
```

-continued

```
Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Thr Ile Ile Asn
        595                 600                 605

Gly Cys Cys Cys Leu Glu Glu Lys Val Arg Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660


<210> SEQ ID NO 19
<211> LENGTH: 3189
<212> TYPE: DNA
<213> ORGANISM: Homo sapiens
<220> FEATURE:
<223> OTHER INFORMATION: Homo sapiens peptidyl arginine deiminase 3
      (PADI3)transcript, mRNA

<400> SEQUENCE: 19

agtgttgggg ttggcggcca cagctaagtc caacaccagc atgtcgctgc agagaatcgt      60

gcgtgtgtcc ctggagcatc ccaccagcgc ggtgtgtgtg gctggcgtgg agaccctcgt     120

ggacatttat gggtcagtgc ctgagggcac agaaatgttt gaggtctatg ggacgcctgg     180

cgtggacatc tacatctctc ccaacatgga gaggggccgg gagcgtgcag acaccaggcg     240

gtggcgcttt gacgcgactt tggagatcat cgtggtcatg aactccccca gcaatgacct     300

caacgacagc catgttcaga tttcctacca ctccagccat gagcctctgc ccctggccta     360

tgcggtgctc tacctcacct gtgttgacat ctctctggat tgcgacctga actgtgaggg     420

aaggcaggac aggaactttg tagacaagcg gcagtgggtc tgggggccca gtgggtatgg     480

cggcatcttg ctggtgaact gtgaccgtga tgatccgagc tgtgatgtcc aggacaattg     540

tgaccagcac gtgcactgcc tgcaagacct ggaagacatg tctgtcatgg tcctgcggac     600

gcagggccct gcagccctct ttgatgacca caaacttgtc ctccatacct ccagctatga     660

tgccaaacgg gcacaggtct tccacatctg cggtcctgag gatgtgtgtg aggcctatag     720

gcatgtgctg ggccaagata aggtgtccta tgaggtaccc cgcttgcatg gggatgagga     780

gcgcttcttc gtggaaggcc tgtccttccc tgatgccggc ttcacaggac tcatctcctt     840

ccatgtcact ctgctggacg actccaacga ggatttctcg gcatccccta tcttcactga     900

cactgtggtg ttccgagtgg caccctggat catgacgccc agcactctgc caccccctaga     960

ggtgtatgtg tgccgtgtga ggaacaacac gtgttttgtg gatgcggtgg cagagctggc    1020

caggaaggcc ggctgcaagc tgaccatctg cccacaggcc gagaaccgca acgaccgctg    1080

gatccaggat gagatggagc tgggctacgt tcaggcgccg cacaagaccc tcccggtggt    1140
```

-continued

```
ctttgactcc ccaaggaatg gggaactgca ggatttccct tacaaaagaa tcctgggtcc   1200

agattttggt tacgtgactc gggaaccacg cgacaggtct gtgagtggcc tggactcctt   1260

tgggaacctg gaggtcagcc ctccagtggt ggccaatggg aaagagtacc ccctggggag   1320

gatcctcatt gggggcaacc tgcctgggtc aagtggccgc agggtcaccc aggtggtgcg   1380

ggacttcctc catgcccaga aggtgcagcc ccccgtggag ctctttgtgg actggttggc   1440

cgtgggccat gtggatgagt ttctgagctt tgtccctgcc cccgatggga agggcttccg   1500

gatgctcctg gccagccctg gggcctgctt caagctcttc caggaaaagc agaagtgtgg   1560

ccacgggagg gccctcctgt tccagggggt tgttgatgat gagcaggtca agaccatctc   1620

catcaaccag gtgctctcca ataaagacct catcaactac aataagtttg tgcagagctg   1680

catcgactgg aaccgtgagg tgctgaagcg ggagctgggc ctggcagagt gtgacatcat   1740

tgacatccca cagctcttca agaccgagag gaaaaaagca acggccttct tccctgactt   1800

ggtgaacatg ctggtgctgg ggaagcacct gggcatcccc aagccctttg ggcccatcat   1860

caatggctgc tgctgcctgg aggagaaggt gcagtccctg ctggagccgc tgggcctcca   1920

ctgcaccttc attgatgact tcactccata ccacatgctg catggggagg tgcactgtgg   1980

caccaatgtg tgcagaaagc ccttctcttt caagtggtgg aacatggtgc cctgagacag   2040

ctcccaccca ccatcctgtc cccctggggc gggcattggc ccaggtggtg gagacagaga   2100

caggcccctg aacgataagc accaagagac cccaaggctc cagatggaac actgagggtg   2160

accgtccctc tcagaagcct ttccctgga agtgtccatg cctcacctgc aacccatgtg   2220

gttctcagac ttgaatcttc tcggcccccc aaaaagaagg acctcatttc ttatagcctc   2280

tcctgtgatt caacacaacc catggagatg tccccttctc actctgaaat catccatttg   2340

gggacaaatc cacattgggg tctagaaaca tccacgtatc tcatcagcca tcttgtcctg   2400

tgcatcctaa cagaggaagg atccatgatt ctgctttggt ccaattgctt cctctctgca   2460

gaggaacaac cctaaaacca gaccactcca cgcaggacag gcaggagaga ttcttcctaa   2520

agcctccccc ataaaaaggg agctgtggat ccacttagat cagggcggaa ccatctttca   2580

cccggccaag ctcctgccca gatgttgacc ctcacccagc gtgagctgtc acatagtagg   2640

agcttctaga tgcatgtgga agcaatgaga gttgtccctt agccttataa actccccatg   2700

atctgacatg cagaaatcca gccttgtcca gaatcctcct ggaatttctt ggagacgaaa   2760

gtatctgggg gattgttggg tactagggag actgggtaca agggtgaaaa gtagttccca   2820

taatacacat ggttgactat ggtgatccac cttgtgatgg ttaatattag gtgtctggag   2880

aaggttgctt cattggccct gggacttctc tctgcaggag gagagaacgc tgcctctcct   2940

ctggattggt ctcaggctct ctgttggcct ttggtcagcg tttccacatc ctgctctgct   3000

gcaggagagg gggctaaggg gctggatcca ccaaggcagc tcacagcggg aaaactctgg   3060

gaatgaacca ctgaattcag gggatggggg tgggggggcg gttctcgagg tgtgtgccag   3120

ctacacgtgt gttctgtatg ggtccagctg cgtttccatc actcgctaat aaatcaacag   3180

aaacacaaa                                                             3189
```

<210> SEQ ID NO 20
<211> LENGTH: 664
<212> TYPE: PRT
<213> ORGANISM: Homo sapiens
<220> FEATURE:
<223> OTHER INFORMATION: protein-arginine deiminase type-3 [Homo sapiens]

<400> SEQUENCE: 20

Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

```
Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
        435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
    530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Gln Ser Leu Leu Glu Pro Leu
    610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660
```

<210> SEQ ID NO 21
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X1, mRNA

<400> SEQUENCE: 21

```
tctccctggt tctgccattt cccctgtggg gggctgccca gggccaaaca ggccagaggg      60

ctccaccagc cctggaaatt acaggctttg ggagtagggt tgccagataa aataaaagat     120

gcctagttaa aattgaattt caggtaaata attaataatt tttttagtat aagtgtatcc     180

caaatacttc acgggagtac caaacaatga ttgactgttc acttgaaatt caagtccaac     240

tgagctttct gtatttttat ttgctaagtc tggcagccct gcttaggagg agaaacaggt     300

gtgtctgtcc ctcccaactg gtgaggacac ctgacagggg cccagacacc agagtgggac     360

ctgcctgatg gagagaagct tgggcttggt ttatttccct tttcataaaa aagctgcttt     420

gagatgtaag agaatcatgt tggtggaaga gtgaagaggt tgttttgggg gaggtctgcc     480

ttactctgag ggaagatggg aagcgggggg agtggccagc tgtggaaatt tggggtagtc     540

ccctacgtat cctgtgcctc agtttcccca tgtgtaaaca ggagtaatta tctcatcctg     600
```

-continued

```
gggctgcagt gaggatcaga tgagctaatg tacaaaaagg cttaggcagg cctgccgtga    660
taagagtgca gaggctgggg gctttttatg ttatggtatt gttgttatta ttactcctgg    720
ggaggtggtg ggcaagagtg tggactgagg agccacatgg ctgggtttgg atcccagccc    780
ggccacagac cttgggcaag ttacttaacc tcggctttct catctgtata atgggagaca    840
ataatagata gtgcctccct tctagggtta ttgagaggat tgcatgatgg gctggcacac    900
agcatgagct cagtaagtgt cagtcactgt tatcccccag gggcatgcat gccgctgcct    960
ccaggaggcc ctccaactcg cagtggcctc tccctacatg ggttcccact gagctgtgat   1020
cctgtggcct tgagccccat ctggctgccc tggacaatgt tggtcctcag ctccccagcg   1080
ggatcaacag tggggagagc agtgggtgga tctgcccgcc aggcagtacc tgagtgcaca   1140
gtgggcaccc cacagtcaaa ggatgcatag tctggtttcc aaggaggaac cccaggctag   1200
gtggaatgag ggaaatgcaa tctcagggcc agataacatc acagatactt taaacctgca   1260
attaatttct ggttgtttga ccaaatccgg ccaagtttcc cgggtgacac tgcagagctg   1320
tggaacagca tgggcttgga gtcagacctg ttgcacatct ggctctgcca tgtgatgcaa   1380
cctcaggctt gtcacgaggc ctccttgagc ctcagttgct aatatgccaa atggggatga   1440
tattgctcac cttacagctt gtaagagtgg agggagctgc gtgcgccagg tgcctggcat   1500
gcagcgggca ctcaaccaga ttgaattccc ttcccaggga agaattcaag gatatcttcc   1560
cacccactaa ggagacatgt gatgggatct ggggtgagaa ttgctctttt taaagctctc   1620
agaactgtaa ggggctccac ccaccaatgg ctggtgttca ctgagctctt cgtgcccaga   1680
cctgcactgg ggatttatcg agcacatggc tggcttctga cttccgaaga gctcgccatt   1740
ctggtcagtg cctgagggca cagaaatgtt tgaggtctat gggacgcctg gcgtggacat   1800
ctacatctct cccaacatgg agaggggccg ggagcgtgca gacaccaggc ggtggcgctt   1860
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctacctcacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
cgtgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
```

-continued

```
tgggggcaac ctgcctgggt caagtggccg cagggtcacc caggtggtgc gggacttcct   3000

ccatgcccag aaggtgcagc cccccgtgga gctctttgtg gactggttgg ccgtgggcca   3060

tgtggatgag tttctgagct ttgtccctgc cccgatggg aagggcttcc ggatgctcct   3120

ggccagccct ggggcctgct tcaagctctt ccaggaaaag cagaagtgtg gccacgggag   3180

ggccctcctg ttccaggggg ttgttgatga tgagcaggtc aagaccatct ccatcaacca   3240

ggtgctctcc aataaagacc tcatcaacta caataagttt gtgcagagct gcatcgactg   3300

gaaccgtgag gtgctgaagc gggagctggg cctggcagag tgtgacatca ttgacatccc   3360

acagctcttc aagaccgaga ggaaaaaagc aacggccttc ttccctgact tggtgaacat   3420

gctggtgctg gggaagcacc tgggcatccc caagcccttt gggcccatca tcaatggctg   3480

ctgctgcctg gaggagaagg tgcggtccct gctggagccg ctgggcctcc actgcacctt   3540

cattgatgac ttcactccat accacatgct gcatggggag gtgcactgtg gcaccaatgt   3600

gtgcagaaag cccttctctt tcaagtggtg gaacatggtg ccctgagaca gctcccaccc   3660

accatcctgt cccccctgggg cggcattgg cccaggtggt ggagacagag acaggcccct   3720

gaacgataag caccaagaga ccccaaggct ccagatggaa cactgagggt gaccgtccct   3780

ctcagaagcc ttttccctgg aagtgtccat gcctcacctg caacccatgt ggttctcaga   3840

cttgaatctt ctcggccccc caaaaagaag gacctcattt cttatagcct ctcctgtgat   3900

tcaacacaac ccatggagat gtccccttct cactctgaaa tcatccattt ggggacaaat   3960

ccacattggg gtctagaaac atccacgtat ctcatcagcc atcttgtcct gtgcatccta   4020

acagaggaag gatccatgat tctgctttgg tccaattgct tcctctctgc agaggaacaa   4080

ccctaaaacc agaccactcc acgcaggaca ggcaggagag attcttccta aagcctcccc   4140

cataaaaagg gagctgtgga tccacttaga tcagggcgga accatctttc acccggccaa   4200

gctcctgccc agatgttgac cctcacccag cgtgagctgt cacatagtag gagcttctag   4260

atgcatgtgg aagcaatgag agttgtccct tagccttata aactccccat gatctgacat   4320

gcagaaatcc agccttgtcc agaatcctcc tggaatttct tggagacgaa agtatctggg   4380

ggattgttgg gtactaggga gactgggtac aagggtgaaa agtagttccc ataatacaca   4440

tggttgacta tggtgatcca ccttgtgatg gttaatatta ggtgtctgga gaaggttgct   4500

tcattggccc tgggacttct ctctgcagga ggagagaacg ctgcctctcc tctggattgg   4560

tctcaggctc tctgttggcc tttggtcagc gtttccacat cctgctctgc tgcaggagag   4620

ggggctaagg ggctggatcc accaaggcag ctcacagcgg gaaaactctg ggaatgaacc   4680

actgaattca ggggatgggg gtgggggggc ggttctcgag gtgtgtgcca gctacacgtg   4740

tgttctgtat gggtccagct gcgtttccat cactcgctaa taaatcaaca gaaacacaaa   4800
```

```
<210> SEQ ID NO 22
<211> LENGTH: 626
<212> TYPE: PRT
<213> ORGANISM: Homo sapiens
<220> FEATURE:
<223> OTHER INFORMATION: protein-arginine deiminase type-3 isoform X1
      [Homo sapiens]

<400> SEQUENCE: 22

Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30
```

-continued

```
Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
```

```
    450                 455                 460

Lys Gln Lys Cys Gly His Gly Arg Ala Leu Leu Phe Gln Gly Val Val
465                 470                 475                 480

Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525

Ile Asp Ile Pro Gln Leu Phe Lys Thr Glu Arg Lys Lys Ala Thr Ala
    530                 535                 540

Phe Phe Pro Asp Leu Val Asn Met Leu Val Leu Gly Lys His Leu Gly
545                 550                 555                 560

Ile Pro Lys Pro Phe Gly Pro Ile Ile Asn Gly Cys Cys Cys Leu Glu
                565                 570                 575

Glu Lys Val Arg Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605

Gly Thr Asn Val Cys Arg Lys Pro Phe Ser Phe Lys Trp Trp Asn Met
    610                 615                 620

Val Pro
625


<210> SEQ ID NO 23
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X1, mRNA

<400> SEQUENCE: 23

tctccctggt tctgccattt cccctgtggg gggctgccca gggccaaaca ggccagaggg     60

ctccaccagc cctggaaatt acaggctttg ggagtagggt tgccagataa aataaaagat    120

gcctagttaa aattgaattt caggtaaata attaataatt tttttagtat aagtgtatcc    180

caaatacttc acgggagtac caaacaatga ttgactgttc acttgaaatt caagtccaac    240

tgagctttct gtatttttat ttgctaagtc tggcagccct gcttaggagg agaaacaggt    300

gtgtctgtcc ctcccaactg gtgaggacac ctgacagggg cccagacacc agagtgggac    360

ctgcctgatg gagagaagct tgggcttggt ttatttccct tttcataaaa aagctgcttt    420

gagatgtaag agaatcatgt tggtggaaga gtgaagaggt tgttttgggg gaggtctgcc    480

ttactctgag ggaagatggg aagcgggggg agtggccagc tgtggaaatt tggggtagtc    540

ccctacgtat cctgtgcctc agtttcccca tgtgtaaaca ggagtaatta tctcatcctg    600

gggctgcagt gaggatcaga tgagctaatg tacaaaaagg cttaggcagg cctgccgtga    660

taagagtgca gaggctgggg gctttttatg ttatggtatt gttgttatta ttactcctgg    720

ggaggtggtg ggcaagagtg tggactgagg agccacatgg ctgggtttgg atcccagccc    780

ggccacagac cttgggcaag ttacttaacc tcggctttct catctgtata atgggagaca    840

ataatagata gtgcctccct tctagggtta ttgagaggat tgcatgatgg gctggcacac    900

agcatgagct cagtaagtgt cagtcactgt tatcccccag gggcatgcat gccgctgcct    960

ccaggaggcc ctccaactcg cagtggcctc tccctacatg ggttcccact gagctgtgat   1020
```

-continued

```
cctgtggcct tgagccccat ctggctgccc tggacaatgt tggtcctcag ctccccagcg   1080
ggatcaacag tggggagagc agtgggtgga tctgcccgcc aggcagtacc tgagtgcaca   1140
gtgggcaccc cacagtcaaa ggatgcatag tctggtttcc aaggaggaac cccaggctag   1200
gtggaatgag ggaaatgcaa tctcagggcc agataacatc acagatactt taaacctgca   1260
attaatttct ggttgtttga ccaaatccgg ccaagtttcc cgggtgacac tgcagagctg   1320
tggaacagca tgggcttgga gtcagacctg ttgcacatct ggctctgcca tgtgatgcaa   1380
cctcaggctt gtcacgaggc ctccttgagc ctcagttgct aatatgccaa atggggatga   1440
tattgctcac cttacagctt gtaagagtgg agggagctgc gtgcgccagg tgcctggcat   1500
gcagcgggca ctcaaccaga ttgaattccc ttcccaggga agaattcaag gatatcttcc   1560
cacccactaa ggagacatgt gatgggatct ggggtgagaa ttgctctttt taaagctctc   1620
agaactgtaa ggggctccac ccaccaatgg ctggtgttca ctgagctctt cgtgcccaga   1680
cctgcactgg ggatttatcg agcacatggc tggcttctga cttccgaaga gctcgccatt   1740
ctggtcagtg cctgagggca cagaaatgtt tgaggtctat gggacgcctg gcgtggacat   1800
ctacgtctct cccaacatgg agaggggccg ggagcgtgca gacaccaggc ggtggcgctt   1860
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctacctcacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
cgtgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
tgggggcaac ctgcctgggt caagtggccg cagggtcacc caggtggtgc gggacttcct   3000
ccatgcccag aaggtgcagc cccccgtgga gctctttgtg gactggttgg ccgtgggcca   3060
tgtggatgag tttctgagct ttgtccctgc ccccgatggg aagggcttcc ggatgctcct   3120
ggccagccct ggggcctgct tcaagctctt ccaggaaaag cagaagtgtg gccacgggag   3180
ggccctcctg ttccaggggg ttgttgatga tgagcaggtc aagaccatct ccatcaacca   3240
ggtgctctcc aataaagacc tcatcaacta caataagttt gtgcagagct gcatcgactg   3300
gaaccgtgag gtgctgaagc gggagctggg cctggcagag tgtgacatca ttgacatccc   3360
```

-continued acagctcttc aagaccgaga ggaaaaaagc aacggccttc ttccctgact tggtgaacat 3420
gctggtgctg gggaagcacc tgggcatccc caagcccttt gggcccatca tcaatggctg 3480
ctgctgcctg gaggagaagg tgcggtccct gctggagccg ctgggcctcc actgcacctt 3540
cattgatgac ttcactccat accacatgct gcatggggag gtgcactgtg gcaccaatgt 3600
gtgcagaaag cccttctctt tcaagtggtg gaacatggtg ccctgagaca gctcccaccc 3660
accatcctgt ccccctgggg cgggcattgg cccaggtggt ggagacagag acaggcccct 3720
gaacgataag caccaagaga ccccaaggct ccagatggaa cactgagggt gaccgtccct 3780
ctcagaagcc ttttccctgg aagtgtccat gcctcacctg caacccatgt ggttctcaga 3840
cttgaatctt ctcggccccc caaaaagaag gacctcattt cttatagcct ctcctgtgat 3900
tcaacacaac ccatggagat gtccccttct cactctgaaa tcatccattt ggggacaaat 3960
ccacattggg gtctagaaac atccacgtat ctcatcagcc atcttgtcct gtgcatccta 4020
acagaggaag gatccatgat tctgctttgg tccaattgct tcctctctgc agaggaacaa 4080
ccctaaaacc agaccactcc acgcaggaca ggcaggagag attcttccta aagcctcccc 4140
cataaaaagg gagctgtgga tccacttaga tcagggcgga accatctttc acccggccaa 4200
gctcctgccc agatgttgac cctcacccag cgtgagctgt cacatagtag gagcttctag 4260
atgcatgtgg aagcaatgag agttgtccct tagccttata aactccccat gatctgacat 4320
gcagaaatcc agccttgtcc agaatcctcc tggaatttct tggagacgaa agtatctggg 4380
ggattgttgg gtactaggga gactgggtac aagggtgaaa agtagttccc ataatacaca 4440
tggttgacta tggtgatcca ccttgtgatg gttaatatta ggtgtctgga gaaggttgct 4500
tcattggccc tgggacttct ctctgcagga ggagagaacg ctgcctctcc tctggattgg 4560
tctcaggctc tctgttggcc tttggtcagc gtttccacat cctgctctgc tgcaggagag 4620
ggggctaagg ggctggatcc accaaggcag ctcacagcgg gaaaactctg ggaatgaacc 4680
actgaattca ggggatgggg gtgggggggc ggttctcgag gtgtgtgcca gctacacgtg 4740
tgttctgtat gggtccagct gcgtttccat cactcgctaa taaatcaaca gaaacacaaa 4800

<210> SEQ ID NO 24
<211> LENGTH: 626
<212> TYPE: PRT
<213> ORGANISM: Homo sapiens
<220> FEATURE:
<223> OTHER INFORMATION: protein-arginine deiminase type-3 isoform X1
      [Homo sapiens]

<400> SEQUENCE: 24

Met Phe Glu Val Tyr Gly Thr Pro Gly Val Asp Ile Tyr Val Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

-continued

```
Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
    450                 455                 460

Lys Gln Lys Cys Gly His Gly Arg Ala Leu Leu Phe Gln Gly Val Val
465                 470                 475                 480

Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525
```

```
Ile Asp Ile Pro Gln Leu Phe Lys Thr Glu Arg Lys Lys Ala Thr Ala
    530                 535                 540

Phe Phe Pro Asp Leu Val Asn Met Leu Val Leu Gly Lys His Leu Gly
545                 550                 555                 560

Ile Pro Lys Pro Phe Gly Pro Ile Ile Asn Gly Cys Cys Cys Leu Glu
                565                 570                 575

Glu Lys Val Arg Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605

Gly Thr Asn Val Cys Arg Lys Pro Phe Ser Phe Lys Trp Trp Asn Met
    610                 615                 620

Val Pro
625


<210> SEQ ID NO 25
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X1, mRNA

<400> SEQUENCE: 25

tctccctggt tctgccattt cccctgtggg gggctgccca gggccaaaca ggccagaggg     60

ctccaccagc cctggaaatt acaggctttg ggagtagggt tgccagataa aataaaagat    120

gcctagttaa aattgaattt caggtaaata attaataatt tttttagtat aagtgtatcc    180

caaatacttc acgggagtac caaacaatga ttgactgttc acttgaaatt caagtccaac    240

tgagctttct gtatttttat ttgctaagtc tggcagccct gcttaggagg agaaacaggt    300

gtgtctgtcc ctcccaactg gtgaggacac ctgacagggg cccagacacc agagtgggac    360

ctgcctgatg gagagaagct tgggcttggt ttatttccct tttcataaaa aagctgcttt    420

gagatgtaag agaatcatgt tggtggaaga gtgaagaggt tgttttgggg gaggtctgcc    480

ttactctgag ggaagatggg aagcgggggg agtggccagc tgtggaaatt tggggtagtc    540

ccctacgtat cctgtgcctc agtttcccca tgtgtaaaca ggagtaatta tctcatcctg    600

gggctgcagt gaggatcaga tgagctaatg tacaaaaagg cttaggcagg cctgccgtga    660

taagagtgca gaggctgggg gctttttatg ttatggtatt gttgttatta ttactcctgg    720

ggaggtggtg ggcaagagtg tggactgagg agccacatgg ctgggtttgg atcccagccc    780

ggccacagac cttgggcaag ttacttaacc tcggctttct catctgtata atgggagaca    840

ataatagata gtgcctccct tctagggtta ttgagaggat tgcatgatgg gctggcacac    900

agcatgagct cagtaagtgt cagtcactgt tatcccccag gggcatgcat gccgctgcct    960

ccaggaggcc ctccaactcg cagtggcctc tccctacatg ggttcccact gagctgtgat   1020

cctgtggcct tgagccccat ctggctgccc tggacaatgt tggtcctcag ctccccagcg   1080

ggatcaacag tggggagagc agtgggtgga tctgcccgcc aggcagtacc tgagtgcaca   1140

gtgggcaccc cacagtcaaa ggatgcatag tctggtttcc aaggaggaac cccaggctag   1200

gtggaatgag ggaaatgcaa tctcagggcc agataacatc acagatactt taaacctgca   1260

attaatttct ggttgtttga ccaaatccgg ccaagtttcc cgggtgacac tgcagagctg   1320

tggaacagca tgggcttgga gtcagacctg ttgcacatct ggctctgcca tgtgatgcaa   1380

cctcaggctt gtcacgaggc ctccttgagc ctcagttgct aatatgccaa atggggatga   1440
```

-continued

```
tattgctcac cttacagctt gtaagagtgg agggagctgc gtgcgccagg tgcctggcat   1500
gcagcgggca ctcaaccaga ttgaattccc ttcccaggga agaattcaag gatatcttcc   1560
cacccactaa ggagacatgt gatgggatct ggggtgagaa ttgctctttt taaagctctc   1620
agaactgtaa ggggctccac ccaccaatgg ctggtgttca ctgagctctt cgtgcccaga   1680
cctgcactgg ggatttatcg agcacatggc tggcttctga cttccgaaga gctcgccatt   1740
ctggtcagtg cctgagggca cagaaatgtt tgaggtctat gggacgcctg gcgtggacat   1800
ctacatctct cccaacatgg agaggggccg ggagcgtgca gacaccaggc ggtggcgctt   1860
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctaccacacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
cgtgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
tgggggcaac ctgcctgggt caagtggccg cagggtcacc caggtggtgc gggacttcct   3000
ccatgcccag aaggtgcagc cccccgtgga gctctttgtg gactggttgg ccgtgggcca   3060
tgtggatgag tttctgagct ttgtccctgc ccccgatggg aagggcttcc ggatgctcct   3120
ggccagccct ggggcctgct tcaagctctt ccaggaaaag cagaagtgtg gccacgggag   3180
ggccctcctg ttccaggggg ttgttgatga tgagcaggtc aagaccatct ccatcaacca   3240
ggtgctctcc aataaagacc tcatcaacta caataagttt gtgcagagct gcatcgactg   3300
gaaccgtgag gtgctgaagc gggagctggg cctggcagag tgtgacatca ttgacatccc   3360
acagctcttc aagaccgaga ggaaaaaagc aacggccttc ttccctgact tggtgaacat   3420
gctggtgctg gggaagcacc tgggcatccc caagcccttt gggcccatca tcaatggctg   3480
ctgctgcctg gaggagaagg tgcggtccct gctggagccg ctgggcctcc actgcacctt   3540
cattgatgac ttcactccat accacatgct gcatggggag gtgcactgtg gcaccaatgt   3600
gtgcagaaag cccttctctt tcaagtggtg gaacatggtg ccctgagaca gctcccaccc   3660
accatcctgt ccccctgggg cgggcattgg cccaggtggt ggagacagag acaggcccct   3720
gaacgataag caccaagaga ccccaaggct ccagatggaa cactgagggt gaccgtccct   3780
```

-continued

```
ctcagaagcc ttttccctgg aagtgtccat gcctcacctg caacccatgt ggttctcaga   3840

cttgaatctt ctcggccccc caaaaagaag gacctcattt cttatagcct ctcctgtgat   3900

tcaacacaac ccatggagat gtccccttct cactctgaaa tcatccattt ggggacaaat   3960

ccacattggg gtctagaaac atccacgtat ctcatcagcc atcttgtcct gtgcatccta   4020

acagaggaag gatccatgat tctgctttgg tccaattgct tcctctctgc agaggaacaa   4080

ccctaaaacc agaccactcc acgcaggaca ggcaggagag attcttccta aagcctcccc   4140

cataaaaagg gagctgtgga tccacttaga tcagggcgga accatctttc acccggccaa   4200

gctcctgccc agatgttgac cctcacccag cgtgagctgt cacatagtag gagcttctag   4260

atgcatgtgg aagcaatgag agttgtccct tagccttata aactccccat gatctgacat   4320

gcagaaatcc agccttgtcc agaatcctcc tggaatttct tggagacgaa agtatctggg   4380

ggattgttgg gtactaggga gactgggtac aagggtgaaa agtagttccc ataatacaca   4440

tggttgacta tggtgatcca ccttgtgatg gttaatatta ggtgtctgga gaaggttgct   4500

tcattggccc tgggacttct ctctgcagga ggagagaacg ctgcctctcc tctggattgg   4560

tctcaggctc tctgttggcc tttggtcagc gtttccacat cctgctctgc tgcaggagag   4620

ggggctaagg ggctggatcc accaaggcag ctcacagcgg gaaaactctg ggaatgaacc   4680

actgaattca ggggatgggg gtggggggc ggttctcgag gtgtgtgcca gctacacgtg   4740

tgttctgtat gggtccagct gcgtttccat cactcgctaa taaatcaaca gaaacacaaa   4800
```

```
<210> SEQ ID NO 26
<211> LENGTH: 626
<212> TYPE: PRT
<213> ORGANISM: Homo sapiens
<220> FEATURE:
<223> OTHER INFORMATION: protein-arginine deiminase type-3 isoform X1
      [Homo sapiens]

<400> SEQUENCE: 26

Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr His Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
```

-continued

```
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
    450                 455                 460

Lys Gln Lys Cys Gly His Gly Arg Ala Leu Leu Phe Gln Gly Val Val
465                 470                 475                 480

Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525

Ile Asp Ile Pro Gln Leu Phe Lys Thr Glu Arg Lys Lys Ala Thr Ala
    530                 535                 540

Phe Phe Pro Asp Leu Val Asn Met Leu Val Leu Gly Lys His Leu Gly
545                 550                 555                 560

Ile Pro Lys Pro Phe Gly Pro Ile Ile Asn Gly Cys Cys Cys Leu Glu
                565                 570                 575

Glu Lys Val Arg Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605
```

```
Gly Thr Asn Val Cys Arg Lys Pro Phe Ser Phe Lys Trp Trp Asn Met
    610                 615                 620

Val Pro
625


<210> SEQ ID NO 27
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X1, mRNA

<400> SEQUENCE: 27

tctccctggt tctgccattt cccctgtggg gggctgccca gggccaaaca ggccagaggg     60

ctccaccagc cctggaaatt acaggctttg ggagtagggt tgccagataa aataaaagat    120

gcctagttaa aattgaattt caggtaaata attaataatt tttttagtat aagtgtatcc    180

caaatacttc acgggagtac caaacaatga ttgactgttc acttgaaatt caagtccaac    240

tgagctttct gtatttttat ttgctaagtc tggcagccct gcttaggagg agaaacaggt    300

gtgtctgtcc ctcccaactg gtgaggacac ctgacagggg cccagacacc agagtgggac    360

ctgcctgatg gagagaagct tgggcttggt ttatttccct tttcataaaa aagctgcttt    420

gagatgtaag agaatcatgt tggtggaaga gtgaagaggt tgttttgggg gaggtctgcc    480

ttactctgag ggaagatggg aagcgggggg agtggccagc tgtggaaatt tggggtagtc    540

ccctacgtat cctgtgcctc agtttcccca tgtgtaaaca ggagtaatta tctcatcctg    600

gggctgcagt gaggatcaga tgagctaatg tacaaaaagg cttaggcagg cctgccgtga    660

taagagtgca gaggctgggg gctttttatg ttatggtatt gttgttatta ttactcctgg    720

ggaggtggtg ggcaagagtg tggactgagg agccacatgg ctgggtttgg atcccagccc    780

ggccacagac cttgggcaag ttacttaacc tcggctttct catctgtata atgggagaca    840

ataatagata gtgcctccct tctagggtta ttgagaggat tgcatgatgg gctggcacac    900

agcatgagct cagtaagtgt cagtcactgt tatcccccag gggcatgcat gccgctgcct    960

ccaggaggcc ctccaactcg cagtggcctc tccctacatg ggttcccact gagctgtgat   1020

cctgtggcct tgagccccat ctggctgccc tggacaatgt tggtcctcag ctccccagcg   1080

ggatcaacag tggggagagc agtgggtgga tctgcccgcc aggcagtacc tgagtgcaca   1140

gtgggcaccc cacagtcaaa ggatgcatag tctggtttcc aaggaggaac cccaggctag   1200

gtggaatgag ggaaatgcaa tctcagggcc agataacatc acagatactt taaacctgca   1260

attaatttct ggttgtttga ccaaatccgg ccaagtttcc cgggtgacac tgcagagctg   1320

tggaacagca tgggcttgga gtcagacctg ttgcacatct ggctctgcca tgtgatgcaa   1380

cctcaggctt gtcacgaggc ctccttgagc ctcagttgct aatatgccaa atggggatga   1440

tattgctcac cttacagctt gtaagagtgg agggagctgc gtgcgccagg tgcctggcat   1500

gcagcgggca ctcaaccaga ttgaattccc ttcccaggga agaattcaag gatatcttcc   1560

cacccactaa ggagacatgt gatgggatct ggggtgagaa ttgctctttt taaagctctc   1620

agaactgtaa ggggctccac ccaccaatgg ctggtgttca ctgagctctt cgtgcccaga   1680

cctgcactgg ggatttatcg agcacatggc tggcttctga cttccgaaga gctcgccatt   1740

ctggtcagtg cctgagggca cagaaatgtt tgaggtctat gggacgcctg gcgtggacat   1800

ctacatctct cccaacatgg agaggggccg ggagcgtgca gacaccaggc ggtggcgctt   1860
```

-continued

```
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctacctcacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
catgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
tgggggcaac ctgcctgggt caagtggccg cagggtcacc caggtggtgc gggacttcct   3000
ccatgcccag aaggtgcagc cccccgtgga gctctttgtg gactggttgg ccgtgggcca   3060
tgtggatgag tttctgagct ttgtccctgc ccccgatggg aagggcttcc ggatgctcct   3120
ggccagccct ggggcctgct tcaagctctt ccaggaaaag cagaagtgtg gccacgggag   3180
ggccctcctg ttccaggggg ttgttgatga tgagcaggtc aagaccatct ccatcaacca   3240
ggtgctctcc aataaagacc tcatcaacta caataagttt gtgcagagct gcatcgactg   3300
gaaccgtgag gtgctgaagc gggagctggg cctggcagag tgtgacatca ttgacatccc   3360
acagctcttc aagaccgaga ggaaaaaagc aacggccttc ttccctgact tggtgaacat   3420
gctggtgctg gggaagcacc tgggcatccc caagcccttt gggcccatca tcaatggctg   3480
ctgctgcctg gaggagaagg tgcggtccct gctggagccg ctgggcctcc actgcacctt   3540
cattgatgac ttcactccat accacatgct gcatggggag gtgcactgtg gcaccaatgt   3600
gtgcagaaag cccttctctt tcaagtggtg gaacatggtg ccctgagaca gctcccaccc   3660
accatcctgt ccccctgggg cgggcattgg cccaggtggt ggagacagag acaggcccct   3720
gaacgataag caccaagaga ccccaaggct ccagatggaa cactgagggt gaccgtccct   3780
ctcagaagcc ttttccctgg aagtgtccat gcctcacctg caacccatgt ggttctcaga   3840
cttgaatctt ctcggccccc caaaaagaag gacctcattt cttatagcct ctcctgtgat   3900
tcaacacaac ccatggagat gtccccttct cactctgaaa tcatccattt ggggacaaat   3960
ccacattggg gtctagaaac atccacgtat ctcatcagcc atcttgtcct gtgcatccta   4020
acagaggaag gatccatgat tctgctttgg tccaattgct tcctctctgc agaggaacaa   4080
ccctaaaacc agaccactcc acgcaggaca ggcaggagag attcttccta aagcctcccc   4140
cataaaaagg gagctgtgga tccacttaga tcagggcgga accatctttc acccggccaa   4200
```

-continued

```
gctcctgccc agatgttgac cctcacccag cgtgagctgt cacatagtag gagcttctag   4260

atgcatgtgg aagcaatgag agttgtccct tagccttata aactccccat gatctgacat   4320

gcagaaatcc agccttgtcc agaatcctcc tggaatttct tggagacgaa agtatctggg   4380

ggattgttgg gtactaggga gactgggtac aagggtgaaa agtagttccc ataatacaca   4440

tggttgacta tggtgatcca ccttgtgatg gttaatatta ggtgtctgga gaaggttgct   4500

tcattggccc tgggacttct ctctgcagga ggagagaacg ctgcctctcc tctggattgg   4560

tctcaggctc tctgttggcc tttggtcagc gtttccacat cctgctctgc tgcaggagag   4620

ggggctaagg ggctggatcc accaaggcag ctcacagcgg gaaaactctg ggaatgaacc   4680

actgaattca ggggatgggg gtgggggggc ggttctcgag gtgtgtgcca gctacacgtg   4740

tgttctgtat gggtccagct gcgtttccat cactcgctaa taaatcaaca gaaacacaaa   4800


<210> SEQ ID NO 28
<211> LENGTH: 626
<212> TYPE: PRT
<213> ORGANISM: Homo sapiens
<220> FEATURE:
<223> OTHER INFORMATION: protein-arginine deiminase type-3 isoform X1
      [Homo sapiens]

<400> SEQUENCE: 28

Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Met His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255
```

-continued

```
Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
    450                 455                 460

Lys Gln Lys Cys Gly His Gly Arg Ala Leu Leu Phe Gln Gly Val Val
465                 470                 475                 480

Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525

Ile Asp Ile Pro Gln Leu Phe Lys Thr Glu Arg Lys Lys Ala Thr Ala
    530                 535                 540

Phe Phe Pro Asp Leu Val Asn Met Leu Val Leu Gly Lys His Leu Gly
545                 550                 555                 560

Ile Pro Lys Pro Phe Gly Pro Ile Ile Asn Gly Cys Cys Cys Leu Glu
                565                 570                 575

Glu Lys Val Arg Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605

Gly Thr Asn Val Cys Arg Lys Pro Phe Ser Phe Lys Trp Trp Asn Met
    610                 615                 620

Val Pro
625
```

<210> SEQ ID NO 29
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X1, mRNA

<400> SEQUENCE: 29
tctccctggt tctgccattt cccctgtggg gggctgccca gggccaaaca ggccagaggg 60
ctccaccagc cctggaaatt acaggctttg ggagtagggt tgccagataa aataaaagat 120
gcctagttaa aattgaattt caggtaaata attaataatt tttttagtat aagtgtatcc 180
caaatacttc acgggagtac caaacaatga ttgactgttc acttgaaatt caagtccaac 240
tgagctttct gtatttttat ttgctaagtc tggcagccct gcttaggagg agaaacaggt 300
gtgtctgtcc ctcccaactg gtgaggacac ctgacagggg cccagacacc agagtgggac 360
ctgcctgatg gagagaagct tgggcttggt ttatttccct tttcataaaa aagctgcttt 420
gagatgtaag agaatcatgt tggtggaaga gtgaagaggt tgttttgggg gaggtctgcc 480
ttactctgag ggaagatggg aagcgggggg agtggccagc tgtggaaatt tggggtagtc 540
ccctacgtat cctgtgcctc agtttcccca tgtgtaaaca ggagtaatta tctcatcctg 600
gggctgcagt gaggatcaga tgagctaatg tacaaaaagg cttaggcagg cctgccgtga 660
taagagtgca gaggctgggg gctttttatg ttatggtatt gttgttatta ttactcctgg 720
ggaggtggtg ggcaagagtg tggactgagg agccacatgg ctgggtttgg atcccagccc 780
ggccacagac cttgggcaag ttacttaacc tcggctttct catctgtata atgggagaca 840
ataatagata gtgcctccct tctagggtta ttgagaggat tgcatgatgg gctggcacac 900
agcatgagct cagtaagtgt cagtcactgt tatcccccag gggcatgcat gccgctgcct 960
ccaggaggcc ctccaactcg cagtggcctc tccctacatg ggttcccact gagctgtgat 1020
cctgtggcct tgagccccat ctggctgccc tggacaatgt tggtcctcag ctccccagcg 1080
ggatcaacag tggggagagc agtgggtgga tctgcccgcc aggcagtacc tgagtgcaca 1140
gtgggcaccc cacagtcaaa ggatgcatag tctggtttcc aaggaggaac cccaggctag 1200
gtggaatgag ggaaatgcaa tctcagggcc agataacatc acagatactt taaacctgca 1260
attaatttct ggttgtttga ccaaatccgg ccaagtttcc cgggtgacac tgcagagctg 1320
tggaacagca tgggcttgga gtcagacctg ttgcacatct ggctctgcca tgtgatgcaa 1380
cctcaggctt gtcacgaggc ctccttgagc ctcagttgct aatatgccaa atggggatga 1440
tattgctcac cttacagctt gtaagagtgg agggagctgc gtgcgccagg tgcctggcat 1500
gcagcgggca ctcaaccaga ttgaattccc ttcccaggga agaattcaag gatatcttcc 1560
cacccactaa ggagacatgt gatgggatct ggggtgagaa ttgctctttt taaagctctc 1620
agaactgtaa ggggctccac ccaccaatgg ctggtgttca ctgagctctt cgtgcccaga 1680
cctgcactgg ggatttatcg agcacatggc tggcttctga cttccgaaga gctcgccatt 1740
ctggtcagtg cctgagggca cagaaatgtt tgaggtctat gggacgcctg gcgtggacat 1800
ctacatctct cccaacatgg agaggggccg ggagcgtgca gacaccaggc ggtggcgctt 1860
tgacgcgact ttggagatca tcgtggtcat gaactccccc agcaatgacc tcaacgacag 1920
ccatgttcag atttcctacc actccagcca tgagcctctg cccctggcct atgcggtgct 1980
ctacctcacc tgtgttgaca tctctctgga ttgcgacctg aactgtgagg gaaggcagga 2040
caggaacttt gtagacaagc ggcagtgggt ctgggggccc agtgggtatg gcggcatctt 2100
gctggtgaac tgtgaccgtg atgatccgag ctgtgatgtc caggacaatt gtgaccagca 2160
cgtgcactgc ctgcaagacc tggaagacat gtctgtcatg gtcctgcgga cgcagggccc 2220
tgcagccctc tttgatgacc acaaacttgt cctccatacc tccagctatg atgccaaacg 2280

-continued

```
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gtaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
tgggggcaac ctgcctgggt caagtggccg cagggtcacc caggtggtgc gggacttcct   3000
ccatgcccag aaggtgcagc cccccgtgga gctctttgtg gactggttgg ccgtgggcca   3060
tgtggatgag tttctgagct ttgtccctgc cccgatggg aagggcttcc ggatgctcct   3120
ggccagccct ggggcctgct tcaagctctt ccaggaaaag cagaagtgtg gccacgggag   3180
ggccctcctg ttccaggggg ttgttgatga tgagcaggtc aagaccatct ccatcaacca   3240
ggtgctctcc aataaagacc tcatcaacta caataagttt gtgcagagct gcatcgactg   3300
gaaccgtgag gtgctgaagc gggagctggg cctggcagag tgtgacatca ttgacatccc   3360
acagctcttc aagaccgaga ggaaaaaagc aacggccttc ttccctgact tggtgaacat   3420
gctggtgctg gggaagcacc tgggcatccc caagcccttt gggcccatca tcaatggctg   3480
ctgctgcctg gaggagaagg tgcggtccct gctggagccg ctgggcctcc actgcacctt   3540
cattgatgac ttcactccat accacatgct gcatggggag gtgcactgtg gcaccaatgt   3600
gtgcagaaag cccttctctt tcaagtggtg gaacatggtg ccctgagaca gctcccaccc   3660
accatcctgt ccccctgggg cgggcattgg cccaggtggt ggagacagag acaggcccct   3720
gaacgataag caccaagaga ccccaaggct ccagatggaa cactgagggt gaccgtccct   3780
ctcagaagcc ttttccctgg aagtgtccat gcctcacctg caacccatgt ggttctcaga   3840
cttgaatctt ctcggccccc caaaaagaag gacctcattt cttatagcct ctcctgtgat   3900
tcaacacaac ccatggagat gtccccttct cactctgaaa tcatccattt ggggacaaat   3960
ccacattggg gtctagaaac atccacgtat ctcatcagcc atcttgtcct gtgcatccta   4020
acagaggaag gatccatgat tctgctttgg tccaattgct tcctctctgc agaggaacaa   4080
ccctaaaacc agaccactcc acgcaggaca ggcaggagag attcttccta aagcctcccc   4140
cataaaaagg gagctgtgga tccacttaga tcagggcgga accatctttc acccggccaa   4200
gctcctgccc agatgttgac cctcacccag cgtgagctgt cacatagtag gagcttctag   4260
atgcatgtgg aagcaatgag agttgtccct tagccttata aactccccat gatctgacat   4320
gcagaaatcc agccttgtcc agaatcctcc tggaatttct tggagacgaa agtatctggg   4380
ggattgttgg gtactaggga gactgggtac aagggtgaaa agtagttccc ataatacaca   4440
tggttgacta tggtgatcca ccttgtgatg gttaatatta ggtgtctgga gaaggttgct   4500
tcattggccc tgggacttct ctctgcagga ggagagaacg ctgcctctcc tctggattgg   4560
tctcaggctc tctgttggcc tttggtcagc gtttccacat cctgctctgc tgcaggagag   4620
```

ggggctaagg ggctggatcc accaaggcag ctcacagcgg gaaaactctg ggaatgaacc 4680
actgaattca ggggatgggg gtgggggggc ggttctcgag gtgtgtgcca gctacacgtg 4740
tgttctgtat gggtccagct gcgtttccat cactcgctaa taaatcaaca gaaacacaaa 4800

<210> SEQ ID NO 30
<211> LENGTH: 626
<212> TYPE: PRT
<213> ORGANISM: Homo sapiens
<220> FEATURE:
<223> OTHER INFORMATION: protein-arginine deiminase type-3 isoform X1
[Homo sapiens]

<400> SEQUENCE: 30

```
Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Val
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335
```

Glu Leu Gln Asp Phe Pro Tyr Lys Arg Ile Leu Gly Pro Asp Phe Gly
340 345 350

Tyr Val Thr Arg Glu Pro Arg Asp Arg Ser Val Ser Gly Leu Asp Ser
355 360 365

Phe Gly Asn Leu Glu Val Ser Pro Pro Val Val Ala Asn Gly Lys Glu
370 375 380

Tyr Pro Leu Gly Arg Ile Leu Ile Gly Gly Asn Leu Pro Gly Ser Ser
385 390 395 400

Gly Arg Arg Val Thr Gln Val Val Arg Asp Phe Leu His Ala Gln Lys
405 410 415

Val Gln Pro Pro Val Glu Leu Phe Val Asp Trp Leu Ala Val Gly His
420 425 430

Val Asp Glu Phe Leu Ser Phe Val Pro Ala Pro Asp Gly Lys Gly Phe
435 440 445

Arg Met Leu Leu Ala Ser Pro Gly Ala Cys Phe Lys Leu Phe Gln Glu
450 455 460

Lys Gln Lys Cys Gly His Gly Arg Ala Leu Leu Phe Gln Gly Val Val
465 470 475 480

Asp Asp Glu Gln Val Lys Thr Ile Ser Ile Asn Gln Val Leu Ser Asn
485 490 495

Lys Asp Leu Ile Asn Tyr Asn Lys Phe Val Gln Ser Cys Ile Asp Trp
500 505 510

Asn Arg Glu Val Leu Lys Arg Glu Leu Gly Leu Ala Glu Cys Asp Ile
515 520 525

Ile Asp Ile Pro Gln Leu Phe Lys Thr Glu Arg Lys Lys Ala Thr Ala
530 535 540

Phe Phe Pro Asp Leu Val Asn Met Leu Val Leu Gly Lys His Leu Gly
545 550 555 560

Ile Pro Lys Pro Phe Gly Pro Ile Ile Asn Gly Cys Cys Cys Leu Glu
565 570 575

Glu Lys Val Arg Ser Leu Leu Glu Pro Leu Gly Leu His Cys Thr Phe
580 585 590

Ile Asp Asp Phe Thr Pro Tyr His Met Leu His Gly Glu Val His Cys
595 600 605

Gly Thr Asn Val Cys Arg Lys Pro Phe Ser Phe Lys Trp Trp Asn Met
610 615 620

Val Pro
625

<210> SEQ ID NO 31
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X1, mRNA

<400> SEQUENCE: 31
tctccctggt tctgccattt cccctgtggg gggctgccca gggccaaaca ggccagaggg 60
ctccaccagc cctggaaatt acaggctttg ggagtagggt tgccagataa aataaaagat 120
gcctagttaa aattgaattt caggtaaata attaataatt tttttagtat aagtgtatcc 180
caaatacttc acgggagtac caaacaatga ttgactgttc acttgaaatt caagtccaac 240
tgagctttct gtatttttat ttgctaagtc tggcagccct gcttaggagg agaaacaggt 300

-continued

```
gtgtctgtcc ctcccaactg gtgaggacac ctgacagggg cccagacacc agagtgggac    360
ctgcctgatg gagagaagct tgggcttggt ttatttccct tttcataaaa aagctgcttt    420
gagatgtaag agaatcatgt tggtggaaga gtgaagaggt tgttttgggg gaggtctgcc    480
ttactctgag ggaagatggg aagcgggggg agtggccagc tgtggaaatt tggggtagtc    540
ccctacgtat cctgtgcctc agtttcccca tgtgtaaaca ggagtaatta tctcatcctg    600
gggctgcagt gaggatcaga tgagctaatg tacaaaaagg cttaggcagg cctgccgtga    660
taagagtgca gaggctgggg gctttttatg ttatggtatt gttgttatta ttactcctgg    720
ggaggtggtg ggcaagagtg tggactgagg agccacatgg ctgggtttgg atcccagccc    780
ggccacagac cttgggcaag ttacttaacc tcggctttct catctgtata atgggagaca    840
ataatagata gtgcctccct tctagggtta ttgagaggat tgcatgatgg gctggcacac    900
agcatgagct cagtaagtgt cagtcactgt tatcccccag gggcatgcat gccgctgcct    960
ccaggaggcc ctccaactcg cagtggcctc tccctacatg ggttcccact gagctgtgat   1020
cctgtggcct tgagccccat ctggctgccc tggacaatgt tggtcctcag ctccccagcg   1080
ggatcaacag tggggagagc agtgggtgga tctgcccgcc aggcagtacc tgagtgcaca   1140
gtgggcaccc cacagtcaaa ggatgcatag tctggtttcc aaggaggaac cccaggctag   1200
gtggaatgag ggaaatgcaa tctcagggcc agataacatc acagatactt taaacctgca   1260
attaatttct ggttgtttga ccaaatccgg ccaagtttcc cgggtgacac tgcagagctg   1320
tggaacagca tgggcttgga gtcagacctg ttgcacatct ggctctgcca tgtgatgcaa   1380
cctcaggctt gtcacgaggc ctccttgagc ctcagttgct aatatgccaa atggggatga   1440
tattgctcac cttacagctt gtaagagtgg agggagctgc gtgcgccagg tgcctggcat   1500
gcagcgggca ctcaaccaga ttgaattccc ttcccaggga agaattcaag gatatcttcc   1560
cacccactaa ggagacatgt gatgggatct ggggtgagaa ttgctctttt taaagctctc   1620
agaactgtaa ggggctccac ccaccaatgg ctggtgttca ctgagctctt cgtgcccaga   1680
cctgcactgg ggatttatcg agcacatggc tggcttctga cttccgaaga gctcgccatt   1740
ctggtcagtg cctgagggca cagaaatgtt tgaggtctat gggacgcctg gcgtggacat   1800
ctacatctct cccaacatgg agaggggccg ggagcgtgca gacaccaggc ggtggcgctt   1860
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctacctcacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
cgtgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
```

tgagatggag ctgggctacg ttcaggcgcc gcacaagacc ctcccggtgg tctttgactc 2760
cccaaggaat ggggaactgc aggatttccc ttacaaaaga atcctgggtc cagattttgg 2820
ttacgtgact cgggaaccac gcgacaggtc tgtgagtggc ctggactcct ttgggaacct 2880
ggaggtcagc cctccagtgg tggccaatgg gaaagagtac cccctgggga ggatcctcat 2940
tgggggcaac ctgcctgggt caagtggccg cagggtcacc caggtggtgc gggacttcct 3000
ccatgcccag aaggtgcagc cccccgtgga gctctttgtg gactggttgg ccgtgggcca 3060
tgtggatgag tttctgagct ttgtccctgc cccgatggg aagggcttcc ggatgctcct 3120
ggccagccct ggggcctgct tcaagctctt ccaggaaaag cagaagtgtg gccacgggag 3180
ggccctcctg ttccaggggg ttgttgatga tgagcaggtc aagaccatct ccatcaacca 3240
ggtgctctcc aataaagacc tcatcaacta caataagttt gtgcagagct gcatcgactg 3300
gaaccgtgag gtgctgaagc gggagctggg cctggcagag tgtgacatca ttgacatccc 3360
acagctcttc aagaccgaga ggaaaaaagc aacgaccttc ttccctgact tggtgaacat 3420
gctggtgctg gggaagcacc tgggcatccc caagcccttt gggcccatca tcaatggctg 3480
ctgctgcctg gaggagaagg tgcggtccct gctggagccg ctgggcctcc actgcacctt 3540
cattgatgac ttcactccat accacatgct gcatggggag gtgcactgtg gcaccaatgt 3600
gtgcagaaag cccttctctt tcaagtggtg gaacatggtg ccctgagaca gctcccaccc 3660
accatcctgt ccccctgggg cgggcattgg cccaggtggt ggagacagag acaggcccct 3720
gaacgataag caccaagaga ccccaaggct ccagatggaa cactgagggt gaccgtccct 3780
ctcagaagcc ttttccctgg aagtgtccat gcctcacctg caacccatgt ggttctcaga 3840
cttgaatctt ctcggccccc caaaaagaag gacctcattt cttatagcct ctcctgtgat 3900
tcaacacaac ccatggagat gtccccttct cactctgaaa tcatccattt ggggacaaat 3960
ccacattggg gtctagaaac atccacgtat ctcatcagcc atcttgtcct gtgcatccta 4020
acagaggaag gatccatgat tctgctttgg tccaattgct tcctctctgc agaggaacaa 4080
ccctaaaacc agaccactcc acgcaggaca ggcaggagag attcttccta aagcctcccc 4140
cataaaaagg gagctgtgga tccacttaga tcagggcgga accatctttc acccggccaa 4200
gctcctgccc agatgttgac cctcacccag cgtgagctgt cacatagtag gagcttctag 4260
atgcatgtgg aagcaatgag agttgtccct tagccttata aactccccat gatctgacat 4320
gcagaaatcc agccttgtcc agaatcctcc tggaatttct tggagacgaa agtatctggg 4380
ggattgttgg gtactaggga gactgggtac aagggtgaaa agtagttccc ataatacaca 4440
tggttgacta tggtgatcca ccttgtgatg gttaatatta ggtgtctgga gaaggttgct 4500
tcattggccc tgggacttct ctctgcagga ggagagaacg ctgcctctcc tctggattgg 4560
tctcaggctc tctgttggcc tttggtcagc gtttccacat cctgctctgc tgcaggagag 4620
ggggctaagg ggctggatcc accaaggcag ctcacagcgg gaaaactctg ggaatgaacc 4680
actgaattca ggggatgggg gtgggggggc ggttctcgag gtgtgtgcca gctacacgtg 4740
tgttctgtat gggtccagct gcgtttccat cactcgctaa taaatcaaca gaaacacaaa 4800

<210> SEQ ID NO 32
<211> LENGTH: 626
<212> TYPE: PRT
<213> ORGANISM: Homo sapiens
<220> FEATURE:
<223> OTHER INFORMATION: protein-arginine deiminase type-3 isoform X1
[Homo sapiens]

<400> SEQUENCE: 32

Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys

-continued

```
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
    450                 455                 460

Lys Gln Lys Cys Gly His Gly Arg Ala Leu Leu Phe Gln Gly Val Val
465                 470                 475                 480

Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525

Ile Asp Ile Pro Gln Leu Phe Lys Thr Glu Arg Lys Lys Ala Thr Thr
    530                 535                 540

Phe Phe Pro Asp Leu Val Asn Met Leu Val Leu Gly Lys His Leu Gly
545                 550                 555                 560

Ile Pro Lys Pro Phe Gly Pro Ile Ile Asn Gly Cys Cys Cys Leu Glu
                565                 570                 575

Glu Lys Val Arg Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605

Gly Thr Asn Val Cys Arg Lys Pro Phe Ser Phe Lys Trp Trp Asn Met
    610                 615                 620

Val Pro
625
```

<210> SEQ ID NO 33
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X1, mRNA

<400> SEQUENCE: 33

```
tctccctggt tctgccattt cccctgtggg gggctgccca gggccaaaca ggccagaggg     60

ctccaccagc cctggaaatt acaggctttg ggagtagggt tgccagataa aataaaagat    120

gcctagttaa aattgaattt caggtaaata attaataatt tttttagtat aagtgtatcc    180

caaatacttc acgggagtac caaacaatga ttgactgttc acttgaaatt caagtccaac    240

tgagctttct gtatttttat ttgctaagtc tggcagccct gcttaggagg agaaacaggt    300

gtgtctgtcc ctcccaactg gtgaggacac ctgacagggg cccagacacc agagtgggac    360

ctgcctgatg gagagaagct tgggcttggt ttatttccct tttcataaaa aagctgcttt    420

gagatgtaag agaatcatgt tggtggaaga gtgaagaggt tgttttgggg gaggtctgcc    480

ttactctgag ggaagatggg aagcgggggg agtggccagc tgtggaaatt tggggtagtc    540

ccctacgtat cctgtgcctc agtttcccca tgtgtaaaca ggagtaatta tctcatcctg    600

gggctgcagt gaggatcaga tgagctaatg tacaaaaagg cttaggcagg cctgccgtga    660

taagagtgca gaggctgggg gctttttatg ttatggtatt gttgttatta ttactcctgg    720
```

```
ggaggtggtg ggcaagagtg tggactgagg agccacatgg ctgggtttgg atcccagccc    780
ggccacagac cttgggcaag ttacttaacc tcggctttct catctgtata atgggagaca    840
ataatagata gtgcctccct tctagggtta ttgagaggat tgcatgatgg gctggcacac    900
agcatgagct cagtaagtgt cagtcactgt tatcccccag gggcatgcat gccgctgcct    960
ccaggaggcc ctccaactcg cagtggcctc tccctacatg ggttcccact gagctgtgat   1020
cctgtggcct tgagccccat ctggctgccc tggacaatgt tggtcctcag ctccccagcg   1080
ggatcaacag tggggagagc agtgggtgga tctgcccgcc aggcagtacc tgagtgcaca   1140
gtgggcaccc cacagtcaaa ggatgcatag tctggtttcc aaggaggaac cccaggctag   1200
gtggaatgag ggaaatgcaa tctcagggcc agataacatc acagatactt taaacctgca   1260
attaatttct ggttgtttga ccaaatccgg ccaagtttcc cgggtgacac tgcagagctg   1320
tggaacagca tgggcttgga gtcagacctg ttgcacatct ggctctgcca tgtgatgcaa   1380
cctcaggctt gtcacgaggc ctccttgagc ctcagttgct aatatgccaa atggggatga   1440
tattgctcac cttacagctt gtaagagtgg agggagctgc gtgcgccagg tgcctggcat   1500
gcagcgggca ctcaaccaga ttgaattccc ttcccaggga agaattcaag gatatcttcc   1560
cacccactaa ggagacatgt gatgggatct ggggtgagaa ttgctctttt taaagctctc   1620
agaactgtaa ggggctccac ccaccaatgg ctggtgttca ctgagctctt cgtgcccaga   1680
cctgcactgg ggatttatcg agcacatggc tggcttctga cttccgaaga gctcgccatt   1740
ctggtcagtg cctgagggca cagaaatgtt tgaggtctat gggacgcctg gcgtggacat   1800
ctacatctct cccaacatgg agaggggccg ggagcgtgca gacaccaggc ggtggcgctt   1860
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctacctcacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
cgtgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
tgggggcaac ctgcctgggt caagtggccg cagggtcacc caggtggtgc gggacttcct   3000
ccatgcccag aaggtgcagc cccccgtgga gctctttgtg gactggttgg ccgtgggcca   3060
tgtggatgag tttctgagct ttgtccctgc ccccgatggg aagggcttcc ggatgctcct   3120
```

```
ggccagccct ggggcctgct tcaagctctt ccaggaaaag cagaagtgtg gccacgggag   3180

ggccctcctg ttccaggggg ttgttgatga tgagcaggtc aagaccatct ccatcaacca   3240

ggtgctctcc aataaagacc tcatcaacta caataagttt gtgcagagct gcatcgactg   3300

gaaccgtgag gtgctgaagc gggagctggg cctggcagag tgtgacatca ttgacatccc   3360

acagctcttc aagaccgaga ggaaaaaagc aacggccttc ttccctgact tggtgaacat   3420

gctggtgctg gggaagcacc tgggcatccc caagcccttt gggaccatca tcaatggctg   3480

ctgctgcctg gaggagaagg tgcggtccct gctggagccg ctgggcctcc actgcacctt   3540

cattgatgac ttcactccat accacatgct gcatggggag gtgcactgtg gcaccaatgt   3600

gtgcagaaag cccttctctt tcaagtggtg gaacatggtg ccctgagaca gctcccaccc   3660

accatcctgt ccccctgggg cgggcattgg cccaggtggt ggagacagag acaggcccct   3720

gaacgataag caccaagaga ccccaaggct ccagatggaa cactgagggt gaccgtccct   3780

ctcagaagcc ttttccctgg aagtgtccat gcctcacctg caacccatgt ggttctcaga   3840

cttgaatctt ctcggccccc caaaaagaag gacctcattt cttatagcct ctcctgtgat   3900

tcaacacaac ccatggagat gtccccttct cactctgaaa tcatccattt ggggacaaat   3960

ccacattggg gtctagaaac atccacgtat ctcatcagcc atcttgtcct gtgcatccta   4020

acagaggaag gatccatgat tctgctttgg tccaattgct tcctctctgc agaggaacaa   4080

ccctaaaacc agaccactcc acgcaggaca ggcaggagag attcttccta aagcctcccc   4140

cataaaaagg gagctgtgga tccacttaga tcagggcgga accatctttc acccggccaa   4200

gctcctgccc agatgttgac cctcacccag cgtgagctgt cacatagtag gagcttctag   4260

atgcatgtgg aagcaatgag agttgtccct tagccttata aactccccat gatctgacat   4320

gcagaaatcc agccttgtcc agaatcctcc tggaatttct tggagacgaa agtatctggg   4380

ggattgttgg gtactaggga gactgggtac aagggtgaaa agtagttccc ataatacaca   4440

tggttgacta tggtgatcca ccttgtgatg gttaatatta ggtgtctgga gaaggttgct   4500

tcattggccc tgggacttct ctctgcagga ggagagaacg ctgcctctcc tctggattgg   4560

tctcaggctc tctgttggcc tttggtcagc gtttccacat cctgctctgc tgcaggagag   4620

ggggctaagg ggctggatcc accaaggcag ctcacagcgg gaaaactctg ggaatgaacc   4680

actgaattca ggggatgggg gtgggggggc ggttctcgag gtgtgtgcca gctacacgtg   4740

tgttctgtat gggtccagct gcgtttccat cactcgctaa taaatcaaca gaaacacaaa   4800
```

<210> SEQ ID NO 34
<211> LENGTH: 626
<212> TYPE: PRT
<213> ORGANISM: Homo sapiens
<220> FEATURE:
<223> OTHER INFORMATION: protein-arginine deiminase type-3 isoform X1
[Homo sapiens]

<400> SEQUENCE: 34

```
Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60
```

```
Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
    450                 455                 460

Lys Gln Lys Cys Gly His Gly Arg Ala Leu Leu Phe Gln Gly Val Val
465                 470                 475                 480
```

-continued

```
Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525

Ile Asp Ile Pro Gln Leu Phe Lys Thr Glu Arg Lys Lys Ala Thr Ala
    530                 535                 540

Phe Phe Pro Asp Leu Val Asn Met Leu Val Leu Gly Lys His Leu Gly
545                 550                 555                 560

Ile Pro Lys Pro Phe Gly Thr Ile Ile Asn Gly Cys Cys Cys Leu Glu
                565                 570                 575

Glu Lys Val Arg Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605

Gly Thr Asn Val Cys Arg Lys Pro Phe Ser Phe Lys Trp Trp Asn Met
    610                 615                 620

Val Pro
625
```

<210> SEQ ID NO 35
<211> LENGTH: 4800
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X1, mRNA

<400> SEQUENCE: 35

```
tctccctggt tctgccattt cccctgtggg gggctgccca gggccaaaca ggccagaggg     60

ctccaccagc cctggaaatt acaggctttg ggagtagggt tgccagataa aataaaagat    120

gcctagttaa aattgaattt caggtaaata attaataatt tttttagtat aagtgtatcc    180

caaatacttc acgggagtac caaacaatga ttgactgttc acttgaaatt caagtccaac    240

tgagctttct gtatttttat ttgctaagtc tggcagccct gcttaggagg agaaacaggt    300

gtgtctgtcc ctcccaactg gtgaggacac ctgacagggg cccagacacc agagtgggac    360

ctgcctgatg gagagaagct tgggcttggt ttatttccct tttcataaaa aagctgcttt    420

gagatgtaag agaatcatgt tggtggaaga gtgaagaggt tgttttgggg gaggtctgcc    480

ttactctgag ggaagatggg aagcgggggg agtggccagc tgtggaaatt tggggtagtc    540

ccctacgtat cctgtgcctc agtttcccca tgtgtaaaca ggagtaatta tctcatcctg    600

gggctgcagt gaggatcaga tgagctaatg tacaaaaagg cttaggcagg cctgccgtga    660

taagagtgca gaggctgggg gctttttatg ttatggtatt gttgttatta ttactcctgg    720

ggaggtggtg ggcaagagtg tggactgagg agccacatgg ctgggtttgg atcccagccc    780

ggccacagac cttgggcaag ttacttaacc tcggctttct catctgtata atgggagaca    840

ataatagata gtgcctccct tctagggtta ttgagaggat tgcatgatgg gctggcacac    900

agcatgagct cagtaagtgt cagtcactgt tatcccccag gggcatgcat gccgctgcct    960

ccaggaggcc ctccaactcg cagtggcctc tccctacatg ggttcccact gagctgtgat   1020

cctgtggcct tgagccccat ctggctgccc tggacaatgt tggtcctcag ctccccagcg   1080

ggatcaacag tggggagagc agtgggtgga tctgcccgcc aggcagtacc tgagtgcaca   1140
```

-continued

```
gtgggcaccc cacagtcaaa ggatgcatag tctggtttcc aaggaggaac cccaggctag   1200
gtggaatgag ggaaatgcaa tctcagggcc agataacatc acagatactt taaacctgca   1260
attaatttct ggttgtttga ccaaatccgg ccaagtttcc cgggtgacac tgcagagctg   1320
tggaacagca tgggcttgga gtcagacctg ttgcacatct ggctctgcca tgtgatgcaa   1380
cctcaggctt gtcacgaggc ctccttgagc ctcagttgct aatatgccaa atggggatga   1440
tattgctcac cttacagctt gtaagagtgg agggagctgc gtgcgccagg tgcctggcat   1500
gcagcgggca ctcaaccaga ttgaattccc ttcccaggga agaattcaag gatatcttcc   1560
cacccactaa ggagacatgt gatgggatct ggggtgagaa ttgctctttt taaagctctc   1620
agaactgtaa ggggctccac ccaccaatgg ctggtgttca ctgagctctt cgtgcccaga   1680
cctgcactgg ggatttatcg agcacatggc tggcttctga cttccgaaga gctcgccatt   1740
ctggtcagtg cctgagggca cagaaatgtt tgaggtctat gggacgcctg gcgtggacat   1800
ctacatctct cccaacatgg agaggggccg ggagcgtgca gacaccaggc ggtggcgctt   1860
tgacgcgact ttggagatca tcgtggtcat gaactccccc agcaatgacc tcaacgacag   1920
ccatgttcag atttcctacc actccagcca tgagcctctg cccctggcct atgcggtgct   1980
ctacctcacc tgtgttgaca tctctctgga ttgcgacctg aactgtgagg gaaggcagga   2040
caggaacttt gtagacaagc ggcagtgggt ctgggggccc agtgggtatg gcggcatctt   2100
gctggtgaac tgtgaccgtg atgatccgag ctgtgatgtc caggacaatt gtgaccagca   2160
cgtgcactgc ctgcaagacc tggaagacat gtctgtcatg gtcctgcgga cgcagggccc   2220
tgcagccctc tttgatgacc acaaacttgt cctccatacc tccagctatg atgccaaacg   2280
ggcacaggtc ttccacatct gcggtcctga ggatgtgtgt gaggcctata ggcatgtgct   2340
gggccaagat aaggtgtcct atgaggtacc ccgcttgcat ggggatgagg agcgcttctt   2400
cgtggaaggc ctgtccttcc ctgatgccgg cttcacagga ctcatctcct tccatgtcac   2460
tctgctggac gactccaacg aggatttctc ggcatcccct atcttcactg acactgtggt   2520
gttccgagtg gcaccctgga tcatgacgcc cagcactctg ccacccctag aggtgtatgt   2580
gtgccgtgtg aggaacaaca cgtgttttgt ggatgcggtg gcagagctgg ccaggaaggc   2640
cggctgcaag ctgaccatct gcccacaggc cgagaaccgc aacgaccgct ggatccagga   2700
tgagatggag ctgggctacg ttcaggcgcc gcacaagacc ctcccggtgg tctttgactc   2760
cccaaggaat ggggaactgc aggatttccc ttacaaaaga atcctgggtc cagattttgg   2820
ttacgtgact cgggaaccac gcgacaggtc tgtgagtggc ctggactcct ttgggaacct   2880
ggaggtcagc cctccagtgg tggccaatgg gaaagagtac cccctgggga ggatcctcat   2940
tgggggcaac ctgcctgggt caagtggccg cagggtcacc caggtggtgc gggacttcct   3000
ccatgcccag aaggtgcagc cccccgtgga gctctttgtg gactggttgg ccgtgggcca   3060
tgtggatgag tttctgagct ttgtccctgc ccccgatggg aagggcttcc ggatgctcct   3120
ggccagccct ggggcctgct tcaagctctt ccaggaaaag cagaagtgtg gccacgggag   3180
ggccctcctg ttccaggggg ttgttgatga tgagcaggtc aagaccatct ccatcaacca   3240
ggtgctctcc aataaagacc tcatcaacta caataagttt gtgcagagct gcatcgactg   3300
gaaccgtgag gtgctgaagc gggagctggg cctggcagag tgtgacatca ttgacatccc   3360
acagctcttc aagaccgaga ggaaaaaagc aacggccttc ttccctgact tggtgaacat   3420
gctggtgctg gggaagcacc tgggcatccc caagcccttt gggcccatca tcaatggctg   3480
ctgctgcctg gaggagaagg tgcagtccct gctggagccg ctgggcctcc actgcacctt   3540
```

-continued

```
cattgatgac ttcactccat accacatgct gcatggggag gtgcactgtg gcaccaatgt   3600

gtgcagaaag cccttctctt tcaagtggtg gaacatggtg ccctgagaca gctcccaccc   3660

accatcctgt ccccctgggg cgggcattgg cccaggtggt ggagacagag acaggcccct   3720

gaacgataag caccaagaga ccccaaggct ccagatggaa cactgagggt gaccgtccct   3780

ctcagaagcc ttttccctgg aagtgtccat gcctcacctg caacccatgt ggttctcaga   3840

cttgaatctt ctcggccccc caaaaagaag gacctcattt cttatagcct ctcctgtgat   3900

tcaacacaac ccatggagat gtccccttct cactctgaaa tcatccattt ggggacaaat   3960

ccacattggg gtctagaaac atccacgtat ctcatcagcc atcttgtcct gtgcatccta   4020

acagaggaag gatccatgat tctgctttgg tccaattgct tcctctctgc agaggaacaa   4080

ccctaaaacc agaccactcc acgcaggaca ggcaggagag attcttccta aagcctcccc   4140

cataaaaagg gagctgtgga tccacttaga tcagggcgga accatctttc acccggccaa   4200

gctcctgccc agatgttgac cctcacccag cgtgagctgt cacatagtag gagcttctag   4260

atgcatgtgg aagcaatgag agttgtccct tagccttata aactccccat gatctgacat   4320

gcagaaatcc agccttgtcc agaatcctcc tggaatttct tggagacgaa agtatctggg   4380

ggattgttgg gtactaggga gactgggtac aagggtgaaa agtagttccc ataatacaca   4440

tggttgacta tggtgatcca ccttgtgatg gttaatatta ggtgtctgga gaaggttgct   4500

tcattggccc tgggacttct ctctgcagga ggagagaacg ctgcctctcc tctggattgg   4560

tctcaggctc tctgttggcc tttggtcagc gtttccacat cctgctctgc tgcaggagag   4620

ggggctaagg ggctggatcc accaaggcag ctcacagcgg gaaaactctg ggaatgaacc   4680

actgaattca ggggatgggg gtgggggggc ggttctcgag gtgtgtgcca gctacacgtg   4740

tgttctgtat gggtccagct gcgtttccat cactcgctaa taaatcaaca gaaacacaaa   4800
```

<210> SEQ ID NO 36
<211> LENGTH: 626
<212> TYPE: PRT
<213> ORGANISM: Homo sapiens
<220> FEATURE:
<223> OTHER INFORMATION: protein-arginine deiminase type-3 isoform X1
      [Homo sapiens]

<400> SEQUENCE: 36

```
Met Phe Glu Val Tyr Gly Thr Pro Gly Val Asp Ile Tyr Ile Ser Pro
1               5                   10                  15

Asn Met Glu Arg Gly Arg Glu Arg Ala Asp Thr Arg Arg Trp Arg Phe
            20                  25                  30

Asp Ala Thr Leu Glu Ile Ile Val Val Met Asn Ser Pro Ser Asn Asp
        35                  40                  45

Leu Asn Asp Ser His Val Gln Ile Ser Tyr His Ser Ser His Glu Pro
    50                  55                  60

Leu Pro Leu Ala Tyr Ala Val Leu Tyr Leu Thr Cys Val Asp Ile Ser
65                  70                  75                  80

Leu Asp Cys Asp Leu Asn Cys Glu Gly Arg Gln Asp Arg Asn Phe Val
                85                  90                  95

Asp Lys Arg Gln Trp Val Trp Gly Pro Ser Gly Tyr Gly Gly Ile Leu
            100                 105                 110

Leu Val Asn Cys Asp Arg Asp Asp Pro Ser Cys Asp Val Gln Asp Asn
        115                 120                 125

Cys Asp Gln His Val His Cys Leu Gln Asp Leu Glu Asp Met Ser Val
```

-continued

```
    130                 135                 140

Met Val Leu Arg Thr Gln Gly Pro Ala Ala Leu Phe Asp Asp His Lys
145                 150                 155                 160

Leu Val Leu His Thr Ser Ser Tyr Asp Ala Lys Arg Ala Gln Val Phe
                165                 170                 175

His Ile Cys Gly Pro Glu Asp Val Cys Glu Ala Tyr Arg His Val Leu
            180                 185                 190

Gly Gln Asp Lys Val Ser Tyr Glu Val Pro Arg Leu His Gly Asp Glu
        195                 200                 205

Glu Arg Phe Phe Val Glu Gly Leu Ser Phe Pro Asp Ala Gly Phe Thr
    210                 215                 220

Gly Leu Ile Ser Phe His Val Thr Leu Leu Asp Asp Ser Asn Glu Asp
225                 230                 235                 240

Phe Ser Ala Ser Pro Ile Phe Thr Asp Thr Val Val Phe Arg Val Ala
                245                 250                 255

Pro Trp Ile Met Thr Pro Ser Thr Leu Pro Pro Leu Glu Val Tyr Val
            260                 265                 270

Cys Arg Val Arg Asn Asn Thr Cys Phe Val Asp Ala Val Ala Glu Leu
        275                 280                 285

Ala Arg Lys Ala Gly Cys Lys Leu Thr Ile Cys Pro Gln Ala Glu Asn
    290                 295                 300

Arg Asn Asp Arg Trp Ile Gln Asp Glu Met Glu Leu Gly Tyr Val Gln
305                 310                 315                 320

Ala Pro His Lys Thr Leu Pro Val Val Phe Asp Ser Pro Arg Asn Gly
                325                 330                 335

Glu Leu Gln Asp Phe Pro Tyr Lys Arg Ile Leu Gly Pro Asp Phe Gly
            340                 345                 350

Tyr Val Thr Arg Glu Pro Arg Asp Arg Ser Val Ser Gly Leu Asp Ser
        355                 360                 365

Phe Gly Asn Leu Glu Val Ser Pro Pro Val Val Ala Asn Gly Lys Glu
    370                 375                 380

Tyr Pro Leu Gly Arg Ile Leu Ile Gly Gly Asn Leu Pro Gly Ser Ser
385                 390                 395                 400

Gly Arg Arg Val Thr Gln Val Val Arg Asp Phe Leu His Ala Gln Lys
                405                 410                 415

Val Gln Pro Pro Val Glu Leu Phe Val Asp Trp Leu Ala Val Gly His
            420                 425                 430

Val Asp Glu Phe Leu Ser Phe Val Pro Ala Pro Asp Gly Lys Gly Phe
        435                 440                 445

Arg Met Leu Leu Ala Ser Pro Gly Ala Cys Phe Lys Leu Phe Gln Glu
    450                 455                 460

Lys Gln Lys Cys Gly His Gly Arg Ala Leu Leu Phe Gln Gly Val Val
465                 470                 475                 480

Asp Asp Glu Gln Val Lys Thr Ile Ser Ile Asn Gln Val Leu Ser Asn
                485                 490                 495

Lys Asp Leu Ile Asn Tyr Asn Lys Phe Val Gln Ser Cys Ile Asp Trp
            500                 505                 510

Asn Arg Glu Val Leu Lys Arg Glu Leu Gly Leu Ala Glu Cys Asp Ile
        515                 520                 525

Ile Asp Ile Pro Gln Leu Phe Lys Thr Glu Arg Lys Lys Ala Thr Ala
    530                 535                 540

Phe Phe Pro Asp Leu Val Asn Met Leu Val Leu Gly Lys His Leu Gly
545                 550                 555                 560
```

```
Ile Pro Lys Pro Phe Gly Pro Ile Ile Asn Gly Cys Cys Cys Leu Glu
                565                 570                 575

Glu Lys Val Gln Ser Leu Leu Glu Pro Leu Gly Leu His Cys Thr Phe
            580                 585                 590

Ile Asp Asp Phe Thr Pro Tyr His Met Leu His Gly Glu Val His Cys
        595                 600                 605

Gly Thr Asn Val Cys Arg Lys Pro Phe Ser Phe Lys Trp Trp Asn Met
    610                 615                 620

Val Pro
625


<210> SEQ ID NO 37
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X2, mRNA

<400> SEQUENCE: 37

agaaatggat ggatgtgact gtgtgctaat aaaactttat ttatacaaac aggcagtagg     60

ccagatttgg cccacagttc ataatgtgct gatcctgacc taggcgagaa gagaaaccaa    120

atatgaaact gttgaagaac ttgggactga attatgttgg aacttggtgc cctgggagtt    180

aagaggagaa ggtcgagcgg cagtgggtct gggggcccag tgggtatggc ggcatcttgc    240

tggtgaactg tgaccgtgat gatccgagct gtgatgtcca ggacaattgt gaccagcacg    300

tgcactgcct gcaagacctg gaagacatgt ctgtcatggt cctgcggacg cagggccctg    360

cagccctctt tgatgaccac aaacttgtcc tccatacctc cagctatgat gccaaacggg    420

cacaggtctt ccacatctgc ggtcctgagg atgtgtgtga ggcctatagg catgtgctgg    480

gccaagataa ggtgtcctat gaggtacccc gcttgcatgg ggatgaggag cgcttcttcg    540

tggaaggcct gtccttccct gatgccggct tcacaggact catctccttc catgtcactc    600

tgctggacga ctccaacgag gatttctcgg catcccctat cttcactgac actgtggtgt    660

tccgagtggc accctggatc atgacgccca gcactctgcc acccctagag gtgtatgtgt    720

gccgtgtgag gaacaacacg tgttttgtgg atgcggtggc agagctggcc aggaaggccg    780

gctgcaagct gaccatctgc ccacaggccg agaaccgcaa cgaccgctgg atccaggatg    840

agatggagct gggctacgtt caggcgccgc acaagaccct cccggtggtc tttgactccc    900

caaggaatgg ggaactgcag gatttccctt acaaaagaat cctgggtcca gattttggtt    960

acgtgactcg ggaaccacgc gacaggtctg tgagtggcct ggactccttt gggaacctgg   1020

aggtcagccc tccagtggtg gccaatggga aagagtaccc cctggggagg atcctcattg   1080

ggggcaacct gcctgggtca agtggccgca gggtcaccca ggtggtgcgg gacttcctcc   1140

atgcccagaa ggtgcagccc cccgtggagc tctttgtgga ctggttggcc gtgggccatg   1200

tggatgagtt tctgagcttt gtccctgccc ccgatgggaa gggcttccgg atgctcctgg   1260

ccagccctgg ggcctgcttc aagctcttcc aggaaaagca gaagtgtggc cacgggaggg   1320

ccctcctgtt ccagggggtt gttgatgatg agcaggtcaa gaccatctcc atcaaccagg   1380

tgctctccaa taaagacctc atcaactaca ataagtttgt gcagagctgc atcgactgga   1440

accgtgaggt gctgaagcgg gagctgggcc tggcagagtg tgacatcatt gacatcccac   1500

agctcttcaa gaccgagagg aaaaaagcaa cggccttctt ccctgacttg gtgaacatgc   1560
```

-continued

```
tggtgctggg gaagcacctg ggcatcccca agccctttgg gcccatcatc aatggctgct   1620
gctgcctgga ggagaaggtg cggtccctgc tggagccgct gggcctccac tgcaccttca   1680
ttgatgactt cactccatac cacatgctgc atggggaggt gcactgtggc accaatgtgt   1740
gcagaaagcc cttctctttc aagtggtgga acatggtgcc ctgagacagc tcccacccac   1800
catcctgtcc ccctggggcg ggcattggcc caggtggtgg agacagagac aggcccctga   1860
acgataagca ccaagagacc ccaaggctcc agatggaaca ctgagggtga ccgtccctct   1920
cagaagcctt ttccctggaa gtgtccatgc ctcacctgca acccatgtgg ttctcagact   1980
tgaatcttct cggcccccca aaaagaagga cctcatttct tatagcctct cctgtgattc   2040
aacacaaccc atggagatgt ccccttctca ctctgaaatc atccatttgg ggacaaatcc   2100
acattggggt ctagaaacat ccacgtatct catcagccat cttgtcctgt gcatcctaac   2160
agaggaagga tccatgattc tgctttggtc caattgcttc ctctctgcag aggaacaacc   2220
ctaaaaccag accactccac gcaggacagg caggagagat tcttcctaaa gcctccccca   2280
taaaaaggga gctgtggatc cacttagatc agggcggaac catctttcac ccggccaagc   2340
tcctgcccag atgttgaccc tcacccagcg tgagctgtca catagtagga gcttctagat   2400
gcatgtggaa gcaatgagag ttgtccctta gccttataaa ctccccatga tctgacatgc   2460
agaaatccag ccttgtccag aatcctcctg gaatttcttg gagacgaaag tatctggggg   2520
attgttgggt actagggaga ctgggtacaa gggtgaaaag tagttcccat aatacacatg   2580
gttgactatg gtgatccacc ttgtgatggt taatattagg tgtctggaga aggttgcttc   2640
attggccctg ggacttctct ctgcaggagg agagaacgct gcctctcctc tggattggtc   2700
tcaggctctc tgttggcctt tggtcagcgt ttccacatcc tgctctgctg caggagaggg   2760
ggctaagggg ctggatccac caaggcagct cacagcggga aaactctggg aatgaaccac   2820
tgaattcagg ggatgggggt ggggggcgg ttctcgaggt gtgtgccagc tacacgtgtg   2880
ttctgtatgg gtccagctgc gtttccatca ctcgctaata aatcaacaga aacacaaa     2938
```

```
<210> SEQ ID NO 38
<211> LENGTH: 485
<212> TYPE: PRT
<213> ORGANISM: Homo sapiens
<220> FEATURE:
<223> OTHER INFORMATION: protein-arginine deiminase type-3 isoform X2
      [Homo sapiens]

<400> SEQUENCE: 38

Met Ser Val Met Val Leu Arg Thr Gln Gly Pro Ala Ala Leu Phe Asp
1               5                   10                  15

Asp His Lys Leu Val Leu His Thr Ser Ser Tyr Asp Ala Lys Arg Ala
            20                  25                  30

Gln Val Phe His Ile Cys Gly Pro Glu Asp Val Cys Glu Ala Tyr Arg
        35                  40                  45

His Val Leu Gly Gln Asp Lys Val Ser Tyr Glu Val Pro Arg Leu His
    50                  55                  60

Gly Asp Glu Glu Arg Phe Phe Val Glu Gly Leu Ser Phe Pro Asp Ala
65                  70                  75                  80

Gly Phe Thr Gly Leu Ile Ser Phe His Val Thr Leu Leu Asp Asp Ser
                85                  90                  95

Asn Glu Asp Phe Ser Ala Ser Pro Ile Phe Thr Asp Thr Val Val Phe
            100                 105                 110

Arg Val Ala Pro Trp Ile Met Thr Pro Ser Thr Leu Pro Pro Leu Glu
```

-continued

```
        115                 120                 125

Val Tyr Val Cys Arg Val Arg Asn Asn Thr Cys Phe Val Asp Ala Val
    130                 135                 140

Ala Glu Leu Ala Arg Lys Ala Gly Cys Lys Leu Thr Ile Cys Pro Gln
145                 150                 155                 160

Ala Glu Asn Arg Asn Asp Arg Trp Ile Gln Asp Glu Met Glu Leu Gly
                165                 170                 175

Tyr Val Gln Ala Pro His Lys Thr Leu Pro Val Val Phe Asp Ser Pro
            180                 185                 190

Arg Asn Gly Glu Leu Gln Asp Phe Pro Tyr Lys Arg Ile Leu Gly Pro
        195                 200                 205

Asp Phe Gly Tyr Val Thr Arg Glu Pro Arg Asp Arg Ser Val Ser Gly
    210                 215                 220

Leu Asp Ser Phe Gly Asn Leu Glu Val Ser Pro Pro Val Val Ala Asn
225                 230                 235                 240

Gly Lys Glu Tyr Pro Leu Gly Arg Ile Leu Ile Gly Gly Asn Leu Pro
                245                 250                 255

Gly Ser Ser Gly Arg Arg Val Thr Gln Val Val Arg Asp Phe Leu His
            260                 265                 270

Ala Gln Lys Val Gln Pro Pro Val Glu Leu Phe Val Asp Trp Leu Ala
        275                 280                 285

Val Gly His Val Asp Glu Phe Leu Ser Phe Val Pro Ala Pro Asp Gly
    290                 295                 300

Lys Gly Phe Arg Met Leu Leu Ala Ser Pro Gly Ala Cys Phe Lys Leu
305                 310                 315                 320

Phe Gln Glu Lys Gln Lys Cys Gly His Gly Arg Ala Leu Leu Phe Gln
                325                 330                 335

Gly Val Val Asp Asp Glu Gln Val Lys Thr Ile Ser Ile Asn Gln Val
            340                 345                 350

Leu Ser Asn Lys Asp Leu Ile Asn Tyr Asn Lys Phe Val Gln Ser Cys
        355                 360                 365

Ile Asp Trp Asn Arg Glu Val Leu Lys Arg Glu Leu Gly Leu Ala Glu
    370                 375                 380

Cys Asp Ile Ile Asp Ile Pro Gln Leu Phe Lys Thr Glu Arg Lys Lys
385                 390                 395                 400

Ala Thr Ala Phe Phe Pro Asp Leu Val Asn Met Leu Val Leu Gly Lys
                405                 410                 415

His Leu Gly Ile Pro Lys Pro Phe Gly Pro Ile Ile Asn Gly Cys Cys
            420                 425                 430

Cys Leu Glu Glu Lys Val Arg Ser Leu Leu Glu Pro Leu Gly Leu His
        435                 440                 445

Cys Thr Phe Ile Asp Asp Phe Thr Pro Tyr His Met Leu His Gly Glu
    450                 455                 460

Val His Cys Gly Thr Asn Val Cys Arg Lys Pro Phe Ser Phe Lys Trp
465                 470                 475                 480

Trp Asn Met Val Pro
                485
```

<210> SEQ ID NO 39
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X2, mRNA

<400> SEQUENCE: 39
agaaatggat ggatgtgact gtgtgctaat aaaactttat ttatacaaac aggcagtagg 60
ccagatttgg cccacagttc ataatgtgct gatcctgacc taggcgagaa gagaaaccaa 120
atatgaaact gttgaagaac ttgggactga attatgttgg aacttggtgc cctgggagtt 180
aagaggagaa ggtcgagcgg cagtgggtct gggggcccag tgggtatggc ggcatcttgc 240
tggtgaactg tgaccgtgat gatccgagct gtgatgtcca ggacaattgt gaccagcacg 300
tgcactgcct gcaagacctg gaagacatgt ctgtcatggt cctgcggacg cagggccctg 360
cagccctctt tgatgaccac aaacttgtcc tccatacctc cagctatgat gccaaacggg 420
cacaggtctt ccacatctgc ggtcctgagg atgtgtgtga ggcctatagg catgtgctgg 480
gccaagataa ggtgtcctat gaggtacccc gcttgcatgg ggatgaggag cgcttcttcg 540
tggaaggcct gtccttccct gatgccggct tcacaggact catctccttc catgtcactc 600
tgctggacga ctccaacgag gatttctcgg catcccctat cttcactgac actgtggtgt 660
tccgagtggc accctggatc atgacgccca gcactctgcc acccctagag gtgtatgtgt 720
gccgtgtgag gaacaacacg tgttttgtgg atgcggtggc agagctggcc aggaaggccg 780
gctgcaagct gaccatctgc ccacaggccg agaaccgcaa cgaccgctgg atccaggatg 840
agatggagct gggctacgtt caggcgccgc acaagaccct cccggtggtc tttgactccc 900
caaggaatgg ggaactgcag gatttccctt acaaaagaat cctgggtcca gattttggtt 960
acgtgactcg ggaaccacgc gacaggtctg tgagtggcct ggactccttt gggaacctgg 1020
aggtcagccc tccagtggtg gccaatggga aagagtaccc cctggggagg atcctcattg 1080
ggggcaacct gcctgggtca agtggccgca gggtcaccca ggtggtgcgg gacttcctcc 1140
atgcccagaa ggtgcagccc cccgtggagc tctttgtgga ctggttggcc gtgggccatg 1200
tggatgagtt tctgagcttt gtccctgccc ccgatgggaa gggcttccgg atgctcctgg 1260
ccagccctgg ggcctgcttc aagctcttcc aggaaaagca gaagtgtggc cacgggaggg 1320
ccctcctgtt ccaggggggtt gttgatgatg agcaggtcaa gaccatctcc atcaaccagg 1380
tgctctccaa taaagacctc atcaactaca ataagtttgt gcagagctgc atcgactgga 1440
accgtgaggt gctgaagcgg gagctgggcc tggcagagtg tgacatcatt gacatcccac 1500
agctcttcaa gaccgagagg aaaaaagcaa cggccttctt ccctgacttg gtgaacatgc 1560
tggtgctggg gaagcacctg ggcatcccca agccctttgg gcccatcatc aatggctgct 1620
gctgcctgga ggagaaggtg cggtccctgc tggagccgct gggcctccac tgcaccttca 1680
ttgatgactt cactccatac cacatgctgc atggggaggt gcactgtggc accaatgtgt 1740
gcagaaagcc cttctctttc aagtggtgga acatggtgcc ctgagacagc tcccacccac 1800
catcctgtcc ccctggggcg ggcattggcc caggtggtgg agacagagac aggcccctga 1860
acgataagca ccaagagacc ccaaggctcc agatggaaca ctgagggtga ccgtccctct 1920
cagaagcctt ttccctggaa gtgtccatgc ctcacctgca acccatgtgg ttctcagact 1980
tgaatcttct cggcccccca aaaagaagga cctcatttct tatagcctct cctgtgattc 2040
aacacaaccc atggagatgt ccccttctca ctctgaaatc atccatttgg ggacaaatcc 2100
acattggggt ctagaaacat ccacgtatct catcagccat cttgtcctgt gcatcctaac 2160
agaggaagga tccatgattc tgctttggtc caattgcttc ctctctgcag aggaacaacc 2220
ctaaaaccag accactccac gcaggacagg caggagagat tcttcctaaa gcctccccca 2280
taaaaaggga gctgtggatc cacttagatc agggcggaac catctttcac ccggccaagc 2340
tcctgcccag atgttgaccc tcacccagcg tgagctgtca catagtagga gcttctagat 2400
gcatgtggaa gcaatgagag ttgtccctta gccttataaa ctccccatga tctgacatgc 2460
agaaatccag ccttgtccag aatcctcctg gaatttcttg gagacgaaag tatctggggg 2520
attgttgggt actagggaga ctgggtacaa gggtgaaaag tagttcccat aatacacatg 2580
gttgactatg gtgatccacc ttgtgatggt taatattagg tgtctggaga aggttgcttc 2640
attggccctg ggacttctct ctgcaggagg agagaacgct gcctctcctc tggattggtc 2700
tcaggctctc tgttggcctt tggtcagcgt ttccacatcc tgctctgctg caggagaggg 2760
ggctaagggg ctggatccac caaggcagct cacagcggga aaactctggg aatgaaccac 2820
tgaattcagg ggatgggggt gggggggcgg ttctcgaggt gtgtgccagc tacacgtgtg 2880
ttctgtatgg gtccagctgc gtttccatca ctcgctaata aatcaacaga aacacaaa 2938

<210> SEQ ID NO 40
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X2, mRNA

<400> SEQUENCE: 40
agaaatggat ggatgtgact gtgtgctaat aaaactttat ttatacaaac aggcagtagg 60
ccagatttgg cccacagttc ataatgtgct gatcctgacc taggcgagaa gagaaaccaa 120
atatgaaact gttgaagaac ttgggactga attatgttgg aacttggtgc cctgggagtt 180
aagaggagaa ggtcgagcgg cagtgggtct gggggcccag tgggtatggc ggcatcttgc 240
tggtgaactg tgaccgtgat gatccgagct gtgatgtcca ggacaattgt gaccagcacg 300
tgcactgcct gcaagacctg gaagacatgt ctgtcatggt cctgcggacg cagggccctg 360
cagccctctt tgatgaccac aaacttgtcc tccatacctc cagctatgat gccaaacggg 420
cacaggtctt ccacatctgc ggtcctgagg atgtgtgtga ggcctatagg catgtgctgg 480
gccaagataa ggtgtcctat gaggtacccc gcttgcatgg ggatgaggag cgcttcttcg 540
tggaaggcct gtccttccct gatgccggct tcacaggact catctccttc catgtcactc 600
tgctggacga ctccaacgag gatttctcgg catcccctat cttcactgac actgtggtgt 660
tccgagtggc accctggatc atgacgccca gcactctgcc acccctagag gtgtatgtgt 720
gccgtgtgag gaacaacacg tgttttgtgg atgcggtggc agagctggcc aggaaggccg 780
gctgcaagct gaccatctgc ccacaggccg agaaccgcaa cgaccgctgg atccaggatg 840
agatggagct gggctacgtt caggcgccgc acaagaccct cccggtggtc tttgactccc 900
caaggaatgg ggaactgcag gatttccctt acaaaagaat cctgggtcca gattttggtt 960
acgtgactcg ggaaccacgc gacaggtctg tgagtggcct ggactccttt gggaacctgg 1020
aggtcagccc tccagtggtg gccaatggga aagagtaccc cctggggagg atcctcattg 1080 gggcaacct gcctgggtca agtggccgca gggtcaccca ggtggtgcgg gacttcctcc 1140
atgcccagaa ggtgcagccc cccgtggagc tctttgtgga ctggttggcc gtgggccatg 1200
tggatgagtt tctgagcttt gtccctgccc ccgatgggaa gggcttccgg atgctcctgg 1260
ccagccctgg ggcctgcttc aagctcttcc aggaaaagca gaagtgtggc cacgggaggg 1320
ccctcctgtt ccagggggtt gttgatgatg agcaggtcaa gaccatctcc atcaaccagg 1380

-continued

```
tgctctccaa taaagacctc atcaactaca ataagtttgt gcagagctgc atcgactgga   1440

accgtgaggt gctgaagcgg gagctgggcc tggcagagtg tgacatcatt gacatcccac   1500

agctcttcaa gaccgagagg aaaaaagcaa cggccttctt ccctgacttg gtgaacatgc   1560

tggtgctggg gaagcacctg ggcatcccca agccctttgg gcccatcatc aatggctgct   1620

gctgcctgga ggagaaggtg cggtccctgc tggagccgct gggcctccac tgcaccttca   1680

ttgatgactt cactccatac cacatgctgc atggggaggt gcactgtggc accaatgtgt   1740

gcagaaagcc cttctctttc aagtggtgga acatggtgcc ctgagacagc tcccacccac   1800

catcctgtcc ccctggggcg ggcattggcc caggtggtgg agacagagac aggcccctga   1860

acgataagca ccaagagacc ccaaggctcc agatggaaca ctgagggtga ccgtccctct   1920

cagaagcctt ttccctggaa gtgtccatgc ctcacctgca acccatgtgg ttctcagact   1980

tgaatcttct cggcccccca aaaagaagga cctcatttct tatagcctct cctgtgattc   2040

aacacaaccc atggagatgt ccccttctca ctctgaaatc atccatttgg ggacaaatcc   2100

acattggggt ctagaaacat ccacgtatct catcagccat cttgtcctgt gcatcctaac   2160

agaggaagga tccatgattc tgctttggtc caattgcttc ctctctgcag aggaacaacc   2220

ctaaaaccag accactccac gcaggacagg caggagagat tcttcctaaa gcctccccca   2280

taaaaaggga gctgtggatc cacttagatc agggcggaac catctttcac ccggccaagc   2340

tcctgcccag atgttgaccc tcacccagcg tgagctgtca catagtagga gcttctagat   2400

gcatgtggaa gcaatgagag ttgtccctta gccttataaa ctccccatga tctgacatgc   2460

agaaatccag ccttgtccag aatcctcctg gaatttcttg gagacgaaag tatctggggg   2520

attgttgggt actagggaga ctgggtacaa gggtgaaaag tagttcccat aatacacatg   2580

gttgactatg gtgatccacc ttgtgatggt taatattagg tgtctggaga aggttgcttc   2640

attggccctg ggacttctct ctgcaggagg agagaacgct gcctctcctc tggattggtc   2700

tcaggctctc tgttggcctt tggtcagcgt ttccacatcc tgctctgctg caggagaggg   2760

ggctaagggg ctggatccac caaggcagct cacagcggga aaactctggg aatgaaccac   2820

tgaattcagg ggatgggggt ggggggcgg ttctcgaggt gtgtgccagc tacacgtgtg   2880

ttctgtatgg gtccagctgc gtttccatca ctcgctaata aatcaacaga aacacaaa     2938
```

<210> SEQ ID NO 41
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X2, mRNA

<400> SEQUENCE: 41

```
agaaatggat ggatgtgact gtgtgctaat aaaactttat ttatacaaac aggcagtagg     60

ccagatttgg cccacagttc ataatgtgct gatcctgacc taggcgagaa gagaaaccaa    120

atatgaaact gttgaagaac ttgggactga attatgttgg aacttggtgc cctgggagtt    180

aagaggagaa ggtcgagcgg cagtgggtct gggggcccag tgggtatggc ggcatcttgc    240

tggtgaactg tgaccgtgat gatccgagct gtgatgtcca ggacaattgt gaccagcacg    300

tgcactgcct gcaagacctg gaagacatgt ctgtcatggt cctgcggacg cagggccctg    360

cagccctctt tgatgaccac aaacttgtcc tccatacctc cagctatgat gccaaacggg    420

cacaggtctt ccacatctgc ggtcctgagg atgtgtgtga ggcctatagg catgtgctgg    480
```

-continued

```
gccaagataa ggtgtcctat gaggtacccc gcttgcatgg ggatgaggag cgcttcttcg    540
tggaaggcct gtccttccct gatgccggct tcacaggact catctccttc catgtcactc    600
tgctggacga ctccaacgag gatttctcgg catcccctat cttcactgac actgtggtgt    660
tccgagtggt accctggatc atgacgccca gcactctgcc acccctagag gtgtatgtgt    720
gccgtgtgag gaacaacacg tgttttgtgg atgcggtggc agagctggcc aggaaggccg    780
gctgcaagct gaccatctgc ccacaggccg agaaccgcaa cgaccgctgg atccaggatg    840
agatggagct gggctacgtt caggcgccgc acaagaccct cccggtggtc tttgactccc    900
caaggaatgg ggaactgcag gatttccctt acaaaagaat cctgggtcca gattttggtt    960
acgtgactcg ggaaccacgc gacaggtctg tgagtggcct ggactccttt gggaacctgg   1020
aggtcagccc tccagtggtg gccaatggga aagagtaccc cctggggagg atcctcattg   1080
ggggcaacct gcctgggtca agtggccgca gggtcaccca ggtggtgcgg gacttcctcc   1140
atgcccagaa ggtgcagccc cccgtggagc tctttgtgga ctggttggcc gtgggccatg   1200
tggatgagtt tctgagcttt gtccctgccc ccgatgggaa gggcttccgg atgctcctgg   1260
ccagccctgg ggcctgcttc aagctcttcc aggaaaagca gaagtgtggc cacgggaggg   1320
ccctcctgtt ccaggggggtt gttgatgatg agcaggtcaa gaccatctcc atcaaccagg   1380
tgctctccaa taaagacctc atcaactaca ataagtttgt gcagagctgc atcgactgga   1440
accgtgaggt gctgaagcgg gagctgggcc tggcagagtg tgacatcatt gacatcccac   1500
agctcttcaa gaccgagagg aaaaaagcaa cggccttctt ccctgacttg gtgaacatgc   1560
tggtgctggg gaagcacctg ggcatcccca agccctttgg gcccatcatc aatggctgct   1620
gctgcctgga ggagaaggtg cggtccctgc tggagccgct gggcctccac tgcaccttca   1680
ttgatgactt cactccatac cacatgctgc atggggaggt gcactgtggc accaatgtgt   1740
gcagaaagcc cttctctttc aagtggtgga acatggtgcc ctgagacagc tcccacccac   1800
catcctgtcc ccctggggcg ggcattggcc caggtggtgg agacagagac aggcccctga   1860
acgataagca ccaagagacc ccaaggctcc agatggaaca ctgagggtga ccgtccctct   1920
cagaagcctt ttccctggaa gtgtccatgc ctcacctgca acccatgtgg ttctcagact   1980
tgaatcttct cggcccccca aaaagaagga cctcatttct tatagcctct cctgtgattc   2040
aacacaaccc atggagatgt ccccttctca ctctgaaatc atccatttgg ggacaaatcc   2100
acattggggt ctagaaacat ccacgtatct catcagccat cttgtcctgt gcatcctaac   2160
agaggaagga tccatgattc tgctttggtc caattgcttc ctctctgcag aggaacaacc   2220
ctaaaaccag accactccac gcaggacagg caggagagat tcttcctaaa gcctccccca   2280
taaaaaggga gctgtggatc cacttagatc agggcggaac catctttcac ccggccaagc   2340
tcctgcccag atgttgaccc tcacccagcg tgagctgtca catagtagga gcttctagat   2400
gcatgtggaa gcaatgagag ttgtccctta gccttataaa ctccccatga tctgacatgc   2460
agaaatccag ccttgtccag aatcctcctg gaatttcttg gagacgaaag tatctggggg   2520
attgttgggt actagggaga ctgggtacaa gggtgaaaag tagttcccat aatacacatg   2580
gttgactatg gtgatccacc ttgtgatggt taatattagg tgtctggaga aggttgcttc   2640
attggccctg ggacttctct ctgcaggagg agagaacgct gcctctcctc tggattggtc   2700
tcaggctctc tgttggcctt tggtcagcgt ttccacatcc tgctctgctg caggagaggg   2760
ggctaagggg ctggatccac caaggcagct cacagcggga aaactctggg aatgaaccac   2820
tgaattcagg ggatgggggt gggggggcgg ttctcgaggt gtgtgccagc tacacgtgtg   2880
```

ttctgtatgg gtccagctgc gtttccatca ctcgctaata aatcaacaga aacacaaa 2938

<210> SEQ ID NO 42
<211> LENGTH: 485
<212> TYPE: PRT
<213> ORGANISM: Homo sapiens
<220> FEATURE:
<223> OTHER INFORMATION: protein-arginine deiminase type-3 isoform X2
[Homo sapiens]

<400> SEQUENCE: 42

Met Ser Val Met Val Leu Arg Thr Gln Gly Pro Ala Ala Leu Phe Asp
1 5 10 15

Asp His Lys Leu Val Leu His Thr Ser Ser Tyr Asp Ala Lys Arg Ala
20 25 30

Gln Val Phe His Ile Cys Gly Pro Glu Asp Val Cys Glu Ala Tyr Arg
35 40 45

His Val Leu Gly Gln Asp Lys Val Ser Tyr Glu Val Pro Arg Leu His
50 55 60

Gly Asp Glu Glu Arg Phe Phe Val Glu Gly Leu Ser Phe Pro Asp Ala
65 70 75 80

Gly Phe Thr Gly Leu Ile Ser Phe His Val Thr Leu Leu Asp Asp Ser
85 90 95

Asn Glu Asp Phe Ser Ala Ser Pro Ile Phe Thr Asp Thr Val Val Phe
100 105 110

Arg Val Val Pro Trp Ile Met Thr Pro Ser Thr Leu Pro Pro Leu Glu
115 120 125

Val Tyr Val Cys Arg Val Arg Asn Asn Thr Cys Phe Val Asp Ala Val
130 135 140

Ala Glu Leu Ala Arg Lys Ala Gly Cys Lys Leu Thr Ile Cys Pro Gln
145 150 155 160

Ala Glu Asn Arg Asn Asp Arg Trp Ile Gln Asp Glu Met Glu Leu Gly
165 170 175

Tyr Val Gln Ala Pro His Lys Thr Leu Pro Val Val Phe Asp Ser Pro
180 185 190

Arg Asn Gly Glu Leu Gln Asp Phe Pro Tyr Lys Arg Ile Leu Gly Pro
195 200 205

Asp Phe Gly Tyr Val Thr Arg Glu Pro Arg Asp Arg Ser Val Ser Gly
210 215 220

Leu Asp Ser Phe Gly Asn Leu Glu Val Ser Pro Pro Val Val Ala Asn
225 230 235 240

Gly Lys Glu Tyr Pro Leu Gly Arg Ile Leu Ile Gly Gly Asn Leu Pro
245 250 255

Gly Ser Ser Gly Arg Arg Val Thr Gln Val Val Arg Asp Phe Leu His
260 265 270

Ala Gln Lys Val Gln Pro Pro Val Glu Leu Phe Val Asp Trp Leu Ala
275 280 285

Val Gly His Val Asp Glu Phe Leu Ser Phe Val Pro Ala Pro Asp Gly
290 295 300

Lys Gly Phe Arg Met Leu Leu Ala Ser Pro Gly Ala Cys Phe Lys Leu
305 310 315 320

Phe Gln Glu Lys Gln Lys Cys Gly His Gly Arg Ala Leu Leu Phe Gln
325 330 335

Gly Val Val Asp Asp Glu Gln Val Lys Thr Ile Ser Ile Asn Gln Val
340 345 350

-continued

Leu Ser Asn Lys Asp Leu Ile Asn Tyr Asn Lys Phe Val Gln Ser Cys
        355                 360                 365

Ile Asp Trp Asn Arg Glu Val Leu Lys Arg Glu Leu Gly Leu Ala Glu
    370                 375                 380

Cys Asp Ile Ile Asp Ile Pro Gln Leu Phe Lys Thr Glu Arg Lys Lys
385                 390                 395                 400

Ala Thr Ala Phe Phe Pro Asp Leu Val Asn Met Leu Val Leu Gly Lys
                405                 410                 415

His Leu Gly Ile Pro Lys Pro Phe Gly Pro Ile Ile Asn Gly Cys Cys
            420                 425                 430

Cys Leu Glu Glu Lys Val Arg Ser Leu Leu Glu Pro Leu Gly Leu His
        435                 440                 445

Cys Thr Phe Ile Asp Asp Phe Thr Pro Tyr His Met Leu His Gly Glu
    450                 455                 460

Val His Cys Gly Thr Asn Val Cys Arg Lys Pro Phe Ser Phe Lys Trp
465                 470                 475                 480

Trp Asn Met Val Pro
                485

<210> SEQ ID NO 43
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X2, mRNA

<400> SEQUENCE: 43
agaaatggat ggatgtgact gtgtgctaat aaaactttat ttatacaaac aggcagtagg 60
ccagatttgg cccacagttc ataatgtgct gatcctgacc taggcgagaa gagaaaccaa 120
atatgaaact gttgaagaac ttgggactga attatgttgg aacttggtgc cctgggagtt 180
aagaggagaa ggtcgagcgg cagtgggtct gggggcccag tgggtatggc ggcatcttgc 240
tggtgaactg tgaccgtgat gatccgagct gtgatgtcca ggacaattgt gaccagcacg 300
tgcactgcct gcaagacctg gaagacatgt ctgtcatggt cctgcggacg cagggccctg 360
cagccctctt tgatgaccac aaacttgtcc tccatacctc cagctatgat gccaaacggg 420
cacaggtctt ccacatctgc ggtcctgagg atgtgtgtga ggcctatagg catgtgctgg 480
gccaagataa ggtgtcctat gaggtacccc gcttgcatgg ggatgaggag cgcttcttcg 540
tggaaggcct gtccttccct gatgccggct tcacaggact catctccttc catgtcactc 600
tgctggacga ctccaacgag gatttctcgg catcccctat cttcactgac actgtggtgt 660
tccgagtggc accctggatc atgacgccca gcactctgcc acccctagag gtgtatgtgt 720
gccgtgtgag gaacaacacg tgttttgtgg atgcggtggc agagctggcc aggaaggccg 780
gctgcaagct gaccatctgc ccacaggccg agaaccgcaa cgaccgctgg atccaggatg 840
agatggagct gggctacgtt caggcgccgc acaagaccct cccggtggtc tttgactccc 900
caaggaatgg ggaactgcag gatttccctt acaaaagaat cctgggtcca gattttggtt 960
acgtgactcg ggaaccacgc gacaggtctg tgagtggcct ggactccttt gggaacctgg 1020
aggtcagccc tccagtggtg gccaatggga aagagtaccc cctggggagg atcctcattg 1080
ggggcaacct gcctgggtca agtggccgca gggtcaccca ggtggtgcgg gacttcctcc 1140
atgcccagaa ggtgcagccc cccgtggagc tctttgtgga ctggttggcc gtgggccatg 1200

-continued

```
tggatgagtt tctgagcttt gtccctgccc ccgatgggaa gggcttccgg atgctcctgg   1260

ccagccctgg ggcctgcttc aagctcttcc aggaaaagca gaagtgtggc cacgggaggg   1320

ccctcctgtt ccaggggggtt gttgatgatg agcaggtcaa gaccatctcc atcaaccagg   1380

tgctctccaa taaagacctc atcaactaca ataagtttgt gcagagctgc atcgactgga   1440

accgtgaggt gctgaagcgg gagctgggcc tggcagagtg tgacatcatt gacatcccac   1500

agctcttcaa gaccgagagg aaaaaagcaa cgaccttctt ccctgacttg gtgaacatgc   1560

tggtgctggg gaagcacctg ggcatcccca agccctttgg gcccatcatc aatggctgct   1620

gctgcctgga ggagaaggtg cggtccctgc tggagccgct gggcctccac tgcaccttca   1680

ttgatgactt cactccatac cacatgctgc atggggaggt gcactgtggc accaatgtgt   1740

gcagaaagcc cttctctttc aagtggtgga acatggtgcc ctgagacagc tcccacccac   1800

catcctgtcc ccctggggcg ggcattggcc caggtggtgg agacagagac aggcccctga   1860

acgataagca ccaagagacc ccaaggctcc agatggaaca ctgagggtga ccgtccctct   1920

cagaagcctt ttccctggaa gtgtccatgc ctcacctgca acccatgtgg ttctcagact   1980

tgaatcttct cggcccccca aaaagaagga cctcatttct tatagcctct cctgtgattc   2040

aacacaaccc atggagatgt ccccttctca ctctgaaatc atccatttgg ggacaaatcc   2100

acattggggt ctagaaacat ccacgtatct catcagccat cttgtcctgt gcatcctaac   2160

agaggaagga tccatgattc tgctttggtc caattgcttc ctctctgcag aggaacaacc   2220

ctaaaaccag accactccac gcaggacagg caggagagat tcttcctaaa gcctccccca   2280

taaaaaggga gctgtggatc cacttagatc agggcggaac catctttcac ccggccaagc   2340

tcctgcccag atgttgaccc tcacccagcg tgagctgtca catagtagga gcttctagat   2400

gcatgtggaa gcaatgagag ttgtccctta gccttataaa ctccccatga tctgacatgc   2460

agaaatccag ccttgtccag aatcctcctg gaatttcttg gagacgaaag tatctggggg   2520

attgttgggt actagggaga ctgggtacaa gggtgaaaag tagttcccat aatacacatg   2580

gttgactatg gtgatccacc ttgtgatggt taatattagg tgtctggaga aggttgcttc   2640

attggccctg ggacttctct ctgcaggagg agagaacgct gcctctcctc tggattggtc   2700

tcaggctctc tgttggcctt tggtcagcgt ttccacatcc tgctctgctg caggagaggg   2760

ggctaagggg ctggatccac caaggcagct cacagcggga aaactctggg aatgaaccac   2820

tgaattcagg ggatgggggt ggggggcgg ttctcgaggt gtgtgccagc tacacgtgtg   2880

ttctgtatgg gtccagctgc gtttccatca ctcgctaata aatcaacaga aacacaaa     2938


<210> SEQ ID NO 44
<211> LENGTH: 485
<212> TYPE: PRT
<213> ORGANISM: Homo sapiens
<220> FEATURE:
<223> OTHER INFORMATION: protein-arginine deiminase type-3 isoform X2
      [Homo sapiens]

<400> SEQUENCE: 44

Met Ser Val Met Val Leu Arg Thr Gln Gly Pro Ala Ala Leu Phe Asp
1               5                   10                  15

Asp His Lys Leu Val Leu His Thr Ser Ser Tyr Asp Ala Lys Arg Ala
            20                  25                  30

Gln Val Phe His Ile Cys Gly Pro Glu Asp Val Cys Glu Ala Tyr Arg
        35                  40                  45

His Val Leu Gly Gln Asp Lys Val Ser Tyr Glu Val Pro Arg Leu His
```

-continued

```
50                  55                  60

Gly Asp Glu Glu Arg Phe Phe Val Glu Gly Leu Ser Phe Pro Asp Ala
65                  70                  75                  80

Gly Phe Thr Gly Leu Ile Ser Phe His Val Thr Leu Leu Asp Asp Ser
                85                  90                  95

Asn Glu Asp Phe Ser Ala Ser Pro Ile Phe Thr Asp Thr Val Val Phe
            100                 105                 110

Arg Val Ala Pro Trp Ile Met Thr Pro Ser Thr Leu Pro Pro Leu Glu
        115                 120                 125

Val Tyr Val Cys Arg Val Arg Asn Asn Thr Cys Phe Val Asp Ala Val
    130                 135                 140

Ala Glu Leu Ala Arg Lys Ala Gly Cys Lys Leu Thr Ile Cys Pro Gln
145                 150                 155                 160

Ala Glu Asn Arg Asn Asp Arg Trp Ile Gln Asp Glu Met Glu Leu Gly
                165                 170                 175

Tyr Val Gln Ala Pro His Lys Thr Leu Pro Val Val Phe Asp Ser Pro
            180                 185                 190

Arg Asn Gly Glu Leu Gln Asp Phe Pro Tyr Lys Arg Ile Leu Gly Pro
        195                 200                 205

Asp Phe Gly Tyr Val Thr Arg Glu Pro Arg Asp Arg Ser Val Ser Gly
    210                 215                 220

Leu Asp Ser Phe Gly Asn Leu Glu Val Ser Pro Pro Val Val Ala Asn
225                 230                 235                 240

Gly Lys Glu Tyr Pro Leu Gly Arg Ile Leu Ile Gly Gly Asn Leu Pro
                245                 250                 255

Gly Ser Ser Gly Arg Arg Val Thr Gln Val Val Arg Asp Phe Leu His
            260                 265                 270

Ala Gln Lys Val Gln Pro Pro Val Glu Leu Phe Val Asp Trp Leu Ala
        275                 280                 285

Val Gly His Val Asp Glu Phe Leu Ser Phe Val Pro Ala Pro Asp Gly
    290                 295                 300

Lys Gly Phe Arg Met Leu Leu Ala Ser Pro Gly Ala Cys Phe Lys Leu
305                 310                 315                 320

Phe Gln Glu Lys Gln Lys Cys Gly His Gly Arg Ala Leu Leu Phe Gln
                325                 330                 335

Gly Val Val Asp Asp Glu Gln Val Lys Thr Ile Ser Ile Asn Gln Val
            340                 345                 350

Leu Ser Asn Lys Asp Leu Ile Asn Tyr Asn Lys Phe Val Gln Ser Cys
        355                 360                 365

Ile Asp Trp Asn Arg Glu Val Leu Lys Arg Glu Leu Gly Leu Ala Glu
    370                 375                 380

Cys Asp Ile Ile Asp Ile Pro Gln Leu Phe Lys Thr Glu Arg Lys Lys
385                 390                 395                 400

Ala Thr Thr Phe Phe Pro Asp Leu Val Asn Met Leu Val Leu Gly Lys
                405                 410                 415

His Leu Gly Ile Pro Lys Pro Phe Gly Pro Ile Ile Asn Gly Cys Cys
            420                 425                 430

Cys Leu Glu Glu Lys Val Arg Ser Leu Leu Glu Pro Leu Gly Leu His
        435                 440                 445

Cys Thr Phe Ile Asp Asp Phe Thr Pro Tyr His Met Leu His Gly Glu
    450                 455                 460

Val His Cys Gly Thr Asn Val Cys Arg Lys Pro Phe Ser Phe Lys Trp
465                 470                 475                 480
```

Trp Asn Met Val Pro
485

<210> SEQ ID NO 45
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X2, mRNA

<400> SEQUENCE: 45
agaaatggat ggatgtgact gtgtgctaat aaaactttat ttatacaaac aggcagtagg 60
ccagatttgg cccacagttc ataatgtgct gatcctgacc taggcgagaa gagaaaccaa 120
atatgaaact gttgaagaac ttgggactga attatgttgg aacttggtgc cctgggagtt 180
aagaggagaa ggtcgagcgg cagtgggtct gggggcccag tgggtatggc ggcatcttgc 240
tggtgaactg tgaccgtgat gatccgagct gtgatgtcca ggacaattgt gaccagcacg 300
tgcactgcct gcaagacctg gaagacatgt ctgtcatggt cctgcggacg cagggccctg 360
cagccctctt tgatgaccac aaacttgtcc tccatacctc cagctatgat gccaaacggg 420
cacaggtctt ccacatctgc ggtcctgagg atgtgtgtga ggcctatagg catgtgctgg 480
gccaagataa ggtgtcctat gaggtacccc gcttgcatgg ggatgaggag cgcttcttcg 540
tggaaggcct gtccttccct gatgccggct tcacaggact catctccttc catgtcactc 600
tgctggacga ctccaacgag gatttctcgg catcccctat cttcactgac actgtggtgt 660
tccgagtggc accctggatc atgacgccca gcactctgcc acccctagag gtgtatgtgt 720
gccgtgtgag gaacaacacg tgttttgtgg atgcggtggc agagctggcc aggaaggccg 780
gctgcaagct gaccatctgc ccacaggccg agaaccgcaa cgaccgctgg atccaggatg 840
agatggagct gggctacgtt caggcgccgc acaagaccct cccggtggtc tttgactccc 900
caaggaatgg ggaactgcag gatttccctt acaaaagaat cctgggtcca gattttggtt 960
acgtgactcg ggaaccacgc gacaggtctg tgagtggcct ggactccttt gggaacctgg 1020
aggtcagccc tccagtggtg gccaatggga aagagtaccc cctggggagg atcctcattg 1080
ggggcaacct gcctgggtca agtggccgca gggtcaccca ggtggtgcgg gacttcctcc 1140
atgcccagaa ggtgcagccc cccgtggagc tctttgtgga ctggttggcc gtgggccatg 1200
tggatgagtt tctgagcttt gtccctgccc ccgatgggaa gggcttccgg atgctcctgg 1260
ccagccctgg ggcctgcttc aagctcttcc aggaaaagca gaagtgtggc cacgggaggg 1320
ccctcctgtt ccaggggggtt gttgatgatg agcaggtcaa gaccatctcc atcaaccagg 1380
tgctctccaa taaagacctc atcaactaca ataagtttgt gcagagctgc atcgactgga 1440
accgtgaggt gctgaagcgg gagctgggcc tggcagagtg tgacatcatt gacatcccac 1500
agctcttcaa gaccgagagg aaaaaagcaa cggccttctt ccctgacttg gtgaacatgc 1560
tggtgctggg gaagcacctg ggcatcccca agccctttgg gaccatcatc aatggctgct 1620
gctgcctgga ggagaaggtg cggtccctgc tggagccgct gggcctccac tgcaccttca 1680
ttgatgactt cactccatac cacatgctgc atggggaggt gcactgtggc accaatgtgt 1740
gcagaaagcc cttctctttc aagtggtgga acatggtgcc ctgagacagc tcccacccac 1800
catcctgtcc ccctggggcg ggcattggcc caggtggtgg agacagagac aggcccctga 1860
acgataagca ccaagagacc ccaaggctcc agatggaaca ctgagggtga ccgtccctct 1920
cagaagcctt ttccctggaa gtgtccatgc ctcacctgca acccatgtgg ttctcagact 1980
tgaatcttct cggcccccca aaaagaagga cctcatttct tatagcctct cctgtgattc 2040
aacacaaccc atggagatgt ccccttctca ctctgaaatc atccatttgg ggacaaatcc 2100
acattggggt ctagaaacat ccacgtatct catcagccat cttgtcctgt gcatcctaac 2160
agaggaagga tccatgattc tgctttggtc caattgcttc ctctctgcag aggaacaacc 2220
ctaaaaccag accactccac gcaggacagg caggagagat tcttcctaaa gcctccccca 2280
taaaaaggga gctgtggatc cacttagatc agggcggaac catctttcac ccggccaagc 2340
tcctgcccag atgttgaccc tcacccagcg tgagctgtca catagtagga gcttctagat 2400
gcatgtggaa gcaatgagag ttgtccctta gccttataaa ctccccatga tctgacatgc 2460
agaaatccag ccttgtccag aatcctcctg gaatttcttg gagacgaaag tatctggggg 2520
attgttgggt actagggaga ctgggtacaa gggtgaaaag tagttcccat aatacacatg 2580
gttgactatg gtgatccacc ttgtgatggt taatattagg tgtctggaga aggttgcttc 2640
attggccctg ggacttctct ctgcaggagg agagaacgct gcctctcctc tggattggtc 2700
tcaggctctc tgttggcctt tggtcagcgt ttccacatcc tgctctgctg caggagaggg 2760
ggctaagggg ctggatccac caaggcagct cacagcggga aaactctggg aatgaaccac 2820
tgaattcagg ggatgggggt ggggggcgg ttctcgaggt gtgtgccagc tacacgtgtg 2880
ttctgtatgg gtccagctgc gtttccatca ctcgctaata aatcaacaga aacacaaa 2938

<210> SEQ ID NO 46
<211> LENGTH: 485
<212> TYPE: PRT
<213> ORGANISM: Homo sapiens
<220> FEATURE:
<223> OTHER INFORMATION: protein-arginine deiminase type-3 isoform X2
[Homo sapiens]

<400> SEQUENCE: 46

Met Ser Val Met Val Leu Arg Thr Gln Gly Pro Ala Ala Leu Phe Asp
1 5 10 15

Asp His Lys Leu Val Leu His Thr Ser Ser Tyr Asp Ala Lys Arg Ala
20 25 30

Gln Val Phe His Ile Cys Gly Pro Glu Asp Val Cys Glu Ala Tyr Arg
35 40 45

His Val Leu Gly Gln Asp Lys Val Ser Tyr Glu Val Pro Arg Leu His
50 55 60

Gly Asp Glu Glu Arg Phe Phe Val Glu Gly Leu Ser Phe Pro Asp Ala
65 70 75 80

Gly Phe Thr Gly Leu Ile Ser Phe His Val Thr Leu Leu Asp Asp Ser
85 90 95

Asn Glu Asp Phe Ser Ala Ser Pro Ile Phe Thr Asp Thr Val Val Phe
100 105 110

Arg Val Ala Pro Trp Ile Met Thr Pro Ser Thr Leu Pro Pro Leu Glu
115 120 125

Val Tyr Val Cys Arg Val Arg Asn Asn Thr Cys Phe Val Asp Ala Val
130 135 140

Ala Glu Leu Ala Arg Lys Ala Gly Cys Lys Leu Thr Ile Cys Pro Gln
145 150 155 160

Ala Glu Asn Arg Asn Asp Arg Trp Ile Gln Asp Glu Met Glu Leu Gly
165 170 175

Tyr Val Gln Ala Pro His Lys Thr Leu Pro Val Val Phe Asp Ser Pro

```
            180                 185                 190

Arg Asn Gly Glu Leu Gln Asp Phe Pro Tyr Lys Arg Ile Leu Gly Pro
        195                 200                 205

Asp Phe Gly Tyr Val Thr Arg Glu Pro Arg Asp Arg Ser Val Ser Gly
    210                 215                 220

Leu Asp Ser Phe Gly Asn Leu Glu Val Ser Pro Pro Val Val Ala Asn
225                 230                 235                 240

Gly Lys Glu Tyr Pro Leu Gly Arg Ile Leu Ile Gly Gly Asn Leu Pro
                245                 250                 255

Gly Ser Ser Gly Arg Arg Val Thr Gln Val Val Arg Asp Phe Leu His
            260                 265                 270

Ala Gln Lys Val Gln Pro Pro Val Glu Leu Phe Val Asp Trp Leu Ala
        275                 280                 285

Val Gly His Val Asp Glu Phe Leu Ser Phe Val Pro Ala Pro Asp Gly
    290                 295                 300

Lys Gly Phe Arg Met Leu Leu Ala Ser Pro Gly Ala Cys Phe Lys Leu
305                 310                 315                 320

Phe Gln Glu Lys Gln Lys Cys Gly His Gly Arg Ala Leu Leu Phe Gln
                325                 330                 335

Gly Val Val Asp Asp Glu Gln Val Lys Thr Ile Ser Ile Asn Gln Val
            340                 345                 350

Leu Ser Asn Lys Asp Leu Ile Asn Tyr Asn Lys Phe Val Gln Ser Cys
        355                 360                 365

Ile Asp Trp Asn Arg Glu Val Leu Lys Arg Glu Leu Gly Leu Ala Glu
    370                 375                 380

Cys Asp Ile Ile Asp Ile Pro Gln Leu Phe Lys Thr Glu Arg Lys Lys
385                 390                 395                 400

Ala Thr Ala Phe Phe Pro Asp Leu Val Asn Met Leu Val Leu Gly Lys
                405                 410                 415

His Leu Gly Ile Pro Lys Pro Phe Gly Thr Ile Ile Asn Gly Cys Cys
            420                 425                 430

Cys Leu Glu Glu Lys Val Arg Ser Leu Leu Glu Pro Leu Gly Leu His
        435                 440                 445

Cys Thr Phe Ile Asp Asp Phe Thr Pro Tyr His Met Leu His Gly Glu
    450                 455                 460

Val His Cys Gly Thr Asn Val Cys Arg Lys Pro Phe Ser Phe Lys Trp
465                 470                 475                 480

Trp Asn Met Val Pro
                485


<210> SEQ ID NO 47
<211> LENGTH: 2938
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X2, mRNA

<400> SEQUENCE: 47

agaaatggat ggatgtgact gtgtgctaat aaaactttat ttatacaaac aggcagtagg      60

ccagatttgg cccacagttc ataatgtgct gatcctgacc taggcgagaa gagaaaccaa     120

atatgaaact gttgaagaac ttgggactga attatgttgg aacttggtgc cctgggagtt     180

aagaggagaa ggtcgagcgg cagtgggtct gggggcccag tgggtatggc ggcatcttgc     240

tggtgaactg tgaccgtgat gatccgagct gtgatgtcca ggacaattgt gaccagcacg     300
```

-continued

```
tgcactgcct gcaagacctg gaagacatgt ctgtcatggt cctgcggacg cagggccctg    360
cagccctctt tgatgaccac aaacttgtcc tccatacctc cagctatgat gccaaacggg    420
cacaggtctt ccacatctgc ggtcctgagg atgtgtgtga ggcctatagg catgtgctgg    480
gccaagataa ggtgtcctat gaggtacccc gcttgcatgg ggatgaggag cgcttcttcg    540
tggaaggcct gtccttccct gatgccggct tcacaggact catctccttc catgtcactc    600
tgctggacga ctccaacgag gatttctcgg catcccctat cttcactgac actgtggtgt    660
tccgagtggc accctggatc atgacgccca gcactctgcc acccctagag gtgtatgtgt    720
gccgtgtgag gaacaacacg tgttttgtgg atgcggtggc agagctggcc aggaaggccg    780
gctgcaagct gaccatctgc ccacaggccg agaaccgcaa cgaccgctgg atccaggatg    840
agatggagct gggctacgtt caggcgccgc acaagaccct cccggtggtc tttgactccc    900
caaggaatgg ggaactgcag gatttccctt acaaaagaat cctgggtcca gattttggtt    960
acgtgactcg ggaaccacgc gacaggtctg tgagtggcct ggactccttt gggaacctgg   1020
aggtcagccc tccagtggtg gccaatggga aagagtaccc cctggggagg atcctcattg   1080
ggggcaacct gcctgggtca agtggccgca gggtcaccca ggtggtgcgg gacttcctcc   1140
atgcccagaa ggtgcagccc cccgtggagc tctttgtgga ctggttggcc gtgggccatg   1200
tggatgagtt tctgagcttt gtccctgccc ccgatgggaa gggcttccgg atgctcctgg   1260
ccagccctgg ggcctgcttc aagctcttcc aggaaaagca gaagtgtggc cacgggaggg   1320
ccctcctgtt ccaggggggtt gttgatgatg agcaggtcaa gaccatctcc atcaaccagg   1380
tgctctccaa taaagacctc atcaactaca ataagtttgt gcagagctgc atcgactgga   1440
accgtgaggt gctgaagcgg gagctgggcc tggcagagtg tgacatcatt gacatcccac   1500
agctcttcaa gaccgagagg aaaaaagcaa cggccttctt ccctgacttg gtgaacatgc   1560
tggtgctggg gaagcacctg ggcatcccca agccctttgg gcccatcatc aatggctgct   1620
gctgcctgga ggagaaggtg cagtccctgc tggagccgct gggcctccac tgcaccttca   1680
ttgatgactt cactccatac cacatgctgc atggggaggt gcactgtggc accaatgtgt   1740
gcagaaagcc cttctctttc aagtggtgga acatggtgcc ctgagacagc tcccacccac   1800
catcctgtcc ccctggggcg ggcattggcc caggtggtgg agacagagac aggcccctga   1860
acgataagca ccaagagacc ccaaggctcc agatggaaca ctgagggtga ccgtccctct   1920
cagaagcctt ttccctggaa gtgtccatgc ctcacctgca acccatgtgg ttctcagact   1980
tgaatcttct cggcccccca aaaagaagga cctcatttct tatagcctct cctgtgattc   2040
aacacaaccc atggagatgt cccccttctca ctctgaaatc atccatttgg ggacaaatcc   2100
acattggggt ctagaaacat ccacgtatct catcagccat cttgtcctgt gcatcctaac   2160
agaggaagga tccatgattc tgctttggtc caattgcttc ctctctgcag aggaacaacc   2220
ctaaaaccag accactccac gcaggacagg caggagagat tcttcctaaa gcctccccca   2280
taaaaaggga gctgtggatc cacttagatc agggcggaac catctttcac ccggccaagc   2340
tcctgcccag atgttgaccc tcacccagcg tgagctgtca catagtagga gcttctagat   2400
gcatgtggaa gcaatgagag ttgtccctta gccttataaa ctccccatga tctgacatgc   2460
agaaatccag ccttgtccag aatcctcctg gaatttcttg gagacgaaag tatctggggg   2520
attgttgggt actagggaga ctgggtacaa gggtgaaaag tagttcccat aatacacatg   2580
gttgactatg gtgatccacc ttgtgatggt taatattagg tgtctggaga aggttgcttc   2640
```

-continued

```
attggccctg ggacttctct ctgcaggagg agagaacgct gcctctcctc tggattggtc   2700

tcaggctctc tgttggcctt tggtcagcgt ttccacatcc tgctctgctg caggagaggg   2760

ggctaagggg ctggatccac caaggcagct cacagcggga aaactctggg aatgaaccac   2820

tgaattcagg ggatggggt ggggggcgg ttctcgaggt gtgtgccagc tacacgtgtg   2880

ttctgtatgg gtccagctgc gtttccatca ctcgctaata aatcaacaga aacacaaa     2938
```

```
<210> SEQ ID NO 48
<211> LENGTH: 485
<212> TYPE: PRT
<213> ORGANISM: Homo sapiens
<220> FEATURE:
<223> OTHER INFORMATION: protein-arginine deiminase type-3 isoform X2
      [Homo sapiens]

<400> SEQUENCE: 48

Met Ser Val Met Val Leu Arg Thr Gln Gly Pro Ala Ala Leu Phe Asp
1               5                   10                  15

Asp His Lys Leu Val Leu His Thr Ser Ser Tyr Asp Ala Lys Arg Ala
            20                  25                  30

Gln Val Phe His Ile Cys Gly Pro Glu Asp Val Cys Glu Ala Tyr Arg
        35                  40                  45

His Val Leu Gly Gln Asp Lys Val Ser Tyr Glu Val Pro Arg Leu His
    50                  55                  60

Gly Asp Glu Glu Arg Phe Phe Val Glu Gly Leu Ser Phe Pro Asp Ala
65                  70                  75                  80

Gly Phe Thr Gly Leu Ile Ser Phe His Val Thr Leu Leu Asp Asp Ser
                85                  90                  95

Asn Glu Asp Phe Ser Ala Ser Pro Ile Phe Thr Asp Thr Val Val Phe
            100                 105                 110

Arg Val Ala Pro Trp Ile Met Thr Pro Ser Thr Leu Pro Pro Leu Glu
        115                 120                 125

Val Tyr Val Cys Arg Val Arg Asn Asn Thr Cys Phe Val Asp Ala Val
    130                 135                 140

Ala Glu Leu Ala Arg Lys Ala Gly Cys Lys Leu Thr Ile Cys Pro Gln
145                 150                 155                 160

Ala Glu Asn Arg Asn Asp Arg Trp Ile Gln Asp Glu Met Glu Leu Gly
                165                 170                 175

Tyr Val Gln Ala Pro His Lys Thr Leu Pro Val Val Phe Asp Ser Pro
            180                 185                 190

Arg Asn Gly Glu Leu Gln Asp Phe Pro Tyr Lys Arg Ile Leu Gly Pro
        195                 200                 205

Asp Phe Gly Tyr Val Thr Arg Glu Pro Arg Asp Arg Ser Val Ser Gly
    210                 215                 220

Leu Asp Ser Phe Gly Asn Leu Glu Val Ser Pro Pro Val Val Ala Asn
225                 230                 235                 240

Gly Lys Glu Tyr Pro Leu Gly Arg Ile Leu Ile Gly Gly Asn Leu Pro
                245                 250                 255

Gly Ser Ser Gly Arg Arg Val Thr Gln Val Val Arg Asp Phe Leu His
            260                 265                 270

Ala Gln Lys Val Gln Pro Pro Val Glu Leu Phe Val Asp Trp Leu Ala
        275                 280                 285

Val Gly His Val Asp Glu Phe Leu Ser Phe Val Pro Ala Pro Asp Gly
    290                 295                 300

Lys Gly Phe Arg Met Leu Leu Ala Ser Pro Gly Ala Cys Phe Lys Leu
```

-continued

```
305                 310                 315                 320

Phe Gln Glu Lys Gln Lys Cys Gly His Gly Arg Ala Leu Leu Phe Gln
                325                 330                 335

Gly Val Val Asp Asp Glu Gln Val Lys Thr Ile Ser Ile Asn Gln Val
            340                 345                 350

Leu Ser Asn Lys Asp Leu Ile Asn Tyr Asn Lys Phe Val Gln Ser Cys
        355                 360                 365

Ile Asp Trp Asn Arg Glu Val Leu Lys Arg Glu Leu Gly Leu Ala Glu
    370                 375                 380

Cys Asp Ile Ile Asp Ile Pro Gln Leu Phe Lys Thr Glu Arg Lys Lys
385                 390                 395                 400

Ala Thr Ala Phe Phe Pro Asp Leu Val Asn Met Leu Val Leu Gly Lys
                405                 410                 415

His Leu Gly Ile Pro Lys Pro Phe Gly Pro Ile Ile Asn Gly Cys Cys
            420                 425                 430

Cys Leu Glu Glu Lys Val Gln Ser Leu Leu Glu Pro Leu Gly Leu His
        435                 440                 445

Cys Thr Phe Ile Asp Asp Phe Thr Pro Tyr His Met Leu His Gly Glu
    450                 455                 460

Val His Cys Gly Thr Asn Val Cys Arg Lys Pro Phe Ser Phe Lys Trp
465                 470                 475                 480

Trp Asn Met Val Pro
                485
```

<210> SEQ ID NO 49
<211> LENGTH: 1452
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X3, mRNA

<400> SEQUENCE: 49

```
cctaaggggc ctcaggggca gtgttggggt tggcggccac agctaagtcc aacaccagca     60

tgtcgctgca gagaatcgtg cgtgtgtccc tggagcatcc caccagcgcg gtgtgtgtgg    120

ctggcgtgga gaccctcgtg gacatttatg ggtcagtgcc tgagggcaca gaaatgtttg    180

aggtctatgg gacgcctggc gtggacatct acatctctcc caacatggag aggggccggg    240

agcgtgcaga caccaggcgg tggcgctttg acgcgacttt ggagatcatc gtggtcatga    300

actcccccag caatgacctc aacgacagcc atgttcagat ttcctaccac tccagccatg    360

agcctctgcc cctggcctat gcggtgctct acctcacctg tgttgacatc tctctggatt    420

gcgacctgaa ctgtgaggga aggcaggaca ggaactttgt agacaagcgg cagtgggtct    480

gggggcccag tgggtatggc ggcatcttgc tggtgaactg tgaccgtgat gatccgagct    540

gtgatgtcca ggacaattgt gaccagcacg tgcactgcct gcaagacctg gaagacatgt    600

ctgtcatggt cctgcggacg cagggccctg cagccctctt tgatgaccac aaacttgtcc    660

tccatacctc cagctatgat gccaaacggg cacaggtctt ccacatctgc ggtcctgagg    720

atgtgtgtga ggcctatagg catgtgctgg gccaagataa ggtgtcctat gaggtacccc    780

gcttgcatgg ggatgaggag cgcttcttcg tggaaggcct gtccttccct gatgccggct    840

tcacaggact catctccttc catgtcactc tgctggacga ctccaacgag gatttctcgg    900

catcccctat cttcactgac actgtggtgt tccgagtggc accctggatc atgacgccca    960

gcactctgcc acccctagag gtgtatgtgt gccgtgtgag gaacaacacg tgttttgtgg   1020
```

```
atgcggtggc agagctggcc aggaaggccg gctgcaagct gaccatctgc ccacaggccg   1080

agaaccgcaa cgaccgctgg atccaggatg agatggagct gggctacgtt caggcgccgc   1140

acaagaccct cccggtggtc tttgactccc caaggaatgg ggaactgcag gatttccctt   1200

acaaaagaat cctggtcaag tggccgcagg gtcacccagg tggtgcggga cttcctccat   1260

gcccagaagg tgcagccccc cgtggagctc tttgtggact ggttggccgt gggccatgtg   1320

gatgagtttc tgagctttgt ccctgccccc gatgggaagg gcttccggat gctcctggcc   1380

agccctgggg cctgcttcaa gctcttccag gaaaagcaga agtgtggcca cgggagggcc   1440

ctcctgttcc ag                                                       1452
```

```
<210> SEQ ID NO 50
<211> LENGTH: 421
<212> TYPE: PRT
<213> ORGANISM: Homo sapiens
<220> FEATURE:
<223> OTHER INFORMATION: protein-arginine deiminase type-3 isoform X3
      [Homo sapiens]

<400> SEQUENCE: 50

Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270
```

-continued

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Val Lys Trp Pro Gln Gly His Pro Gly Gly Ala Gly Leu Pro Pro
385                 390                 395                 400

Cys Pro Glu Gly Ala Ala Pro Arg Gly Ala Leu Cys Gly Leu Val Gly
                405                 410                 415

Arg Gly Pro Cys Gly
            420

<210> SEQ ID NO 51
<211> LENGTH: 1452
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X3, mRNA

<400> SEQUENCE: 51
cctaaggggc ctcaggggca gtgttggggt tggcggccac agctaagtcc aacaccagca 60
tgtcgctgca gagaatcgtg cgtgtgtccc tggagcatcc caccagcgcg gtgtgtgtgg 120
ctggcgtgga gaccctcgtg gacatttatg ggtcagtgcc tgagggcaca gaaatgtttg 180
aggtctatgg gacgcctggc gtggacatct acgtctctcc caacatggag aggggccggg 240
agcgtgcaga caccaggcgg tggcgctttg acgcgacttt ggagatcatc gtggtcatga 300
actcccccag caatgacctc aacgacagcc atgttcagat ttcctaccac tccagccatg 360
agcctctgcc cctggcctat gcggtgctct acctcacctg tgttgacatc tctctggatt 420
gcgacctgaa ctgtgaggga aggcaggaca ggaactttgt agacaagcgg cagtgggtct 480
gggggcccag tgggtatggc ggcatcttgc tggtgaactg tgaccgtgat gatccgagct 540
gtgatgtcca ggacaattgt gaccagcacg tgcactgcct gcaagacctg gaagacatgt 600
ctgtcatggt cctgcggacg cagggccctg cagccctctt tgatgaccac aaacttgtcc 660
tccatacctc cagctatgat gccaaacggg cacaggtctt ccacatctgc ggtcctgagg 720
atgtgtgtga ggcctatagg catgtgctgg gccaagataa ggtgtcctat gaggtacccc 780
gcttgcatgg ggatgaggag cgcttcttcg tggaaggcct gtccttccct gatgccggct 840
tcacaggact catctccttc catgtcactc tgctggacga ctccaacgag gatttctcgg 900
catcccctat cttcactgac actgtggtgt tccgagtggc accctggatc atgacgccca 960
gcactctgcc acccctagag gtgtatgtgt gccgtgtgag gaacaacacg tgttttgtgg 1020
atgcggtggc agagctggcc aggaaggccg gctgcaagct gaccatctgc ccacaggccg 1080
agaaccgcaa cgaccgctgg atccaggatg agatggagct gggctacgtt caggcgccgc 1140

-continued

```
acaagaccct cccggtggtc tttgactccc caaggaatgg ggaactgcag gatttccctt   1200

acaaaagaat cctggtcaag tggccgcagg gtcacccagg tggtgcggga cttcctccat   1260

gcccagaagg tgcagccccc cgtggagctc tttgtggact ggttggccgt gggccatgtg   1320

gatgagtttc tgagctttgt ccctgccccc gatgggaagg gcttccggat gctcctggcc   1380

agccctgggg cctgcttcaa gctcttccag gaaaagcaga agtgtggcca cgggagggcc   1440

ctcctgttcc ag                                                         1452
```

<210> SEQ ID NO 52
<211> LENGTH: 421
<212> TYPE: PRT
<213> ORGANISM: Homo sapiens
<220> FEATURE:
<223> OTHER INFORMATION: protein-arginine deiminase type-3 isoform X3
      [Homo sapiens]

<400> SEQUENCE: 52

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Val Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300
```

```
Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Val Lys Trp Pro Gln Gly His Pro Gly Gly Ala Gly Leu Pro Pro
385                 390                 395                 400

Cys Pro Glu Gly Ala Ala Pro Arg Gly Ala Leu Cys Gly Leu Val Gly
                405                 410                 415

Arg Gly Pro Cys Gly
            420


<210> SEQ ID NO 53
<211> LENGTH: 1452
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X3, mRNA

<400> SEQUENCE: 53

cctaaggggc ctcaggggca gtgttggggt tggcggccac agctaagtcc aacaccagca     60

tgtcgctgca gagaatcgtg cgtgtgtccc tggagcatcc caccagcgcg gtgtgtgtgg    120

ctggcgtgga gaccctcgtg gacatttatg ggtcagtgcc tgagggcaca gaaatgtttg    180

aggtctatgg gacgcctggc gtggacatct acatctctcc caacatggag aggggccggg    240

agcgtgcaga caccaggcgg tggcgctttg acgcgacttt ggagatcatc gtggtcatga    300

actcccccag caatgacctc aacgacagcc atgttcagat ttcctaccac tccagccatg    360

agcctctgcc cctggcctat gcggtgctct accacacctg tgttgacatc tctctggatt    420

gcgacctgaa ctgtgaggga aggcaggaca ggaactttgt agacaagcgg cagtgggtct    480

gggggcccag tgggtatggc ggcatcttgc tggtgaactg tgaccgtgat gatccgagct    540

gtgatgtcca ggacaattgt gaccagcacg tgcactgcct gcaagacctg gaagacatgt    600

ctgtcatggt cctgcggacg cagggccctg cagccctctt tgatgaccac aaacttgtcc    660

tccatacctc cagctatgat gccaaacggg cacaggtctt ccacatctgc ggtcctgagg    720

atgtgtgtga ggcctatagg catgtgctgg gccaagataa ggtgtcctat gaggtacccc    780

gcttgcatgg ggatgaggag cgcttcttcg tggaaggcct gtccttccct gatgccggct    840

tcacaggact catctccttc catgtcactc tgctggacga ctccaacgag gatttctcgg    900

catcccctat cttcactgac actgtggtgt tccgagtggc accctggatc atgacgccca    960

gcactctgcc acccctagag gtgtatgtgt gccgtgtgag gaacaacacg tgttttgtgg   1020

atgcggtggc agagctggcc aggaaggccg gctgcaagct gaccatctgc ccacaggccg   1080

agaaccgcaa cgaccgctgg atccaggatg agatggagct gggctacgtt caggcgccgc   1140

acaagaccct cccggtggtc tttgactccc caaggaatgg ggaactgcag gatttccctt   1200

acaaaagaat cctggtcaag tggccgcagg gtcacccagg tggtgcggga cttcctccat   1260

gcccagaagg tgcagccccc cgtggagctc tttgtggact ggttggccgt gggccatgtg   1320
```

gatgagtttc tgagctttgt ccctgccccc gatgggaagg gcttccggat gctcctggcc 1380
agccctgggg cctgcttcaa gctcttccag gaaaagcaga agtgtggcca cgggagggcc 1440
ctcctgttcc ag 1452

<210> SEQ ID NO 54
<211> LENGTH: 421
<212> TYPE: PRT
<213> ORGANISM: Homo sapiens
<220> FEATURE:
<223> OTHER INFORMATION: protein-arginine deiminase type-3 isoform X3
[Homo sapiens]

<400> SEQUENCE: 54

Met Ser Leu Gln Arg Ile Val Arg Val Ser Leu Glu His Pro Thr Ser
1 5 10 15

Ala Val Cys Val Ala Gly Val Glu Thr Leu Val Asp Ile Tyr Gly Ser
20 25 30

Val Pro Glu Gly Thr Glu Met Phe Glu Val Tyr Gly Thr Pro Gly Val
35 40 45

Asp Ile Tyr Ile Ser Pro Asn Met Glu Arg Gly Arg Glu Arg Ala Asp
50 55 60

Thr Arg Arg Trp Arg Phe Asp Ala Thr Leu Glu Ile Ile Val Val Met
65 70 75 80

Asn Ser Pro Ser Asn Asp Leu Asn Asp Ser His Val Gln Ile Ser Tyr
85 90 95

His Ser Ser His Glu Pro Leu Pro Leu Ala Tyr Ala Val Leu Tyr His
100 105 110

Thr Cys Val Asp Ile Ser Leu Asp Cys Asp Leu Asn Cys Glu Gly Arg
115 120 125

Gln Asp Arg Asn Phe Val Asp Lys Arg Gln Trp Val Trp Gly Pro Ser
130 135 140

Gly Tyr Gly Gly Ile Leu Leu Val Asn Cys Asp Arg Asp Asp Pro Ser
145 150 155 160

Cys Asp Val Gln Asp Asn Cys Asp Gln His Val His Cys Leu Gln Asp
165 170 175

Leu Glu Asp Met Ser Val Met Val Leu Arg Thr Gln Gly Pro Ala Ala
180 185 190

Leu Phe Asp Asp His Lys Leu Val Leu His Thr Ser Ser Tyr Asp Ala
195 200 205

Lys Arg Ala Gln Val Phe His Ile Cys Gly Pro Glu Asp Val Cys Glu
210 215 220

Ala Tyr Arg His Val Leu Gly Gln Asp Lys Val Ser Tyr Glu Val Pro
225 230 235 240

Arg Leu His Gly Asp Glu Glu Arg Phe Phe Val Glu Gly Leu Ser Phe
245 250 255

Pro Asp Ala Gly Phe Thr Gly Leu Ile Ser Phe His Val Thr Leu Leu
260 265 270

Asp Asp Ser Asn Glu Asp Phe Ser Ala Ser Pro Ile Phe Thr Asp Thr
275 280 285

Val Val Phe Arg Val Ala Pro Trp Ile Met Thr Pro Ser Thr Leu Pro
290 295 300

Pro Leu Glu Val Tyr Val Cys Arg Val Arg Asn Asn Thr Cys Phe Val
305 310 315 320

Asp Ala Val Ala Glu Leu Ala Arg Lys Ala Gly Cys Lys Leu Thr Ile

-continued

```
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Val Lys Trp Pro Gln Gly His Pro Gly Gly Ala Gly Leu Pro Pro
385                 390                 395                 400

Cys Pro Glu Gly Ala Ala Pro Arg Gly Ala Leu Cys Gly Leu Val Gly
                405                 410                 415

Arg Gly Pro Cys Gly
            420
```

```
<210> SEQ ID NO 55
<211> LENGTH: 1452
<212> TYPE: DNA
<213> ORGANISM: Homo sapiens
<220> FEATURE:
<223> OTHER INFORMATION: PREDICTED: Homo sapiens peptidyl arginine
      deiminase 3 (PADI3), transcript variant X3, mRNA

<400> SEQUENCE: 55

cctaaggggc ctcaggggca gtgttggggt tggcggccac agctaagtcc aacaccagca     60

tgtcgctgca gagaatcgtg cgtgtgtccc tggagcatcc caccagcgcg gtgtgtgtgg    120

ctggcgtgga gaccctcgtg gacatttatg ggtcagtgcc tgagggcaca gaaatgtttg    180

aggtctatgg gacgcctggc gtggacatct acatctctcc caacatggag aggggccggg    240

agcgtgcaga caccaggcgg tggcgctttg acgcgacttt ggagatcatc gtggtcatga    300

actcccccag caatgacctc aacgacagcc atgttcagat ttcctaccac tccagccatg    360

agcctctgcc cctggcctat gcggtgctct acctcacctg tgttgacatc tctctggatt    420

gcgacctgaa ctgtgaggga aggcaggaca ggaactttgt agacaagcgg cagtgggtct    480

gggggcccag tgggtatggc ggcatcttgc tggtgaactg tgaccgtgat gatccgagct    540

gtgatgtcca ggacaattgt gaccagcaca tgcactgcct gcaagacctg gaagacatgt    600

ctgtcatggt cctgcggacg cagggccctg cagccctctt tgatgaccac aaacttgtcc    660

tccatacctc cagctatgat gccaaacggg cacaggtctt ccacatctgc ggtcctgagg    720

atgtgtgtga ggcctatagg catgtgctgg gccaagataa ggtgtcctat gaggtacccc    780

gcttgcatgg ggatgaggag cgcttcttcg tggaaggcct gtccttccct gatgccggct    840

tcacaggact catctccttc catgtcactc tgctggacga ctccaacgag gatttctcgg    900

catcccctat cttcactgac actgtggtgt tccgagtggc accctggatc atgacgccca    960

gcactctgcc acccctagag gtgtatgtgt gccgtgtgag gaacaacacg tgttttgtgg   1020

atgcggtggc agagctggcc aggaaggccg gctgcaagct gaccatctgc ccacaggccg   1080

agaaccgcaa cgaccgctgg atccaggatg agatggagct gggctacgtt caggcgccgc   1140

acaagaccct cccggtggtc tttgactccc caaggaatgg ggaactgcag gatttccctt   1200

acaaaagaat cctggtcaag tggccgcagg gtcacccagg tggtgcggga cttcctccat   1260

gcccagaagg tgcagccccc cgtggagctc tttgtggact ggttggccgt gggccatgtg   1320

gatgagtttc tgagctttgt ccctgccccc gatgggaagg gcttccggat gctcctggcc   1380

agccctgggg cctgcttcaa gctcttccag gaaaagcaga agtgtggcca cgggagggcc   1440
```

-continued

```
ctcctgttcc ag                                                         1452


<210> SEQ ID NO 56
<211> LENGTH: 421
<212> TYPE: PRT
<213> ORGANISM: Homo sapiens
<220> FEATURE:
<223> OTHER INFORMATION: protein-arginine deiminase type-3 isoform X3
      [Homo sapiens]

<400> SEQUENCE: 56

Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Met His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350
```

-continued

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380

Leu Val Lys Trp Pro Gln Gly His Pro Gly Gly Ala Gly Leu Pro Pro
385                 390                 395                 400

Cys Pro Glu Gly Ala Ala Pro Arg Gly Ala Leu Cys Gly Leu Val Gly
                405                 410                 415

Arg Gly Pro Cys Gly
            420

<210> SEQ ID NO 57
<211> LENGTH: 1452
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X3, mRNA

<400> SEQUENCE: 57
cctaaggggc ctcaggggca gtgttggggt tggcggccac agctaagtcc aacaccagca 60
tgtcgctgca gagaatcgtg cgtgtgtccc tggagcatcc caccagcgcg gtgtgtgtgg 120
ctggcgtgga gaccctcgtg gacatttatg ggtcagtgcc tgagggcaca gaaatgtttg 180
aggtctatgg gacgcctggc gtggacatct acatctctcc caacatggag aggggccggg 240
agcgtgcaga caccaggcgg tggcgctttg acgcgacttt ggagatcatc gtggtcatga 300
actcccccag caatgacctc aacgacagcc atgttcagat ttcctaccac tccagccatg 360
agcctctgcc cctggcctat gcggtgctct acctcacctg tgttgacatc tctctggatt 420
gcgacctgaa ctgtgaggga aggcaggaca ggaactttgt agacaagcgg cagtgggtct 480
gggggcccag tgggtatggc ggcatcttgc tggtgaactg tgaccgtgat gatccgagct 540
gtgatgtcca ggacaattgt gaccagcacg tgcactgcct gcaagacctg gaagacatgt 600
ctgtcatggt cctgcggacg cagggccctg cagccctctt tgatgaccac aaacttgtcc 660
tccatacctc cagctatgat gccaaacggg cacaggtctt ccacatctgc ggtcctgagg 720
atgtgtgtga ggcctatagg catgtgctgg gccaagataa ggtgtcctat gaggtacccc 780
gcttgcatgg ggatgaggag cgcttcttcg tggaaggcct gtccttccct gatgccggct 840
tcacaggact catctccttc catgtcactc tgctggacga ctccaacgag gatttctcgg 900
catcccctat cttcactgac actgtggtgt tccgagtggt accctggatc atgacgccca 960
gcactctgcc acccctagag gtgtatgtgt gccgtgtgag gaacaacacg tgttttgtgg 1020
atgcggtggc agagctggcc aggaaggccg gctgcaagct gaccatctgc ccacaggccg 1080
agaaccgcaa cgaccgctgg atccaggatg agatggagct gggctacgtt caggcgccgc 1140
acaagaccct cccggtggtc tttgactccc caaggaatgg ggaactgcag gatttccctt 1200
acaaaagaat cctggtcaag tggccgcagg gtcacccagg tggtgcggga cttcctccat 1260
gcccagaagg tgcagccccc cgtggagctc tttgtggact ggttggccgt gggccatgtg 1320
gatgagtttc tgagctttgt ccctgccccc gatgggaagg gcttccggat gctcctggcc 1380
agccctgggg cctgcttcaa gctcttccag gaaaagcaga agtgtggcca cgggagggcc 1440
ctcctgttcc ag 1452

<210> SEQ ID NO 58
<211> LENGTH: 421

<212> TYPE: PRT
<213> ORGANISM: Homo sapiens
<220> FEATURE:
<223> OTHER INFORMATION: protein-arginine deiminase type-3 isoform X3
[Homo sapiens]

<400> SEQUENCE: 58

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Val Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
    370                 375                 380
```

Leu Val Lys Trp Pro Gln Gly His Pro Gly Gly Ala Gly Leu Pro Pro
385 390 395 400

Cys Pro Glu Gly Ala Ala Pro Arg Gly Ala Leu Cys Gly Leu Val Gly
405 410 415

Arg Gly Pro Cys Gly
420

<210> SEQ ID NO 59
<211> LENGTH: 1452
<212> TYPE: DNA
<213> ORGANISM: Homo sapiens
<220> FEATURE:
<223> OTHER INFORMATION: PREDICTED: Homo sapiens peptidyl arginine deiminase 3 (PADI3), transcript variant X3, mRNA

<400> SEQUENCE: 59
cctaaggggc ctcaggggca gtgttggggt tggcggccac agctaagtcc aacaccagca 60
tgtcgctgca gagaatcgtg cgtgtgtccc tggagcatcc caccagcgcg gtgtgtgtgg 120
ctggcgtgga gaccctcgtg gacatttatg ggtcagtgcc tgagggcaca gaaatgtttg 180
aggtctatgg gacgcctggc gtggacatct acatctctcc caacatggag aggggccggg 240
agcgtgcaga caccaggcgg tggcgctttg acgcgacttt ggagatcatc gtggtcatga 300
actcccccag caatgacctc aacgacagcc atgttcagat ttcctaccac tccagccatg 360
agcctctgcc cctggcctat gcggtgctct acctcacctg tgttgacatc tctctggatt 420
gcgacctgaa ctgtgaggga aggcaggaca ggaactttgt agacaagcgg cagtgggtct 480
gggggcccag tgggtatggc ggcatcttgc tggtgaactg tgaccgtgat gatccgagct 540
gtgatgtcca ggacaattgt gaccagcacg tgcactgcct gcaagacctg gaagacatgt 600
ctgtcatggt cctgcggacg cagggccctg cagccctctt tgatgaccac aaacttgtcc 660
tccatacctc cagctatgat gccaaacggg cacaggtctt ccacatctgc ggtcctgagg 720
atgtgtgtga ggcctatagg catgtgctgg gccaagataa ggtgtcctat gaggtacccc 780
gcttgcatgg ggatgaggag cgcttcttcg tggaaggcct gtccttccct gatgccggct 840
tcacaggact catctccttc catgtcactc tgctggacga ctccaacgag gatttctcgg 900
catcccctat cttcactgac actgtggtgt tccgagtggc accctggatc atgacgccca 960
gcactctgcc acccctagag gtgtatgtgt gccgtgtgag gaacaacacg tgttttgtgg 1020
atgcggtggc agagctggcc aggaaggccg gctgcaagct gaccatctgc ccacaggccg 1080
agaaccgcaa cgaccgctgg atccaggatg agatggagct gggctacgtt caggcgccgc 1140
acaagaccct cccggtggtc tttgactccc caaggaatgg ggaactgcag gatttccctt 1200
acaaaagaat cctggtcaag tggccgcagg gtcacccagg tggtgcggga cttcctccat 1260
gcccagaagg tgcagccccc cgtggagctc tttgtggact ggttggccgt gggccatgtg 1320
gatgagtttc tgagctttgt ccctgccccc gatgggaagg gcttccggat gctcctggcc 1380
agccctgggg cctgcttcaa gctcttccag gaaaagcaga agtgtggcca cgggagggcc 1440
ctcctgttcc ag 1452

<210> SEQ ID NO 60

<400> SEQUENCE: 60

000

```
<210> SEQ ID NO 61
<211> LENGTH: 2267
<212> TYPE: DNA
<213> ORGANISM: Homo sapiens
<220> FEATURE:
<223> OTHER INFORMATION: Homo sapiens peptidyl arginine deiminase 4
      (PADI4), mRNA

<400> SEQUENCE: 61

agccagaggg acgagctagc ccgacgatgg cccaggggac attgatccgt gtgaccccag     60

agcagcccac ccatgccgtg tgtgtgctgg gcaccttgac tcagcttgac atctgcagct    120

ctgcccctga ggactgcacg tccttcagca tcaacgcctc cccaggggtg gtcgtggata    180

ttgcccacgg ccctccagcc aagaagaaat ccacaggttc ctccacatgg cccctggacc    240

ctggggtaga ggtgaccctg acgatgaaag tggccagtgg tagcacaggc gaccagaagg    300

ttcagatttc atactacgga cccaagactc caccagtcaa agctctactc tacctcaccg    360

gggtggaaat ctccttgtgc gcagacatca cccgcaccgg caaagtgaag ccaaccagag    420

ctgtgaaaga tcagaggacc tggacctggg gcccttgtgg acagggtgcc atcctgctgg    480

tgaactgtga cagagacaat ctcgaatctt ctgccatgga ctgcgaggat gatgaagtgc    540

ttgacagcga agacctgcag gacatgtcgc tgatgaccct gagcacgaag acccccaagg    600

acttcttcac aaaccataca ctggtgctcc acgtggccag gtctgagatg gacaaagtga    660

gggtgtttca ggccacacgg ggcaaactgt cctccaagtg cagcgtagtc ttgggtccca    720

agtggccctc tcactacctg atggtccccg gtggaaagca caacatggac ttctacgtgg    780

aggccctcgc tttcccggac accgacttcc cggggctcat taccctcacc atctccctgc    840

tggacacgtc caacctggag ctccccgagg ctgtggtgtt ccaagacagc gtggtcttcc    900

gcgtggcgcc ctggatcatg acccccaaca cccagccccc gcaggaggtg tacgcgtgca    960

gtatttttga aaatgaggac ttcctgaagt cagtgactac tctggccatg aaagccaagt   1020

gcaagctgac catctgccct gaggaggaga acatggatga ccagtggatg caggatgaaa   1080

tggagatcgg ctacatccaa gccccacaca aaacgctgcc cgtggtcttc gactctccaa   1140

ggaacagagg cctgaaggag tttcccatca aacgcgtgat gggtccagat tttggctatg   1200

taactcgagg gccccaaaca gggggtatca gtggactgga ctcctttggg aacctggaag   1260

tgagcccccc agtcacagtc aggggcaagg aatacccgct gggcaggatt ctcttcgggg   1320

acagctgtta tcccagcaat gacagccggc agatgcacca ggccctgcag gacttcctca   1380

gtgcccagca ggtgcaggcc cctgtgaagc tctattctga ctggctgtcc gtgggccacg   1440

tggacgagtt cctgagcttt gtgccagcac ccgacaggaa gggcttccgg ctgctcctgg   1500

ccagccccag gtcctgctac aaactgttcc aggagcagca gaatgagggc cacgggggagg   1560

ccctgctgtt cgaagggatc aagaaaaaaa aacagcagaa aataaagaac attctgtcaa   1620

acaagacatt gagagaacat aattcatttg tggagagatg catcgactgg aaccgcgagc   1680

tgctgaagcg ggagctgggc ctggccgaga gtgacatcat tgacatcccg cagctcttca   1740

agctcaaaga gttctctaag gcggaagctt ttttccccaa catggtgaac atgctggtgc   1800

tagggaagca cctgggcatc cccaagccct tcgggcccgt catcaacggc cgctgctgcc   1860

tggaggagaa ggtgtgttcc ctgctggagc cactgggcct ccagtgcacc ttcatcaacg   1920

acttcttcac ctaccacatc aggcatgggg aggtgcactg cggcaccaac gtgcgcagaa   1980

agcccttctc cttcaagtgg tggaacatgg tgccctgagc ccatcttccc tggcgtcctc   2040

tccctcctgg ccagatgtcg ctgggtcctc tgcagtgtgg caagcaagag ctcttgtgaa   2100
```

tattgtggct ccctgggggc ggccagccct cccagcagtg gcttgctttc ttctcctgtg 2160
atgtcccagt ttcccactct gaagatccca acatggtcct agcactgcac actcagttct 2220
gctctaagaa gctgcaataa agttttttta agtcactttg tacatga 2267

<210> SEQ ID NO 62
<211> LENGTH: 663
<212> TYPE: PRT
<213> ORGANISM: Homo sapiens
<220> FEATURE:
<223> OTHER INFORMATION: protein-arginine deiminase type-4 [Homo sapiens]

<400> SEQUENCE: 62

Met Ala Gln Gly Thr Leu Ile Arg Val Thr Pro Glu Gln Pro Thr His
1 5 10 15

Ala Val Cys Val Leu Gly Thr Leu Thr Gln Leu Asp Ile Cys Ser Ser
20 25 30

Ala Pro Glu Asp Cys Thr Ser Phe Ser Ile Asn Ala Ser Pro Gly Val
35 40 45

Val Val Asp Ile Ala His Gly Pro Pro Ala Lys Lys Lys Ser Thr Gly
50 55 60

Ser Ser Thr Trp Pro Leu Asp Pro Gly Val Glu Val Thr Leu Thr Met
65 70 75 80

Lys Val Ala Ser Gly Ser Thr Gly Asp Gln Lys Val Gln Ile Ser Tyr
85 90 95

Tyr Gly Pro Lys Thr Pro Pro Val Lys Ala Leu Leu Tyr Leu Thr Gly
100 105 110

Val Glu Ile Ser Leu Cys Ala Asp Ile Thr Arg Thr Gly Lys Val Lys
115 120 125

Pro Thr Arg Ala Val Lys Asp Gln Arg Thr Trp Thr Trp Gly Pro Cys
130 135 140

Gly Gln Gly Ala Ile Leu Leu Val Asn Cys Asp Arg Asp Asn Leu Glu
145 150 155 160

Ser Ser Ala Met Asp Cys Glu Asp Asp Glu Val Leu Asp Ser Glu Asp
165 170 175

Leu Gln Asp Met Ser Leu Met Thr Leu Ser Thr Lys Thr Pro Lys Asp
180 185 190

Phe Phe Thr Asn His Thr Leu Val Leu His Val Ala Arg Ser Glu Met
195 200 205

Asp Lys Val Arg Val Phe Gln Ala Thr Arg Gly Lys Leu Ser Ser Lys
210 215 220

Cys Ser Val Val Leu Gly Pro Lys Trp Pro Ser His Tyr Leu Met Val
225 230 235 240

Pro Gly Gly Lys His Asn Met Asp Phe Tyr Val Glu Ala Leu Ala Phe
245 250 255

Pro Asp Thr Asp Phe Pro Gly Leu Ile Thr Leu Thr Ile Ser Leu Leu
260 265 270

Asp Thr Ser Asn Leu Glu Leu Pro Glu Ala Val Val Phe Gln Asp Ser
275 280 285

Val Val Phe Arg Val Ala Pro Trp Ile Met Thr Pro Asn Thr Gln Pro
290 295 300

Pro Gln Glu Val Tyr Ala Cys Ser Ile Phe Glu Asn Glu Asp Phe Leu
305 310 315 320

Lys Ser Val Thr Thr Leu Ala Met Lys Ala Lys Cys Lys Leu Thr Ile

-continued

```
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
        435                 440                 445

Asp Phe Leu Ser Ala Gln Gln Val Gln Ala Pro Val Lys Leu Tyr Ser
    450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
            500                 505                 510

Leu Leu Phe Glu Gly Ile Lys Lys Lys Lys Gln Gln Lys Ile Lys Asn
        515                 520                 525

Ile Leu Ser Asn Lys Thr Leu Arg Glu His Asn Ser Phe Val Glu Arg
    530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
            580                 585                 590

Gly Lys His Leu Gly Ile Pro Lys Pro Phe Gly Pro Val Ile Asn Gly
        595                 600                 605

Arg Cys Cys Leu Glu Glu Lys Val Cys Ser Leu Leu Glu Pro Leu Gly
    610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660
```

<210> SEQ ID NO 63
<211> LENGTH: 2267
<212> TYPE: DNA
<213> ORGANISM: Homo sapiens
<220> FEATURE:
<223> OTHER INFORMATION: Homo sapiens peptidyl arginine deiminase 4
(PADI4), mRNA

<400> SEQUENCE: 63

```
agccagaggg acgagctagc ccgacgatgg cccaggggac attgatccat gtgaccccag      60

agcagcccac ccatgccgtg tgtgtgctgg gcaccttgac tcagcttgac atctgcagct     120
```

ctgcccctga ggactgcacg tccttcagca tcaacgcctc cccaggggtg gtcgtggata 180
ttgcccacgg ccctccagcc aagaagaaat ccacaggttc ctccacatgg cccctggacc 240
ctggggtaga ggtgaccctg acgatgaaag tggccagtgg tagcacaggc gaccagaagg 300
ttcagatttc atactacgga cccaagactc caccagtcaa agctctactc tacctcaccg 360
gggtggaaat ctccttgtgc gcagacatca cccgcaccgg caaagtgaag ccaaccagag 420
ctgtgaaaga tcagaggacc tggacctggg gcccttgtgg acagggtgcc atcctgctgg 480
tgaactgtga cagagacaat ctcgaatctt ctgccatgga ctgcgaggat gatgaagtgc 540
ttgacagcga agacctgcag gacatgtcgc tgatgaccct gagcacgaag acccccaagg 600
acttcttcac aaaccataca ctggtgctcc acgtggccag gtctgagatg gacaaagtga 660
gggtgtttca ggccacacgg ggcaaactgt cctccaagtg cagcgtagtc ttgggtccca 720
agtggccctc tcactacctg atggtccccg gtggaaagca caacatggac ttctacgtgg 780
aggccctcgc tttcccggac accgacttcc cggggctcat taccctcacc atctccctgc 840
tggacacgtc caacctggag ctccccgagg ctgtggtgtt ccaagacagc gtggtcttcc 900
gcgtggcgcc ctggatcatg acccccaaca cccagccccc gcaggaggtg tacgcgtgca 960
gtatttttga aaatgaggac ttcctgaagt cagtgactac tctggccatg aaagccaagt 1020
gcaagctgac catctgccct gaggaggaga acatggatga ccagtggatg caggatgaaa 1080
tggagatcgg ctacatccaa gccccacaca aaacgctgcc cgtggtcttc gactctccaa 1140
ggaacagagg cctgaaggag tttcccatca aacgcgtgat gggtccagat tttggctatg 1200
taactcgagg gccccaaaca gggggtatca gtggactgga ctcctttggg aacctggaag 1260
tgagcccccc agtcacagtc aggggcaagg aatacccgct gggcaggatt ctcttcgggg 1320
acagctgtta tcccagcaat gacagccggc agatgcacca ggccctgcag gacttcctca 1380
gtgcccagca ggtgcaggcc cctgtgaagc tctattctga ctggctgtcc gtgggccacg 1440
tggacgagtt cctgagcttt gtgccagcac ccgacaggaa gggcttccgg ctgctcctgg 1500
ccagccccag gtcctgctac aaactgttcc aggagcagca gaatgagggc cacggggagg 1560
ccctgctgtt cgaagggatc aagaaaaaaa aacagcagaa aataaagaac attctgtcaa 1620
acaagacatt gagagaacat aattcatttg tggagagatg catcgactgg aaccgcgagc 1680
tgctgaagcg ggagctgggc ctggccgaga gtgacatcat tgacatcccg cagctcttca 1740
agctcaaaga gttctctaag gcggaagctt ttttccccaa catggtgaac atgctggtgc 1800
tagggaagca cctgggcatc cccaagccct tcgggcccgt catcaacggc cgctgctgcc 1860
tggaggagaa ggtgtgttcc ctgctggagc cactgggcct ccagtgcacc ttcatcaacg 1920
acttcttcac ctaccacatc aggcatgggg aggtgcactg cggcaccaac gtgcgcagaa 1980
agcccttctc cttcaagtgg tggaacatgg tgccctgagc ccatcttccc tggcgtcctc 2040
tccctcctgg ccagatgtcg ctgggtcctc tgcagtgtgg caagcaagag ctcttgtgaa 2100
tattgtggct ccctgggggc ggccagccct cccagcagtg gcttgctttc ttctcctgtg 2160
atgtcccagt ttcccactct gaagatccca acatggtcct agcactgcac actcagttct 2220
gctctaagaa gctgcaataa agttttttta agtcactttg tacatga 2267

<210> SEQ ID NO 64
<211> LENGTH: 663
<212> TYPE: PRT
<213> ORGANISM: Homo sapiens
<220> FEATURE:

<223> OTHER INFORMATION: protein-arginine deiminase type-4 [Homo sapiens]

<400> SEQUENCE: 64

```
Met Ala Gln Gly Thr Leu Ile His Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gly Pro Asp Phe Gly Tyr Val Thr Arg Gly Pro Gln Thr Gly Gly
385                 390                 395                 400
```

```
Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
        435                 440                 445

Asp Phe Leu Ser Ala Gln Gln Val Gln Ala Pro Val Lys Leu Tyr Ser
    450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
            500                 505                 510

Leu Leu Phe Glu Gly Ile Lys Lys Lys Lys Gln Gln Lys Ile Lys Asn
        515                 520                 525

Ile Leu Ser Asn Lys Thr Leu Arg Glu His Asn Ser Phe Val Glu Arg
    530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
            580                 585                 590

Gly Lys His Leu Gly Ile Pro Lys Pro Phe Gly Pro Val Ile Asn Gly
        595                 600                 605

Arg Cys Cys Leu Glu Glu Lys Val Cys Ser Leu Leu Glu Pro Leu Gly
    610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660
```

<210> SEQ ID NO 65
<211> LENGTH: 2267
<212> TYPE: DNA
<213> ORGANISM: Homo sapiens
<220> FEATURE:
<223> OTHER INFORMATION: Homo sapiens peptidyl arginine deiminase 4 (PADI4), mRNA

<400> SEQUENCE: 65

```
agccagaggg acgagctagc ccgacgatgg cccaggggac attgatcctt gtgaccccag      60

agcagcccac ccatgccgtg tgtgtgctgg gcaccttgac tcagcttgac atctgcagct     120

ctgcccctga ggactgcacg tccttcagca tcaacgcctc cccaggggtg gtcgtggata     180

ttgcccacgg ccctccagcc aagaagaaat ccacaggttc ctccacatgg cccctggacc     240

ctggggtaga ggtgaccctg acgatgaaag tggccagtgg tagcacaggc gaccagaagg     300

ttcagatttc atactacgga cccaagactc caccagtcaa agctctactc tacctcaccg     360

gggtggaaat ctccttgtgc gcagacatca cccgcaccgg caaagtgaag ccaaccagag     420

ctgtgaaaga tcagaggacc tggacctggg gcccttgtgg acagggtgcc atcctgctgg     480
```

```
tgaactgtga cagagacaat ctcgaatctt ctgccatgga ctgcgaggat gatgaagtgc    540

ttgacagcga agacctgcag gacatgtcgc tgatgaccct gagcacgaag acccccaagg    600

acttcttcac aaaccataca ctggtgctcc acgtggccag gtctgagatg gacaaagtga    660

gggtgtttca ggccacacgg ggcaaactgt cctccaagtg cagcgtagtc ttgggtccca    720

agtggccctc tcactacctg atggtccccg gtggaaagca caacatggac ttctacgtgg    780

aggccctcgc tttcccggac accgacttcc cggggctcat taccctcacc atctccctgc    840

tggacacgtc caacctggag ctccccgagg ctgtggtgtt ccaagacagc gtggtcttcc    900

gcgtggcgcc ctggatcatg acccccaaca cccagccccc gcaggaggtg tacgcgtgca    960

gtatttttga aaatgaggac ttcctgaagt cagtgactac tctggccatg aaagccaagt   1020

gcaagctgac catctgccct gaggaggaga acatggatga ccagtggatg caggatgaaa   1080

tggagatcgg ctacatccaa gccccacaca aaacgctgcc cgtggtcttc gactctccaa   1140

ggaacagagg cctgaaggag tttcccatca aacgcgtgat gggtccagat tttggctatg   1200

taactcgagg gccccaaaca gggggtatca gtggactgga ctcctttggg aacctggaag   1260

tgagcccccc agtcacagtc aggggcaagg aatacccgct gggcaggatt ctcttcgggg   1320

acagctgtta tcccagcaat gacagccggc agatgcacca ggccctgcag gacttcctca   1380

gtgcccagca ggtgcaggcc cctgtgaagc tctattctga ctggctgtcc gtgggccacg   1440

tggacgagtt cctgagcttt gtgccagcac ccgacaggaa gggcttccgg ctgctcctgg   1500

ccagccccag gtcctgctac aaactgttcc aggagcagca gaatgagggc cacgggggagg  1560

ccctgctgtt cgaagggatc aagaaaaaaa aacagcagaa aataaagaac attctgtcaa   1620

acaagacatt gagagaacat aattcatttg tggagagatg catcgactgg aaccgcgagc   1680

tgctgaagcg ggagctgggc ctggccgaga gtgacatcat tgacatcccg cagctcttca   1740

agctcaaaga gttctctaag gcggaagctt ttttccccaa catggtgaac atgctggtgc   1800

tagggaagca cctgggcatc cccaagccct tcgggcccgt catcaacggc cgctgctgcc   1860

tggaggagaa ggtgtgttcc ctgctggagc cactgggcct ccagtgcacc ttcatcaacg   1920

acttcttcac ctaccacatc aggcatgggg aggtgcactg cggcaccaac gtgcgcagaa   1980

agcccttctc cttcaagtgg tggaacatgg tgccctgagc ccatcttccc tggcgtcctc   2040

tccctcctgg ccagatgtcg ctgggtcctc tgcagtgtgg caagcaagag ctcttgtgaa   2100

tattgtggct ccctgggggc ggccagccct cccagcagtg gcttgctttc ttctcctgtg   2160

atgtcccagt ttcccactct gaagatccca acatggtcct agcactgcac actcagttct   2220

gctctaagaa gctgcaataa agttttttta agtcactttg tacatga                 2267
```

<210> SEQ ID NO 66
<211> LENGTH: 663
<212> TYPE: PRT
<213> ORGANISM: Homo sapiens
<220> FEATURE:
<223> OTHER INFORMATION: protein-arginine deiminase type-4 [Homo sapiens]

<400> SEQUENCE: 66

```
Met Ala Gln Gly Thr Leu Ile Leu Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45
```

```
Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
        435                 440                 445

Asp Phe Leu Ser Ala Gln Gln Val Gln Ala Pro Val Lys Leu Tyr Ser
    450                 455                 460
```

-continued

```
Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
            500                 505                 510

Leu Leu Phe Glu Gly Ile Lys Lys Lys Lys Gln Gln Lys Ile Lys Asn
        515                 520                 525

Ile Leu Ser Asn Lys Thr Leu Arg Glu His Asn Ser Phe Val Glu Arg
    530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
            580                 585                 590

Gly Lys His Leu Gly Ile Pro Lys Pro Phe Gly Pro Val Ile Asn Gly
        595                 600                 605

Arg Cys Cys Leu Glu Glu Lys Val Cys Ser Leu Leu Glu Pro Leu Gly
    610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660
```

<210> SEQ ID NO 67
<211> LENGTH: 1801
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X3, mRNA

<400> SEQUENCE: 67

```
tctacctcac cggggtggaa atctccttgt gcgcagacat cacccgcacc ggcaaagtga     60

agccaaccag agctgtgaaa gatcagacct gcaggacatg tcgctgatga ccctgagcac    120

gaagaccccc aaggacttct tcacaaacca tacactggtg ctccacgtgg ccaggtctga    180

gatggacaaa gtgagggtgt ttcaggccac acggggcaaa ctgtcctcca agtgcagcgt    240

agtcttgggt cccaagtggc cctctcacta cctgatggtc cccggtggaa agcacaacat    300

ggacttctac gtggaggccc tcgctttccc ggacaccgac ttcccggggc tcattacct    360

caccatctcc ctgctggaca cgtccaacct ggagctcccc gaggctgtgg tgttccaaga    420

cagcgtggtc ttccgcgtgg cgccctggat catgaccccc aacacccagc cccgcagga    480

ggtgtacgcg tgcagtattt ttgaaaatga ggacttcctg aagtcagtga ctactctggc    540

catgaaagcc aagtgcaagc tgaccatctg ccctgaggag gagaacatgg atgaccagtg    600

gatgcaggat gaaatggaga tcggctacat ccaagcccca cacaaaacgc tgcccgtggt    660

cttcgactct ccaaggaaca gaggcctgaa ggagtttccc atcaaacgcg tgatgggtcc    720

agattttggc tatgtaactc gagggcccca aacagggggt atcagtggac tggactcctt    780

tgggaacctg gaagtgagcc ccccagtcac agtcaggggc aaggaatacc cgctgggcag    840

gattctcttc ggggacagct gttatcccag caatgacagc cggcagatgc accaggccct    900
```

gcaggacttc ctcagtgccc agcaggtgca ggcccctgtg aagctctatt ctgactggct 960
gtccgtgggc cacgtggacg agttcctgag ctttgtgcca gcacccgaca ggaagggctt 1020
ccggctgctc ctggccagcc ccaggtcctg ctacaaactg ttccaggagc agcagaatga 1080
gggccacggg gaggccctgc tgttcgaagg gatcaagaaa aaaaaacagc agaaaataaa 1140
gaacattctg tcaaacaaga cattgagaga acataattca tttgtggaga gatgcatcga 1200
ctggaaccgc gagctgctga agcgggagct gggcctggcc gagagtgaca tcattgacat 1260
cccgcagctc ttcaagctca aagagttctc taaggcggaa gctttttcc ccaacatggt 1320 gaacatgctg gtgctaggga agcacctggg catccccaag cccttcgggc ccgtcatcaa 1380
cggccgctgc tgcctggagg agaaggtgtg ttccctgctg gagccactgg gcctccagtg 1440
caccttcatc aacgacttct tcacctacca catcaggcat ggggaggtgc actgcggcac 1500
caacgtgcgc agaaagccct tctccttcaa gtggtggaac atggtgccct gagcccatct 1560
tccctggcgt cctctccctc ctggccagat gtcgctgggt cctctgcagt gtggcaagca 1620
agagctcttg tgaatattgt ggctccctgg gggcggccag ccctcccagc agtggcttgc 1680
tttcttctcc tgtgatgtcc cagtttccca ctctgaagat cccaacatgg tcctagcact 1740
gcacactcag ttctgctcta agaagctgca ataaagtttt tttaagtcac tttgtacatg 1800
a 1801

<210> SEQ ID NO 68
<211> LENGTH: 1748
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X8, mRNA

<400> SEQUENCE: 68
agctctactc tacctcaccg gggtggaaat ctccttgtgc gcagacatca cccgcaccgg 60
caaagtgaag ccaaccagag ctgtgaaaga tcagaggacc tggacctggg gcccttgtgg 120
acagggtgcc atcctgctgg tgaactgtga cagagacaat ctcgaatctt ctgccatgga 180
ctgcgaggat gatgaagtgc ttgacagcga agacctgcag gacatgtcgc tgatgaccct 240
gagcacgaag acccccaagg acttcttcac aaaccataca ctggtgctcc acgtggccag 300
gtctgagatg gacaaagtga gggtgtttca ggccacacga gctccccgag gctgtggtgt 360
tccaagacag cgtggtcttc cgcgtggcgc cctggatcat gacccccaac acccagcccc 420
cgcaggaggt gtacgcgtgc agtatttttg aaaatgagga cttcctgaag tcagtgacta 480
ctctggccat gaaagccaag tgcaagctga ccatctgccc tgaggaggag aacatggatg 540
accagtggat gcaggatgaa atggagatcg gctacatcca agccccacac aaaacgctgc 600
ccgtggtctt cgactctcca aggaacagag gcctgaagga gtttcccatc aaacgcgtga 660
tgggtccaga ttttggctat gtaactcgag ggccccaaac agggggtatc agtggactgg 720
actcctttgg gaacctggaa gtgagccccc cagtcacagt caggggcaag gaatacccgc 780
tgggcaggat tctcttcggg gacagctgtt atcccagcaa tgacagccgg cagatgcacc 840
aggccctgca ggacttcctc agtgcccagc aggtgcaggc ccctgtgaag ctctattctg 900
actggctgtc cgtgggccac gtggacgagt tcctgagctt tgtgccagca cccgacagga 960
agggcttccg gctgctcctg gccagcccca ggtcctgcta caaactgttc caggagcagc 1020
agaatgaggg ccacggggag gccctgctgt tcgaagggat caagaaaaaa aaacagcaga 1080

```
aaataaagaa cattctgtca aacaagacat tgagagaaca taattcattt gtggagagat   1140
gcatcgactg gaaccgcgag ctgctgaagc gggagctggg cctggccgag agtgacatca   1200
ttgacatccc gcagctcttc aagctcaaag agttctctaa ggcggaagct tttttcccca   1260
acatggtgaa catgctggtg ctagggaagc acctgggcat ccccaagccc ttcgggcccg   1320
tcatcaacgg ccgctgctgc ctggaggaga aggtgtgttc cctgctggag ccactgggcc   1380
tccagtgcac cttcatcaac gacttcttca cctaccacat caggcatggg gaggtgcact   1440
gcggcaccaa cgtgcgcaga aagcccttct ccttcaagtg gtggaacatg gtgccctgag   1500
cccatcttcc ctggcgtcct ctccctcctg gccagatgtc gctgggtcct ctgcagtgtg   1560
gcaagcaaga gctcttgtga atattgtggc tccctggggg cggccagccc tcccagcagt   1620
ggcttgcttt cttctcctgt gatgtcccag tttcccactc tgaagatccc aacatggtcc   1680
tagcactgca cactcagttc tgctctaaga agctgcaata aagtttttt aagtcacttt    1740
gtacatga                                                            1748
```

<210> SEQ ID NO 69
<211> LENGTH: 2081
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X1, mRNA

<400> SEQUENCE: 69

```
agccagaggg acgagctagc ccgacgatgg cccaggggac attgatccgt gtgaccccag     60
agcagcccac ccatgccgtg tgtgtgctgg gcaccttgac tcagcttgac atctgcagct    120
ctgcccctga ggactgcacg tccttcagca tcaacgcctc cccaggggtg gtcgtggata    180
ttgcccacgg ccctccagcc aagaagaaat ccacaggttc ctccacatgg cccctggacc    240
ctggggtaga ggtgaccctg acgatgaaag tggccagtgg tagcacaggc gaccagaagg    300
ttcagatttc atactacgga cccaagactc caccagtcaa agctctactc tacctcaccg    360
gggtggacct gcaggacatg tcgctgatga ccctgagcac gaagaccccc aaggacttct    420
tcacaaacca tacactggtg ctccacgtgg ccaggtctga gatggacaaa gtgagggtgt    480
ttcaggccac acggggcaaa ctgtcctcca agtgcagcgt agtcttgggt cccaagtggc    540
cctctcacta cctgatggtc cccggtggaa agcacaacat ggacttctac gtggaggccc    600
tcgctttccc ggacaccgac ttcccggggc tcattaccct caccatctcc ctgctggaca    660
cgtccaacct ggagctcccc gaggctgtgg tgttccaaga cagcgtggtc ttccgcgtgg    720
cgccctggat catgaccccc aacacccagc cccgcagga ggtgtacgcg tgcagtattt     780
ttgaaaatga ggacttcctg aagtcagtga ctactctggc catgaaagcc aagtgcaagc    840
tgaccatctg ccctgaggag gagaacatgg atgaccagtg gatgcaggat gaaatggaga    900
tcggctacat ccaagcccca cacaaaacgc tgcccgtggt cttcgactct ccaaggaaca    960
gaggcctgaa ggagtttccc atcaaacgcg tgatgggtcc agattttggc tatgtaactc   1020
gagggcccca aacagggggt atcagtggac tggactcctt tgggaacctg gaagtgagcc   1080
ccccagtcac agtcaggggc aaggaatacc cgctgggcag gattctcttc ggggacagct   1140
gttatcccag caatgacagc cggcagatgc accaggccct gcaggacttc ctcagtgccc   1200
agcaggtgca ggcccctgtg aagctctatt ctgactggct gtccgtgggc cacgtggacg   1260
agttcctgag ctttgtgcca gcacccgaca ggaagggctt ccggctgctc ctggccagcc   1320
```

```
ccaggtcctg ctacaaactg ttccaggagc agcagaatga gggccacggg gaggccctgc   1380

tgttcgaagg gatcaagaaa aaaaaacagc agaaaataaa gaacattctg tcaaacaaga   1440

cattgagaga acataattca tttgtggaga gatgcatcga ctggaaccgc gagctgctga   1500

agcgggagct gggcctggcc gagagtgaca tcattgacat cccgcagctc ttcaagctca   1560

aagagttctc taaggcggaa gctttttttcc ccaacatggt gaacatgctg gtgctaggga   1620

agcacctggg catccccaag cccttcgggc ccgtcatcaa cggccgctgc tgcctggagg   1680

agaaggtgtg ttccctgctg gagccactgg gcctccagtg caccttcatc aacgacttct   1740

tcacctacca catcaggcat ggggaggtgc actgcggcac caacgtgcgc agaaagccct   1800

tctccttcaa gtggtggaac atggtgccct gagcccatct tccctggcgt cctctccctc   1860

ctggccagat gtcgctgggt cctctgcagt gtggcaagca agagctcttg tgaatattgt   1920

ggctccctgg gggcggccag ccctcccagc agtggcttgc tttcttctcc tgtgatgtcc   1980

cagtttccca ctctgaagat cccaacatgg tcctagcact gcacactcag ttctgctcta   2040

agaagctgca ataaagtttt tttaagtcac tttgtacatg a                       2081
```

```
<210> SEQ ID NO 70
<211> LENGTH: 601
<212> TYPE: PRT
<213> ORGANISM: Homo sapiens
<220> FEATURE:
<223> OTHER INFORMATION: protein-arginine deiminase type-4 isoform X1
      [Homo sapiens]

<400> SEQUENCE: 70

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Asp Leu Gln Asp Met Ser Leu Met Thr Leu Ser Thr Lys Thr Pro
        115                 120                 125

Lys Asp Phe Phe Thr Asn His Thr Leu Val Leu His Val Ala Arg Ser
    130                 135                 140

Glu Met Asp Lys Val Arg Val Phe Gln Ala Thr Arg Gly Lys Leu Ser
145                 150                 155                 160

Ser Lys Cys Ser Val Val Leu Gly Pro Lys Trp Pro Ser His Tyr Leu
                165                 170                 175

Met Val Pro Gly Gly Lys His Asn Met Asp Phe Tyr Val Glu Ala Leu
            180                 185                 190

Ala Phe Pro Asp Thr Asp Phe Pro Gly Leu Ile Thr Leu Thr Ile Ser
        195                 200                 205

Leu Leu Asp Thr Ser Asn Leu Glu Leu Pro Glu Ala Val Val Phe Gln
    210                 215                 220
```

```
Asp Ser Val Val Phe Arg Val Ala Pro Trp Ile Met Thr Pro Asn Thr
225                 230                 235                 240

Gln Pro Pro Gln Glu Val Tyr Ala Cys Ser Ile Phe Glu Asn Glu Asp
                245                 250                 255

Phe Leu Lys Ser Val Thr Thr Leu Ala Met Lys Ala Lys Cys Lys Leu
            260                 265                 270

Thr Ile Cys Pro Glu Glu Glu Asn Met Asp Asp Gln Trp Met Gln Asp
        275                 280                 285

Glu Met Glu Ile Gly Tyr Ile Gln Ala Pro His Lys Thr Leu Pro Val
    290                 295                 300

Val Phe Asp Ser Pro Arg Asn Arg Gly Leu Lys Glu Phe Pro Ile Lys
305                 310                 315                 320

Arg Val Met Gly Pro Asp Phe Gly Tyr Val Thr Arg Gly Pro Gln Thr
                325                 330                 335

Gly Gly Ile Ser Gly Leu Asp Ser Phe Gly Asn Leu Glu Val Ser Pro
            340                 345                 350

Pro Val Thr Val Arg Gly Lys Glu Tyr Pro Leu Gly Arg Ile Leu Phe
        355                 360                 365

Gly Asp Ser Cys Tyr Pro Ser Asn Asp Ser Arg Gln Met His Gln Ala
    370                 375                 380

Leu Gln Asp Phe Leu Ser Ala Gln Gln Val Gln Ala Pro Val Lys Leu
385                 390                 395                 400

Tyr Ser Asp Trp Leu Ser Val Gly His Val Asp Glu Phe Leu Ser Phe
                405                 410                 415

Val Pro Ala Pro Asp Arg Lys Gly Phe Arg Leu Leu Leu Ala Ser Pro
            420                 425                 430

Arg Ser Cys Tyr Lys Leu Phe Gln Glu Gln Gln Asn Glu Gly His Gly
        435                 440                 445

Glu Ala Leu Leu Phe Glu Gly Ile Lys Lys Lys Lys Gln Gln Lys Ile
    450                 455                 460

Lys Asn Ile Leu Ser Asn Lys Thr Leu Arg Glu His Asn Ser Phe Val
465                 470                 475                 480

Glu Arg Cys Ile Asp Trp Asn Arg Glu Leu Leu Lys Arg Glu Leu Gly
                485                 490                 495

Leu Ala Glu Ser Asp Ile Ile Asp Ile Pro Gln Leu Phe Lys Leu Lys
            500                 505                 510

Glu Phe Ser Lys Ala Glu Ala Phe Phe Pro Asn Met Val Asn Met Leu
        515                 520                 525

Val Leu Gly Lys His Leu Gly Ile Pro Lys Pro Phe Gly Pro Val Ile
    530                 535                 540

Asn Gly Arg Cys Cys Leu Glu Glu Lys Val Cys Ser Leu Leu Glu Pro
545                 550                 555                 560

Leu Gly Leu Gln Cys Thr Phe Ile Asn Asp Phe Phe Thr Tyr His Ile
                565                 570                 575

Arg His Gly Glu Val His Cys Gly Thr Asn Val Arg Arg Lys Pro Phe
            580                 585                 590

Ser Phe Lys Trp Trp Asn Met Val Pro
        595                 600
```

<210> SEQ ID NO 71
<211> LENGTH: 2081
<212> TYPE: DNA
<213> ORGANISM: Homo sapiens
<220> FEATURE:

<223> OTHER INFORMATION: PREDICTED: Homo sapiens peptidyl arginine deiminase 4 (PADI4), transcript variant X1, mRNA

<400> SEQUENCE: 71

```
agccagaggg acgagctagc ccgacgatgg cccaggggac attgatccgt gtgaccccag     60
agcagcccac ccatgccgtg tgtgtgctgg gcaccttgac tcagcttgac atctgcagct    120
ctgcccctga ggactgcacg tccttcagca tcaacgcctc cccaggggtg gtcgtggata    180
ttgcccacgg ccctccagcc aagaagaaat ccacaggttc ctccacatgg cccctggacc    240
ctggggtaga ggtgaccctg acgatgaaag tggccagtgg tagcacaggc gaccagaagg    300
ttcagatttc atactacgga cccaagactc caccagtcaa agctctactc tacctcaccg    360
gggtggacct gcaggacatg tcgctgatga ccctgagcac gaagaccccc aaggacttct    420
tcacaaacca tacactggtg ctccacgtgg ccaggtctga gatggacaaa gtgagggtgt    480
ttcaggccac acggggcaaa ctgtcctcca agtgcagcgt agtcttgggt cccaagtggc    540
cctctcacta cctgatggtc cccggtggaa agcacaacat ggacttctac gtggaggccc    600
tcgctttccc ggacaccgac ttcccggggc tcattaccct caccatctcc ctgctggaca    660
cgtccaacct ggagctcccc gaggctgtgg tgttccaaga cagcgtggtc ttccgcgtgg    720
cgccctggat catgaccccc aacacccagc cccgcagga ggtgtacgcg tgcagtattt     780
ttgaaaatga ggacttcctg aagtcagtga ctactctggc catgaaagcc aagtgcaagc    840
tgaccatctg ccctgaggag gagaacatgg atgaccagtg gatgcaggat gaaatggaga    900
tcggctacat ccaagcccca cacaaaacgc tgcccgtggt cttcgactct ccaaggaaca    960
gaggcctgaa ggagtttccc atcaaacgcg tgatgggtcc agattttggc tatgtaactc   1020
gagggcccca aacagggggt atcagtggac tggactcctt tgggaacctg gaagtgagcc   1080
ccccagtcac agtcaggggc aaggaatacc cgctgggcag gattctcttc ggggacagct   1140
gttatcccag caatgacagc cggcagatgc accaggccct gcaggacttc ctcagtgccc   1200
agcaggtgca ggcccctgtg aagctctatt ctgactggct gtccgtgggc cacgtggacg   1260
agttcctgag ctttgtgcca gcacccgaca ggaagggctt ccggctgctc ctggccagcc   1320
ccaggtcctg ctacaaactg ttccaggagc agcagaatga gggccacggg gaggccctgc   1380
tgttcgaagg gatcaagaaa aaaaaacagc agaaaataaa gaacattctg tcaaacaaga   1440
cattgagaga acataattca tttgtggaga gatgcatcga ctggaaccgc gagctgctga   1500
agcgggagct gggcctggcc gagagtgaca tcattgacat cccgcagctc ttcaagctca   1560
aagagttctc taaggcggaa gctttttcc ccaacatggt gaacatgctg gtgctaggga    1620
agcacctggg catccccaag cccttcgggc ccgtcatcaa cggccgctgc tgcctggagg   1680
agaaggtgtg ttccctgctg gagccactgg gcctccagtg caccttcatc aacgacttct   1740
tcacctacca catcaggcat ggggaggtgc actgcggcac caacgtgcgc agaaagccct   1800
tctccttcaa gtggtggaac atggtgccct gagcccatct tccctggcgt cctctccctc   1860
ctggccagat gtcgctgggt cctctgcagt gtggcaagca agagctcttg tgaatattgt   1920
ggctccctgg gggcggccag ccctcccagc agtggcttgc tttcttctcc tgtgatgtcc   1980
cagtttccca ctctgaagat cccaacatgg tcctagcact gcacactcag ttctgctcta   2040
agaagctgca ataaagtttt tttaagtcac tttgtacatg a                       2081
```

<210> SEQ ID NO 72
<211> LENGTH: 601
<212> TYPE: PRT

```
<213> ORGANISM: Homo sapiens
<220> FEATURE:
<223> OTHER INFORMATION: protein-arginine deiminase type-4 isoform X1
      [Homo sapiens]

<400> SEQUENCE: 72

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Asp Leu Gln Asp Met Ser Leu Met Thr Leu Ser Thr Lys Thr Pro
        115                 120                 125

Lys Asp Phe Phe Thr Asn His Thr Leu Val Leu His Val Ala Arg Ser
    130                 135                 140

Glu Met Asp Lys Val Arg Val Phe Gln Ala Thr Arg Gly Lys Leu Ser
145                 150                 155                 160

Ser Lys Cys Ser Val Val Leu Gly Pro Lys Trp Pro Ser His Tyr Leu
                165                 170                 175

Met Val Pro Gly Gly Lys His Asn Met Asp Phe Tyr Val Glu Ala Leu
            180                 185                 190

Ala Phe Pro Asp Thr Asp Phe Pro Gly Leu Ile Thr Leu Thr Ile Ser
        195                 200                 205

Leu Leu Asp Thr Ser Asn Leu Glu Leu Pro Glu Ala Val Val Phe Gln
    210                 215                 220

Asp Ser Val Val Phe Arg Val Ala Pro Trp Ile Met Thr Pro Asn Thr
225                 230                 235                 240

Gln Pro Pro Gln Glu Val Tyr Ala Cys Ser Ile Phe Glu Asn Glu Asp
                245                 250                 255

Phe Leu Lys Ser Val Thr Thr Leu Ala Met Lys Ala Lys Cys Lys Leu
            260                 265                 270

Thr Ile Cys Pro Glu Glu Glu Asn Met Asp Asp Gln Trp Met Gln Asp
        275                 280                 285

Glu Met Glu Ile Gly Tyr Ile Gln Ala Pro His Lys Thr Leu Pro Val
    290                 295                 300

Val Phe Asp Ser Pro Arg Asn Arg Gly Leu Lys Glu Phe Pro Ile Lys
305                 310                 315                 320

Arg Val Met Gly Pro Asp Phe Gly Tyr Val Thr Arg Gly Pro Gln Thr
                325                 330                 335

Gly Gly Ile Ser Gly Leu Asp Ser Phe Gly Asn Leu Glu Val Ser Pro
            340                 345                 350

Pro Val Thr Val Arg Gly Lys Glu Tyr Pro Leu Gly Arg Ile Leu Phe
        355                 360                 365

Gly Asp Ser Cys Tyr Pro Ser Asn Asp Ser Arg Gln Met His Gln Ala
    370                 375                 380
```

-continued

```
Leu Gln Asp Phe Leu Ser Ala Gln Gln Val Gln Ala Pro Val Lys Leu
385                 390                 395                 400

Tyr Ser Asp Trp Leu Ser Val Gly His Val Asp Glu Phe Leu Ser Phe
                405                 410                 415

Val Pro Ala Pro Asp Arg Lys Gly Phe Arg Leu Leu Leu Ala Ser Pro
            420                 425                 430

Arg Ser Cys Tyr Lys Leu Phe Gln Glu Gln Gln Asn Glu Gly His Gly
        435                 440                 445

Glu Ala Leu Leu Phe Glu Gly Ile Lys Lys Lys Lys Gln Gln Lys Ile
    450                 455                 460

Lys Asn Ile Leu Ser Asn Lys Thr Leu Arg Glu His Asn Ser Phe Val
465                 470                 475                 480

Glu Arg Cys Ile Asp Trp Asn Arg Glu Leu Leu Lys Arg Glu Leu Gly
                485                 490                 495

Leu Ala Glu Ser Asp Ile Ile Asp Ile Pro Gln Leu Phe Lys Leu Lys
            500                 505                 510

Glu Phe Ser Lys Ala Glu Ala Phe Phe Pro Asn Met Val Asn Met Leu
        515                 520                 525

Val Leu Gly Lys His Leu Gly Ile Pro Lys Pro Phe Gly Pro Val Ile
    530                 535                 540

Asn Gly Arg Cys Cys Leu Glu Glu Lys Val Cys Ser Leu Leu Glu Pro
545                 550                 555                 560

Leu Gly Leu Gln Cys Thr Phe Ile Asn Asp Phe Phe Thr Tyr His Ile
                565                 570                 575

Arg His Gly Glu Val His Cys Gly Thr Asn Val Arg Arg Lys Pro Phe
            580                 585                 590

Ser Phe Lys Trp Trp Asn Met Val Pro
        595                 600
```

<210> SEQ ID NO 73
<211> LENGTH: 1969
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X2, mRNA

<400> SEQUENCE: 73

```
acagccagag ggacgagcta gcccgacgat ggcccagggg acattgatcc gtgtgacccc     60

agagcagccc acccatgccg tgtgtgtgct gggcaccttg actcagcttg acatctgcag    120

ctctgcccct gaggactgca cgtccttcag catcaacgcc tccccagggg tggtcgtgga    180

tattgcccac ggccctccag ccaagaagaa atccacaggt tcctccacat ggcccctgga    240

ccctggggta gaggtgaccc tgacgatgaa agtggccagt ggtagcacag gcgaccagaa    300

ggttcagatt tcatactacg gacccaagac tccaccagtc aaagctctac tctacctcac    360

cggggtggaa atctccttgt gcgcagacat cacccgcacc ggcaaagtga agccaaccag    420

agctgtgaaa gatcagagga cctggacctg ggggcccttgt ggacagggtg ccatcctgct    480

ggtgaactgt gacagagaca atctcgaatc ttctgccatg gactgcgagg atgatgaagt    540

gcttgacagc gaagacctgc aggacatgtc gctgatgacc ctgagcacga agacccccaa    600

ggacttcttc acaaaccata cactggtgct ccacgtggcc aggtctgaga tggacaaagt    660

gagggtgttt caggccacac ggggcaaact gtcctccaag tgcagcgtag tcttgggtcc    720

caagtggccc tctcactacc tgatggtccc cggtggaaag cacaacatgg acttctacgt    780
```

-continued

```
ggaggccctc gctttcccgg acaccgactt cccggggctc attaccctca ccatctccct    840

gctggacacg tccaacctgg agctccccga ggctgtggtg ttccaagaca gcgtggtctt    900

ccgcgtggcg ccctggatca tgacccccaa cacccagccc ccgcaggagg tgtacgcgtg    960

cagtattttt gaaaatgagg acttcctgaa gtcagtgact actctggcca tgaaagccaa   1020

gtgcaagctg accatctgcc ctgaggagga gaacatggat gaccagtgga tgcaggatga   1080

aatggagatc ggctacatcc aagccccaca caaaacgctg cccgtggtct tcgactctcc   1140

aaggaacaga ggcctgaagg agtttcccat caaacgcgtg atgggcttcc ggctgctcct   1200

ggccagcccc aggtcctgct acaaactgtt ccaggagcag cagaatgagg gccacgggga   1260

ggccctgctg ttcgaaggga tcaagaaaaa aaaacagcag aaaataaaga acattctgtc   1320

aaacaagaca ttgagagaac ataattcatt tgtggagaga tgcatcgact ggaaccgcga   1380

gctgctgaag cgggagctgg gcctggccga gagtgacatc attgacatcc cgcagctctt   1440

caagctcaaa gagttctcta aggcggaagc ttttttcccc aacatggtga acatgctggt   1500

gctagggaag cacctgggca tccccaagcc cttcgggccc gtcatcaacg gccgctgctg   1560

cctggaggag aaggtgtgtt ccctgctgga gccactgggc ctccagtgca ccttcatcaa   1620

cgacttcttc acctaccaca tcaggcatgg ggaggtgcac tgcggcacca acgtgcgcag   1680

aaagcccttc tccttcaagt ggtggaacat ggtgccctga gcccatcttc cctggcgtcc   1740

tctccctcct ggccagatgt cgctgggtcc tctgcagtgt ggcaagcaag agctcttgtg   1800

aatattgtgg ctccctgggg gcggccagcc ctcccagcag tggcttgctt tcttctcctg   1860

tgatgtccca gtttcccact ctgaagatcc caacatggtc ctagcactgc acactcagtt   1920

ctgctctaag aagctgcaat aaagtttttt taagtcactt tgtacatga               1969
```

<210> SEQ ID NO 74
<211> LENGTH: 563
<212> TYPE: PRT
<213> ORGANISM: Homo sapiens
<220> FEATURE:
<223> OTHER INFORMATION: protein-arginine deiminase type-4 isoform X2
[Homo sapiens]

<400> SEQUENCE: 74

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
```

-continued

```
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gly Phe Arg Leu Leu Leu Ala Ser Pro Arg Ser Cys Tyr Lys Leu
385                 390                 395                 400

Phe Gln Glu Gln Gln Asn Glu Gly His Gly Glu Ala Leu Leu Phe Glu
                405                 410                 415

Gly Ile Lys Lys Lys Lys Gln Gln Lys Ile Lys Asn Ile Leu Ser Asn
            420                 425                 430

Lys Thr Leu Arg Glu His Asn Ser Phe Val Glu Arg Cys Ile Asp Trp
        435                 440                 445

Asn Arg Glu Leu Leu Lys Arg Glu Leu Gly Leu Ala Glu Ser Asp Ile
    450                 455                 460

Ile Asp Ile Pro Gln Leu Phe Lys Leu Lys Glu Phe Ser Lys Ala Glu
465                 470                 475                 480

Ala Phe Phe Pro Asn Met Val Asn Met Leu Val Leu Gly Lys His Leu
                485                 490                 495

Gly Ile Pro Lys Pro Phe Gly Pro Val Ile Asn Gly Arg Cys Cys Leu
            500                 505                 510

Glu Glu Lys Val Cys Ser Leu Leu Glu Pro Leu Gly Leu Gln Cys Thr
        515                 520                 525

Phe Ile Asn Asp Phe Phe Thr Tyr His Ile Arg His Gly Glu Val His
    530                 535                 540

Cys Gly Thr Asn Val Arg Arg Lys Pro Phe Ser Phe Lys Trp Trp Asn
545                 550                 555                 560

Met Val Pro
```

<210> SEQ ID NO 75
<211> LENGTH: 1969
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X2, mRNA

<400> SEQUENCE: 75

```
acagccagag ggacgagcta gcccgacgat ggcccagggg acattgatcc gtgtgacccc     60
agagcagccc acccatgccg tgtgtgtgct gggcaccttg actcagcttg acatctgcag    120
ctctgcccct gaggactgca cgtccttcag catcaacgcc tccccagggg tggtcgtgga    180
tattgcccac ggccctccag ccaagaagaa atccacaggt tcctccacat ggcccctgga    240
ccctggggta gaggtgaccc tgacgatgaa agtggccagt ggtagcacag gcgaccagaa    300
ggttcagatt tcatactacg gacccaagac tccaccagtc aaagctctac tctacctcac    360
cggggtggaa atctccttgt gcgcagacat cacccgcacc ggcaaagtga agccaaccag    420
agctgtgaaa gatcagagga cctggacctg ggggcccttgt ggacagggtg ccatcctgct    480
ggtgaactgt gacagagaca atctcgaatc ttctgccatg gactgcgagg atgatgaagt    540
gcttgacagc gaagacctgc aggacatgtc gctgatgacc ctgagcacga agacccccaa    600
ggacttcttc acaaaccata cactggtgct ccacgtggcc aggtctgaga tggacaaagt    660
gagggtgttt caggccacac ggggcaaact gtcctccaag tgcagcgtag tcttgggtcc    720
caagtggccc tctcactacc tgatggtccc cggtggaaag cacaacatgg acttctacgt    780
ggaggccctc gctttcccgg acaccgactt cccggggctc attaccctca ccatctccct    840
gctggacacg tccaacctgg agctccccga ggctgtggtg ttccaagaca gcgtggtctt    900
ccgcgtggcg ccctggatca tgacccccaa cacccagccc ccgcaggagg tgtacgcgtg    960
cagtattttt gaaaatgagg acttcctgaa gtcagtgact actctggcca tgaaagccaa   1020
gtgcaagctg accatctgcc ctgaggagga gaacatggat gaccagtgga tgcaggatga   1080
aatggagatc ggctacatcc aagccccaca caaaacgctg cccgtggtct tcgactctcc   1140
aaggaacaga ggcctgaagg agtttcccat caaacgcgtg atgggcttcc ggctgctcct   1200
ggccagcccc aggtcctgct acaaactgtt ccaggagcag cagaatgagg gccacgggga   1260
ggccctgctg ttcgaaggga tcaagaaaaa aaaacagcag aaaataaaga acattctgtc   1320
aaacaagaca ttgagagaac ataattcatt tgtggagaga tgcatcgact ggaaccgcga   1380
gctgctgaag cgggagctgg gcctggccga gagtgacatc attgacatcc cgcagctctt   1440
caagctcaaa gagttctcta aggcggaagc ttttttcccc aacatggtga acatgctggt   1500
gctagggaag cacctgggca tccccaagcc cttcgggccc gtcatcaacg gccgctgctg   1560
cctggaggag aaggtgtgtt ccctgctgga gccactgggc ctccagtgca ccttcatcaa   1620
cgacttcttc acctaccaca tcaggcatgg ggaggtgcac tgcggcacca acgtgcgcag   1680
aaagcccttc tccttcaagt ggtggaacat ggtgccctga gcccatcttc cctggcgtcc   1740
tctccctcct ggccagatgt cgctgggtcc tctgcagtgt ggcaagcaag agctcttgtg   1800
aatattgtgg ctccctgggg gcggccagcc ctcccagcag tggcttgctt tcttctcctg   1860
tgatgtccca gtttcccact ctgaagatcc caacatggtc ctagcactgc acactcagtt   1920
ctgctctaag aagctgcaat aaagtttttt taagtcactt tgtacatga              1969
```

<210> SEQ ID NO 76

```
<211> LENGTH: 563
<212> TYPE: PRT
<213> ORGANISM: Homo sapiens
<220> FEATURE:
<223> OTHER INFORMATION: protein-arginine deiminase type-4 isoform X2
      [Homo sapiens]

<400> SEQUENCE: 76

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
```

-continued

```
    370                 375                 380

Met Gly Phe Arg Leu Leu Leu Ala Ser Pro Arg Ser Cys Tyr Lys Leu
385                 390                 395                 400

Phe Gln Glu Gln Gln Asn Glu Gly His Gly Glu Ala Leu Leu Phe Glu
                405                 410                 415

Gly Ile Lys Lys Lys Lys Gln Gln Lys Ile Lys Asn Ile Leu Ser Asn
            420                 425                 430

Lys Thr Leu Arg Glu His Asn Ser Phe Val Glu Arg Cys Ile Asp Trp
        435                 440                 445

Asn Arg Glu Leu Leu Lys Arg Glu Leu Gly Leu Ala Glu Ser Asp Ile
    450                 455                 460

Ile Asp Ile Pro Gln Leu Phe Lys Leu Lys Glu Phe Ser Lys Ala Glu
465                 470                 475                 480

Ala Phe Phe Pro Asn Met Val Asn Met Leu Val Leu Gly Lys His Leu
                485                 490                 495

Gly Ile Pro Lys Pro Phe Gly Pro Val Ile Asn Gly Arg Cys Cys Leu
            500                 505                 510

Glu Glu Lys Val Cys Ser Leu Leu Glu Pro Leu Gly Leu Gln Cys Thr
        515                 520                 525

Phe Ile Asn Asp Phe Phe Thr Tyr His Ile Arg His Gly Glu Val His
    530                 535                 540

Cys Gly Thr Asn Val Arg Arg Lys Pro Phe Ser Phe Lys Trp Trp Asn
545                 550                 555                 560

Met Val Pro
```

<210> SEQ ID NO 77
<211> LENGTH: 1358
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X4, mRNA

<400> SEQUENCE: 77

```
acagccagag ggacgagcta gcccgacgat ggcccagggg acattgatcc gtgtgacccc     60

agagcagccc acccatgccg tgtgtgtgct gggcaccttg actcagcttg acatctgcag    120

ctctgcccct gaggactgca cgtccttcag catcaacgcc tccccagggg tggtcgtgga    180

tattgcccac ggccctccag ccaagaagaa atccacaggt tcctccacat ggcccctgga    240

ccctggggta gaggtgaccc tgacgatgaa agtggccagt ggtagcacag gcgaccagaa    300

ggttcagatt tcatactacg gacccaagac tccaccagtc aaagctctac tctacctcac    360

cggggtggaa atctccttgt gcgcagacat cacccgcacc ggcaaagtga agccaaccag    420

agctgtgaaa gatcagagga cctggacctg gggcccttgt ggacagggtg ccatcctgct    480

ggtgaactgt gacagagaca atctcgaatc ttctgccatg gactgcgagg atgatgaagt    540

gcttgacagc gaagacctgc aggacatgtc gctgatgacc ctgagcacga agacccccaa    600

ggacttcttc acaaaccata cactggtgct ccacgtggcc aggtctgaga tggacaaagt    660

gagggtgttt caggccacac ggggcaaact gtcctccaag tgcagcgtag tcttgggtcc    720

caagtggccc tctcactacc tgatggtccc cggtggaaag cacaacatgg acttctacgt    780

ggaggccctc gctttcccgg acaccgactt cccggggctc attaccctca ccatctccct    840

gctggacacg tccaacctgg agctccccga ggctgtggtg ttccaagaca gcgtggtctt    900

ccgcgtggcg ccctggatca tgacccccaa cacccagccc ccgcaggagg tgtacgcgtg    960
```

```
cagtattttt gaaaatgagg acttcctgaa gtcagtgact actctggcca tgaaagccaa   1020

gtgcaagctg accatctgcc ctgaggagga gaacatggat gaccagtgga tgcaggatga   1080

aatggagatc ggctacatcc aagccccaca caaaacgctg cccgtggtct tcgactctcc   1140

aaggaacaga ggcctgaagg agtttcccat caaacgcgtg atgattctat caataggccc   1200

attttataga agaagaaact gaggctcaga gtggagaagt tggaattcaa acccggccag   1260

tccggcttgg gtccagattt tggctatgta actcgagggc cccaaacagg gggtatcagt   1320

ggactggact cctttgggaa cctggaagtg agcccccc                           1358
```

```
<210> SEQ ID NO 78
<211> LENGTH: 397
<212> TYPE: PRT
<213> ORGANISM: Homo sapiens
<220> FEATURE:
<223> OTHER INFORMATION: protein-arginine deiminase type-4 isoform X4
      [Homo sapiens]

<400> SEQUENCE: 78

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285
```

```
Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Ile Leu Ser Ile Gly Pro Phe Tyr Arg Arg Arg Asn
385                 390                 395


<210> SEQ ID NO 79
<211> LENGTH: 1358
<212> TYPE: DNA
<213> ORGANISM: Homo sapiens
<220> FEATURE:
<223> OTHER INFORMATION: PREDICTED: Homo sapiens peptidyl arginine
      deiminase 4 (PADI4), transcript variant X4, mRNA

<400> SEQUENCE: 79

acagccagag ggacgagcta gcccgacgat ggcccagggg acattgatcc gtgtgacccc     60

agagcagccc acccatgccg tgtgtgtgct gggcaccttg actcagcttg acatctgcag    120

ctctgcccct gaggactgca cgtccttcag catcaacgcc tccccagggg tggtcgtgga    180

tattgcccac ggccctccag ccaagaagaa atccacaggt tcctccacat ggcccctgga    240

ccctggggta gaggtgaccc tgacgatgaa agtggccagt ggtagcacag gcgaccagaa    300

ggttcagatt tcatactacg gacccaagac tccaccagtc aaagctctac tctacctcac    360

cggggtggaa atctccttgt gcgcagacat cacccgcacc ggcaaagtga agccaaccag    420

agctgtgaaa gatcagagga cctggacctg ggccccttgt ggacagggtg ccatcctgct    480

ggtgaactgt gacagagaca atctcgaatc ttctgccatg gactgcgagg atgatgaagt    540

gcttgacagc gaagacctgc aggacatgtc gctgatgacc ctgagcacga agacccccaa    600

ggacttcttc acaaaccata cactggtgct ccacgtggcc aggtctgaga tggacaaagt    660

gagggtgttt caggccacac ggggcaaact gtcctccaag tgcagcgtag tcttgggtcc    720

caagtggccc tctcactacc tgatggtccc cggtggaaag cacaacatgg acttctacgt    780

ggaggccctc gctttcccgg acaccgactt cccggggctc attaccctca ccatctccct    840

gctggacacg tccaacctgg agctccccga ggctgtggtg ttccaagaca gcgtggtctt    900

ccgcgtggcg ccctggatca tgacccccaa cacccagccc ccgcaggagg tgtacgcgtg    960

cagtattttt gaaaatgagg acttcctgaa gtcagtgact actctggcca tgaaagccaa   1020

gtgcaagctg accatctgcc ctgaggagga gaacatggat gaccagtgga tgcaggatga   1080

aatggagatc ggctacatcc aagccccaca caaaacgctg cccgtggtct tcgactctcc   1140

aaggaacaga ggcctgaagg agtttcccat caaacgcgtg atgattctat caataggccc   1200

attttataga agaagaaact gaggctcaga gtggagaagt tggaattcaa acccggccag   1260

tccggcttgg gtccagattt tggctatgta actcgagggc cccaaacagg gggtatcagt   1320

ggactggact cctttgggaa cctggaagtg agcccccc                            1358
```

<210> SEQ ID NO 80
<211> LENGTH: 397
<212> TYPE: PRT
<213> ORGANISM: Homo sapiens
<220> FEATURE:
<223> OTHER INFORMATION: protein-arginine deiminase type-4 isoform X4
[Homo sapiens]

<400> SEQUENCE: 80

Met Ala Gln Gly Thr Leu Ile Arg Val Thr Pro Glu Gln Pro Thr His
1 5 10 15

Ala Val Cys Val Leu Gly Thr Leu Thr Gln Leu Asp Ile Cys Ser Ser
20 25 30

Ala Pro Glu Asp Cys Thr Ser Phe Ser Ile Asn Ala Ser Pro Gly Val
35 40 45

Val Val Asp Ile Ala His Gly Pro Pro Ala Lys Lys Lys Ser Thr Gly
50 55 60

Ser Ser Thr Trp Pro Leu Asp Pro Gly Val Glu Val Thr Leu Thr Met
65 70 75 80

Lys Val Ala Ser Gly Ser Thr Gly Asp Gln Lys Val Gln Ile Ser Tyr
85 90 95

Tyr Gly Pro Lys Thr Pro Pro Val Lys Ala Leu Leu Tyr Leu Thr Gly
100 105 110

Val Glu Ile Ser Leu Cys Ala Asp Ile Thr Arg Thr Gly Lys Val Lys
115 120 125

Pro Thr Arg Ala Val Lys Asp Gln Arg Thr Trp Thr Trp Gly Pro Cys
130 135 140

Gly Gln Gly Ala Ile Leu Leu Val Asn Cys Asp Arg Asp Asn Leu Glu
145 150 155 160

Ser Ser Ala Met Asp Cys Glu Asp Asp Glu Val Leu Asp Ser Glu Asp
165 170 175

Leu Gln Asp Met Ser Leu Met Thr Leu Ser Thr Lys Thr Pro Lys Asp
180 185 190

Phe Phe Thr Asn His Thr Leu Val Leu His Val Ala Arg Ser Glu Met
195 200 205

Asp Lys Val Arg Val Phe Gln Ala Thr Arg Gly Lys Leu Ser Ser Lys
210 215 220

Cys Ser Val Val Leu Gly Pro Lys Trp Pro Ser His Tyr Leu Met Val
225 230 235 240

Pro Gly Gly Lys His Asn Met Asp Phe Tyr Val Glu Ala Leu Ala Phe
245 250 255

Pro Asp Thr Asp Phe Pro Gly Leu Ile Thr Leu Thr Ile Ser Leu Leu
260 265 270

Asp Thr Ser Asn Leu Glu Leu Pro Glu Ala Val Val Phe Gln Asp Ser
275 280 285

Val Val Phe Arg Val Ala Pro Trp Ile Met Thr Pro Asn Thr Gln Pro
290 295 300

Pro Gln Glu Val Tyr Ala Cys Ser Ile Phe Glu Asn Glu Asp Phe Leu
305 310 315 320

Lys Ser Val Thr Thr Leu Ala Met Lys Ala Lys Cys Lys Leu Thr Ile
325 330 335

Cys Pro Glu Glu Asn Met Asp Asp Gln Trp Met Gln Asp Glu Met
340 345 350

Glu Ile Gly Tyr Ile Gln Ala Pro His Lys Thr Leu Pro Val Val Phe
355 360 365

Asp Ser Pro Arg Asn Arg Gly Leu Lys Glu Phe Pro Ile Lys Arg Val
370 375 380

Met Ile Leu Ser Ile Gly Pro Phe Tyr Arg Arg Arg Asn
385 390 395

<210> SEQ ID NO 81
<211> LENGTH: 1842
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X6, mRNA

<400> SEQUENCE: 81
acagccagag ggacgagcta gcccgacgat ggcccagggg acattgatcc gtgtgacccc 60
agagcagccc acccatgccg tgtgtgtgct gggcaccttg actcagcttg acatctgcag 120
ctctgcccct gaggactgca cgtccttcag catcaacgcc tccccagggg tggtcgtgga 180
tattgcccac ggccctccag ccaagaagaa atccacaggt tcctccacat ggcccctgga 240
ccctggggta gaggtgaccc tgacgatgaa agtggccagt ggtagcacag gcgaccagaa 300
ggttcagatt tcatactacg gacccaagac tccaccagtc aaagctctac tctacctcac 360
cggggtggaa atctccttgt gcgcagacat cacccgcacc ggcaaagtga agccaaccag 420
agctgtgaaa gatcagagga cctggacctg ggggcccttgt ggacagggtg ccatcctgct 480
ggtgaactgt gacagagaca atctcgaatc ttctgccatg gactgcgagg atgatgaagt 540
gcttgacagc gaagacctgc aggacatgtc gctgatgacc ctgagcacga agacccccaa 600
ggacttcttc acaaaccata cactggtgct ccacgtggcc aggtctgaga tggacaaagt 660
gagggtgttt caggccacac ggggcaaact gtcctccaag tgcagcgtag tcttgggtcc 720
caagtggccc tctcactacc tgatggtccc cggtggaaag cacaacatgg acttctacgt 780
ggaggccctc gctttcccgg acaccgactt cccggggctc attaccctca ccatctccct 840
gctggacacg tccaacctgg agctccccga ggctgtggtg ttccaagaca gcgtggtctt 900
ccgcgtggcg ccctggatca tgacccccaa cacccagccc ccgcaggagg tgtacgcgtg 960
cagtattttt gaaaatgagg acttcctgaa gtcagtgact actctggcca tgaaagccaa 1020
gtgcaagctg accatctgcc ctgaggagga gaacatggat gaccagtgga tgcaggatga 1080
aatggagatc ggctacatcc aagccccaca caaaacgctg cccgtggtct tcgactctcc 1140
aaggaacaga ggcctgaagg agtttcccat caaacgcgtg atggaagacc ccaggcctgc 1200
gctctgagtc ctggcagccc cttggctcaa ggtgcccagg gaaaacgacg gaaggagtgt 1260
ggggtccaag gtttgctagg acaaatggct ttccgacaag catctgtact gtgccccaag 1320
ggaggggaga gtggccctgc ccacacagaa ggcttcagaa tgaaacttca gttaaactca 1380
acaacttgtc ccgagtctcg cttcctcctg gccaagctgt gcgctgagca gtggagatgc 1440
agagatgctg ttggattcac agtgtgtact cagccatggg gtcgagttca tcctgtttca 1500
gcagcgttgg ggcgaaccag ccagctgcta ccgtgacttt gccctctttc tgctgctttc 1560
agtcctgcct ggttcagtgg ctgtgtctac tttgatgctc caagtataac aaaggccaga 1620
ttttctgatg ccacaagtcc tgctggacag acagacggac acctcggcac cattgttgtc 1680
ccctttccca cagacaactt tggatgaagg caggcagcac tggtccctca gctaagcaca 1740
tctgtgtatt ccaactcaaa tcactcagaa tgaggccagg tgtggtggct gacacctgta 1800
atcccagcag tttgggaggc caaggaggat ggatcacctg ag 1842

<210> SEQ ID NO 82
<211> LENGTH: 392
<212> TYPE: PRT
<213> ORGANISM: Homo sapiens
<220> FEATURE:
<223> OTHER INFORMATION: protein-arginine deiminase type-4 isoform X5 [Homo sapiens]

<400> SEQUENCE: 82

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
```

355 360 365

Asp Ser Pro Arg Asn Arg Gly Leu Lys Glu Phe Pro Ile Lys Arg Val
370 375 380

Met Glu Asp Pro Arg Pro Ala Leu
385 390

<210> SEQ ID NO 83
<211> LENGTH: 1842
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X6, mRNA

<400> SEQUENCE: 83
acagccagag ggacgagcta gcccgacgat ggcccagggg acattgatcc gtgtgacccc 60
agagcagccc acccatgccg tgtgtgtgct gggcaccttg actcagcttg acatctgcag 120
ctctgcccct gaggactgca cgtccttcag catcaacgcc tccccagggg tggtcgtgga 180
tattgcccac ggccctccag ccaagaagaa atccacaggt tcctccacat ggcccctgga 240
ccctggggta gaggtgaccc tgacgatgaa agtggccagt ggtagcacag gcgaccagaa 300
ggttcagatt tcatactacg gacccaagac tccaccagtc aaagctctac tctacctcac 360
cggggtggaa atctccttgt gcgcagacat cacccgcacc ggcaaagtga agccaaccag 420
agctgtgaaa gatcagagga cctggacctg ggcccttgt ggacagggtg ccatcctgct 480
ggtgaactgt gacagagaca atctcgaatc ttctgccatg gactgcgagg atgatgaagt 540
gcttgacagc gaagacctgc aggacatgtc gctgatgacc ctgagcacga agacccccaa 600
ggacttcttc acaaaccata cactggtgct ccacgtggcc aggtctgaga tggacaaagt 660
gagggtgttt caggccacac ggggcaaact gtcctccaag tgcagcgtag tcttgggtcc 720
caagtggccc tctcactacc tgatggtccc cggtggaaag cacaacatgg acttctacgt 780
ggaggccctc gctttcccgg acaccgactt cccggggctc attaccctca ccatctccct 840
gctggacacg tccaacctgg agctccccga ggctgtggtg ttccaagaca gcgtggtctt 900
ccgcgtggcg ccctggatca tgacccccaa cacccagccc ccgcaggagg tgtacgcgtg 960
cagtattttt gaaaatgagg acttcctgaa gtcagtgact actctggcca tgaaagccaa 1020
gtgcaagctg accatctgcc ctgaggagga gaacatggat gaccagtgga tgcaggatga 1080
aatggagatc ggctacatcc aagccccaca caaaacgctg cccgtggtct tcgactctcc 1140
aaggaacaga ggcctgaagg agtttcccat caaacgcgtg atggaagacc ccaggcctgc 1200
gctctgagtc ctggcagccc cttggctcaa ggtgcccagg gaaaacgacg gaaggagtgt 1260
ggggtccaag gtttgctagg acaaatggct ttccgacaag catctgtact gtgccccaag 1320
ggaggggaga gtggccctgc ccacacagaa ggcttcagaa tgaaacttca gttaaactca 1380
acaacttgtc ccgagtctcg cttcctcctg gccaagctgt gcgctgagca gtggagatgc 1440
agagatgctg ttggattcac agtgtgtact cagccatggg gtcgagttca tcctgtttca 1500
gcagcgttgg ggcgaaccag ccagctgcta ccgtgacttt gccctctttc tgctgctttc 1560
agtcctgcct ggttcagtgg ctgtgtctac tttgatgctc caagtataac aaaggccaga 1620
ttttctgatg ccacaagtcc tgctggacag acagacggac acctcggcac cattgttgtc 1680
ccctttccca cagacaactt tggatgaagg caggcagcac tggtccctca gctaagcaca 1740
tctgtgtatt ccaactcaaa tcactcagaa tgaggccagg tgtggtggct gacacctgta 1800
atcccagcag tttgggaggc caaggaggat ggatcacctg ag 1842

<210> SEQ ID NO 84
<211> LENGTH: 392
<212> TYPE: PRT
<213> ORGANISM: Homo sapiens
<220> FEATURE:
<223> OTHER INFORMATION: protein-arginine deiminase type-4 isoform X5
[Homo sapiens]

<400> SEQUENCE: 84

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350
```

```
Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Glu Asp Pro Arg Pro Ala Leu
385                 390
```

<210> SEQ ID NO 85
<211> LENGTH: 1275
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X7, mRNA

<400> SEQUENCE: 85

```
acagccagag ggacgagcta gcccgacgat ggcccagggg acattgatcc gtgtgacccc      60
agagcagccc acccatgccg tgtgtgtgct gggcaccttg actcagcttg acatctgcag     120
ctctgcccct gaggactgca cgtccttcag catcaacgcc tccccagggg tggtcgtgga     180
tattgcccac ggccctccag ccaagaagaa atccacaggt tcctccacat ggcccctgga     240
ccctggggta gaggtgaccc tgacgatgaa agtggccagt ggtagcacag gcgaccagaa     300
ggttcagatt tcatactacg gacccaagac tccaccagtc aaagctctac tctacctcac     360
cggggtggaa atctccttgt gcgcagacat cacccgcacc ggcaaagtga agccaaccag     420
agctgtgaaa gatcagagga cctggacctg ggcccttgt ggacagggtg ccatcctgct      480
ggtgaactgt gacagagaca atctcgaatc ttctgccatg gactgcgagg atgatgaagt     540
gcttgacagc gaagacctgc aggacatgtc gctgatgacc ctgagcacga agaccccaa      600
ggacttcttc acaaaccata cactggtgct ccacgtggcc aggtctgaga tggacaaagt     660
gagggtgttt caggccacac ggggcaaact gtcctccaag tgcagcgtag tcttgggtcc     720
caagtggccc tctcactacc tgatggtccc cggtggaaag cacaacatgg acttctacgt     780
ggaggccctc gctttcccgg acaccgactt cccggggctc attaccctca ccatctccct     840
gctggacacg tccaacctgg agctccccga ggctgtggtg ttccaagaca gcgtggtctt     900
ccgcgtggcg ccctggatca tgacccccaa cacccagccc ccgcaggagg tgtacgcgtg     960
cagtattttt gaaaatgagg acttcctgaa gtcagtgact actctggcca tgaaagccaa    1020
gtgcaagctg accatctgcc ctgaggagga gaacatggat gaccagtgga tgcaggatga    1080
aatggagatc ggctacatcc aagccccaca caaaacgctg cccgtggtct tcgactctcc    1140
aaggaacaga ggcctgaagg agtttcccat caaacgcgtg atgcaatgac agccggcaga    1200
tgcaccaggc cctgcaggac ttcctcagtg cccagcaggt gcaggcccct gtgaagctct    1260
attctgactg gctgt                                                     1275
```

<210> SEQ ID NO 86
<211> LENGTH: 386
<212> TYPE: PRT
<213> ORGANISM: Homo sapiens
<220> FEATURE:
<223> OTHER INFORMATION: protein-arginine deiminase type-4 isoform X6 [Homo sapiens]

<400> SEQUENCE: 86

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
```

```
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gln
385
```

<210> SEQ ID NO 87
<211> LENGTH: 1275
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X7, mRNA

<400> SEQUENCE: 87

```
acagccagag ggacgagcta gcccgacgat ggcccagggg acattgatcc gtgtgacccc     60
agagcagccc acccatgccg tgtgtgtgct gggcaccttg actcagcttg acatctgcag    120
ctctgcccct gaggactgca cgtccttcag catcaacgcc tccccagggg tggtcgtgga    180
tattgcccac ggccctccag ccaagaagaa atccacaggt tcctccacat ggcccctgga    240
ccctggggta gaggtgaccc tgacgatgaa agtggccagt ggtagcacag gcgaccagaa    300
ggttcagatt tcatactacg gacccaagac tccaccagtc aaagctctac tctacctcac    360
cggggtggaa atctccttgt gcgcagacat cacccgcacc ggcaaagtga agccaaccag    420
agctgtgaaa gatcagagga cctggacctg gggcccttgt ggacagggtg ccatcctgct    480
ggtgaactgt gacagagaca atctcgaatc ttctgccatg gactgcgagg atgatgaagt    540
gcttgacagc gaagacctgc aggacatgtc gctgatgacc ctgagcacga agacccccaa    600
ggacttcttc acaaaccata cactggtgct ccacgtggcc aggtctgaga tggacaaagt    660
gagggtgttt caggccacac ggggcaaact gtcctccaag tgcagcgtag tcttgggtcc    720
caagtggccc tctcactacc tgatggtccc cggtggaaag cacaacatgg acttctacgt    780
ggaggccctc gctttcccgg acaccgactt cccggggctc attaccctca ccatctccct    840
gctggacacg tccaacctgg agctccccga ggctgtggtg ttccaagaca gcgtggtctt    900
ccgcgtggcg ccctggatca tgacccccaa cacccagccc ccgcaggagg tgtacgcgtg    960
cagtattttt gaaaatgagg acttcctgaa gtcagtgact actctggcca tgaaagccaa   1020
gtgcaagctg accatctgcc ctgaggagga gaacatggat gaccagtgga tgcaggatga   1080
aatggagatc ggctacatcc aagccccaca caaaacgctg cccgtggtct tcgactctcc   1140
aaggaacaga ggcctgaagg agtttcccat caaacgcgtg atgcaatgac agccggcaga   1200
tgcaccaggc cctgcaggac ttcctcagtg cccagcaggt gcaggcccct gtgaagctct   1260
attctgactg gctgt                                                    1275
```

<210> SEQ ID NO 88
<211> LENGTH: 386
<212> TYPE: PRT
<213> ORGANISM: Homo sapiens
<220> FEATURE:
<223> OTHER INFORMATION: protein-arginine deiminase type-4 isoform X6
[Homo sapiens]

<400> SEQUENCE: 88

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110
```

-continued

```
Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Gln
385
```

<210> SEQ ID NO 89
<211> LENGTH: 1340
<212> TYPE: DNA
<213> ORGANISM: Homo sapiens
<220> FEATURE:
<223> OTHER INFORMATION: PREDICTED: Homo sapiens peptidyl arginine deiminase 4 (PADI4), transcript variant X5, mRNA

<400> SEQUENCE: 89

```
acagccagag ggacgagcta gcccgacgat ggcccagggg acattgatcc gtgtgacccc      60

agagcagccc acccatgccg tgtgtgtgct gggcaccttg actcagcttg acatctgcag     120

ctctgcccct gaggactgca cgtccttcag catcaacgcc tccccagggg tggtcgtgga     180

tattgcccac ggccctccag ccaagaagaa atccacaggt tcctccacat ggcccctgga     240

ccctggggta gaggtgaccc tgacgatgaa agtggccagt ggtagcacag gcgaccagaa     300

ggttcagatt tcatactacg gacccaagac tccaccagtc aaagctctac tctacctcac     360

cggggtggaa atctccttgt gcgcagacat cacccgcacc ggcaaagtga agccaaccag     420
```

```
agctgtgaaa gatcagagga cctggacctg gggcccttgt ggacagggtg ccatcctgct    480

ggtgaactgt gacagagaca atctcgaatc ttctgccatg gactgcgagg atgatgaagt    540

gcttgacagc gaagacctgc aggacatgtc gctgatgacc ctgagcacga agacccccaa    600

ggacttcttc acaaaccata cactggtgct ccacgtggcc aggtctgaga tggacaaagt    660

gagggtgttt caggccacac ggggcaaact gtcctccaag tgcagcgtag tcttgggtcc    720

caagtggccc tctcactacc tgatggtccc cggtggaaag cacaacatgg acttctacgt    780

ggaggccctc gctttcccgg acaccgactt cccggggctc attaccctca ccatctccct    840

gctggacacg tccaacctgg agctccccga ggctgtggtg ttccaagaca gcgtggtctt    900

ccgcgtggcg ccctggatca tgacccccaa cacccagccc ccgcaggagg tgtacgcgtg    960

cagtattttt gaaaatgagg acttcctgaa gtcagtgact actctggcca tgaaagccaa   1020

gtgcaagctg accatctgcc ctgaggagga gaacatggat gaccagtgga tgcaggatga   1080

aatggagatc ggctacatcc aagccccaca caaaacgctg cccgtggtct tcgactctcc   1140

aaggaacaga ggcctgaagg agtttcccat caaacgcgtg atgattctat caataggccc   1200

attttataga agaagaaact gaggctcaga gtggagaagt tggaattcaa acccggccag   1260

tccggcttgc aatgacagcc ggcagatgca ccaggccctg caggacttcc tcagtgccca   1320

gcaggtgcag gcccctgtga                                                1340
```

<210> SEQ ID NO 90
<211> LENGTH: 397
<212> TYPE: PRT
<213> ORGANISM: Homo sapiens
<220> FEATURE:
<223> OTHER INFORMATION: protein-arginine deiminase type-4 isoform X4
[Homo sapiens]

<400> SEQUENCE: 90

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190
```

-continued

```
Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Ile Leu Ser Ile Gly Pro Phe Tyr Arg Arg Arg Asn
385                 390                 395


<210> SEQ ID NO 91
<211> LENGTH: 1340
<212> TYPE: DNA
<213> ORGANISM: Homo sapiens
<220> FEATURE:
<223> OTHER INFORMATION: PREDICTED: Homo sapiens peptidyl arginine
      deiminase 4 (PADI4), transcript variant X5, mRNA

<400> SEQUENCE: 91

acagccagag ggacgagcta gcccgacgat ggcccagggg acattgatcc gtgtgacccc      60

agagcagccc acccatgccg tgtgtgtgct gggcaccttg actcagcttg acatctgcag     120

ctctgcccct gaggactgca cgtccttcag catcaacgcc tccccagggg tggtcgtgga     180

tattgcccac ggccctccag ccaagaagaa atccacaggt tcctccacat ggcccctgga     240

ccctggggta gaggtgaccc tgacgatgaa agtggccagt ggtagcacag gcgaccagaa     300

ggttcagatt tcatactacg gacccaagac tccaccagtc aaagctctac tctacctcac     360

cggggtggaa atctccttgt gcgcagacat cacccgcacc ggcaaagtga agccaaccag     420

agctgtgaaa gatcagagga cctggacctg ggggcccttgt ggacagggtg ccatcctgct     480

ggtgaactgt gacagagaca atctcgaatc ttctgccatg gactgcgagg atgatgaagt     540

gcttgacagc gaagacctgc aggacatgtc gctgatgacc ctgagcacga agacccccaa     600

ggacttcttc acaaaccata cactggtgct ccacgtggcc aggtctgaga tggacaaagt     660

gagggtgttt caggccacac ggggcaaact gtcctccaag tgcagcgtag tcttgggtcc     720

caagtggccc tctcactacc tgatggtccc cggtggaaag cacaacatgg acttctacgt     780

ggaggccctc gctttcccgg acaccgactt cccggggctc attaccctca ccatctccct     840

gctggacacg tccaacctgg agctccccga ggctgtggtg ttccaagaca gcgtggtctt     900
```

```
ccgcgtggcg ccctggatca tgacccccaa cacccagccc ccgcaggagg tgtacgcgtg    960

cagtattttt gaaaatgagg acttcctgaa gtcagtgact actctggcca tgaaagccaa   1020

gtgcaagctg accatctgcc ctgaggagga gaacatggat gaccagtgga tgcaggatga   1080

aatggagatc ggctacatcc aagccccaca caaaacgctg cccgtggtct tcgactctcc   1140

aaggaacaga ggcctgaagg agtttcccat caaacgcgtg atgattctat caataggccc   1200

attttataga agaagaaact gaggctcaga gtggagaagt tggaattcaa acccggccag   1260

tccggcttgc aatgacagcc ggcagatgca ccaggccctg caggacttcc tcagtgccca   1320

gcaggtgcag gcccctgtga                                                1340


<210> SEQ ID NO 92
<211> LENGTH: 397
<212> TYPE: PRT
<213> ORGANISM: Homo sapiens
<220> FEATURE:
<223> OTHER INFORMATION: protein-arginine deiminase type-4 isoform X4
      [Homo sapiens]

<400> SEQUENCE: 92

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270
```

-continued

```
Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365

Asp Ser Pro Arg Asn Arg Gly Leu Lys Glu Phe Pro Ile Lys Arg Val
    370                 375                 380

Met Ile Leu Ser Ile Gly Pro Phe Tyr Arg Arg Arg Asn
385                 390                 395
```

COMPOSITIONS AND METHODS FOR DIAGNOSING AND ASSESSING RHEUMATOID ARTHRITIS

This application claims the benefit of U.S. Provisional Application No. 62/806,607 filed Feb. 15, 2019, the entire contents of which are incorporated herein by reference.

This application incorporates herein by reference a Sequence Listing as an ASCII text file entitled "13510-034-999_SEQ_LISTING" created on Feb. 12, 2020, and having a size of 385,711 bytes.

FIELD

The present disclosure relates to the field of molecular biology and more specifically to methods for detecting anti-PAD IgA in the serum of rheumatoid arthritis (RA) patients.

BACKGROUND

Rheumatoid Arthritis (RA) is a chronic autoimmune disease characterized by inflammation, pain and subsequent damage to synovial-lined joints. Unlike other arthritis conditions, RA is a systemic disease that can affect other organ systems including but not limited to the cardiovascular system, the respiratory system and musculature. While the exact pathogenesis of the disease is unknown, RA is characterized by the production of antibodies to self-proteins (autoantibodies) by the immune system. The most common autoantibodies implicated in RA include rheumatoid factor (RF) and anti-citrullinated protein antibodies (ACPAs), which are part of the classification criteria for this disease. ACPAs are a hallmark amongst serologic factors detected in RA patients, and as such, serve as valuable diagnostic and prognostic markers. Aletaha D. et al., Ann. Rheum. Dis. 2010, 69, 1580-1588); Taylor et al., Autoimmune Dis; 2011:815038 (2011). However, clinical heterogeneity of RA precludes the use of ACPAs and RF alone as reliable biomarkers. Patients with erosive disease require more aggressive treatment in the early phase of the disease to prevent joint damage. More precise biomarkers that specifically identify sufferers of RA and disease severity are needed.

Peptidylarginine deiminases (PAD)s are calcium-dependent enzymes that play a central role in generating autoantigens in RA through the conversion of arginine residues to citrulline, process known as citrullination. Beyond ACPA and RF, autoantibodies which target the PAD enzymes, have also been described in RA, see for example, Takizawa et al., Scand. J. Rheumatol. 3: 212-215 (2005); Roth et al., Clin. Exp. Rheumatol. 1: 12-18 (2006); Halvorsen et al., Ann. Rheumatol. Dis. 67:414-417 (2008); Zhao et al., J. Rheumatol., 35:969-974 (2008); Darrah et al., Sci. Trans. Med., 5(186):186ra65 (2013); Darrah et al., Front. Immunol., 9:2696 (2018). As such, PADs appear to play a central role in RA pathogenesis.

Thus, there exists a need for additional biomarkers for the diagnosis of RA and assessment of disease severity, including erosive conditions. The present disclosure satisfies this need and provides related advantages as well.

SUMMARY

In some embodiments, the present disclosure provides a method of diagnosing rheumatoid arthritis (RA). The method includes: (a) contacting a biological sample from a subject suspected of having RA with a peptidyl arginine deiminase (PAD) or an antigenic fragment thereof, and (b) detecting the presence of an anti-PAD IgA in the biological sample, wherein the presence of the anti-PAD IgA is indicative of RA.

In some embodiments, the present disclosure provides a method of assessing disease severity in a subject having RA. The method includes: (a) contacting a biological sample from a subject having RA with a PAD or an antigenic fragment thereof, and (b) detecting the presence of an anti-PAD IgA in the biological sample, wherein the presence of the anti-PAD IgA is indicative of severity of RA.

In some embodiments, the biological sample includes whole blood, plasma, serum, synovial fluid or sputum. In some embodiments, the biological sample includes serum or plasma.

In some embodiments, the present disclosure provides a method of assessing disease severity, wherein the severity of RA includes the presence of joint erosion. In other embodiments, the severity of RA includes severe joint erosion. In other embodiments, anti-PAD IgA levels correlate with extent of joint erosion.

In some embodiments, the extent of joint erosion includes reduced mobility. In other embodiments, the reduced mobility includes a disability index of approximately 3.

In some embodiments, the PAD or antigenic fragment thereof used in the method of diagnosing RA or assessing disease severity is selected from the group consisting of PAD2, PAD3 and PAD4.

In some embodiments, the PAD or antigenic fragment thereof includes an amino acid sequence selected from an even numbered SEQ ID NO within SEQ ID NOS:2-92 or an amino acid sequence comprising at least six consecutive amino acids selected from an even numbered SEQ ID NO within SEQ ID NOS:2-92. In some embodiments, the antigenic fragment includes from 6-120, 12-100, 18-80, 24-60, 30-50 or 35-45 amino acid residues.

In some embodiments, the PAD or antigenic fragment thereof is obtained by a method comprising isolation from a natural source, chemical synthesis or recombinant expression.

In some embodiments, detection includes an immunoassay. In some embodiments, the immunoassay is selected from the group consisting of a fluorescent immunosorbent assay (FIA), a chemiluminescent immunoassay (CIA), a radioimmunoassay (RIA), multiplex immunoassay, a protein/peptide array immunoassay, a solid phase radioimmunoassay (SPRIA), an indirect immunofluorescence assay (IIF), an enzyme linked immunosorbent assay (ELISA) and a particle based multianalyte test (PMAT), or a Dot Blot assay.

In some embodiments, the method described herein can be performed by (a) contacting the anti-PAD IgA with a detection probe specific for the anti-PAD IgA and (b) detecting specific binding of the detection probe. In some embodiments, the detection probe is specific to PAD. In other embodiments, the detection probe includes an antibody or functional fragment. In some embodiments, the functional fragment is anti-IgA. In some embodiments, the detection probe is a reporter tag.

In some embodiments, the reporter tag includes a label. In some embodiments, the label is selected from the group consisting of a fluorophore, enzyme, chemiluminescent moiety, radioactive moiety, organic dye and small molecule. In some embodiments, the label is a fluorescent label. In some embodiments, the fluorescent label is phycoerytherin (PE).

In some embodiments, the reporter tag includes a ligand or particle. In some embodiments, the ligand includes biotin. In some embodiments, the particle includes a nanoparticle.

In other embodiments, the reporter tag is a ligand or particle. In some embodiments, the ligand is biotin and the particle is a nanoparticle.

In some embodiments, the present disclosure provides a kit. The kit includes: (a) a PAD, or antigenic fragment thereof; (b) a detection probe specific to anti-PAD IgA, and (c) a solid support.

In some embodiments, the kit further includes a label. In some embodiments, the kit includes a label selected from the group consisting of a fluorophore, enzyme, chemiluminescent moiety, radioactive moiety, organic dye and small molecule.

In some embodiments, the kit includes a positive control. In some embodiments, the positive control includes an anti-PAD IgA.

In some embodiments, the kit further includes one or more ancillary reagents. In some embodiments, the one or more ancillary reagents is selected from the group consisting of an incubation buffer, a wash buffer, a detection buffer and a detection instrument.

In some embodiments, the kit includes a PAD or antigenic fragment thereof selected from the group consisting of PAD2, PAD3 and PAD4.

In some embodiments, the PAD or antigenic fragment thereof in the kit includes an amino acid sequence selected from an even numbered SEQ ID NO within SEQ ID NOS:2-92 or an amino acid sequence comprising at least six consecutive amino acids selected from an even numbered SEQ ID NO within SEQ ID NOS:2-92.

In some embodiments, the kit contains an antigenic fragment including from 6-120, 12-100, 18-80, 24-60, 30-50 or 35-45 amino acid residues.

In some embodiments, the detection probe includes an antibody or functional fragment thereof. In some embodiments, the antibody or functional fragment thereof includes anti-IgA.

In some embodiments, the detection probe includes a reporter tag. In some embodiments, the reporter tag includes a label. In some embodiments, the label is selected from the group consisting of a fluorophore, enzyme, chemiluminescent moiety, radioactive moiety, organic dye and small molecule.

In some embodiments, the label is a fluorescent label. In some embodiments, the fluorescent label is (PE).

In some embodiments, the reporter tag includes a ligand or particle. In some embodiments, the ligand includes biotin. In some embodiments, the particle includes a nanoparticle.

In some embodiments, the solid support is selected from the group consisting of a bead, sphere, particle, membrane, chip, slide, plate, well and test tube. In some embodiments, the bead, sphere or particle includes micrometer or nanometer dimensions.

In some embodiments, the membrane is selected from the group consisting of nitrocellulose, nylon, polyvinylidene fluoride (PVDF) and polyvinylidene difluoride.

In some embodiments, the PAD or antigenic fragment thereof is conjugated to the solid support.

BRIEF DESCRIPTION OF THE DRAWINGS

FIG. 3 shows a receiver operating characteristic (ROC) analysis of anti-PAD2 IgA (square) and anti-PAD4 IgA (triangle) illustrating the discrimination between erosive and non-erosive disease in RA patients. Area Under the Curve (AUC) for each marker is shown in the legend.

FIG. 4 shows SEQ ID NO:1 which includes the mRNA nucleotide sequence of a human wild-type PAD2. The accession number for SEQ ID NO:1 is NM_007365.3.

FIG. 5 shows sequence number-2 which includes the amino acid sequence of a human wild-type PAD2. The accession number for SEQ ID NO:2 is NP_031391.2. SEQ ID NO:2 is the polypeptide encoded by SEQ ID NO:1.

FIG. 6 shows SEQ ID NO:3 which includes the mRNA nucleotide sequence of human PAD2 transcript variant X2. The accession number for SEQ ID NO:3 is XM_017000148.2. SEQ ID NO:3 is a transcript variant of SEQ ID NO:1.

FIG. 7 shows SEQ ID NO:4 which includes the amino acid sequence of a human PAD2 isoform X1. The accession number for SEQ ID NO:4 is XP_016855637.1. SEQ ID NO:4 is the polypeptide encoded by SEQ ID NO:3.

FIG. 8 shows SEQ ID NO:5 which includes the mRNA nucleotide sequence of a human wild-type PAD3. The accession number for SEQ ID NO:5 is NM_016233.2.

FIG. 9 shows SEQ ID NO:6 which includes the amino acid sequence of a human wild-type PAD3. The accession number for SEQ ID NO:6 is NP_057317.2. SEQ ID NO:6 is the polypeptide encoded by SEQ ID NO:5.

FIG. 10 shows SEQ ID NO:21 which includes the mRNA nucleotide sequence of a human PAD3 transcript variant X1. The accession number is XM_011541571.2. SEQ ID NO:21 is a transcript variant of SEQ ID NO:5.

FIG. 11 shows SEQ ID NO:22 which includes the amino acid sequence of a human PAD3 isoform X1. The accession number is XP_011539873.1. SEQ ID NO:22 is the polypeptide encoded by SEQ ID NO:21.

FIG. 12 shows SEQ ID NO:37 which includes the mRNA nucleotide sequence of a human PAD3 transcript variant X2. The accession number is XM_017001463.1. SEQ ID NO:37 is a transcript variant of SEQ ID NO:5.

FIG. 13 shows SEQ ID NO:38 which includes the amino acid sequence of a human PAD3 isoform X2. The accession number is XP_016856952.1. SEQ ID NO:38 is the polypeptide encoded by SEQ ID NO:37.

FIG. 14 shows SEQ ID NO:39 which includes the mRNA nucleotide sequence of a human PAD3 transcript variant X2. The accession number is XM_017001463.1:c. SEQ ID NO:39 is a transcript variant of SEQ ID NO:5.

FIG. 15 shows SEQ ID NO:40 which includes the mRNA nucleotide sequence of a human PAD3 transcript variant X2. The accession number is XM_017001463.1:c. SEQ ID NO:40 is a transcript variant of SEQ ID NO:5.

FIG. 16 shows SEQ ID NO:49 which includes the mRNA nucleotide sequence of a human PAD3 transcript variant X3. The accession number is XM_011541572.2. SEQ ID NO:49 is a transcript variant of SEQ ID NO:5.

FIG. 17 shows SEQ ID NO:50 which includes the amino acid sequence of a human PAD3 isoform X3. The accession number is XP_011539874.1. SEQ ID NO:50 is the polypeptide encoded by SEQ ID NO:49.

FIG. 18 shows SEQ ID NO:59 which includes the mRNA nucleotide sequence of a human PAD3 transcript variant X3. The accession number is XM_011541572.2:c. SEQ ID NO:59 is a transcript variant of SEQ ID NO:5.

FIG. 19 shows SEQ ID NO:61 which includes the mRNA nucleotide sequence of a human wild-type PAD4. The accession number is NM_012387.3.

FIG. 20 shows SEQ ID NO:62 which includes the amino acid sequence of a human wild-type PAD4. The accession number is NP_036519.2. SEQ ID NO:62 is the polypeptide encoded by SEQ ID NO:61.

FIG. 21 shows SEQ ID NO:67 which includes the mRNA nucleotide sequence of a human PAD4 transcript, variant X3. The accession number is XM_011541152.1. SEQ ID NO:67 is a transcript variant of SEQ ID NO:61.

FIG. 22 shows SEQ ID NO:68 which includes the mRNA nucleotide sequence of a human PAD4 transcript variant X8. The accession number is XM_0115411571 SEQ ID NO:68 is a transcript variant of SEQ ID NO:61.

DETAILED DESCRIPTION

Figure 1:
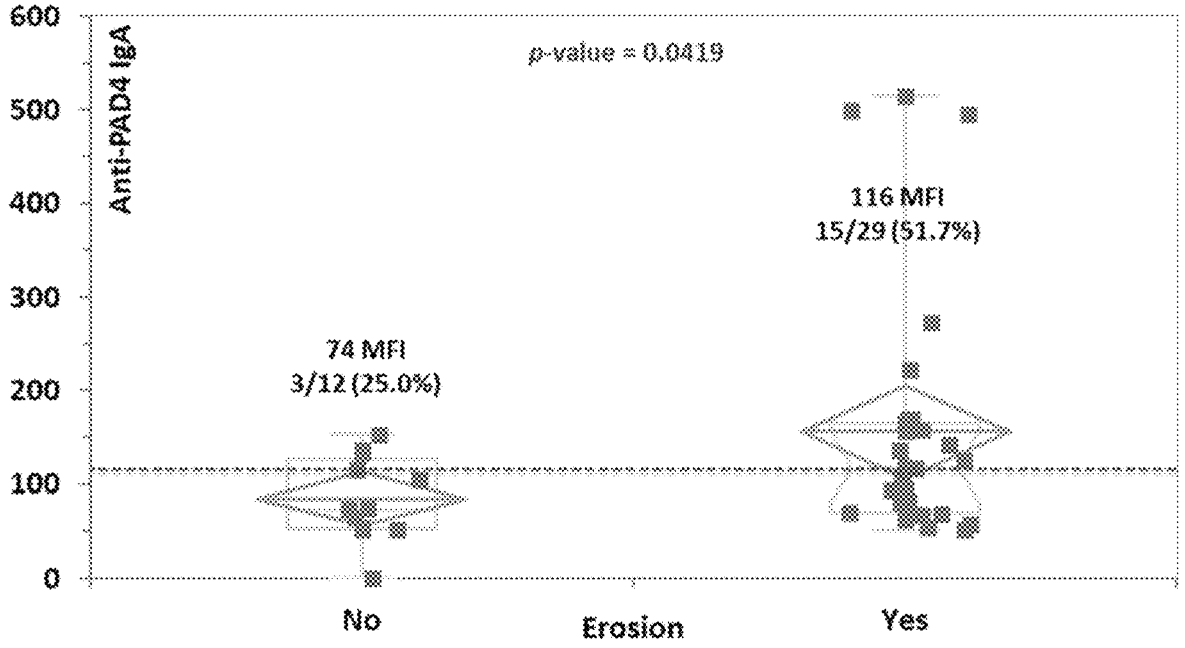
FIG. 1 shows association of anti-PAD4 IgA with joint erosion status. Results are expressed in Median Fluorescence Intensity (MFI). P-value of the Mann-Whitney analysis is shown in red (p-value <0.05 considered significant). Median MFI for the subgroup and number of patients and % are shown. Red dashed line represents the preliminary cut-off.

The present disclosure is based, in part, on the discovery that anti-PAD IgA serves as a diagnostic biomarker for RA and also as an indicator of disease severity for RA. Thus, the present disclosure benefits RA patients by providing a new biomarker which can indicate the presence of RA, disease severity, including erosive arthritis, and facilitate the early detection of RA and treatment escalation. Such benefits further enable at risk or early-stage RA patients to reduce or prevent disease progression and related erosive conditions such as joint erosion.

It must be noted that, as used in this specification and the appended claims, the singular forms “a”, “an” and “the” also include plural referents unless the content clearly dictates otherwise.

It must also be noted that, as used in this specification and the appended claims, where a range of numeric values is provided, it is understood that the ranges are inclusive of the numbers defining the range. It is also understood that each intervening integer within the recited range as well as fractions thereof, including for example, every tenth of a unit of a selected intervening integer or a lower limit of the recited range is intended to be included within the disclosure, unless the context clearly dictates otherwise.

As used herein, the terms “comprises,” “comprising,” “includes,” “including,” “has,” “having,” “contains,” “containing,” and any variations thereof, are intended to cover a non-exclusive inclusion, such that a process, method, product-by-process, or composition of matter that includes has or contains an element or list of elements, does not include only those elements but can include other elements not expressly listed or inherent to such process, method, product-by-process, or composition of matter.

The present disclosure provides a method of diagnosing RA. The method includes: (a) contacting a biological sample from a subject suspected of having RA with a PAD or an antigenic fragment thereof, and (b) detecting the presence of anti-PAD IgA in the biological sample, wherein the presence of the anti-PAD IgA is indicative of RA.

The present disclosure also provides a method of assessing disease severity in a subject having RA. The method includes: (a) contacting a biological sample from a subject having RA with PAD or an antigenic fragment thereof, and (b) detecting the presence of anti-PAD IgA in the biological sample, wherein the presence of the anti-PAD IgA is indicative of severity of RA. Disease severity can be the presence of joint erosion, including assessing the extent of joint erosion.

The term “autoantibody” refers to an immunoglobulin directed against a constituent of tissue of the subject that produces the autoantibody. The term is intended to include an antibody produced by a subject’s immune system that is directed against one or more of the subject’s own polypeptides or antigens. Accordingly, autoantibodies can be produced by a subject’s immune system when the immune system fails to distinguish, in whole or in part, between self and non-self tissue constituents. As provided herein an autoantibody directed to or specific for PAD having an IgA isotype is a beneficial biomarker for diagnosing RA, assessing disease severity of RA and/or diagnosing or determining the severity of joint erosion.

As used herein, the terms “anti-PAD IgA” when used in reference to an autoantibody is intended to mean an IgA autoantibody directed against PAD or an antigenic fragment thereof. An IgA autoantibody is distinguishable from other antibody classes including, for example, gamma (IgG), mu (IgM), delta (IgD) and epsilon (IgE) antibody classes based in part on the constant region sequence and/or structure and other characteristics well-known in the art. IgA includes, for example, IgA1 and IgA2 subclasses as well as secretory IgA. IgA1 and IgA2 exist in monomer and dimer configurations and can form polymers with IgM. The term “anti-PAD IgA” is intended to include all IgA subclasses as well as the monomer, dimer and polymer configurations.

The presence of increased anti-PAD IgA in a subject compared to a healthy control individual can be indicative of the presence of RA, the severity of disease or the risk of developing RA. Accordingly, a measurable increase in an autoantibody to PAD having an IgA isotype, and any IgA subtypes, is used to diagnose RA, determine the severity of RA and/or diagnose or determine the severity levels of joint erosion. Exemplary methods for detection and comparison of anti-PAD IgA levels to a control are provided herein and described further below.

In some embodiments, detection of an increased level of anti-PAD IgA compared to a healthy control individual is indicative of a subject having RA. In some embodiments, following diagnosis of RA using the compositions and methods provided herein, the presence of RA can be further corroborated based on a variety of symptoms associated with the onset or presence of RA. Clinical symptoms associated with RA include, for example, pain and swelling of small and large bilateral joints, palindromic onset, monoarticular presentation, and extra-articular synovitis, like tenosynovitis and bursitis, polymyalgic-like onset and other symptoms including malaise, weight loss, fatigue, fever and disability. Grassi et al., Eur. J. Radiol., Suppl 1:S 18-24 (1998); Aletaha and Smolen, JAMA, 320(13):1360-1372 (2018).

In some embodiments, detection of an increased level of anti-PAD IgA in a subject compared to a healthy control is indicative of having severe RA. In other embodiments, detection of an increased level of anti-PAD IgA in a subject compared to an RA subject without an increased level of anti-PAD IgA, is indicative of having severe RA. In some embodiments, having severe RA is considered by the degree of joint erosion or the risk of radiographic progression as determined by methods in the art. Detection of an increased level of anti-PAD IgA in a subject compared to a healthy control or compared to an RA subject without an increased level of anti-PAD IgA is indicative that the subject has a higher probability of having more progressed RA wherein joint erosion is severe. In some embodiments, a subject having increased anti-PAD IgA can be more than 5%, more than 10%, more than 15%, more than 20%, more than 25%, more than 30%, more than 35%, more than 40%, more than 45%, more than 50%, more than 60%, more than 70%, more than 80% or more than 90% likely to have more progressed RA where severe joint erosion is present. In other embodiments, a subject having increased anti-PAD IgA can be more than 2-fold, more than 3-fold, more than 4-fold, more than 5-fold, more than 6-fold, more than 7-fold, more than 8-fold, more than 9-fold, or more than 10-fold likely to have more progressed RA where severe joint erosion is present.

In severe RA, joint erosion occurs when there is loss of bone and cartilage in the joint. Severity of joint erosion can be determined by, for example, the Sharp score method. See Sharp, Arthritis Rheum., 32:221-229 (1989); Brower, Arthritis Rheum., 33:316-324 (1990). The Sharp score assesses joints for narrowness and erosions, based upon radiographic images. Erosion scores range from 0-3.5 and joint space narrowing scores range from 0-4. A score of 0 indicates a normal joint with no narrowing or erosions and a score of 3.5-4 indicates an abnormal joint with erosions and narrowing. In some embodiments of the present disclosure, joint erosion in a subject is determined by use of the Sharp score.

In other embodiments, having severe RA is determined by the Health Assessment Questionnaire (HAQ) Disability Index (DI). Fries et al., Arthritis Rheum, 23(2):137-145 (1980); Bruce and Fries, Health Qual Life Outcomes, 1(1): 20 (2003). The HAQ assesses physical ability in 8 sections including dressing, arising, eating, walking, hygiene, reach, grip and activities. Performing each session is allotted a score ranging from 0 (without any difficulty) to 3 (unable to do). The scores of the 8 sections are summed and divided by 8 to produce the DI. The DI, which ranges from 0 to 3, predicts disability, with a person able to complete a task without any difficulty (DI of 0), with some difficulty (DI of 1), with much difficulty (DI of 2), or unable to do (DI of 3).

Thus, in some embodiments, the presence of increased anti-PAD IgA in a subject compared to a healthy control individual is indicative of the presence of joint erosion. In other embodiments, detection of an increased level of anti-PAD IgA in a subject compared to an RA subject without an increased level of anti-PAD IgA is indicative of having joint erosion. In other embodiments, the presence of increased anti-PAD IgA compared to a healthy individual is indicative of the presence of severe joint erosion. In some embodiments, detection of an increased level of anti-PAD IgA compared to an RA subject without having an increased level of anti-PAD IgA is indicative of having severe joint erosion. In another embodiment, the presence of anti-PAD IgA is indicative of a DI of 2 or more, or of 3 or more.

In alternative embodiments, having joint erosion includes having worse radiographic joint damage. In some embodiments, having severe joint erosion includes having worse baseline radiographic joint damage. Accordingly, detection of an increased level of anti-PAD IgA in a subject compared to a healthy control individual is indicative of having worse radiographic joint damage and/or worse baseline radiographic joint damage. In other embodiments, detection of an increased level of anti-PAD IgA in a subject compared to a RA subject without having an increased level of anti-PAD IgA is indicative of having worse radiographic joint damage and/or worse baseline radiographic joint damage. One skilled in the art will recognize that methods for determining and assessing radiographic joint damage are well known in the art. Additionally, those skilled in the art will recognize and employ suitable techniques to quantify radiographic joint damage. As a non-limiting example, the Sharp scoring method can be used.

In some embodiments, detection of an increased level of anti-PAD IgA compared to a healthy control individual indicates that the subject is at risk of developing clinical symptoms of RA. In some embodiments, a subject can be at risk of developing clinical symptoms of RA within less than 3 months, less than 6 months, less than 9 months, less than 12 months, less than 18 months, less than 2 years, less than 3 years, less than 4 years, less than 5 years, less than 6 years, less than 7 years, less than 8 years, less than 9 years, less than 10 years, less than 12 years, less than 14 years, or less than 16 years from the determination of the increased anti-PAD IgA level.

In some embodiments, the presence of an increased level of anti-PAD IgA compared to a healthy control individual indicates that the subject is more than 5%, more than 10%, more than 15%, more than 20%, more than 25%, more than 30%, more than 35%, more than 40%, more than 45%, more than 50%, more than 60%, more than 70%, or more than 80% or more than 90% likely to develop clinical symptoms of RA within 5 years following the determination of increased anti-PAD IgA. In some embodiments, the presence of an increased level of anti-PAD IgA can indicate that the subject is more than 2-fold, more than 3-fold, more than 4-fold, more than 5-fold, more than 6-fold, more than 7-fold, more than 8-fold, more than 9-fold, or more than 10-fold likely to develop clinical symptoms of RA within 5 years following determination of increased anti-PAD IgA level compared to a healthy control individual.

Anti-PAD IgA can be detected in a variety of different biological samples obtained from a subject. Such samples include, for example, solid tissue and biological fluids. As used herein, the term "biological sample" refers to any specimen from the body of an organism that can be used for analysis or diagnosis. In the context of the present disclosure, a biological sample obtained from a subject can be any sample that contains or is suspected to contain autoantibodies and encompasses any material in which an anti-PAD autoantibody can be detected. For example, a biological sample can include a liquid sample such as whole blood, plasma, serum, synovial fluid, amniotic fluid, sputum, pleural fluid, peritoneal fluid, central spinal fluid, urine, saliva, tears or other body fluid that contains autoantibodies. A biological sample can also include a solid tissue sample such as bone marrow, tissue, buccal or other solid or semi-solid aggregate of cells.

In some embodiments, anti-PAD IgA is detected in whole blood, plasma, serum, synovial fluid or sputum. In some embodiments of the present disclosure, the level of anti-PAD IgA is detected. In other embodiments, anti-PAD IgA-PAD complex can be formed using the compositions and methods described herein and an anti-PAD IgA in the complex can be detected. Accordingly, the disclosure provides compositions that include an anti-PAD IgA-PAD complex.

The biological samples of this disclosure can be obtained from any organism including, for example, mammals such as humans, primates such as monkeys, chimpanzees, orangutans and gorillas, cats, dogs, rabbits, farm animals such as cows, horses, goats, sheep and pigs, and rodents such as mice, rats, hamsters and guinea pigs.

In some embodiments, the biological sample can be a plurality of samples. In some embodiments the plurality of samples can be obtained periodically over the course of more than 12 hours, more than 1 day, more than 2 days, more than 3 days, more than 4 days, more than 5 days, more than 6 days, more than 7 days, more than 10 days, more than 14 days, more than 3 weeks, more than 1 month, more than 2 months, more than 3 months, more than 4 months, more than 5 months, more than 6 months, more than 9 months, more than 12 months, more than 18 months, more than 24 months, more than 30 months, more than 3 years months, more than 4 years or more than 5 years.

In some embodiments, the samples of the present disclosure can be collected and processed fresh. In other embodiments, the samples of the present disclosure can be frozen, stored and processed at a later date.

In some embodiments, the present disclosure provides a method of determining the level of anti-PAD IgA in a subject to determine if that subject has RA, severe RA or joint erosion, including severe joint erosion. It is noted that, as used herein, the terms "subject," "organism," "individual" or "patient" are used as synonyms and interchangeably, and refer to a vertebrate mammal. Mammals include humans, primates such as monkeys, chimpanzees, orangutans and gorillas, cats, dogs, rabbits, farm animals such as cows, horses, goats, sheep and pigs, and rodents such as mice, rats, hamsters and guinea pigs. The subjects of this disclosure can include healthy subjects, asymptomatic subjects, and diseased subjects.

In some embodiments, the diseased subjects can suffer from any disease associated with aberrant anti-PAD IgA levels. It is noted that the term "aberrant anti-PAD IgA levels" refers to anti-PAD IgA levels in a sample that measurably deviate from the median anti-PAD IgA levels found in a population of healthy subjects. In some embodiments, the aberrant anti-PAD IgA levels can be higher than the median anti-PAD IgA levels. In some embodiments, the aberrant anti-PAD IgA levels can be lower than the median anti-PAD IgA levels.

In some embodiments, the healthy subjects can have never suffered from a certain disease. In some embodiments, the healthy subjects can be previously diseased. In some embodiments, the healthy subjects can be undergoing a routine medical checkup. In some embodiments, the healthy subjects can be members of a control group in, for example, a clinical trial. In some embodiments, the healthy subjects can be at risk of contracting a disease, as determined by the presence of certain risk factors that are well known in the art. Such risk factors include, without limitation, a genetic predisposition, a personal disease history, a familial disease history, a lifestyle factor, an environmental factor, a diagnostic indicator, and the like.

In some embodiments, the subject can be asymptomatic. Asymptomatic subjects include healthy subjects who have essentially no risk or only a low risk of developing RA (e.g., there is a less than 10%, less than 5%, less than 3%, or less than 1% probability that the asymptomatic patient will develop RA over the following five year period). Asymptomatic subjects further include healthy subjects who have a high risk of developing RA (e.g., there is a greater than 50%, greater than 70%, greater than 90%, or greater than 95% probability that the asymptomatic patient will develop RA over the following five year period). Asymptomatic subjects further include diseased subjects, who can display mild early diagnostic indicators of RA, but who are otherwise disease or complaint free (e.g., no synovial joint pain, no systemic inflammatory disorder). In some embodiments, the asymptomatic patient can be an arthralgia patient.

In some embodiments, the subject can have RA. In some embodiments, the subject can have RA with joint pain. In some embodiments, the subject can have RA with a systematic inflammatory disorder. In some embodiments, the subject can have juvenile idiopathic arthritis (JIA). In some embodiments, the subject can have a pre-RA syndrome. In some embodiments, the pre-RA syndrome can be arthralgia.

In some embodiments, the subject can be suspected of having RA. As used herein, a subject can be "suspected of having RA" as determined by the presence of certain risk factors that are well known in the art. Such risk factors include, without limitation, a genetic predisposition, a personal disease history, a lifestyle factor, an environmental factor, a diagnostic indicator and the like.

In some embodiments, the subject can be at risk of developing RA. In some embodiments, the subject can have a genetic predisposition for developing RA or a family history of RA or other autoimmune diseases. In some embodiments, the subject can be exposed to certain lifestyle factors (e.g., smoking cigarettes) promoting the development of RA or the subject can show clinical disease manifestations of RA. In some embodiments, the subject can be a patient who is receiving a clinical workup to diagnose RA or to assess the risk of developing RA.

In some embodiments, the subjects can have anti-PAD IgA present, e.g., in their blood or another bodily tissue or fluid, (anti-PAD IgA-positive subjects). In some embodiments, the subjects can have elevated anti-PAD IgA levels, e.g., in their blood or another bodily tissue or fluid, relative to normal healthy subjects. In some embodiments, the subjects can have no anti-PAD IgA present, e.g., in their blood or another bodily tissue or fluid (anti-PAD IgA-negative subjects).

In some embodiments, the subjects can have anti-PAD IgA present, e.g., in their blood or another tissue or bodily fluid, (anti-PAD IgA-positive subjects) or the subjects can have elevated anti-PAD IgA levels, e.g., in their blood or another tissue or bodily fluid, relative to normal healthy subjects. In some embodiments, the subjects can be negative for anti-PAD IgA.

In some embodiments, the subject can be treatment naïve. In some embodiments, the subject can be undergoing treatments for RA (e.g., drug treatments). In some embodiments, the subject can be in remission. In some embodiments, the remission can be drug-induced. In some embodiments, the remission can be drug-free.

In some embodiments, the subject can be an animal model for RA. In some embodiments, the animal model can be a mouse, rabbit, or primate model of RA. In some embodiments, the animal model can involve inducing anti-PAD IgA responses by immunizing or vaccinating an animal with PAD It should be noted that the terms "healthy control individual," "healthy subjects," and grammatical equivalents herein are used interchangeably and refer to subjects who do not have increased anti-PAD IgA levels, RA or joint erosion above baseline or a standard known or determined to represent non-RA subjects.

The baseline or standard which determines or defines a subject as a non-RA subject is the reference interval. In diagnostic or health-related fields, the reference interval is a range of values observed in the reference subjects, which can be healthy control individuals, designated by specific percentiles. The reference interval can be any range of values as determined by those having skill in the art. See CLSI, "How to define and determine reference intervals in the clinical laboratory: approved guideline," C28:A2 (2000). In some cases, the reference interval can be stringent or less stringent depending on the specific analyte being measured or disease being studied. A person having skill in the art will understand the appropriate stringency to use when determining the reference interval. Thus, in some embodiments, the reference interval can be set at the 95th percentile. In order to increase specificity and decrease sensitivity, e.g. increase stringency, a higher cut-off can be used such as the 96th percentile or the 97th, or the $98^{th}$, or the 99th.

In the present disclosure, anti-PAD IgA can be considered increased in a subject if anti-PAD IgA levels are at least above the 95th percentile relative to anti-PAD IgA levels in healthy control subjects. In other embodiments, anti-PAD IgA can be considered increased in a subject if anti-PAD IgA levels are above the $96^{th}$, $97^{th}$, $98^{th}$ or $99^{th}$ percentile. A subject of the present disclosure with anti-PAD IgA levels at or above any of the disclosed reference intervals is considered to have RA and joint erosion In some embodiments, the presence of anti-PAD IgA can be based on a comparison of signal against background in a healthy subject. In some embodiments, the presence of anti-PAD IgA can be increased or decreased relative to an average or median anti-PAD IgA level observed in a population of healthy subjects. In some embodiments, anti-PAD IgA can be absent in healthy subjects. In some embodiments, anti-PAD IgA level cannot be detected above the noise of the respective assay used to determine anti-PAD IgA level. In some embodiments, anti-PAD IgA can be considered present in a sample if an anti-PAD IgA level can be detected above the noise of the respective assay used to determine an anti-PAD IgA level. In some embodiments, anti-PAD IgA can be considered increased in a sample if the signal in an anti-PAD IgA detection assay is at least two standard deviations above noise such as the average or mean signal for control samples. In some embodiments, anti-PAD IgA can be considered present in a sample if the level of anti-PAD IgA exceeds a predetermined threshold level. An anti-PAD IgA threshold level can be determined by a skilled artisan, such as a clinical physician, based on a variety of factors, such as the specific objectives of a clinical trial or the diagnostic and prognostic significance of a certain anti-PAD IgA level or the results of another diagnostic test for RA that does not involve the detection of anti-PAD IgA levels.

In some embodiments, the present disclosure provides a polypeptide including a PAD or antigenic fragment thereof. The PAD can be used in the methods provided herein or included in the kits provided herein.

As used herein, the term "peptidyl arginine deiminase" or "PAD," also known as PADI, refers to a family of enzymes that catalyze the post-translational modifications of protein arginine residues by deimination or demethylimination to produce citrulline (Wang and Wang, Biochim. Biophys. Acta., 1829:1126-35 (2013)). Five isotypes of PADs have been identified in humans and include PAD1, PAD2, PAD3, PAD4 and PAD6. All of such PAD polypeptides, PAD1, PAD2, PAD3, PAD4 and PAD6 are included within the meaning of the term "PAD" as it is used herein.

As used herein, the term "peptidyl arginine deiminase 2" or "PAD2," also known as PADI2, PAD-H19 and PDI2, refers to a member of the PAD family of enzymes. PAD2 is abundantly expressed in secretory glands, brain, uterus, spleen, pancreas and skeletal muscle. Known substrates of PAD2 include myelin basic protein, vimentin and macrophages. See Vossenaar et al., Annals of the Rheumatic Diseases, 63:373-81 (2004); Watanbe et al., Biochim Biophys Acta., 966:375-383 (1988); Watanabe et al., J. Biol Chem., 264:15255-15260 (1989); Nagata et al., Experientia, 46:72-74 (1990); Urano et al., Am J Dermatopathol., 12(3): 249-55 (1990), Vossenaar et al., Arthritis and Rheum., 48:2489-2500 (2003). Approximately 726 coding single nucleotide polymorphisms (SNP) have been identified for PAD2 and at least 184 known orthologs (see, for example, NCBI Gene ID: 11240). The term "PAD2" includes all of such PAD2 variants and PAD2 orthologs. An exemplary human PAD2 (hPAD2) nucleotide sequence can be found in GenBank under GenBank Accession number NM_007365 (SEQ ID NO:1) and encodes an exemplary human PAD2 having the amino acid sequence found under found under GenBank Accession number NP_031391 (SEQ ID NO:2). The GenBank Accession numbers and GenBank GI numbers of this PAD2 and other exemplary PAD2 enzymes can be found below in Table 1. All of such PAD2 polypeptides and variants thereof are included within the meaning of the term "PAD2" as it is used herein.

In some embodiments, a PAD2, or antigenic fragment thereof, includes the amino acid in SEQ ID NO:2, of a mature human PAD2 (hPAD2; amino acids 25-665 of NCBI Accession Number NP_031391; GI: 122939159), or naturally occurring variants thereof:

```
                                          SEQ ID NO: 2
MLRERTVRLQYGSRVEAVYVLGTYLWTDVYSAAPAGAQTFSLKHSEHVWV

EVVRDGEAEEVATNGKQRWLLSPSTTLRVTMSQASTEASSDKVTVNYYDE

EGSIPIDQAGLFLTAIEISLDVDADRDGVVEKNNPKKASWTWGPEGQGAI

LLVNCDRETPWLPKEDCRDEKVYSKEDLKDMSQMILRTKGPDRLPAGYEI

VLYISMSDSDKVGVFYVENPFFGQRYIHILGRRKLYHVVKYTGGSAELLF

FVEGLCFPDEGFSGLVSIHVSLLEYMAQDIPLTPIFTDTVIFRIAPWIMT

PNILPPVSVFVCCMKDNYLFLKEVKNLVEKTNCELKVCFQYLNRGDRWIQ

DEIEFGYIEAPHKGFPVVLDSPRDGNLKDFPVKELLGPDFGYVTREPLFE

SVTSLDSFGNLEVSPPVTVNGKTYPLGRILIGSSFPLSGGRRMTKVVRDF

LKAQQVQAPVELYSDWLTVGHVDEFMSFVPIPGTKKFLLLMASTSACYKL

FREKQKDGHGEAIMFKGLGGMSSKRITINKILSNESLVQENLYFQRCLDW
```

-continued

NRDILKKELGLTEQDIIDLPALFKMDEDHRARAFFPNMVNMIVLDKDLGI

PKPFGPQVEEECCLEMHVRGLLEPLGLECTFIDDISAYHKFLGEVHCGTN

VRRKPFTFKWWHMVP

As used herein, the term "peptidyl arginine deiminase 3" or "PAD3," also known as PADI3, PDI3 and UHS1, refers to a member of the PAD family of enzymes. PAD3 is detected in the epidermis where it plays a role in terminal differentiation and in hair follicles where it modulates structural proteins including filaggrin and trichoyalin. See Chavanas et al., J Dermatol Sci., 44:63-72 (2006); Kanno et al., J. Invest Dermatol. 115(5):813-23 (2000); Nachat et al., J Investig Dermatol., 125:34-41 (2005). Approximately 738 coding SNPs have been identified for PAD3 and at least 109 known orthologs (see, for example, NCBI Gene ID: 51702). The term "PAD3" includes all of such PAD3 variants and PAD3 orthologs. An exemplary human PAD3 (hPAD3) nucleotide sequence can be found in GenBank under GenBank Accession number NM_016233 (SEQ ID NO:5) and encodes an exemplary human PAD3 having the amino acid sequence found under found under GenBank Accession number NP_057317 (SEQ ID NO:6). The GenBank Accession numbers and GenBank GI numbers of this PAD3 and other exemplary PADS enzymes can be found below in Table 2. All of such PAD3 polypeptides and variants thereof are included within the meaning of the term "PAD3" as it is used herein.

In some embodiments, a PAD3, or antigenic fragment thereof, includes the amino acid in SEQ ID NO:6 of a mature human PAD3 (hPAD3; amino acids 25-664 of NCBI Accession Number NP_057317; GI: 122939161), or naturally occurring variants thereof:

SEQ ID NO: 6

MSLQRIVRVSLEHPTSAVCVAGVETLVDIYGSVPEGTEMFEVYGTPGVDI

YISPNMERGRERADTRRWRFDATLEIIVVMNSPSNDLNDSHVQISYHSSH

EPLPLAYAVLYLTCVDISLDCDLNCEGRQDRNFVDKRQWVWGPSGYGGIL

LVNCDRDDPSCDVQDNCDQHVHCLQDLEDMSVMVLRTQGPAALFDDHKLV

LHTSSYDAKRAQVFHICGPEDVCEAYRHVLGQDKVSYEVPRLHGDEERFF

VEGLSFPDAGFTGLISFHVTLLDDSNEDFSASPIFTDTVVFRVAPWIMTP

STLPPLEVYVCRVRNNTCFVDAVAELARKAGCKLTICPQAENRNDRWIQD

EMELGYVQAPHKTLPVVFDSPRNGELQDFPYKRILGPDFGYVTREPRDRS

VSGLDSFGNLEVSPPVVANGKEYPLGRILIGGNLPGSSGRRVTQVVRDFL

HAQKVQPPVELFVDWLAVGHVDEFLSFVPAPDGKGFRMLLASPGACFKLF

QEKQKCGHGRALLFQGVVDDEQVKTISINQVLSNKDLINYNKFVQSCIDW

NREVLKRELGLAECDIIDIPQLFKTERKKATAFFPDLVNMLVLGKHLGIP

KPFGPIINGCCCLEEKVRSLLEPLGLHCTFIDDFTPYHMLHGEVHCGTNV

CRKPFSFKWWNMVP

As used herein, the term "peptidyl arginine deiminase 4" or "PAD4," also known as PAD, PADI4, PDI4, PADV, PDI5 and PADI5, refers to a member of the PAD family of enzymes. PAD4 can be detected in white blood cells including granulocytes and monocytes under normal physiological conditions (Vossenaar et al., Annals of the Rheumatic Diseases, 63:373-81 (2004); Asaga et al., J. Leukocyte Biology 70:46-51 (2001)) and is generally localized in the nucleus (Nakashima et al., JBC 277:49562-68 (2002)). Approximately 737 coding SNPs have been identified for PAD4 and at least 108 known orthologs (see, for example, NCBI Gene ID: 23569). The term "PAD4" includes all of such PAD4 variants and PAD4 orthologs. An exemplary human PAD4 (hPAD4) nucleotide sequence can be found in GenBank under GenBank Accession number NM_012387.2 (SEQ ID NO:61) and encodes an exemplary human PAD4 having the amino acid sequence found under found under GenBank Accession number NP_036519.2 (SEQ ID NO:62). The GenBank Accession numbers and GenBank GI numbers of this PAD4 and other exemplary PAD4 enzymes can be found below in Table 3. All of such PAD4 polypeptides and variants thereof are included within the meaning of the term "PAD4" as it is used herein.

In some embodiments, a PAD4, or antigenic fragment thereof, includes the amino acid in SEQ ID NO:62, of a mature human PAD4 (hPAD4; amino acids 25-663 of NCBI Accession Number NP_036519; GI: 216548487), or naturally occurring variants thereof:

SEQ ID NO: 62

MAQGTLIRVTPEQPTHAVCVLGTLTQLDICSSAPEDCTSFSINASPGVVV

DIAHGPPAKKKSTGSSTWPLDPGVEVTLTMKVASGSTGDQKVQISYYGPK

TPPVKALLYLTGVEISLCADITRTGKVKPTRAVKDQRTWTWGPCGQGAIL

LVNCDRDNLESSAMDCEDDEVLDSEDLQDMSLMTLSTKTPKDFFTNHTLV

LHVARSEMDKVRVFQATRGKLSSKCSVVLGPKWPSHYLMVPGGKHNMDFY

VEALAFPDTDFPGLITLTISLLDTSNLELPEAVVFQDSVVFRVAPWIMTP

NTQPPQEVYACSIFENEDFLKSVTTLAMKAKCKLTICPEEENMDDQWMQD

EMEIGYIQAPHKTLPVVFDSPRNRGLKEFPIKRVMGPDFGYVTRGPQTGG

ISGLDSFGNLEVSPPVTVRGKEYPLGRILFGDSCYPSNDSRQMHQALQDF

LSAQQVQAPVKLYSDWLSVGHVDEFLSFVPAPDRKGFRLLLASPRSCYKL

FQEQQNEGHGEALLFEGIKKKKQQKIKNILSNKTLREHNSFVERCIDWNR

ELLKRELGLAESDIIDIPQLFKLKEFSKAEAFFPNMVNMLVLGKHLGIPK

PFGPVINGRCCLEEKVCSLLEPLGLQCTFINDFFTYHIRHGEVHCGTNVR

RKPFSFKWWNMVP

Tables 1, 2 and 3 contain two sequence identifiers, the GI number and the GenBank accession number. The GI number and GenBank accession number run in parallel as unique identifiers to access the referenced sequence in publicly available databases. Table 1 includes GI numbers and GenBank Accession numbers for PAD2, Table 2 includes GI numbers and GenBank Accession numbers for PAD3 and Table 3 includes GI numbers and GenBank accession numbers for PAD4.

The sequence identifiers in Tables 1, 2 and 3 are provided for wild-type PAD2, 3 and 4, respectively. It should be understood that wild-type nucleic acid and amino acid sequences herein refer to those nucleic acid and amino acid sequences prevalent among a population and serve as a reference for their respective variants. As an example, SEQ ID NO:61 in Table 3 (GI number: 1519314340 and Accession number: NM_012387) identifies the wild-type nucleic acid sequence for hPAD4 while SEQ ID NO:62 (GI number: 216548487 and Accession number: NP_036519) identifies the wild-type amino acid sequence for hPAD4.

The sequence identifiers in Tables 1, 2 and 3 also are provided for variants of PAD2, 3 and 4 respectively. It should be understood that a variant refers to a nucleic acid sequence that is similar but different from the wild-type nucleic acid sequence.

A variant in any of the Tables below can include a nucleic acid substitution that can be the result of, for example, alternative splicing (e.g. splice variant). As an example, SEQ ID NO:69 in Table 3 (GI number: 767903519 and Accession number: XM_011541150.1:c.23G>A) is a hPAD4 nucleic acid splice variant of SEQ ID NO:61.

A variant in any of the Tables below can also include, for example, a nucleic acid substitution (e.g. SNP). As an example, SEQ ID NO:63 in Table 3 (GI number: 216548486 and Accession number: NM_012387.2:c.23G>A) is a hPAD4 nucleic acid variant of SEQ ID NO:61 and includes a single nucleic acid substitution at nucleic acid position 23, resulting in the substitution of G (guanosine) for A (adenine).

It should be understood that a variant also refers to an amino acid sequence that is similar but different to the wild-type amino acid sequence.

A variant in any of the Tables below can further include amino acid substitutions that can be the result of, for example, alternative splicing (e.g. splice variant). As an example, SEQ ID NO:70 in Table 3 (GI number: 767903520 and Accession number: XP_011539452.1:p.Arg8His), which is encoded by SEQ ID NO:69 described above, is a hPAD4 that includes an amino acid substitution at position 8, resulting in a substitution of Arg (arginine) for His (histidine).

A variant in any of the Tables below can include, for example, amino acid substitutions that can be the result of genetic inheritance (e.g. SNP). As an example, SEQ ID NO:64 in Table 3 (GI number: 216548487 and Accession number: NP_036519.2:p.Arg8His), which is encoded by SEQ ID NO:63 described above, is a hPAD4 that includes an amino acid substitution at position 8, resulting in a substitution of Arg (arginine) for His (histidine).

TABLE 1

| Molecule Type | SEQ ID NO | GI Number | GenBank Accession Number |
|---|---|---|---|
| Homo sapiens peptidyl arginine deiminase 2 (PADI2), mRNA | 1 | 1519245591 | NM_007365 |
| protein-arginine deiminase type-2 [Homo sapiens] | 2 | 122939159 | NP_031391 |
| PREDICTED: Homo sapiens peptidyl arginine deiminase 2 (PADI2), transcript variant X2, mRNA | 3 | 1370451734 | XM_017000148 |
| protein-arginine deiminase type-2 isoform X1 [Homo sapiens] | 4 | 1034554998 | XP_016855637 |

TABLE 2

| Molecule Type | SEQ ID NO | GI Number | GenBank Accession Number | Amino Acid [Codon] | SO Term |
|---|---|---|---|---|---|
| Homo sapiens peptidyl arginine deiminase 3 (PADI3), mRNA | 5 | 122939160 | NM_016233 | N/A | N/A |
| protein-arginine deiminase type-3 [Homo sapiens] | 6 | 122939161 | NP_057317 | N/A | N/A |
| PADI3 transcript | 7 | 122939160 | NM_016233.2:c.154A > G | I [ATC] > V [GTC] | Coding Sequence Variant |
| protein-arginine deiminase type-3 | 8 | 122939161 | NP_057317.2:p.Ile52Val | I (Ile) > V (Val) | Missense Variant |
| PADI3 transcript | 9 | 122939160 | NM_016233.2:c.335T > A | L [CTC] > H [CAC] | Coding Sequence Variant |
| protein-arginine deiminase type-3 | 10 | 122939161 | NP_057317.2:p.Leu112His | L (Leu) > H (His) | Missense Variant |
| PADI3 transcript | 11 | 122939160 | NM_016233.2:c.511G > A | V [GTG] > M [ATG] | Coding Sequence Variant |
| protein-arginine deiminase type-3 | 12 | 122939161 | NP_057317.2:p.Val171Met | V (Val) > M (Met) | Missense Variant |
| PADI3 transcript | 13 | 122939160 | NM_016233.2:c.881C > T | A [GCA] > V [GTA] | Coding Sequence Variant |
| protein-arginine deiminase type-3 | 14 | 122939161 | NP_057317.2:p.Ala294Val | A (Ala) > V (Val) | Missense Variant |
| PADI3 transcript | 15 | 122939160 | NM_016233.2:c.1744G > A | A [GCC] > T [ACC] | Coding Sequence Variant |
| protein-arginine deiminase type-3 | 16 | 122939161 | NP_057317.2:p.Ala582Thr | A (Ala) > T (Thr) | Missense Variant |
| PADI3 transcript | 17 | 122939160 | NM_016233.2:c.1813C > A | P [CCC] > T [ACC] | Coding Sequence Variant |
| protein-arginine deiminase type-3 | 18 | 122939161 | NP_057317.2:p.Pro605Thr | P (Pro) > T (Thr) | Missense Variant |
| PADI3 transcript | 19 | 122939160 | NM_016233.2:c.1853G > A | R [CGG] > Q [CAG] | Coding Sequence Variant |
| protein-arginine deiminase type-3 | 20 | 122939161 | NP_057317.2:p.Arg618Gln | R (Arg) > Q (Gln) | Missense Variant |
| Predicted: Homo sapiens peptidyl arginine deiminase 3 (PADI3), transcript variant X1, mRNA | 21 | 1034559140 | XM_011541571 | N/A | N/A |
| protein-arginine deiminase type-3 isoform X1 [Homo sapiens] | 22 | 767904616 | XP_011539873 | N/A | N/A |

TABLE 2-continued

| Molecule Type | SEQ ID NO | GI Number | GenBank Accession Number | Amino Acid [Codon] | SO Term |
|---|---|---|---|---|---|
| Predicted: PADI3 transcript variant X1 | 23 | 1034559140 | XM_011541571.2 :c.40A > G | I [ATC] > V [GTC] I (Ile) > V (Val) | Coding Sequence Variant |
| protein-arginine deiminase type-3 isoform X1 | 24 | 767904616 | XP_011539873.1: p.Ile14Val | | Missense Variant |
| Predicted: PADI3 transcript variant X1 | 25 | 1034559140 | XM_011541571.2 :c.221T > A | L [CTC] > H [CAC] | Coding Sequence Variant |
| protein-arginine deiminase type-3 isoform X1 | 26 | 767904616 | XP_011539873.1: p.Leu74His | L (Leu) > H (His) | Missense Variant |
| Predicted: PADI3 transcript variant X1 | 27 | 1034559140 | XM_011541571.2 :c.397G > A | V [GTG] > M [ATG] | Coding Sequence Variant |
| protein-arginine deiminase type-3 isoform X1 | 28 | 767904616 | XP_011539873.1: p.Val133Met | V (Val) > M (Met) | Missense Variant |
| PADI3 transcript variant X1 | 29 | 1034559140 | XM_011541571.2 :c.767C > T | A [GCA] > V [GTA] | Coding Sequence Variant |
| protein-arginine deiminase type-3 isoform X1 | 30 | 767904616 | XP_011539873.1: p.Ala256Val | A (Ala) > V (Val) | Missense Variant |
| PADI3 transcript variant X1 | 31 | 1034559140 | XM_011541571.2 :c.1630G > A | A [GCC] >T [ACC] | Coding Sequence Variant |
| protein-arginine deiminase type-3 isoform X1 | 32 | 767904616 | XP_011539873.1: p.Ala544Thr | A (Ala) > T (Thr) | Missense Variant |
| PADI3 transcript variant X1 | 33 | 1034559140 | XM_011541571.2 :c.1699C > A | P [CCC] > T [ACC] | Coding Sequence Variant |
| protein-arginine deiminase type-3 isoform X1 | 34 | 767904616 | XP_011539873.1: p.Pro567Thr | P (Pro) > T (Thr) | Missense Variant |
| PADI3 transcript variant X1 | 35 | 1034559140 | XM_011541571.2 :c.1739G > A | R [CGG] > Q [CAG] | Coding Sequence Variant |
| protein-arginine deiminase type-3 isoform X1 | 36 | 767904616 | XP_011539873.1: p.Arg580Gln | R (Arg) > Q (Gln) | Missense Variant |
| Homo sapiens peptidyl arginine deiminase 3 (PADI3), transcript variant X2, mRNA | 37 | 1034559141 | XM_017001463 | N/A | N/A |
| protein-arginine deiminase type-3 isoform X2 [Homo sapiens] | 38 | 1034559142 | XP_016856952 | N/A | N/A |
| PADI3 transcript variant X2 | 39 | 1034559141 | XM_017001463.1 :c | N/A | Genic Upstream Transcript Variant |
| PADI3 transcript variant X2 | 40 | 1034559141 | XM_017001463.1 :c | N/A | 5 Prime UTR Variant |
| PADI3 transcript variant X2 | 41 | 1034559141 | XM_017001463.1 :c.344C > T | A [GCA] > V [GTA] | Coding Sequence Variant |
| protein-arginine deiminase type-3 isoform X2 | 42 | 1034559142 | XP_016856952.1: p.Ala115Val | A (Ala) > V (Val) | Missense Variant |
| PADI3 transcript variant X2 | 43 | 1034559141 | XM_017001463.1 :c.1207G > A | A [GCC] > T [ACC] | Coding Sequence Variant |
| protein-arginine deiminase type-3 isoform X2 | 44 | 1034559142 | XP_016856952.1: p.Ala403Thr | A (Ala) > T (Thr) | Missense Variant |
| PADI3 transcript variant X2 | 45 | 1034559141 | XM_017001463.1 :c.1276C > A | P [CCC] > T [ACC] | Coding Sequence Variant |
| protein-arginine deiminase type-3 isoform X2 | 46 | 1034559142 | XP_016856952.1: p.Pro426Thr | P (Pro) > T (Thr) | Missense Variant |
| PADI3 transcript variant X2 | 47 | 1034559141 | XM_017001463.1 :c.1316G > A | R [CGG] > Q [CAG] | Coding Sequence Variant |
| protein-arginine deiminase type-3 isoform X2 | 48 | 1034559142 | XP_016856952.1: p.Arg439Gln | R (Arg) > Q (Gln) | Missense Variant |
| Homo sapiens peptidyl arginine deiminase 3 (PADI3), transcript variant X3, mRNA | 49 | 1034559143 | XM_011541572 | N/A | N/A |
| protein-arginine deiminase type-3 isoform X3 [Homo sapiens] | 50 | 767904618 | XP_011539874 | N/A | N/A |
| PADI3 transcript variant X3 | 51 | 1034559143 | XM_011541572.2 :c.154A > G | I [ATC] > V [GTC] | Coding Sequence Variant |
| protein-arginine deiminase type-3 isoform X3 | 52 | 767904618 | XP_011539874.1: p.Ile52Val | I (Ile) > V (Val) | Missense Variant |
| PADI3 transcript variant X3 | 53 | 1034559143 | XM_011541572.2 :c.335T > A | L [CTC] > H [CAC] | Coding Sequence Variant |
| protein-arginine deiminase type-3 isoform X3 | 54 | 767904618 | XP_011539874.1: p.Leu112His | L (Leu) > H (His) | Missense Variant |
| PADI3 transcript variant X3 | 55 | 1034559143 | XM_011541572.2 :c.511G > A | V [GTG] > M [ATG] | Coding Sequence Variant |

TABLE 2-continued

| Molecule Type | SEQ ID NO | GI Number | GenBank Accession Number | Amino Acid [Codon] | SO Term |
|---|---|---|---|---|---|
| protein-arginine deiminase type-3 isoform X3 | 56 | 767904618 | XP_011539874.1: p.Val171Met | V (Val) > M (Met) | Missense Variant |
| PADI3 transcript variant X3 | 57 | 1034559143 | XM_011541572.2 :c.881C > T | A [GCA] > V [GTA] | Coding Sequence Variant |
| protein-arginine deiminase type-3 isoform X3 | 58 | 767904618 | XP_011539874.1: p.Ala294Val | A (Ala) > V (Val) | Missense Variant |
| PADI3 transcript variant X3 | 59 | 1034559143 | XM_011541572.2 :c. | N/A | Genic Downstream Transcript Variant |

TABLE 3

| Molecule Type | SEQ ID NO | GI Number | GenBank Accession Number | Amino Acid [Codon] | SO Term |
|---|---|---|---|---|---|
| Homo sapiens peptidyl arginine deiminase 4 (PADI4), mRNA | 61 | 1519314340 | NM_012387 | N/A | N/A |
| protein-arginine deiminase type-4 [Homo sapiens] | 62 | 216548487 | NP_036519 | N/A | N/A |
| PADI4 transcript | 63 | 216548486 | NM_012387.2: c.23G > A | R [CGT] > H [CAT] | Coding Sequence Variant |
| protein-arginine deiminase type-4 | 64 | 216548487 | NP_036519.2:p .Arg8His | R (Arg) > H (His) | Missense Variant |
| PADI4 transcript | 65 | 216548486 | NM_012387.2: c.23G > T | R [CGT] > L [CTT] | Coding Sequence Variant |
| protein-arginine deiminase type-4 | 66 | 216548487 | NP_036519.2:p .Arg8Leu | R (Arg) > L (Leu) | Missense Variant |
| PADI4 transcript variant X3 | 67 | 767903523 | XM_01154115 2.1:c. | N/A | Genic Upstream Transcript Variant |
| PADI4 transcript variant X8 | 68 | 767903533 | XM_01154115 7.1:c. | N/A | Genic Upstream Transcript Variant |
| PADI4 transcript variant X1 | 69 | 767903519 | XM_01154115 0.1:c.23G > A | R [CGT] > H [CAT] | Coding Sequence Variant |
| protein-arginine deiminase type-4 isoform X1 | 70 | 767903520 | XP_011539452. 1:p.Arg8His | R (Arg) > H (His) | Missense Variant |
| PADI4 transcript variant X1 | 71 | 767903519 | XM_01154115 0.1:c.23G > T | R [CGT] > L [CTT] | Coding Sequence Variant |
| protein-arginine deiminase type-4 isoform X1 | 72 | 767903520 | XP_011539452. 1:p.Arg8Leu | R (Arg) > L (Leu) | Missense Variant |
| PADI4 transcript variant X2 | 73 | 767903521 | XM_01154115 1.1:c.23G > A | R [CGT] > H [CAT] | Coding Sequence Variant |
| protein-arginine deiminase type-4 isoform X2 | 74 | 767903522 | XP_011539453. 1:p.Arg8His | R (Arg) > H (His) | Missense Variant |
| PADI4 transcript variant X2 | 75 | 767903521 | XM_01154115 1.1:c.23G > T | R [CGT] > L [CTT] | Coding Sequence Variant |
| protein-arginine deiminase type-4 isoform X2 | 76 | 767903522 | XP_011539453. 1:p.Arg8Leu | R (Arg) > L (Leu) | Missense Variant |
| PADI4 transcript variant X4 | 77 | 767903525 | XM_01154115 3.1:c.23G > A | R [CGT] > H [CAT] | Coding Sequence Variant |
| protein-arginine deiminase type-4 isoform X4 | 78 | 767903526 | XP_011539455. 1:p.Arg8His | R (Arg) > H (His) | Missense Variant |
| PADI4 transcript variant X4 | 79 | 767903525 | XM_01154115 3.1:c.23G > T | R [CGT] > L [CTT] | Coding Sequence Variant |
| protein-arginine deiminase type-4 isoform X4 | 80 | 767903526 | XP_011539455. 1:p.Arg8Leu | R (Arg) > L (Leu) | Missense Variant |
| PADI4 transcript variant X6 | 81 | 767903529 | XM_01154115 5.1:c.23G > A | R [CGT] > H [CAT] | Coding Sequence Variant |
| protein-arginine deiminase type-4 isoform X5 | 82 | 767903530 | XP_011539457. 1:p.Arg8His | R (Arg) > H (His) | Missense Variant |
| PADI4 transcript variant X6 | 83 | 767903529 | XM_01154115 5.1:c.23G > T | R [CGT] > L [CTT] | Coding Sequence Variant |
| protein-arginine deiminase type-4 isoform X5 | 84 | 767903530 | XP_011539457. 1:p.Arg8Leu | R (Arg) > L (Leu) | Missense Variant |
| PADI4 transcript variant X7 | 85 | 767903531 | XM_01154115 6.1:c.23G > A | R [CGT] > H [CAT] | Coding Sequence Variant |
| protein-arginine deiminase type-4 isoform X6 | 86 | 767903532 | XP_011539458. 1:p.Arg8His | R (Arg) > H (His) | Missense Variant |
| PADI4 transcript variant X7 | 87 | 767903531 | XM_01154115 6.1:c.23G > T | R [CGT] > L [CTT] | Coding Sequence Variant |

TABLE 3-continued

| Molecule Type | SEQ ID NO | GI Number | GenBank Accession Number | Amino Acid [Codon] | SO Term |
|---|---|---|---|---|---|
| protein-arginine deiminase type-4 isoform X6 | 88 | 767903532 | XP_011539458. 1:p.Arg8Leu | R (Arg) > L (Leu) | Missense Variant |
| PADI4 transcript variant X5 | 89 | 1034557308 | XM_01154115 4.2:c.23G > A | R [CGT] > H [CAT] | Coding Sequence Variant |
| protein-arginine deiminase type-4 isoform X4 | 90 | 767903528 | XP_011539456. 1:p.Arg8His | R (Arg) > H (His) | Missense Variant |
| PADI4 transcript variant X5 | 91 | 1034557308 | XM_01154115 4.2:c.23G > T | R [CGT] > L [CTT] | Coding Sequence Variant |
| protein-arginine deiminase type-4 isoform X4 | 92 | 767903528 | XP_011539456. 1:p.Arg8Leu | R (Arg) > L (Leu) | Missense Variant |

It should be noted that "polypeptide" includes a short oligopeptide having between 2 and 30 amino acids (e.g., 2, 3, 4, 5, 6, 7, 8, 9, 10, 12, 14, 16, 18, 20, 25 or 30 amino acids) as well as longer amino acid chains, e.g., more than 30 amino acids, more than 50 amino acids, more than 100 amino acids, more than 150 amino acids, more than 200 amino acids, more than 300 amino acids, more than 400 amino acids, more than 500 amino acids, or more than 600 amino acids. In some embodiments, the PAD can be a full-length, wild-type polypeptide. PAD polypeptides can include unnatural amino acids not encoded by the natural genetic code.

In some embodiments, the purified polypeptide includes a PAD antigenic fragment. In some embodiments, a PAD antigenic fragment includes more than 3, more than 5, more than 10, more than 15, more than 20, more than 25, more than 50, more than 75, more than 100, more than 125, more than 150, more than 200, more than 250, more than 300, more than 350, more than 400, more than 500, or more than 600 consecutive amino acids of a full-length PAD polypeptide. In some embodiments, a PAD antigenic fragment includes less than 100%, less than 95%, less than 90%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of consecutive amino acids of full-length PAD. In some embodiments, a PAD antigenic fragment is a PAD peptide fragment.

In some embodiments, a PAD or antigenic fragment thereof can be a mammalian PAD. In some embodiments, a PAD or antigenic fragment thereof can be human. In some embodiments, a PAD or antigenic fragment thereof can be a PAD or antigenic fragment thereof of one of the organisms of the present disclosure. In some embodiments, a PAD or antigenic fragment thereof can include any of the variants or single nucleotide polymorphisms in Tables 1-3.

A PAD or antigenic fragment thereof can be obtained using various methods well known in the art. For example, a PAD or antigenic fragment thereof can be isolated from a natural source, produced by chemical synthesis or produced by recombinant protein expression.

Exemplary methods for expressing and purifying recombinant polypeptides, for purifying polypeptides from cells, tissues or bodily fluids, and for chemically synthesizing polypeptides are well known in the art and can be found described in Scopes R. K., Protein Purification—Principles and Practice, Springer Advanced Texts in Chemistry, 3rd Edition (1994); Simpson R. J. et al., Basic Methods in Protein Purification and Analysis: A Laboratory Manual, Cold Spring Harbor Laboratory Press, 1st Edition (2008); Green M. R. and Sambrook J., Molecular Cloning: A Laboratory Manual, Cold Spring Harbor Laboratory Press, 4th Edition (2012); Jensen K. J. et al., Peptide Synthesis and Applications (Methods in Molecular Biology), Humana Press, 2nd Edition (2013).

Polypeptides purified or isolated from a natural source refers to the isolation and purification of a polypeptide from a source where it is naturally expressed. In some embodiments, a natural source of a PAD can be from a cell, tissue or bodily fluid of an organism. In some embodiments, the cells, tissues or bodily fluids can include, for example, whole blood, serum, plasma, synovial fluid or sputum from an organism of the present disclosure. A PAD or antigenic fragment thereof can similarly be isolated from any biological sample described and provided herein.

It should be noted that the terms "purified" or "isolated" refer to a polypeptide that is isolated, partially or completely, from a complex mixture of components, as found in nature. Thus, in some embodiments, a PAD of the present disclosure can be partially purified or substantially purified. Partial purification results in isolation from one or more components as found in nature. Substantial purification results in isolation from all components as found in nature. Partial purification, as disclosed herein, can be achieved by the methods and compositions provided herein. In some embodiments, a partially purified PAD can be performed with a capture probe. In some embodiments, the capture probe is a polypeptide or functional fragment thereof specific to PAD. In some embodiments, the capture probe is an anti-PAD antibody. Substantial purification, as exemplified herein, can be achieved by methods known in the art. In some embodiments, a PAD is purified substantially by a process of extraction, precipitation and solubilization.

Recombinant polypeptides can be expressed in and purified from bacterial cells (e.g., *E. coli*), yeast cells (e.g., *S. cerevisiae*), insect cells (e.g., Sf9), in mammalian cells (e.g., CHO) and others. Recombinant polypeptides can be expressed and purified as fusion proteins including tags for protein detection or affinity purification tags (e.g., His-tag, GST-tag, Myc-tag), including cleavable tags (e.g., tags including a TEV-cleavage site). In some embodiments, the PAD provided herein can be purified from a cell, tissue or bodily fluid obtained from an organism. Tissues or bodily fluids can include any tissue or bodily fluids obtained from the organism. In some embodiments, the tissues or bodily fluids can include blood, serum, plasma, synovial fluid, urine or milk (e.g., from goats, cows, sheep). One skilled in the art will recognize that methods for the purification of polypeptides from cells, tissues or bodily fluids are well known in the art.

In some embodiments, a PAD or antigenic fragment thereof is chemically synthesized using, for example, methods described in Jensen, K. J. (supra).

In some embodiments, a PAD antigenic fragment can be produced by enzymatically digesting full-length PAD. The full-length PAD can be obtained by, for example, any of the exemplary methods described above. The enzymatic digest can be carried out with, for example, a protease or peptidase. In some embodiments, the protease or peptidase can be an exoprotease or an exopeptidase. In some embodiments, the protease or peptidase can be an endoprotease or endopeptidase. In some embodiments, the protease or peptidase can include a serine protease, threonine protease, cysteine protease, aspartate protease, glutamic acid protease, or metalloprotease. In some embodiments, the protease or peptidase can include trypsin, chymotrypsin, pepsin, papain and any cathepsin including cathepsin B, L, D, K, or G.

In some embodiments, a PAD or antigenic fragment thereof can be a native PAD. In some embodiments, the PAD or antigenic fragment thereof can be a denatured or unfolded PAD. In some embodiments, the PAD or antigenic fragment thereof can include unnatural amino acids. In some embodiments, the unnatural amino acids can be methylated at the a-amino-group to produce polypeptides with methylated backbones. In some embodiments, the unnatural amino acids can be R-amino acids. In some embodiments, the unnatural amino acids can include dyes (e.g., fluorescent dyes) or affinity tags. In some embodiments, the PAD or antigenic fragment thereof can include chemical modifications. Chemical modifications can include, e.g., chemical modifications with biotin, fluorescent dyes. A skilled artisan will recognize that methods for introducing unnatural amino acids into polypeptides and for chemically modifying polypeptides are well known in the art.

In some embodiments, an isolated, chemically synthesized or recombinant PAD or antigenic fragment thereof can be a plurality of PADs. It should be noted that the term "plurality" refers to a population of two or more members, such as polypeptide members or other referenced molecules. In some embodiments, the two or more members of a plurality of members can be the same members. For example, a plurality of polypeptides can include two or more polypeptide members having the same amino acid sequence. By way of exemplification, a plurality of members having the same amino acid sequence can include two or more members of any one of PAD exemplified in Table 1. In some embodiments, the two or more members of a plurality of members can be different members. For example, a plurality of polypeptides can include two or more polypeptide members having different amino acid sequences. By way of exemplification, a plurality of members having different amino acid sequences can include at least one member of two or more PADs exemplified in Table 1. A plurality includes 2, 3, 4, 5, 6, 7, 8, 9, 10, 20, 30, 40, 50, 60, 70, 80, 90 or a 100 or more different members. A plurality can also include 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$ or more different members. A plurality includes, for example, all integer numbers in between the above exemplary plurality numbers. In some embodiments, a PAD can be a plurality of PADs from the organisms of the present disclosure.

As provided herein, RA, RA severity and joint erosion can be determined in subjects of the present disclosure by the detection of anti-PAD2, anti-PAD3 or anti-PAD4 IgA. Detection of any of the anti-PAD IgA described herein can be performed through the use of, for example, an antibody specific to IgA or other binding molecule specific to IgA. An IgA binding molecule in the art can be used. An antibody or other binding molecule specific to any of the anti-PAD IgA described herein can also be employed.

As used herein, the term "antibody" is used interchangeably with immunoglobulin (Ig) and refers to a polypeptide product of B-cells that is able to bind to a specific molecular antigen and is composed of two heavy chains and two light chains. Each amino-terminal portion of each chain includes a variable region that confers binding specificity. See Borrebaeck (ed.) (1995) Antibody Engineering, Second Edition, Oxford University Press; Kuby (1997) Immunology, Third Edition, W.H. Freeman and Company, New York. The term includes autoantibodies and antibodies used as detection probes in the disclosed methods. The antibody can exhibit specific binding affinity where it binds to a single molecular species or pan-specific binding where it binds selectively to more than one related molecular species. In the context of the present disclosure, the specific molecular antigen that can be bound by an antibody of the disclosure includes, for example, IgA, PAD (e.g., PAD2, PAD3 and/or PAD4), PAD:anti-PAD IgA complex (e.g., anti-PAD 2, 3 and/or 4 IgA complexes), and/or anti-PAD IgA (e.g., anti-PAD2 IgA, anti-PAD3 IgA and/or anti-PAD4 IgA). An antibody of the present disclosure can be derived from any mammalian organism, including mouse, rabbit, goat, chicken, donkey and the like. Furthermore, a primary or secondary antibody can be monoclonal, polyclonal, chimeric or humanized. The antibodies provided herein can be used in the methods and compositions of the disclosure.

As used herein, the term "functional fragment" when used in reference to an antibody is intended to refer to a portion of the antibody including heavy or light chain polypeptides that retain some or all of the binding activity as the antibody from which the fragment was derived. Such functional fragments can include, for example, an Fd, Fv, Fab, F(ab'), F(ab) 2, F(ab') 2, single chain Fv (scFv), diabody, triabody, tetrabody and minibody. Such antibody binding fragments can be found described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., Cell Biophysics, 22:189-224 (1993); Plückthun and Skerra, Meth. Enzymol., 178:497-515 (1989) and in Day, E. D., Advanced Immunochemistry, Second Ed., Wiley-Liss, Inc., New York, N.Y. (1990). The antibody functional fragments provided herein can be used in the methods and compositions of the disclosure. Ligands are provided herein and include any molecule having specific binding to a target. Exemplary ligands include a polypeptide, IgA binding molecules including, for example, IgA binding proteins, an affibody, an aptamer, a small molecule and the like. Specific examples of polypeptide ligands include receptors, chimeric receptors and polypeptides identified from screening of random or combinatorial libraries. Exemplary polypeptide ligands of the present disclosure include PAD (e.g., PAD2, PAD3 and/or PAD4) or an antigenic fragment thereof or an IgA binding polypeptide. An exemplary IgA binding polypeptide includes KW-0388. Other exemplary ligands that bind to IgA can be found described in Rönnmark et al., "Human immunoglobulin A (IgA)-specific ligands from combinatorial engineering of protein A," Eur. J. Biochem. 269:2647-55 (2002) and Kruljec et al., "Alternative Affinity Ligands for Immunoglobulins," Bioconjugate Chem. 28:2009-30 (2017). A ligand of the present disclosure can be obtained or synthesized by methods described herein or known in the art, including for example, chemically synthesized, purified from a natural source or recombinantly made. Thus, a ligand detection probe described herein can be mammalian, including mouse, rabbit, goat, chicken, donkey and the like. All of such ligands provided herein can be used in the methods and compositions of the disclosure.

As used herein, the term “detection probe” refers to a binding agent capable of specific binding to a target. Such binding agents include, for example, antibodies and ligands. Antibodies include full length antibodies as well as functional fragments such as those exemplified above. Ligands include full length polypeptides such as those exemplified above and functional binding fragments thereof. Ligands also include the non-polypeptide ligands exemplified above. When referring to specific binding to a target, a detection probe of the disclosure can bind the target directly or it can be made specific to the target by indirect means. For example, a detection probe that binds directly to anti-PAD IgA includes PAD. A direct binder also includes, for example, an antibody or other ligand that specifically recognizes a PAD:anti-PAD IgA complex as well as an antibody or other ligand that specifically binds to anti-PAD IgA. A detection probe of the disclosure that can be made specific to anti-PAD IgA by indirect means includes, for example, anti-IgA or other ligand that binds IgA. Such antibodies and ligands can be made specific to anti-PAD IgA by, for example, capturing the anti-PAD IgA with PAD and washing away non-anti-PAD IgA prior to adding anti-IgA. Numerous other configurations for isolating such a binding complex in order to achieve specific binding to a target are well known in the art and all of which can be used as an indirect means to make a detection probe specific to a target. Thus, a “detection probe specific for anti-PAD IgA” includes, for example, PAD, a PAD:anti-PAD IgA complex binding agent, an anti-PAD IgA binding agent and an IgA binding agent. The anti-PAD IgA detection probes include binding agents to anti-PAD2 IgA, anti-PAD3 IgA and/or anti-PAD4 IgA.

Accordingly, in one embodiment an exemplary detection probe of the current disclosure which can bind anti-PAD IgA directly is a labeled PAD. A detection probe made specific to anti-PAD IgA by indirect means includes a labeled anti-IgA. These and other exemplary detection probes as well as means for capturing a PAD:anti-PAD IgA complex for specific detection are further described below.

As used herein, the term “reporter tag” refers to a molecule capable of producing a signal indicative of the detection of a biomarker. An exemplary biomarker in the present disclosure includes anti-PAD IgA. Reporter tags can be attached, for example conjugated, to the detection probe through non-covalent or covalent cross-linkage to the detection probe. Non-covalent and covalent immobilization of reporter tags to detection probes can be performed by any means known in the art described in Dennler et al., “Antibody conjugates: from heterogeneous populations to defined reagents,” Antibodies. 4:197-224 (2015). Reporter tags produce various signals, depending on the type of reporter tag. A person skilled in the art appreciates that there are various labels encompassed by reporter tags.

As used herein, the term “label” refers to a molecular entity that emits a signal and can be used as a readout or measurement for detection of an analyte. Various classes of labels exist. Such labels include a fluorophore, an enzyme, a chemiluminescent moiety, a radioactive moiety, an organic dye, a small molecule, a polypeptide or functional fragment thereof. Examples of fluorophores include fluorescent dyes like phycoerytherin (PE), fluorescein isothiocyanate (FITC), tetramethylrhodamine (TRITC), BODIPY and AlexaFluor® dyes. Fluorescent dyes can also include fluorescence resonance energy transfer (FRET)-dyes or time-resolved (TR)-FRET dyes. Fluorophore labels also include fluorescent proteins such as green fluorescent protein (GFP) and cyan fluorescent protein (CFP). Examples of enzyme labels include alkaline phosphatase (AP) or horseradish peroxidase (HRP). When any of the substrates 3,3'5,5'-Tetramethylbenzidine (TMB), 3,3'-Diaminobenzidene (DAB), or 2,2'-azino-bis(3-ethylbenzothiazoline-6-sulphonic acid) (ABTS) are applied to HRP, a colored (chromogenic) or light (chemiluminescent) signal is produced. Radioactive moiety labels include carbon-14 or Tritium. Small molecule labels include biotin, resins such as agarose beads and fluorescently labeled magnetic beads, or nanoparticles such as colloidal gold. Polypeptide or functional fragment labels include Avidin, Streptavidin or NeutrAvidin which have an affinity for biotin. Polypeptide or functional fragment labels also include hemagglutinin (HA), glutathione-S-transferase (GST) or c-myc.

A label of the present disclosure can be conjugated to any of the detection probes identified herein. Conjugation can include non-covalent or covalent cross-linkage as described above. In some configurations, a label conjugated to a detection probe requires an additional substrate or binding agent described above. As an example, an HRP label conjugated to a detection probe requires a substrate, disclosed above, to detect a detection probe. Numerous other configurations for a label are known in the art. The present disclosure includes all label configurations exemplified herein and/or known in the art. In some embodiments, a label configuration can include PE conjugated to a PAD, a PAD:anti-PAD IgA complex binding agent, an anti-PAD IgA or an anti-IgA. In alternative embodiments, a label configuration can include PE conjugated to a specific PAD including, for example, PAD2, PAD3 and/or PAD4. In further embodiments, a label configuration can include a PE conjugated to an anti-PAD IgA including, for example, anti-PAD2 IgA, anti-PAD3 IgA and/or anti-PAD4 IgA.

Methods for detecting, measuring and/or quantifying a signal produced by a label of the present disclosure are well known in the art and include detection of fluorescence, luminescence, chemiluminescence or absorbance, reflectance, transmittance, birefringence or refractive index. Optical methods include imaging methods such as confocal and non-confocal microscopy and non-imaging methods such as microplate readers. In some embodiments, methods of detecting anti-PAD IgA in biological sample can include visualization, quantification or both of a fluorescent, colorimetric or absorbance signal in a biological sample.

In some embodiments of the present disclosure, anti-PAD IgA presence can be detected by immunoassay. Methods and protocols for conducting immunoassays and biophysical protein-interaction assays are well known in the art. See, e.g., Wild D., *The Immunoassay Handbook*, Elsevier Science, $4^{th}$ Edition (2013); Fu H., Protein-Protein Interactions, Humana Press, $4^{th}$ Edition (2004). Exemplary immunoassays include fluorescent immunosorbent assay (FIA), a chemiluminescent immunoassay (CIA), a radioimmunoassay (MA), multiplex immunoassay, a protein/peptide array immunoassay, a solid phase radioimmunoassay (SPRIA), an indirect immunofluorescence assay (IIF), an enzyme linked immunosorbent assay (ELISA) and a particle based multi-analyte test (PMAT), or a Dot Blot assay.

In some embodiments, the ELISA can be a sandwich ELISA. In some embodiments, the sandwich ELISA can include the initial step of immobilizing a purified polypeptide of this disclosure on a solid support as exemplified below. For example, a PAD or antigenic fragment thereof can be immobilized on a wall of a microtiter plate well or of a cuvette. In some embodiments, contacting the sample from the subject with the PAD or antigenic fragment thereof of this disclosure can include exposing the sample to the immobilized PAD or antigenic fragment thereof.

In some embodiments, the ELISA can be a direct ELISA. In some embodiments, the direct ELISA can include the initial step of immobilizing a PAD or antigenic fragment thereof on any of the solid supports disclosed herein. For example, a PAD or antigenic fragment thereof can be immobilized to a wall of a microtiter plate well or of a cuvette. In some embodiments, contacting the sample from the subject with a PAD or antigenic fragment thereof of this disclosure can include exposing the anti-PAD IgA contained in the patient's sample to the immobilized PAD. Any of the immunoassays disclosed herein (see above) and in the art can be used, or modified to be used, in any of the methods disclosed herein.

In some embodiments, anti-PAD IgA can be detected by a particle based multianalyte test. As used herein, the term "particle based multianalyte test (PMAT)" refers to an immunoassay that allows simultaneous measurement of two or more analytes in a single assay. For example, in PMAT, different types of particles are used simultaneously, with each type having immobilized a specific binding partner for a specific molecule species on the surface of its particles. In a solution, the analyte molecules to be detected are bound to their binding partners on the corresponding particle type. The bonds are then detected optically through the addition of a secondary marker that marks all particle-bound analyte molecules of the multiplex assay. A PMAT can be performed using a variety of formats known in the art, such as flow cytometry, a capture sandwich immunoassay, or a competitive immunoassay. For example, using a dual-laser flow-based detection instrument, the binding of analyte fractions, such as autoantibodies, can be detected through the fluorescence of the secondary marker. In some embodiments, the PMAT particle can be a bead. In effecting the PMAT, the presence of one or more autoantibodies specifically associated with an autoimmune disease can be identified, and the patient can be diagnosed with the autoimmune disease that is specifically associated with the autoantibody identified by the PMAT.

In some embodiments, a Dot-Blot or line immunoassay (LIA) can be used to detect anti-PAD IgA in a biological sample. Methods and protocols for dot blot are well known in the art, including estimating polypeptide concentration. See Joint ProteomicS Laboratory (JPSL) of the Ludwig Institute for Cancer Research, Estimating protein concentration by dot blotting of multiple samples, Cold Spring Harbor Protocols, New York (2006).

In some embodiments, the immunoassay can be performed by immobilizing a capture probe to a solid support for a sufficient time to allow binding to occur. A capture probe includes a binding agent that binds to an analyte of interest. With respect to detection of an anti-PAD IgA of this disclosure, a capture probe can be any binding agent that specifically binds to anti-PAD IgA, PAD:anti-PAD IgA complex or anti-PAD IgA. Exemplary capture probes includes, PAD and/or a particular PAD such as PAD2, PAD3 and/or PAD4, as well as antigenic fragments thereof. Other exemplary capture probes include anti-IgA antibodies and functional fragments thereof, anti-IgA binding polypeptides and functional fragments thereof, anti-PAD IgA binding polypeptides, including antibodies, and functional fragments thereof and/or PAD:anti-PAD IgA complex binding polypeptides and functional fragments and binding agents.

Accordingly, in some embodiments, an immunoassay can utilize anti-IgA immobilized to a solid support to capture IgA. In some embodiments, a PAD or antigenic fragment thereof can be immobilized to a solid support to capture anti-PAD IgA. In other embodiments, an anti-PAD IgA binding polypeptide can be immobilized to a solid support to detect IgA. Anti-PAD IgA captured by the above exemplary capture probes can be detected using a detection probe provided in this disclosure.

The immunoassay can further include blocking steps, washing steps and additionally or alternatively, elution steps. Blocking steps can include contacting a solid support of the immunoassay in a blocking buffer for a sufficient time and temperature to allow blocking. Exemplary blocking buffers are identified below as are exemplary solid supports. Washing steps include contacting a solid support of the immunoassay with a washing buffer to remove non-specific binding of polypeptides to the solid support. Exemplary washing buffers are described below. Elution buffers can include any of a variety of elution buffers known in the art or disclosed herein. Elution buffers include, for example, a 0.1 M glycine:HCl solution between pH 2.5 and 3. Polypeptide complexes can be eluted from the solid support of the immunoassay to aid in detection and measurement of, for example, PAD and anti-IgA complexes.

The present disclosure provides a kit which can be used to diagnosis RA, severity of disease and joint erosion. The kit can include a PAD of the present disclosure as exemplified in Tables 1-3 or an antigenic fragment thereof. In some embodiments, a PAD or antigenic fragment thereof can include any mammalian PAD as provided herein. Exemplary PADs include, for example, PAD2, PAD3 and PAD4.

The kit can include any of the detection probes provided herein as well as others well known in the art. For example, a detection probe can include an antibody or a ligand. A detection probe can be immobilized on a solid support. It should be noted that the term "immobilized" is used interchangeably with "attached" and both terms are intended to include covalent and non-covalent attachment, unless indicated otherwise, either explicitly or by context. In some embodiments, a PAD or antigenic fragment thereof is immobilized to a solid support. h As provided herein and exemplified with respect to the methods of this disclosure, a kit of this disclosure can include a reporter tag. Reporter tags function to produce a signal for detection of a biomarker. Reporter tags can be attached, for example, to any of the detection probes used herein through non-covalent or covalent cross-linkage. As exemplified with respect to the methods of this disclosure, a kit can include any of the labels described or exemplified herein. For example, a label of the kit can include a fluorophore, an enzyme, a chemiluminescent moiety, a radioactive moiety, an organic dye, a small molecule, a polypeptide or functional fragment thereof. In some embodiments, a label of the kit includes PE. In some embodiments, a label of the kit includes FITC. In some embodiments, a label of the present disclosure is conjugated to a detection probe of the disclosure as exemplified above.

A kit can include any solid support provided herein or identified in the art. As used herein, the terms "solid support," "solid surface" and other grammatical equivalents refer to any material that is appropriate for or can be modified to be appropriate for the attachment of PAD or an antigenic fragment thereof of this disclosure. Possible materials include, without limitation, glass and modified or functionalized glass, plastics (including acrylics, polystyrene, methylstyrene, polyurethanes, Teflon", etc.), paramagnetic materials, thoria sol, carbon graphite, titanium oxide, latex or cross-linked dextrans such as Sepharose, cellulose polysaccharides, nylon or nitrocellulose, ceramics, resins, silica or silica-based materials including silicon and modified silicon, carbon metals, inorganic glasses, optical fiber bundles, and a variety of other polymers. In some embodiments, the solid supports can be located in microtiter well plates (e.g., a 96-well, 384-well or 1536-well plate). In some embodiments, the solid supports can be located within a flow cell or flow cell apparatus (e.g., a flow cell on a Biacore™ chip or a protein chip).

In some embodiments, the solid support can be a bead, microsphere, particle, membrane, chip, slide, well, and test tube. Beads include microspheres or particles. By “microspheres” or “particles” or grammatical equivalents herein is meant small, discrete, non-planar particles in the micrometer or nanometer dimensions. In some embodiments the bead can be spherical, in other embodiments the bead is irregular. Alternatively or additionally, the beads can be porous. The bead sizes range from nanometers to millimeters with beads from about 0.2 to about 200 microns being preferred in some embodiments. In other embodiments, bead size can range from about 0.5 to about 5 microns. In some embodiments, beads smaller than 0.2 microns and larger than 200 microns can be used. In some embodiments, the solid support can include an array of wells or depressions in a surface. This can be fabricated as is known in the art using a variety of techniques, including, photolithography, stamping techniques, molding techniques and microetching techniques. As will be appreciated by those skilled in the art, the technique used will depend on the composition and shape of the array substrate.

In some embodiments, the solid support can include a patterned surface suitable for immobilization of purified proteins in an ordered pattern (e.g., a protein chip). A “patterned surface” refers to an arrangement of different regions in or on an exposed layer of a solid support. For example, one or more of the regions can be features where one or more purified proteins are present. The features can be separated by interstitial regions where purified proteins are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. App. Publ. No. 2008/0280785 A1, U.S. Pat. App. Publ. No. 2004/0253640 A1, U.S. Pat. App. Publ. No. 2003/0153013 A1 and International Publication No. WO 2009/039170 A2.

In some embodiments, a solid support can have attached to its surface a PAD or an antigenic fragment thereof or anti-IgA. Any PAD exemplified by, for example, Tables 1-3, including antigenic fragments thereof can be attached to a solid support. In some embodiments, any PAD or antigenic fragment thereof of the present disclosure can be immobilized to a solid support via a linker molecule. In some embodiments, all that is required is that molecules, such as any PAD or antigenic fragment thereof of the present disclosure, remain immobilized or attached to the support under the conditions in which it is intended to use the support, for example, in applications requiring antibody binding or detection.

A kit can include a positive control. In some embodiments, a positive control can be a sample containing a detectable amount of anti-PAD IgA or levels above the threshold. In some embodiments, a positive control can be obtained from a diseased subject who has levels of anti-PAD IgA above threshold. Additionally or alternatively, a positive control can contain anti-PAD IgA synthesized in vitro using any of the methods described herein. In other embodiments, the kit can include a negative control. A negative control can be a sample containing no detectable amount of anti-PAD IgA or levels below the threshold. In some embodiments, a negative control can be obtained from a healthy control individual or can be synthesized in vitro. For example, a negative control can include water or buffer.

The kit or the disclosure can further include one or more ancillary reagents. As used herein, “ancillary reagents” refer to a substance, mixture, material or component that is useful to carry out an intended purpose of the kit. Ancillary reagents can include a reagent, including a conjugation reagent, a buffer, standard, positive control, label, instructions and the like.

In some embodiments, a reagent of the kit of the present disclosure can include any conjugation reagent known in the art, including covalent and non-covalent conjugation reagents. Covalent conjugation reagents can include any chemical or biological reagent that can be used to covalently immobilize a polypeptide of this disclosure on a surface. Covalent conjugation reagents can include a carboxyl-to-amine reactive group such as carbodiimides such as EDC or DCC, an amine reactive group such as N-hydroxysuccinimide (NHS) ester or imidoesters, a sulfhydryl-reactive crosslinker such as maleimides, haloacetyls, or pyridyl disulfides, a carbonyl-reactive crosslinker groups such as, hydrazides or alkoxyamines, a photoreactive crosslinker such as aryl azides or dizirines, or a chemoselective ligation group such as a Staudinger reaction pair. Non-covalent immobilization reagents can include any chemical or biological reagent that can be used to immobilize a polypeptide of this disclosure non-covalently on a surface, such as affinity tags such as biotin or capture reagents such as streptavidin or anti-tag antibodies, such as anti-His6 or anti-Myc antibodies.

The kits of this disclosure can include combinations of conjugation reagents. Such combinations include, e.g., EDC and NHS, which can be used, e.g., to immobilize a protein of this disclosure on a surface, such as a carboxylated dextrane matrix (e.g., on a BIAcore™ CM5 chip or a dextrane-based bead). Combinations of conjugation reagents can be stored as premixed reagent combinations or with one or more conjugation reagents of the combination being stored separately from other conjugation reagents.

In other embodiments, a reagent of the kit can include a reagent such as a coating buffer. A coating buffer can include sodium carbonate-sodium hydroxide or phosphate. In some embodiments, the coating buffer can be 0.1M $NaHCO_3$ (e.g., about pH 9.6).

In some embodiments, a reagent of a kit can include a washing buffer. A washing buffer can include tris(hydroxymethyl)aminomethane (Tris)-based buffers like Tris-buffered saline (TB S) or phosphate buffers like phosphate-buffered saline (PBS). Washing buffers can be composed of detergents, such as ionic or non-ionic detergents. In some embodiments, the washing buffer can be a PBS buffer at about pH 7.4 including Tween® 20 at about 0.05%. In other embodiments, the washing buffer can be the BIO-FLASH™ Special Wash Solution (Inova Diagnostics, Inc., San Diego, CA).

In some embodiments, a reagent of the kit can include a dilution buffer. Any dilution buffer known in the art can be included in the kit of the present disclosure. Typical dilution buffers include a carrier protein such as bovine serum albumin (BSA) and a detergent such as Tween® 20. In some embodiments, the dilution buffer can be PBS at about pH 7.4 including BSA at about 1% BSA and Tween 20 at about 0.05%.

In some embodiments, a reagent can include a detection or assay buffer. Any detection or assay buffer known in the art can be included in the kit of the present disclosure. The detection or assay buffer can be a colorimetric detection or assay buffer, a fluorescent detection or assay buffer or a chemiluminescent detection or assay buffer. Colorimetric detection or assay buffers include PNPP (p-nitrophenyl phosphate), ABTS (2,2'-azino-bis(3-ethylbenzothiazoline-6-sulphonic acid)) or OPD (o-phenylenediamine). Fluorescent detection or assay buffers include QuantaBlu™ or QuantaRed™ (Thermo Scientific, Waltham, MA). Chemiluminescent detection or assay buffers can include luminol or luciferin. Detection or assay buffers can also include a trigger such as $H_2O_2$ and a tracer such as isoluminol-conjugate. In some embodiments, the detection reagent can include one or more BIO-FLASH™ Trigger solutions (Inova Diagnostics, Inc., San Diego, CA). In some embodiments, a reagent of the kit of the present disclosure can include solutions useful for calibration or testing.

In some embodiments, a reagent of the kit can include a stop solution. Any stop solution known in the art can be included in a kit of this disclosure. The stop solutions of this disclosure terminate or delay the further development of the detection reagent and corresponding assay signals. Stop solutions can include, e.g., low-pH buffers (e.g., glycine-buffer, pH 2.0), chaotrophic agents (e.g., guanidinium chloride, sodium-dodecylsulfate (SDS)) or reducing agents (e.g., dithiothreitol, β-mercaptoethanol), or the like.

In some embodiments, a reagent of the kit of this disclosure can include cleaning reagents. Cleaning reagents can include any cleaning reagent known in the art. In some embodiments, the cleaning reagents can be the cleaning reagents recommended by the manufacturers of the automated assay systems. In some embodiments, the cleaning reagents can include the BIO-FLASH™ System Rinse or the BIO-FLASH™ System Cleaning solutions (Inova Diagnostics, Inc., San Diego, CA).

A detection probe of the kit can include any of the detection probes described above. In brief, a detection probe of the kit can include antibodies and ligands. Thus, a "detection probe specific for anti-PAD IgA" includes, for example, PAD, a PAD:anti-PAD IgA complex binding agent, an anti-PAD IgA binding agent and an IgA binding agent. The anti-PAD IgA detection probes include binding agents to anti-PAD2 IgA, anti-PAD3 IgA and/or anti-PAD4 IgA.

A detection probe of the kit can be conjugated to any of the labels previously disclosed herein. For example, a detection probe can be conjugated to a fluorophore, an enzyme, a chemiluminescent moiety, a radioactive moiety, an organic dye, a small molecule, a polypeptide or functional fragment thereof. Examples of fluorophores include fluorescent dyes like phycoerytherin (PE), fluorescein isothiocyanate (FITC), tetramethylrhodamine (TRITC), BODIPY and AlexaFluor® dyes. Fluorescent dyes can also include fluorescence resonance energy transfer (FRET)-dyes or time-resolved (TR)-FRET dyes. Fluorophore labels also include fluorescent proteins such as green fluorescent protein (GFP) and cyan fluorescent protein (CFP). Examples of enzyme labels include alkaline phosphatase (AP) or horseradish peroxidase (HRP). When any of the substrates 3,3'5,5'-Tetramethylbenzidine (TMB), 3,3'-Diaminobenzidene (DAB), or 2,2'-azino-bis(3-ethylbenzothiazoline-6-sulphonic acid) (ABTS) are applied to HRP, a colored (chromogenic) or light (chemiluminescent) signal is produced. Radioactive moiety labels include carbon-14 or Tritium. Small molecule labels include biotin, resins such as agarose beads and fluorescently labeled magnetic beads, or nanoparticles such as colloidal gold. Polypeptide or functional fragment labels include Avidin, Streptavidin or NeutrAvidin which have an affinity for biotin. Polypeptide or functional fragment labels also include hemagglutinin (HA), glutathione-S-transferase (GST) or c-myc.

In some embodiments, the kit provided in this disclosure can include a component suitable for collecting a biological sample. A component can include collection tubes, columns, syringes, needles and the like. In some embodiments, the kit can include instructions for using the components of the kit. Instructions can be in any form, inside or outside of the kit. The instructions provide details regarding protocol and analytical techniques.

In some embodiments, a kit of the disclosure can include an instrument to an automated assay system. Automated assay systems can include systems by any manufacturer. In some embodiments, the automated assay systems can include, e.g., the BIO-FLASH™, the BEST 2000™, the DS2™, the ELx50 WASHER, the ELx800 WASHER, the ELx800 READER, and the Autoblot S20™ (Inova Diagnostics, Inc., San Diego, CA). In other embodiments, an instrument of the kit can be a detection instrument. A detection instrument can include any detection instrument in the art. Detection instruments are capable of detecting or measuring a label of the reporter tags of the present disclosure. Thus, detection instruments are capable of detecting or measuring fluorescence, luminescence, chemiluminescence or absorbance, reflectance, transmittance, birefringence or refractive index. In some embodiments, detection instruments can include confocal and non-confocal microscopy, a microplate reader, a flow cytometer and the like.

Components of a kit of the disclosure can be in varying physical states. For example, some or all of the components can be lyophilized or in aqueous solution or frozen. Such components include a PAD, a detection probe, and ancillary reagents. Ancillary reagents include immobilization buffer, incubation buffer, washing buffer, dilution buffer, detection or assay buffer and blocking buffer. A person skilled in the art recognizes that there are various types of incubation, washing, detection and blocking buffers.

A kit of this disclosure can be tailored to specific assay technologies. In some embodiments, a kit can be tailored to assay technologies exemplified herein. For example, in some embodiments, the kits can be a FIA kit, a CIA kit, a RIA kit, a multiplex immunoassay kit, a protein/peptide array immunoassay kit, a SPRIA kit, an IIF kit, an ELISA, a PMAT kit, or a Dot Blot kit. In some embodiments, the ELSA kits can include a washing buffer, a sample diluents, a secondary antibody-enzyme conjugate, a detection reagent and a stop solution. In some embodiments, the Dot Blot kits can include a washing buffer, a sample diluents, a secondary antibody-enzyme conjugate, a detection reagent, and a stop solution. In some embodiments, the CIA kit can include a washing buffer, a sample diluent, a tracer (e.g., isoluminol-conjugate) and a trigger (e.g., $H_2O_2$). In some embodiments, the multiplex kit can include a washing buffer, a sample diluent and a secondary antibody-enzyme conjugate. In some embodiments, the kits can be tailored to the Luminex platform and include, as an example, xMAP® beads.

A kit can be used to diagnose RA, severity of disease or joint erosion by providing a means for detecting anti-IgA bound to PAD or an antigenic fragment thereof. A kit can detect anti-IgA by any of the methods disclosed herein (see above). Complexes of anti-PAD IgA and a PAD, or antigenic fragment thereof, can have a stoichiometry of one to one or more than one to one anti-PAD IgA. In some embodiments, the complexes can have one anti-PAD IgA antibody per PAD or antigenic fragment thereof. In some embodiments, the complexes can have two anti-PAD IgA per PAD or antigenic fragment thereof. In some embodiments, the complexes can have more than two anti-PAD IgA per PAD or antigenic fragment thereof. Methods for measuring binding stoichiometries of two antigens are well known in the art and include, e.g., isothermal titration calorimetry (ITC) and ultracentrifugation.

In some embodiments, the complexes of anti-PAD IgA and PAD, or antigenic fragment thereof, can be a plurality of complexes with identical stoichiometry. For example, all complexes in the plurality of complexes have one anti-PAD IgA per purified PAD or antigenic fragment thereof. In some embodiments, the complexes of anti-PAD IgA and PAD or antigenic fragment thereof, can be a plurality of complexes with different stoichiometries. For example, some complexes in the plurality of complexes can have one anti-PAD IgA per PAD or antigenic fragment thereof and some other complexes in the plurality of complexes can have more than one anti-PAD IgA per PAD or antigenic fragment thereof.

In some embodiments, a PAD or antigenic fragment thereof can be bound by anti-PAD IgA with higher affinity. In some embodiments, anti-PAD IgA binding sites can be bound by anti-PAD IgA with more than 2-fold, more than 3-fold, more than 4-fold, more than 5-fold, more than 8-fold, more than 10-fold, more than 15-fold, more than 20-fold, more than 25-fold, more than 50-fold, more than 100-fold, more than 300-fold, more than 1,000-fold, more than 3,000-fold, more than 10,000-fold, more than 30,000-fold, or more than 100,000-fold greater binding affinity. Greater binding affinities are evidenced by lower dissociation constants ($K_D$s) for anti-PAD IgA-PAD complex or by higher association constants ($K_A$s) for the respective anti-PAD IgA and PAD. In some embodiments, the dissociation constants for ($K_D$s) for the anti-PAD IgA-PAD complexes can be less than 1 mM, less than 300 nM, less than 100 nM, less than 30 nM, less than 10 nM, less than 3 nM, less than 1 nM, less than 300 pM, less than 100 pM, less than 30 pM, less than 10 pM, less than 3 pM, or less than 1 pM. Methods for measuring binding affinities of antibodies to antigens are well known in the art and include ELISA, isothermal titration calorimetry (ITC) and surface plasmon resonance (SPR).

Example I

Detection of Anti-PAD4, Anti-PAD2 IgA and Joint Erosion in Rheumatoid Arthritis Patients This example illustrates the use of anti-PAD4 IgA and anti-PAD2 IgA as biomarkers for the detection of joint erosion in rheumatoid arthritis (RA).

Anti-PAD4 IgA and anti-PAD2 IgA were measured using a particle-based multianalyte test (PMAT, Inova Diagnostics, San Diego, US). For this test, human recombinant full-length PAD4 polypeptide (Cayman Chemical, Ann Arbor, MI; cat no. 10500) and human recombinant full-length PAD2 polypeptide (John Hopkins University, Baltimore, MD) were coupled to paramagnetic beads with unique signatures. The coupling procedure includes bead activation, antigen coupling and bead blocking.

Bead activation was performed by incubating the beads for 30 min at room temperature with an activation buffer. Once the beads were activated, they were incubated with the antigen for 1 hour at room temperature in coupling buffer at a concentration of 22.2 μg of antigen/million of beads for PAD4 and 10 μg of antigen/million for PAD2. Finally, the beads were blocked for 1 hour at room temperature with PBS-TBN buffer. Once the beads were coupled, they were resuspended in a PBS-based assay resuspension buffer at a concentration of 1500 beads/test.

Measurement of anti-PAD4 IgA and anti-PAD2 IgA was performed as follows. First, sera from 41 RA patients with known erosion status were diluted 1:7 in Hemosil Rinse Solution (Inova Diagnostics, San Diego, CA). Next, PAD4 and PAD2 coupled beads were incubated for 9.5 min at 37° C. with patients' serum and assay buffer. After three washes with Hemosil Rinse Solution, the beads were then incubated for 9.5 min at 37° C. with a phycoerythrin (PE)-labeled anti-human IgA detector (Inova Diagnostics, San Diego, CA) at a concentration of 5 μg/mL in QUANTA Flash Diluent (Inova Diagnostics, San Diego, CA). After incubation, beads were washed again in Hemosil Rinse Solution and the particles were analyzed through digital imaging technology. Finally, the Median Fluorescence Intensity (MFI) was calculated on the particles.

Figure 2:
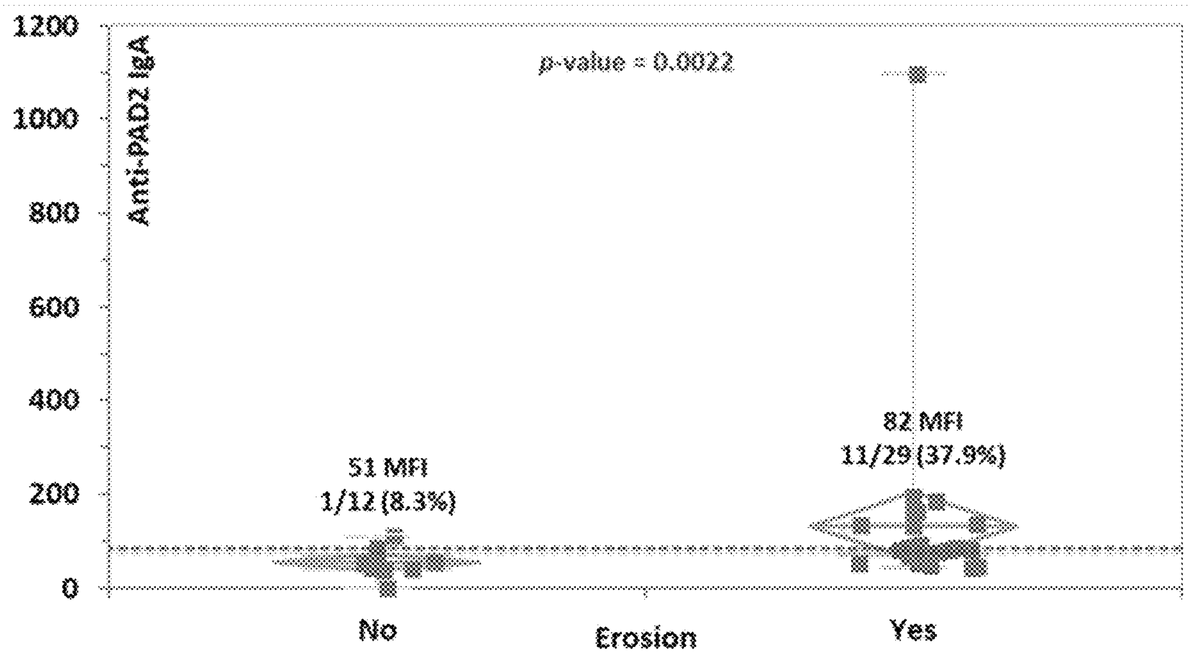
FIG. 2 shows association of anti-PAD2 IgA with joint erosion status. Results are expressed in Median Fluorescence Intensity (MFI). P-value of the Mann-Whitney analysis is shown in red (p-value <0.05 considered significant). Median MFI for the subgroup and number of patients and % are shown. Red dashed line represents the preliminary cut-off.

Anti-PAD4 IgA and anti-PAD2 IgA were significantly higher in RA patients with erosions compared to individuals without erosions ($p=0.0022$ and $p=0.0419$, respectively). See, FIG. 1 and FIG. 2. Discrimination between the populations of subjects with and without erosive disease reported an Area Under the Curve (AUC) of 0.704 (95% CI 0.529-0.879) for anti-PAD4 IgA. See FIG. 1. With an assay preliminary cut-off of 88 MFI determined by Receiver Operating Characteristic (ROC) curve analysis, anti-PAD2 IgA positive patients were 6.7 (95% CI 0.9-45.6) times more likely to have erosive disease. With an assay preliminary cut-off of 116 MFI, anti-PAD4 IgA positive patients were 3.2 (95% CI 0.8-13.4) times more likely to have erosive disease.

In conclusion, this example demonstrates that anti-PAD4 IgA and anti-PAD2 IgA are indicative of erosive disease in RA. These data further demonstrate that anti-PAD4 IgA and anti-PAD2 IgA represent useful biomarkers for patient stratification.

Example II

Detection of Anti-PAD4 IgA, IgG and IgM in Rheumatoid Arthritis Patients

This example illustrates the use of anti-PAD4 IgA, IgG and IgM as biomarkers for the detection of joint erosion in rheumatoid arthritis (RA).

Bead activation was performed by incubating the beads for 30 min at room temperature with an activation buffer. Once the beads were activated, they were incubated with the antigen for 1 hour at room temperature in coupling buffer at a concentration of 22.2 μg of antigen/million of beads for PAD4 and 10 μg of antigen/million for PAD2. Finally, the beads were blocked for 1 hour at room temperature with a PBS-TBN buffer. Once the beads were coupled, they were resuspended in a PBS-based assay resuspension buffer at a concentration of 1500 beads/test.

Measurement of anti-PAD4 IgA, IgG and IgM was performed as follows. First, sera from 62 RA patients with known erosion status were diluted 1:7 in Hemosil Rinse Solution (Inova Diagnostics, San Diego, CA). Next, PAD4 coupled beads were incubated for 9.5 min at 37° C. with patients' serum and assay buffer. After three washes with Hemosil Rinse Solution, the beads were then incubated for 9.5 min at 37° C. with a PE-labeled anti-human IgA, IgG or IgM detector (Inova Diagnostics, San Diego, CA) at the concentrations of 5, 1 and 5 μg/mL, respectively, and diluted in QUANTA Flash Diluent (Inova Diagnostics, San Diego, CA). After incubation, beads were washed again in Hemosil Rinse Solution and the particles were analyzed through digital imaging technology. Finally, the Median Fluorescence Intensity (MFI) was calculated on the particles.

Figure 23:
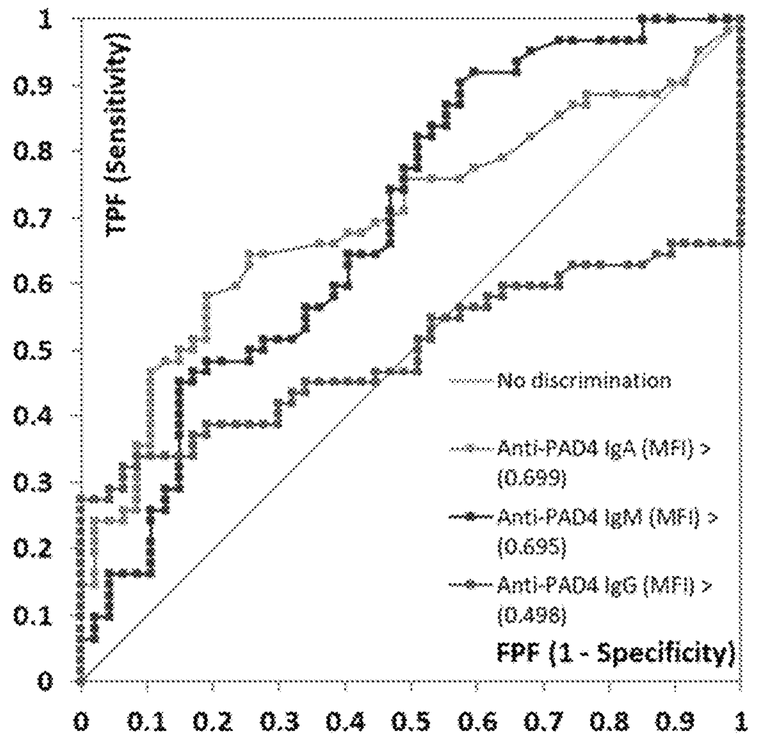
FIG. 23 shows receiver operating characteristic (ROC) analysis of anti-PAD4 IgA (blue), anti-PAD4 IgG (grey) and anti-PAD4 IgM (red), illustrating the discrimination between RA and controls. Area Under the Curve (AUC) for each marker is shown in the legend.
Figure 24:
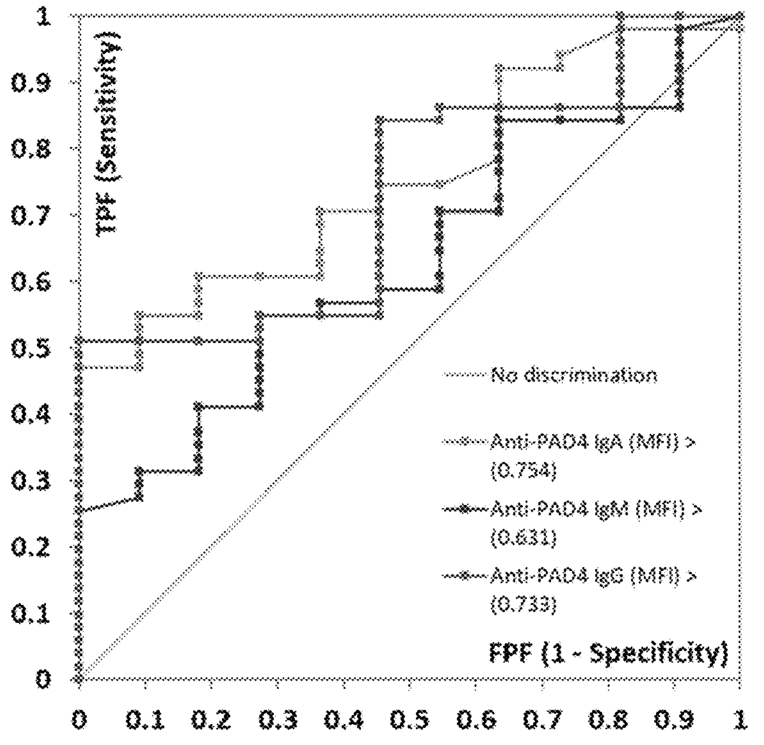
FIG. 24 shows receiver operating characteristic (ROC) analysis of anti-PAD4 IgA (blue), anti-PAD4 IgG (grey) and anti-PAD4 IgM (red), illustrating discrimination for RA erosive disease. Area Under the Curve (AUC) for each marker is shown in the legend.
Figure 25:
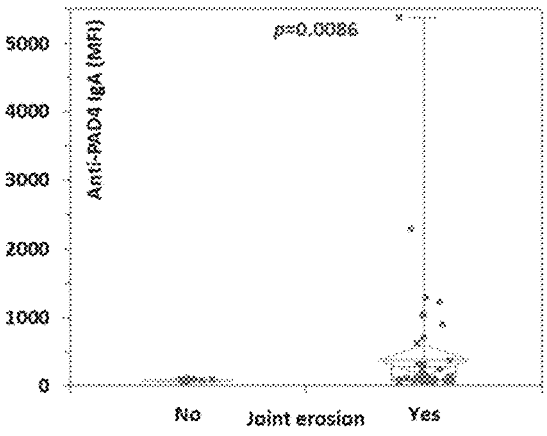
FIG. 25 shows association of anti-PAD4 IgA with joint erosion status. Results are expressed in Median Fluorescence Intensity (MFI). P-value of the Mann-Whitney analysis is shown in the graph (p-value <0.05 considered significant).
Figure 26:
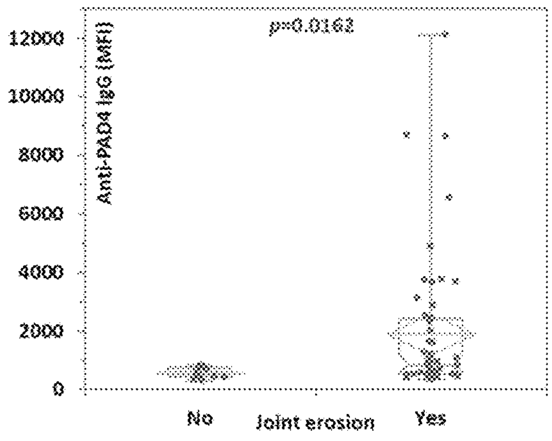
FIG. 26 shows association of anti-PAD4 IgG with joint erosion status. Results are expressed in Median Fluorescence Intensity (MFI). P-value of the Mann-Whitney analysis is shown in the graph (p-value <0.05 considered significant).
Figure 27:
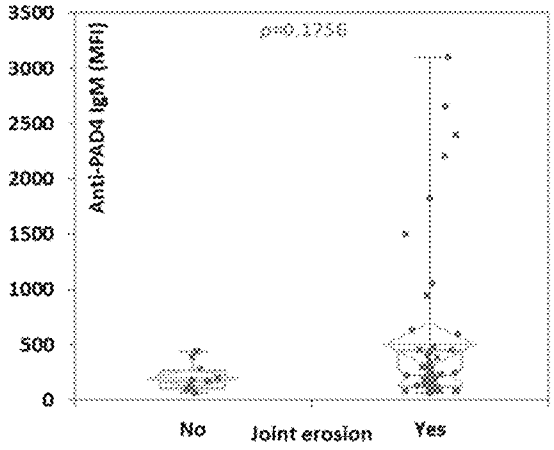
FIG. 27 shows association of anti-PAD4 IgM with joint erosion status. Results are expressed in Median Fluorescence Intensity (MFI). P-value of the Mann-Whitney analysis is shown in the graph (p-value <0.05 considered significant).

Anti-PAD4 IgA and IgM, but not IgG, were significantly higher in RA patients with erosions compared to individuals without erosions (p=0.0004, p=0.0005 and p=0.9'70'7, respectively). ROC analysis showed higher AUC values for the discrimination between RA and controls for anti-PAD4 IgA and IgM [0.70 (95% CI 0.60-0.80) and 0.70 (95% CI 0.59-0.80), respectively] than for anti-PAD4 IgG [0.50 (95% CI 0.39-0.61)]. At the relevant diagnostic area (>90% specificity), IgG outperformed the other two markers. See, FIG. 23. Discrimination for erosive disease was observed with anti-PAD4 IgA, followed by IgG and IgM. See, FIG. 24. Spearman correlation analysis showed moderate significant association between IgA and IgG (Spearman's rs=0.45, p<0.0001) and between IgA and IgM (Spearman's rs=0.45, p<0.0001), and a weak correlation between IgG and IgM (Spearman's rs=0.27, p=0.0053). When subjects with RA were stratified by presence or absence of erosive disease, higher titers of the three isotypes were observed in patients with erosive disease compared to individuals without erosions. However, this association was only significant for anti-PAD4 IgA and IgG (p=0.0086 and p=0.0162) (See, FIG. 25 and FIG. 26) but not anti-PAD4 IgM (p=0.1756) (See, FIG. 27).

In conclusion, the anti-PAD4 response in RA patients involves all three isotypes in RA. Anti-PAD4 IgA and IgG are associated with erosive disease in RA and represent useful markers for patient stratification.

It is understood that modifications, which do not substantially affect the activity of the various embodiments of this disclosure, are also included within the definition of the disclosure provided herein. Accordingly, the following examples are intended to illustrate but not limit the present disclosure.

What is claimed is:

1. One or more detection kits comprising:
(a) a peptidyl arginine deiminase 4 (PAD4) or antigenic fragment thereof;
(b) a first antibody or functional fragment thereof capable of binding to anti-PAD4 IgA;
(c) a second antibody or functional fragment thereof capable of binding to anti-PAD4 IgG;
(d) a solid support; and
(e) a peptidyl arginine deiminase 1 (PAD1) or antigenic fragment thereof;
wherein the one or more detection kits are used usable in the a method for assessing disease severity in a subject having rheumatoid arthritis (RA); and
wherein a severity of the RA is based on presence of joint erosion or severe joint erosion in the subject.

2. The one or more detection kits of claim 1, wherein the first antibody or functional fragment thereof and the second antibody or functional fragment thereof each comprises a reporter tag.

3. The one or more detection kits of claim 2, wherein each reporter tag is independently selected from the group consisting of a fluorophore, an enzyme, a chemiluminescent moiety, a radioactive moiety, or an organic dye.

4. The one or more kits of claim 1, wherein said the solid support is selected from the group consisting of a bead, a sphere, a particle, a membrane, a chip, a slide, a plate, a well, or a test tube.

5. The one or more detection kits of claim 1, wherein the PAD4 or antigenic fragment thereof is conjugated to the solid support.

6. A detection kit comprising:
(a) a peptidyl arginine deiminase 4 (PAD4) and a peptidyl arginine deiminase (PAD1) or antigenic fragments of PAD4 and PAD1;
(b) two or more antibodies or functional fragments thereof, wherein a first antibody or functional fragment thereof is capable of binding to anti-PAD4 IgA and a second antibody or functional fragment thereof is capable of binding to anti-PAD4 IgG; and
(c) a solid support;
wherein the detection kit is usable in a method for assessing disease severity in a subject having rheumatoid arthritis (RA), and wherein a severity of the RA is based on a presence of joint erosion or severe joint erosion in the subject.

7. The one or more detection kits of claim 1, further comprising:
a positive control comprising anti-PAD4 IgA.

8. The one or more detection kits of claim 1, further comprising:
a positive control comprising anti-PAD4 IgG.

9. The one or more detection kits of claim 1, further comprising:
a first positive control comprising anti-PAD4 IgA; and
a second positive control comprising anti-PAD4 IgG.

10. The one or more detection kits of claim 1, further comprising:
one or more ancillary reagents selected from the group consisting of an incubation buffer, a wash buffer, a detection buffer, or a detection instrument.

11. The one or more detection kits of claim 1, further comprising:
a first positive control comprising anti-PAD4 IgA;
a second positive control comprising anti-PAD4 IgG; and
one or more ancillary reagents selected from the group consisting of an incubation buffer, a wash buffer, a detection buffer, or a detection instrument.

12. The one or more detection kits of claim 2, wherein the reporter tag is a label.

13. The one or more kits of claim 4, wherein the bead, the sphere, or the particle has micrometer or nanometer dimensions.

14. The detection kit of claim 6, further comprising:
a positive control comprising anti-PAD4 IgA.

15. The detection kit of claim 6, further comprising:
one or more ancillary reagents selected from the group consisting of an incubation buffer,
a wash buffer, a detection buffer, or a detection instrument.

16. The detection kit of claim 6, further comprising:
a positive control comprising anti-PAD4 IgA; and
one or more ancillary reagents selected from the group consisting of an incubation buffer, a wash buffer, a detection buffer, or a detection instrument.

* * * * *